United States Patent
Sunagawa et al.

(10) Patent No.: US 7,163,936 B2
(45) Date of Patent: Jan. 16, 2007

(54) β-LACTAM COMPOUNDS AND PROCESS FOR PRODUCING THE SAME

(75) Inventors: Makoto Sunagawa, Itami (JP); Katsumi Kubota, New York, NY (US); Masanori Itoh, Toyonaka (JP); Erwin Goetschi, Reinach (CH)

(73) Assignee: Dainippon Sumitomo Pharma Co., Ltd., Osaka-fu (JP)

( * ) Notice: Subject to any disclaimer, the term of this patent is extended or adjusted under 35 U.S.C. 154(b) by 37 days.

(21) Appl. No.: 10/416,334

(22) PCT Filed: Nov. 6, 2001

(86) PCT No.: PCT/JP01/09664

§ 371 (c)(1),
(2), (4) Date: May 8, 2003

(87) PCT Pub. No.: WO02/38564

PCT Pub. Date: May 16, 2002

(65) Prior Publication Data

US 2004/0102433 A1    May 27, 2004

(30) Foreign Application Priority Data

Nov. 8, 2000  (JP) .............................. 2000-341063
Apr. 24, 2001 (JP) .............................. 2001-126296
Sep. 10, 2001 (JP) .............................. 2001-273615

(51) Int. Cl.
*A61K 31/40* (2006.01)
*C07D 487/04* (2006.01)
(52) U.S. Cl. .................. 514/210.12; 540/350
(58) Field of Classification Search ................ 540/350; 514/210.12
See application file for complete search history.

(56) References Cited

U.S. PATENT DOCUMENTS 5,750,686 A * 5/1998 Sunagawa et al. .......... 540/350

FOREIGN PATENT DOCUMENTS

EP    0 704 446    4/1996
WO    98/09965    3/1998

* cited by examiner

*Primary Examiner*—Golam M. M. Shameeh
*Assistant Examiner*—Ebenezer Sackey
(74) *Attorney, Agent, or Firm*—Wenderoth, Lind & Ponack, L.L.P.

(57) ABSTRACT

1. A β-lactam compound of the formula [1];

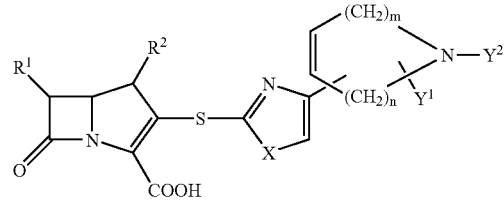

wherein $R^1$ is a lower alkyl, a lower alkyl substituted by a hydroxy; $R^2$ is a hydrogen, a lower alkyl; X is O, S, NH; m and n are 0 to 4, $Y^1$ is a halogen, cyano, a hydroxy, an amino, a lower alkyloxy, a lower alkylamino, a carboxy, a carbamoyl, a lower alkyl, etc., $Y^2$ is hydrogen, an alkyl, cyano, —C($R^3$)=$NR^4$ (wherein $R^3$ and $R^4$ are hydrogen, an amino, an alkyl, etc., or $R^3$ and $R^4$ may combine each other together with the nitrogen atom to form a 5- to 7-membered heterocyclic group), or a pharmaceutically acceptable salt thereof, or a non-toxic ester thereof, which has an excellent antibacterial activity against Gram-positive bacteria, especially against MRSA and MRCNS.

19 Claims, No Drawings

β-LACTAM COMPOUNDS AND PROCESS FOR PRODUCING THE SAME

This application is a U.S. national stage of International Application No. PCT/JP01/09664 filed Nov. 6, 2001.

TECHNICAL FIELD

The present invention relates to a novel β-lactam compound represented by the formula [1] as described below.

BACKGROUND ART

By the wide clinical application of the third-generation cephalosporins, Gram-positive bacteria have become to be frequently isolated. Particularly, methicillin-resistant *Staphylococcus aureus* (hereinafter, abbreviated as MRSA) has been more frequently isolated, and becomes a serious problem in clinical field, because infectious diseases caused by MRSA are difficult to be treated. Although vancomycin has been broadly used for infectious diseases caused by MRSA in these days, it has a defect in difficulty of administration because of its side effects, and further glycopeptide-resistant bacteria are supposed to increase in future by administration thereof. Moreover, it has recently been reported increase in isolation of methicillin-resistant and coagulase-negative *Staphylococci* (MRCNS). Under these circumstances, it has been desired to develop a safer medicament having excellent anti-MRSA and anti-MRCNS activities.

DISCLOSURE OF INVENTION

An object of the present invention is to provide β-lactam antibiotic having an excellent antibacterial activity against Gram-positive bacteria, especially against MRSA and MRCNS.

The present inventors have intensively studied, and have found that a compound of the following formula [1] shows a potent effect on Gram-positive bacteria, and shows an excellent antibacterial activity especially against MRSA and MRCNS, and have accomplished the present invention.

That is, the present invention relates to (1) a β-lactam compound of the following formula [1];

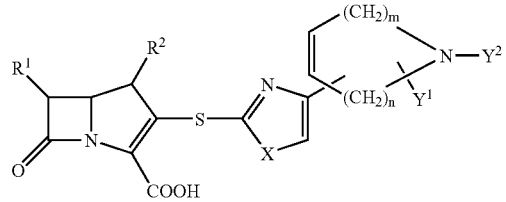
[1]

wherein $R^1$ is a lower alkyl group or a lower alkyl group substituted by a hydroxy group; $R^2$ is a hydrogen atom or a lower alkyl group; X is an oxygen atom, a sulfur atom or an imino group (NH); m and n are independently an integer of 0 to 4 and the sum of m and n is 0 to 4, $Y^1$ is a halogen atom, cyano group, a hydroxy group optionally protected, an amino group optionally protected, a lower alkyloxy group, a lower alkylamino group, a carboxy group optionally protected, a carbamoyl group optionally substituted, or a lower alkyl group optionally substituted, $Y^2$ is hydrogen atom, a lower alkyl group optionally substituted, cyano group, or $-C(R^3)=NR^4$ (wherein $R^3$ and $R^4$ are independently, hydrogen atom, an amino group optionally substituted or, or a lower alkyl group optionally substituted, or $R^3$ and $R^4$ may combine each other together with the nitrogen atom to which they bond to form a 5- to 7-membered heterocyclic group), provided that 1 to 4 $Y^1$s may present on the same ring and 2 $Y^1$s may present on the same carbon atom, or a pharmaceutically acceptable salt thereof, or a non-toxic ester thereof, (2) the β-lactam compound according to the above (1), wherein the sum of m and n is 2, or a pharmaceutically acceptable salt thereof, or a non-toxic ester thereof, (3) the β-lactam compound according to the above (1), wherein the sum of m and n is 3, or a pharmaceutically acceptable salt thereof, or a non-toxic ester thereof, (4) the β-lactam compound according to the above (1) wherein the β-lactam compound is a β-lactam compound of the following formula [1a];

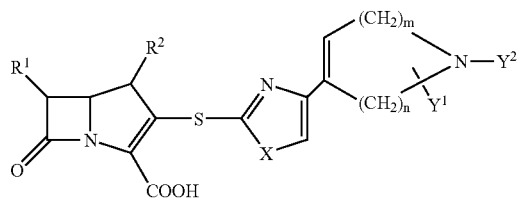
[1a]

wherein $R^1$, $R^2$, X, m, n, $Y^1$ and $Y^2$ are the same as defined above, or a pharmaceutically acceptable salt thereof, or a non-toxic ester thereof, (5) the β-lactam compound according to the above (4), wherein the sum of m and n is 2, or a pharmaceutically acceptable salt thereof, or a non-toxic ester thereof, (6) the β-lactam compound according to the above (4), wherein the sum of m and n is 3, or a pharmaceutically acceptable salt thereof, or a non-toxic ester thereof, (7) the β-lactam compound according to any of the above (1) to (6), wherein X is a sulfur atom, or a pharmaceutically acceptable salt thereof, or a non-toxic ester thereof, (8) the β-lactam compound according to any one of the above (1) to (7), wherein $R^1$ is a 1-(R)-hydroxyethyl group, or a pharmaceutically acceptable salt thereof, or a non-toxic ester thereof, (9) a process for producing a β-lactam compound of the formula [1]:

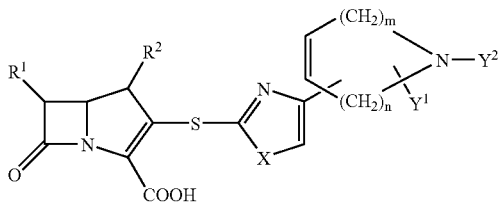
[1]

wherein $R^1$ is a lower alkyl group or a lower alkyl group substituted by a hydroxy group; $R^2$ is a hydrogen atom or a lower alkyl group; X is an oxygen atom, a sulfur atom or an imino group; m and n are independently an integer of 0 to 4 and the sum of m and n is 0 to 4, $Y^1$ is a halogen atom, cyano group, a hydroxy group optionally protected, an amino group optionally protected, a lower alkyloxy group, a lower alkylamino group, a carboxy group optionally protected, a carbamoyl group optionally substituted, or a lower alkyl group optionally substituted, $Y^2$ is hydrogen atom, a lower alkyl group optionally substituted, cyano group, or —C($R^3$)=$NR^4$ (wherein $R^3$ and $R^4$ are independently hydrogen atom, an amino group optionally substituted or protected, or a lower alkyl group optionally substituted, or $R^3$ and $R^4$ may combine each other together with the nitrogen atom to which they bond to form a 5- to 7-membered heterocyclic group), provided that 1 to 4 $Y^1$s may present on the same ring and 2 $Y^1$s may present on the same carbon atom, or a salt thereof, which comprises reacting a compound of the formula [2]:

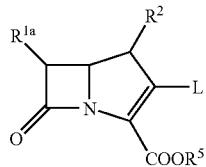

[2]

wherein $R^{1a}$ is a lower alkyl group, a lower alkyl group substituted by a hydroxy group, or a lower alkyl group substituted by a hydroxy group protected by a protecting group, $R^2$ is the same as defined above, $R^5$ is a protecting group of a carboxyl group, and L is an active ester of a hydroxy group, with a compound of the formula [3]:

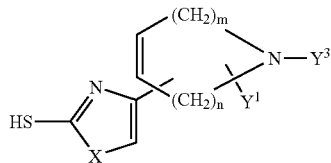

[3]

wherein m, n, X and $Y^1$ are the same as defined above, and $Y^3$ is hydrogen atom, a lower alkyl group optionally substituted, cyano group, or —C($R^3$)=$NR^{4a}$ (wherein $R^3$ is the same as defined above, and $R^{4a}$ are hydrogen atom, an amino group optionally substituted or protected, or a lower alkyl group optionally substituted, or a protective group of an imidoyl group, or $R^3$ and $R^{4a}$ may combine each other together with the nitrogen atom to which they bond to form a 5- to 7-membered heterocyclic group), in the presence of a base, or reacting the compound of the formula [2] with a thiolate of the compound of the formula [3] to give a compound of the formula [4]:

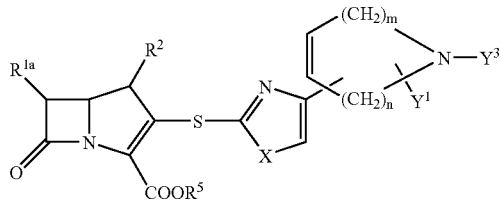

[4]

wherein $R^{1a}$, $R^2$, $R^5$, m, n, X, $Y^1$ and $Y^3$ are the same as defined above, followed by an appropriate combination of reactions which are properly selected from the removal of the protecting group of a hydroxy group for $R^{1a}$ and $Y^1$, the removal of protecting group of an amino group for $Y^3$, the removal of protecting group of an amino group for $Y^1$, the optionally subsequent imidoylization reaction of an amino group of which protecting group was removed for $Y^3$, or the removal of protecting group of an imidoyl group for $Y^3$ and the removal of protecting group of a carboxyl group for $R^5$ and $Y^1$,

(10) a pharmaceutical composition containing the β-lactam compound as set forth in any one of the above (1) to (8), or a pharmaceutically acceptable salt thereof, or a non-toxic ester thereof, and

(11) an antibacterial agent containing the β-lactam compound as set forth in any one of the above (1) to (8), or a pharmaceutically acceptable salt thereof, or a non-toxic ester thereof.

BEST MODE FOR CARRYING OUT THE INVENTION

The lower alkyl group in the present invention includes a straight chain or branched chain $C_1$–$C_6$ alkyl group, for example, methyl, ethyl, n-propyl, isopropyl, n-butyl, isobutyl, tert-butyl, n-pentyl and n-hexyl.

The lower alkyl group substituted by a hydroxy group includes ones having 1 to 6 carbon atoms, for example, hydroxymethyl, 1-hydroxyethyl, 2-hydroxyethyl, 1-hydroxy-1-methylethyl, 1-hydroxypropyl, and 2-hydroxypropyl. The lower alkoxy group includes a straight chain or branched chain $C_{1-6}$ alkyloxy group, for example methoxy, ethoxy, n-propoxy, isopropoxy, n-butoxy, isobutoxy, tert-butoxy, n-pentoxy and n-hexoxy. The lower alkylamino group includes mono or di-substituted amino group substituted by a straight chain or branched chain $C_{1-6}$ alkyl group, for example methylamino, ethylamino, n-propylamino, isopropylamino, n-butylamino, isobutylamino, tert-butylamino, n-pentylamino, n-hexylamino, methyl ethylamino, dimethylamino, diethylamino, di(n-propyl)amino, di(isopropyl)amino, di(n-butyl)amino, di(n-pentyl)amino and di(n-hexyl)amino. The halogen atom includes fluorine atom, chlorine atom, bromine atom and iodine atom. The 5 to 7 membered hetero ring includes, for example 3,4-dihydro-2-H-pyrrole ring, 2,3,4,5-tetrahydropyridine ring, 3,4,5,6-tetrahydro-2-H-azepine ring, etc. The substituent of lower alkyl group optionally substituted includes a hydroxy group, a lower alkoxy group, a lower alkylthio group, a lower alkylsulfinyl group, a lower alkylsulfonyl group, a lower alkylcarbonyl group, a lower alkylcarbonyloxy group, a lower alkoxycarbonyl group, a carboxyl group, a halogen atom, cyano group, —$NR^6R^7$ (wherein $R^6$ and $R^7$ are independently hydrogen atom or a lower alkyl group, or $R^6$ and $R^7$ may be combined together with the nitrogen atom to form a 5–7 membered ring such as pyrrolidine, piperidine, azepane, morpholine, piperazine, or a N-lower alkyl piperazine), —$CONR^6R^7$ (wherein $R^6$ and $R^7$ are the same as defined above), —$NR^{6a}COR^{7a}$ (wherein $R^{6a}$ and $R^{7a}$ are independently hydrogen atom or a lower alkyl group), —$OCONR^6R^7$ (wherein $R^6$ and $R^7$ are the same as defined above), —$SO_2NR^6R^7$ (wherein $R^6$ and $R^7$ are the same as defined above), —$NR^{6a}SO_2NR^6R^7$ (wherein $R^{6a}$, $R^6$ and $R^7$ are the same as defined above), —$NR^{6a}CONR^6R^7$ (wherein $R^{6a}$, $R^6$ and $R^7$ are the same as defined above), and —$COOCH_2OCOR^8$ (wherein $R^8$ is a lower alkyl group). These substituents may be protected by a suitable protective group. The substituted positions are not limited as far as chemically possible, but one or more substituents are possible.

The lower alkylcarbonyl group includes a straight chain or branched chain $C_{2-7}$ alkylcarbonyl group, for example methylcarbonyl, ethylcarbonyl, n-propylcarbonyl, isopropylcarbonyl, n-butylcarbonyl, isobutylcarbonyl, tert-butylcarbonyl, n-pentylcarbonyl and n-hexylcarbonyl. The lower alkylcarbonyloxy group includes a straight chain or branched chain $C_{2-7}$ alkylcarbonyloxy group, for example methylcarbonyloxy, ethylcarbonyloxy, n-propylcarbonyloxy, isopropylcarbonyloxy, n-butylcarbonyloxy, isobutylcarbonyloxy, tert-butylcarbonyloxy, n-pentylcarbonyloxy and n-hexylcarbonyloxy.

The lower alkoxycarbonyl group includes a straight chain or branched chain $C_{2-7}$ alkoxycarbonyl group, for example methoxycarbonyl, ethoxycarbonyl, n-propoxycarbonyl, isopropoxycarbonyl, n-butoxycarbonyl, isobutoxycarbonyl, tert-butoxycarbonyl, n-pentoxycarbonyl and n-hexoxycarbonyl.

The lower alkyl portion of a lower alkylthio group, a lower alkylsulfinyl group and a lower alkylsulfonyl group includes a straight chain or branched chain $C_1$–$C_6$ alkyl group, for example, methyl, ethyl, n-propyl, isopropyl, n-butyl, isobutyl, tert-butyl, n-pentyl and n-hexyl.

The substituent of a carbamoyl group optionally substituted includes one or two lower alkyl groups, pyrrolidine, piperidine, and azepine, which is formed with a nitrogen atom of the carbamoyl group.

The substituent of the amino group optionally substituted includes one or two lower alkyl groups, and the amino group substituted includes pyrrolidine, piperidine, and azepane, which is formed with a nitrogen atom of the amino group.

The substituent of the 5 to 7 membered heterocyclic group optionally substituted includes, for example, a lower alkyl group, a hydroxy group, a lower alkoxy group, a lower alkylcarbonyl group, a lower alkylcarbonyloxy group, a lower alkyloxycarbonyl group, a carboxyl group, a halogen atom, and cyano group.

The protecting group for a carboxyl group may be any conventional protecting groups, but preferably for example, a straight chain or branched chain lower alkyl group having 1 to 5 carbon atoms (e.g., methyl, ethyl, isopropyl, tert-butyl, etc.), a halogeno lower alkyl-group having 1 to 5 carbon atoms (e.g., 2-iodoethyl, 2,2,2-trichloroethyl), an alkoxymethyl group having 1 to 5 carbon atoms (e.g., methoxymethyl, ethoxymethyl, isobutoxymethyl), a lower aliphatic acyloxymethyl group having 1 to 5 carbon atoms (e.g., acetoxymethyl, propionyloxymethyl, butyryloxymethyl, pivaloyloxymethyl), a 1-($C_1$–$C_5$) lower alkoxycarbonyloxyethyl group (e.g., 1-ethoxycarbonyloxyethyl), a substituted or unsubstituted aralkyl group (e.g., benzyl, p-methoxybenzyl, o-nitrobenzyl, p-nitrobenzyl), a lower alkenyl group having 3 to 7 carbon atoms (e.g., allyl, 3-methylallyl), a benzhydryl group, or a phthalidyl group.

The protecting group for a hydroxy group or an amino group may be any conventional ones, and preferably a lower alkoxycarbonyl group having 1 to 5 carbon atoms (e.g., tert-butyloxycarbonyl), a halogenoalkoxycarbonyl group having 1 to 5 carbon atoms (e.g., 2-iodoethyloxycarbonyl, 2,2,2-trichloroethyloxycarbonyl), a substituted or unsubstituted lower alkenyloxycarbonyl group having 3 to 7 carbon atoms (e.g., allyloxycarbonyl), a substituted or unsubstituted aralkyloxycarbonyl group (e.g., benzyloxycarbonyl, p-methoxybenzyloxycarbonyl, o-nitro benzyloxycarbonyl, p-nitrobenzyloxycarbonyl), or a trialkylsilyl group (e.g., trimethylsilyl, triethylsilyl, tert-butyldimethylsilyl).

The preferable substituents of $Y^1$ on the β-lactam compound of the formula [1a] are a $C_{1-3}$ alkyl group such as methyl, ethyl, isopropyl, etc., hydroxymethyl, chloromethyl, fluoromethyl, methoxymethyl, carbamoyloxymethyl, ureidomethyl, sulfamoylmethyl, sulfamoylaminomethyl, carbamoyl, etc., and preferable substituents of $Y^2$ are preferably hydrogen atom, a $C_{1-3}$ alkyl group such as methyl, ethyl, isopropyl, etc., iminomethyl (—CH=NH), —C(CH$_3$)=NH, etc.

The pharmaceutically acceptable salt of the compound of the above formula [1] is a conventional non-toxic salt. Such salts include, as a salt with an intramolecular carboxylic acid, a salt with an inorganic base such as sodium, potassium, calcium, magnesium, ammonium, a salt with an organic base such as triethylammonium, pyridinium, diisopropylammonium, or an intramolecular salt being formed with a cation at the 3-side chain such as a quaternary ammonium ion. As a salt with an intramolecular base, a salt with an inorganic acid such as hydrochloric acid, sulfuric acid, phosphoric acid, or a salt with an organic acid such as formic acid, acetic acid, oxalic acid, methanesulfonic acid, benzenesulfonic acid can be exemplified.

The non-toxic ester of the formula [1] includes a conventional pharmaceutically acceptable ester at the 2-carboxyl group of carbapenem antibacterial agents, and may be esters being able to be easily hydrolyzed in the living body, for example, esters with acetoxymethyl, pivaloyloxymethyl, 1-(ethoxycarbonyloxy)ethyl, and phthalidyl.

The β-lactam compound of the formula [1], or a pharmaceutically acceptable salt thereof, or a non-toxic ester thereof may be in the form of an anhydride thereof, a hydrate thereof, or a solvate thereof.

The process for producing the present compound is illustrated in more detail below.

The compound of the formula [4]:

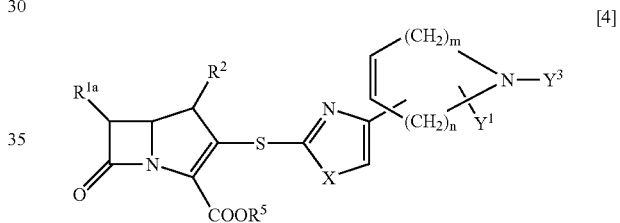

wherein $R^{1a}$, $R^2$, $R^5$, m, n, X, $Y^1$ and $Y^3$ are the same as defined above, can be prepared by reacting a compound of the formula [2]:

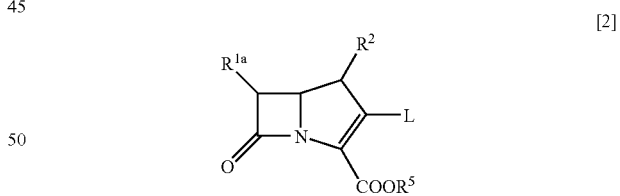

wherein $R^{1a}$, $R^2$, $R^5$ and L are the same as defined above, with a compound of the formula [3]:

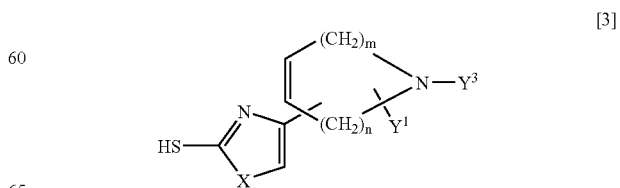

wherein m, n, X, $Y^1$ and $Y^3$ are the same as defined above, in the presence of a base, or by reacting a compound of the formula [2] with a thiolate salt of the compound of the formula [3] in an inert solvent.

The active ester of a hydroxy group includes, for example, a substituted or unsubstituted arylsulfonic acid ester (e.g., benzenesulfonic acid ester, p-toluenesulfonic acid ester, p-nitrobenzenesulfonic acid ester, p-bromobenzene sulfonic acid ester, etc.), a lower alkanesulfonic acid ester having 1 to 5 carbon atoms (e.g., methanesulfonic acid ester, ethanesulfonic acid ester, etc.), a halogenoalkanesulfonic acid ester having 1 to 5 carbon atoms (e.g., trifluoromethanesulfonic acid ester, etc.), an arylphosphoric acid ester (e.g., diphenylphosphoric acid ester, etc.), or a halide compound such as chloride, bromide, iodide which is an ester with a hydrogen halide. The preferable reactive ester of a hydroxy group may be p-toluenesulfonic acid ester, methanesulfonic acid ester, trifluoromethanesulfonic acid ester, and diphenylphosphoric acid ester.

The inert solvent, which is used in the reaction between the compound [2] and the compound [3] in the presence of a base to give the compound [4], includes, for example, dioxane, tetrahydrofuran, dimethylsulfoxide, dimethylformamide, acetonitrile, benzene, toluene, hexamethylphosphoramide, or a mixture of these solvents.

The base includes, for example, an inorganic base such as sodium carbonate, potassium carbonate, sodium hydride, potassium hydride, or an organic base such as pyridine, dimethylaminopyridine, triethylamine, diisopropylethylamine, 1,8-diazabicyclo[5.4.0]undec-7-ene (DBU). Especially preferable one is DBU. The base should be used in an amount sufficient for carrying out the reaction, and it is usually used in an amount of 1 to 3 equivalents, to the amount of the mercaptan compound [3].

The mercaptan compound [3] should be used in an amount sufficient for carrying out the reaction, and can be used in a large excess amount, but it is usually used in an amount of 1 to 2 equivalents, to the amount of the compound [2].

The reaction is carried out at a temperature of from $-78°$ C. to $+60°$ C., preferably at a temperature of from $-40°$ C. to $+40°$ C. Besides, after the reaction is completely over, the product thus obtained is isolated by a conventional technique of organic chemistry.

The inert solvent, which is used in the reaction between the compound [2] and a thiolate salt of the compound [3] to give the compound [4], includes, for example, dioxane, tetrahydrofuran, dimethylsulfoxide, dimethylformamide, acetonitrile, benzene, toluene, hexamethylphosphoramide, or a mixture of these solvents.

In the above reaction, the thiolate salt should be used in an amount sufficient for carrying out the reaction, and can be used in a large excess amount, but it is usually used in an amount of 1 to 2 equivalents, to the amount of the compound [2].

The reaction is carried out at a temperature of from $-78°$ C. to $+60°$ C., more preferably at a temperature of from $-40°$ C. to $+40°$ C. After the reaction is completely over, the product thus obtained is isolated by a conventional technique of organic chemistry.

The thiolate salt is prepared by reacting the mercaptan compound [3] with a base. The base includes, for example, an inorganic base (e.g., sodium hydride, potassium hydride), a metal alkoxide (e.g., potassium tert-butoxide, sodium methoxide), or a metal amide (e.g., sodium amide, lithium diisopropylamide, lithium disilazide).

The β-lactam compound of the formula [1] is obtained from the compound [4] in a conventional manner by carrying out, optionally combining or simultaneously, reactions such as the removal of the protecting group for a hydroxy group for $R^{1a}$ or $Y^1$, the removal of the protecting group of an amino group for $Y^1$, the removal of protecting group of an amino group for $Y^3$, the subsequent imidoylization reaction of the amino group of which protecting group was removed, or the removal of protecting group of an imidoyl group for $Y^3$ and removing the protecting group of a carboxyl group for $R^5$ and $Y^1$.

The removal of these protecting groups is carried out by treating with an acid, a base, or a reducing agent, and these methods per se are well known methods, as disclosed, for example, in T. W. Greene: Protective Groups in Organic Synthesis, J. Wiley & Sons Inc., 1981. The acid is preferably trifluoroacetic acid, formic acid, boron trifluoride, aluminum chloride, etc., or a mixture of these acids. The base is preferably an alkali metal carbonate (e.g., sodium carbonate, potassium carbonate, etc.), an alkali metal sulfide (e.g., sodium sulfide, potassium sulfide, etc.), or tetrabutylammonium fluoride. The reduction method includes, for example, hydrogenation with zinc and acetic acid, hydrogen and palladium-carbon or platinum, etc. There may be also used palladium (0) compound.

The solvent may be any ones which do not disadvantageously affect the reaction, and includes, for example, water, alcohols (e.g., methanol, ethanol), ethers (e.g., tetrahydrofuran, dioxane), fatty acids (e.g., acetic acid), or a mixture of these solvents. The reaction can possibly be suppressed or promoted by properly lowering or raising the reaction temperature. The preferable reaction temperature is in the range from $-30°$ C. to $+40°$ C. After the reaction is completely over, the product thus obtained can be isolated by a conventional technique of organic chemistry, for example, by neutralizing the reaction mixture, subjecting it to column chromatography on absorption resin, etc., collecting the fractions containing the desired compound, and then followed by lyophilizing the resultant.

The compounds of the generic formula (2) are known, and can be prepared by the method disclosed in JP 63-55514 B.

The mercaptan compounds of the generic formula (3) are, according to the following scheme, prepared by changing it into a mercaptothiazole derivative (C) after preparing a cyclic amine derivative (B) having a unsaturated ester portion from an appropriate amino acid. If necessary, an optically active mercaptothiazole derivative (C) is prepared by using an optically active intermediate.

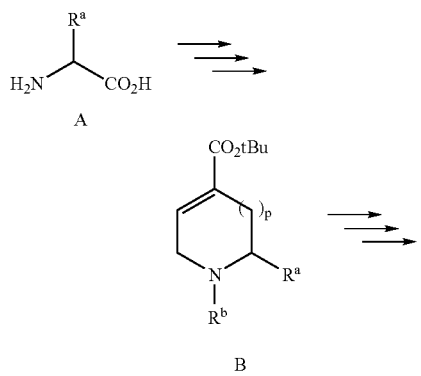

-continued

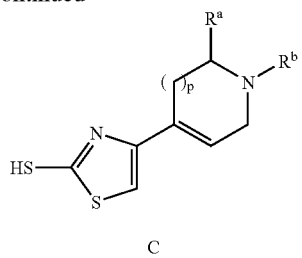

wherein $R^a$ is an optionally substituted lower alkyl group, $R^b$ is a protective group of an amino group, and p is an integer of 0 or 1.

When a compound B is prepared starting from a compound A, the method described in JP 1-233270 B is used. When a compound C is prepared starting from a compound B, the compound C is prepared by the known methods such as K. Hofmann, Heterocyclic Chemistry vol. 6 (1953), J. V. Metzger, ibid vol. 34 (1979), I. J. Turchi, ibid vol. 45 (1986), Interscience Publishers, Inc. or A. R. Katritzky, Advances in Heterocyclic Chemistry, vol. 32 (1982), Academic Press or a combination thereof.

The compound of the above mentioned formula [1] may have optical isomers based on the asymmetric carbon atoms at the 4-, 5- and 6-positions of the carbapenem nucleus, as shown in the following formula:

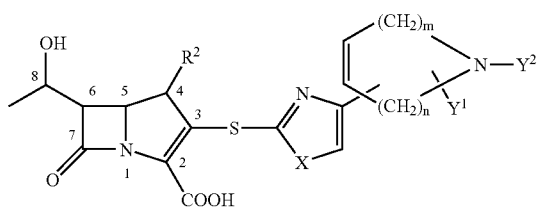

and these isomers are all conveniently expressed by only one formula. However, the scope of the present invention should not be construed to be limited thereby, and includes all isomers and a mixture of isomers based on each asymmetric carbon atom. In addition, the preferable isomers are ones wherein the 5-carbon atom has an R-configuration such as (5R,6R)-compounds or (5R, 6S)-compounds when $R^2$ is a hydrogen atom, and one wherein the 4-carbon atom has an R-configuration and the 5-carbon atom has an S-configuration, such as (4R,5S,6S)-compounds or (4R,5S,6R)-compounds, when $R^2$ is a lower alkyl group. Moreover, when $R^1$ is 1-hydroxyethyl group, the compound [1] may have isomers having an R-configuration or an S-configuration at the 8-position, as shown in the above formula, the preferable one is ones having an R-configuration at the 8-position. There is an isomer due to a substituent, $Y^1$.

Isomers having such configurations are prepared by using each corresponding isomer of the starting compounds [2] and (3).

The present compounds of the formula [1] are novel β-lactam compounds having an azolethio group having various substituents at the 3-position of the carbapenem nucleus, and these compounds show an excellent antibacterial activity, and are useful as a medicament.

Representative compounds of the formula [1] obtained by the present invention are exemplified in the following Table 1.

TABLE 1-1

| Compound No. | $R^1$ | $R^2$ | X | A |
|---|---|---|---|---|
| 1 | CH(OH)CH$_3$ | CH$_3$ | S | ![](structure with HO, N—H) |
| 2 | CH(OH)CH$_3$ | CH$_3$ | S | ![](structure with NHSO$_2$NH$_2$, N—H) |
| 3 | CH(OH)CH$_3$ | CH$_3$ | S | ![](structure with CONH$_2$, N—H) |
| 4 | CH(OH)CH$_3$ | CH$_3$ | S | ![](structure with MeO, N—H) |
| 5 | CH(OH)CH$_3$ | CH$_3$ | S | ![](structure with OCON-pyrrolidine, N—H) |
| 6 | CH(OH)CH$_3$ | CH$_3$ | S | ![](structure with SO$_2$N-piperidine, N—H) |
| 7 | CH$_2$CH$_3$ | CH$_3$ | O | ![](structure with Me, N—H) |

TABLE 1-1-continued

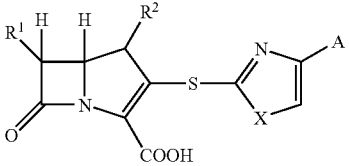

| Compound No. | R¹ | R² | X | A |
|---|---|---|---|---|
| 8 | CH₂OH | H | NH | ![pyrrole with Me, N-H] |

TABLE 1-2

| Compound No. | R¹ | R² | X | A |
|---|---|---|---|---|
| 9 | CH(OH)CH₃ | CH₃ | S | (N-C(Me)=NH, CH₂OH substituted pyrroline) |
| 10 | CH(OH)CH₃ | CH₃ | S | (N-CH=NH, CH₂OH substituted pyrroline) |
| 11 | CH(OH)CH₃ | CH₃ | S | (CH₂OH, N-C(Me)=NH substituted pyrroline) |
| 12 | CH(OH)CH₃ | CH₃ | S | (CH₂OH, N-CH=NH substituted pyrroline) |
| 13 | CH(OH)CH₃ | CH₃ | S | (N-H, CH₂NHCONH₂ substituted pyrroline) |

TABLE 1-2-continued

| Compound No. | R¹ | R² | X | A |
|---|---|---|---|---|
| 14 | CH(OH)CH₃ | CH₃ | S | (N-H, CH₂OCONH₂ substituted pyrroline) |
| 15 | CH(OH)CH₃ | CH₃ | S | (N-Me, CH₂OH substituted pyrroline) |
| 16 | CH(OH)CH₃ | CH₃ | S | (N-Me, CH₂OH substituted pyrroline) |

TABLE 1-3

| Compound No. | R¹ | R² | X | A |
|---|---|---|---|---|
| 17 | CH(OH)CH₃ | CH₃ | S | (N-H, Me substituted pyrroline) |
| 18 | CH(OH)CH₃ | CH₃ | S | (N-H, CH₂OH substituted pyrroline) |
| 19 | CH(OH)CH₃ | CH₃ | S | (Me, N-H substituted tetrahydropyridine) |

TABLE 1-3-continued

[Structure: carbapenem core with R¹, R², and thiazole-S substituent bearing group A]

| Compound No. | R¹ | R² | X | A |
|---|---|---|---|---|
| 20 | CH(OH)CH₃ | CH₃ | S | tetrahydropyridine with CH₂OH, NH |
| 21 | CH(OH)CH₃ | CH₃ | S | tetrahydropyridine with CH₂OH, N-CH=NH |
| 22 | CH(OH)CH₃ | CH₃ | S | tetrahydropyridine with CH₂OMe, N-C(Me)=NH |
| 23 | CH(OH)CH₃ | CH₃ | S | tetrahydropyridine with 2,2-diMe, NH |
| 24 | CH(OH)CH₃ | CH₃ | S | tetrahydropyridine with 2,6-diMe, NH |

TABLE 1-4

[Structure: carbapenem core with R¹, R², and thiazole-S substituent bearing group A]

| Compound No. | R¹ | R² | X | A |
|---|---|---|---|---|
| 25 | CH(OH)CH₃ | CH₃ | S | tetrahydropyridine N-CH₂CH₂OH, 2-Me |
| 26 | CH(OH)CH₃ | CH₃ | S | tetrahydropyridine NH, 2-OH |
| 27 | CH(OH)CH₃ | CH₃ | S | tetrahydropyridine NH, CH₂OMe |
| 28 | CH(OH)CH₃ | CH₃ | S | tetrahydropyridine NH, 2,6-bis(CH₂CONHMe) |
| 29 | CH(OH)CH₃ | CH₃ | S | tetrahydropyridine N-CH₂CH₂OCONH₂, CH₂OMe |
| 30 | CH(OH)CH₃ | CH₃ | S | MeNHSO₂NH—CH₂-tetrahydropyridine NH |
| 31 | CH(OH)CH₃ | CH₃ | S | Me₂NSO₂CH₂-tetrahydropyridine NH |

TABLE 1-4-continued
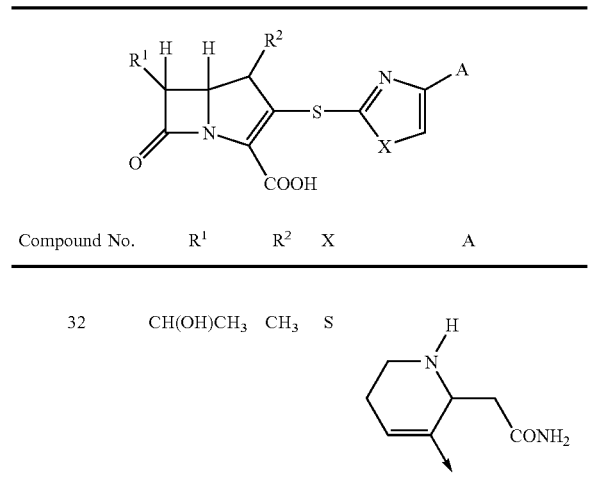
| Compound No. | $R^1$ | $R^2$ | X | A |
|---|---|---|---|---|
| 32 | CH(OH)CH$_3$ | CH$_3$ | S | |
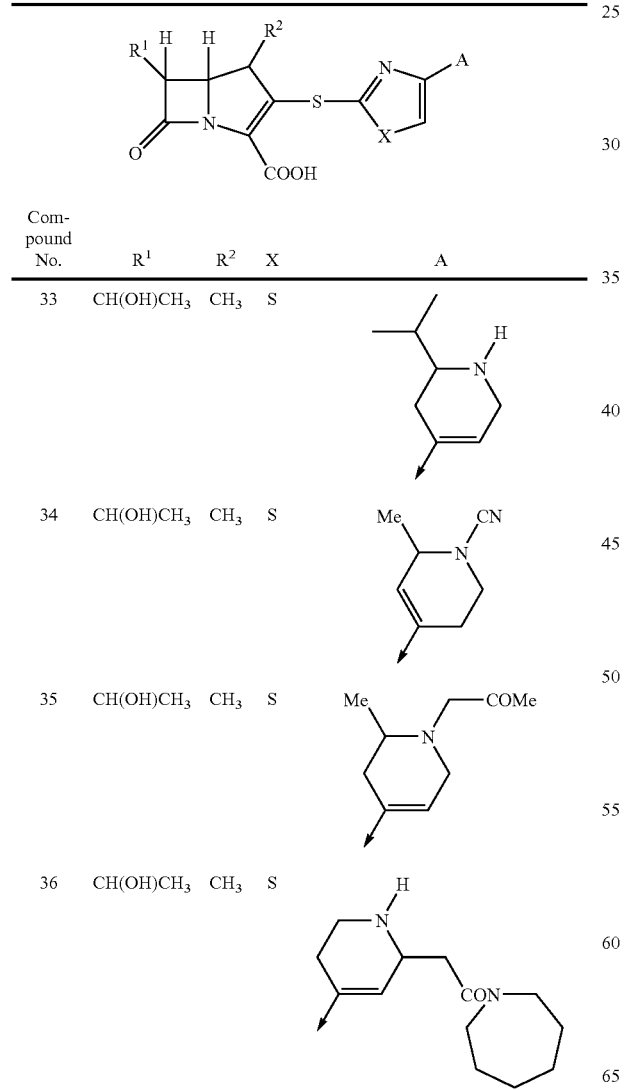
TABLE 1-5
| Compound No. | $R^1$ | $R^2$ | X | A |
|---|---|---|---|---|
| 33 | CH(OH)CH$_3$ | CH$_3$ | S | |
| 34 | CH(OH)CH$_3$ | CH$_3$ | S | |
| 35 | CH(OH)CH$_3$ | CH$_3$ | S | |
| 36 | CH(OH)CH$_3$ | CH$_3$ | S | |
TABLE 1-5-continued
| Compound No. | $R^1$ | $R^2$ | X | A |
|---|---|---|---|---|
| 37 | CH(OH)CH$_3$ | CH$_3$ | S | |
| 38 | CH(OH)CH$_3$ | CH$_3$ | S | |
| 39 | CH(OH)CH$_3$ | CH$_3$ | S | |
| 40 | CH(OH)CH$_3$ | CH$_3$ | S | |
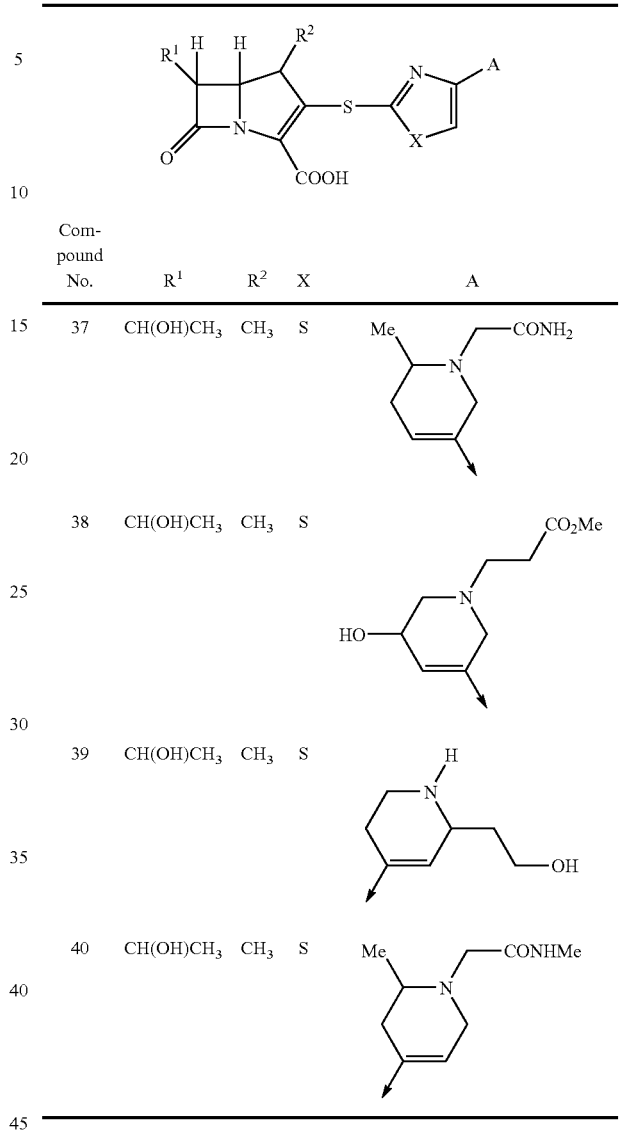
TABLE 1-6
| Compound No. | $R^1$ | $R^2$ | X | A |
|---|---|---|---|---|
| 41 | CH(OH)CH$_3$ | CH$_3$ | S | |
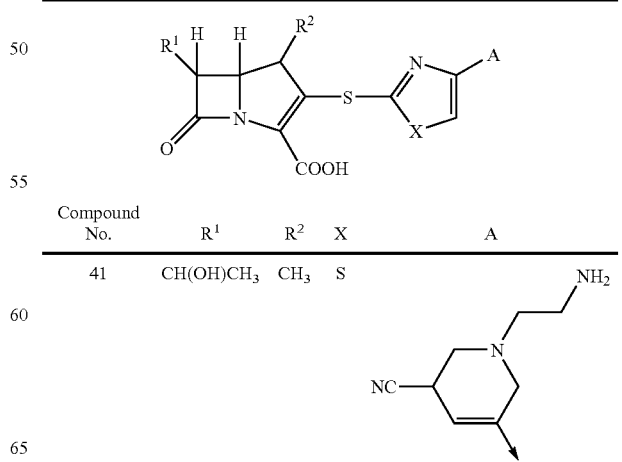

TABLE 1-6-continued

| Compound No. | R¹ | R² | X | A |
|---|---|---|---|---|
| 42 | CH(OH)CH₃ | CH₃ | S | (tetrahydropyridine with N-CH=NMe and HO₂C substituent) |
| 43 | CH(OH)CH₃ | CH₃ | S | (tetrahydropyridine with N-CH=NH and CH₂OH substituent) |
| 44 | CH(OH)CH₃ | CH₃ | S | (tetrahydropyridine with N-CH₂CH₂CONHMe and CH₂CO₂CH₂OAc substituents) |
| 45 | CH(OH)CH₃ | CH₃ | S | (tetrahydroazepine with CH₂OH and NH) |
| 46 | CH(OH)CH₃ | CH₃ | S | (tetrahydroazepine with N-CH=NH and Me substituent) |
| 47 | CH(OH)CH₃ | CH₃ | S | (tetrahydroazepine with N-CH₂CH₂OH and CONH₂ substituent) |
| 48 | CH(OH)CH₃ | CH₃ | S | (tetrahydroazepine with CH₂CH₂OCO₂Et and N-C(=NH)NH₂ guanidine) |

TABLE 1-7

| Compound No. | R¹ | R² | X | A |
|---|---|---|---|---|
| 49 | CH(OH)CH₃ | CH₃ | S | (pyrroline with isopropyl, N-H, and CH₂NHSO₂NH₂ substituents) |
| 50 | CH(OH)CH₃ | CH₃ | S | (pyrroline with CH₂OH and N-C(=NH)NHMe guanidine) |
| 51 | CH(OH)CH₃ | CH₃ | S | (pyrroline with N-C(=NMe)NMe₂ and CH₂OH substituents) |
| 52 | CH(OH)CH₃ | CH₃ | NH | (pyrroline with F and N attached to dihydropyrrole) |
| 53 | CH(OH)CH₃ | CH₃ | S | (pyrroline with Cl and N-CH₂CH₂NHMe) |

TABLE 1-7-continued

Structure: β-lactam core with R¹, R², and thiazole substituent bearing A group, COOH.

| Compound No. | R¹ | R² | X | A |
|---|---|---|---|---|
| 54 | CH(OH)CH₃ | CH₃ | S | tetrahydropyridinyl-CH₂-NHCONH₂ |
| 55 | CH(OH)CH₃ | CH₃ | S | MeO₂C-substituted tetrahydropyridinyl with N=piperidinylidene |
| 56 | CH(OH)CH₃ | CH₃ | S | N-Me tetrahydropyridinyl-CH₂-OCONH₂ |

TABLE 1-8

Structure: β-lactam core with R¹, R², and thiazole substituent bearing A group, COOH.

| Compound No. | R¹ | R² | X | A |
|---|---|---|---|---|
| 57 | CH(OH)CH₃ | CH₃ | S | pyrrolinyl with Bu substituent, N-CH₂CH₂-OAc |
| 58 | CH(OH)CH₃ | CH₃ | S | HO₂C-pyrrolidinyl, N-CH₂-CONH₂ |
| 59 | CH(OH)CH₃ | CH₃ | S | pyrrolinyl-CH(NH)-CONMe₂ |
| 60 | CHMe₂ | CH₃ | O | tetrahydropyridinyl-CH₂OH (NH) |
| 61 | CH₂CH₃ | H | NH | tetrahydropyridinyl-CH₂OH (NH) |
| 62 | CH(OH)CH₃ | CH₃ | S | N-Me tetrahydropyridinyl-CH₂OH |
| 63 | CH(OH)CH₃ | CH₃ | S | N-Me tetrahydropyridinyl-CH₂OH |
| 64 | CH(OH)CH₃ | CH₃ | S | tetrahydropyridinyl-CH₂OH with N-C(=NMe)Me |

The compounds as listed in Table 1 have stereoisomers as described above, and these exemplified compounds include all of their isomers as well.

The novel β-lactam compounds of the present invention represented by the above formula [1] exhibit antibacterial activities against a wide variety of pathogenic bacteria including Gram-positive bacteria such as *Staphylococcus aureus, Staphylococcus epidermidis, Streptococcus pyogenes, Streptococcus pneumoniae, Enterococcus faecalis,* and Gram-negative bacteria such as *Escherichia coli,* the genus *Proteus, Klebsiella pneumoniae, Haemophilus influenzae, Neisseria gonorrhoeae,* the genus *Branhamella,* and especially exhibit excellent antibacterial activities against Gram-positive bacteria, as well as against MRSA and MRCNS.

Further the compounds [1] of the present invention are different in the degree on each compound, but the central nervous side effect is more reduced and the physicochemical property of the compound [1] such as solubility in water which should be equipped as the medicine, is more improved. These properties are exemplified as a characteristic property of the present invention.

It is well known that dehydropeptidase-I (DHP-I), a renal enzyme, can easily hydrolyze carbapenem compounds derived from natural resources, but some of the present compounds [1], which are also carbapenem compounds, are stable over DHP-I, and can be used alone, but a DHP-I inhibitor may be used together with the present compound, if necessary.

When used as an antibacterial agent in the treatment of infectious diseases caused by bacteria, the present compounds are administered, for example, orally in the form of a tablet, capsule, powder, syrup, etc., or parenterally such as intravenous injection, intramuscular injection, or intrarectal administration.

The suitable administration forms as mentioned above may be prepared by mixing an active ingredient with a conventional pharmaceutically acceptable carrier, excipient, binder, stabilizer, etc. When administered in the form of an injection, a pharmaceutically acceptable buffering agent, solubilizer, isotonic agent, etc. may be added thereto.

The dosage of the compound [1] varies according to the symptoms, ages, body weights, the administration form, the frequency of the administration, etc., but it is usually in the range of 100 to 3000 mg per day for an adult, which is administered once or divided into several dosage units. Besides, the dosage of the compound [1] may be increased or decreased, if necessary.

The present invention is illustrated in more detail by Examples, but should not be construed to be limited thereto.

The following abbreviations are used in Examples.

PNB: p-Nitrobenzyl group
PMB: p-Methoxybenzyl group
Ph: Phenyl group
TMS: Trimethylsilyl group
TBDMS: tert-Butyl(dimethyl)silyl group
ALOC: (Allyloxy)carbonyl group
Z: (Benzyloxy)carbonyl group
Me: Methyl group
Et: Ethyl group
iPr: Isopropyl group
t-Bu: tert-Butyl group
Bn: Benzyl group
MOM: Methoxymethyl group
Ms: Methanesulfonyl group
Tf: Trifluoromethanesulfonyl group
THF: Tetrahydrofuran
DMF: N,N-dimethylformamide
DBU: 1,8-Diazabicyclo[5.4.0]undec-7-ene

EXAMPLE 1

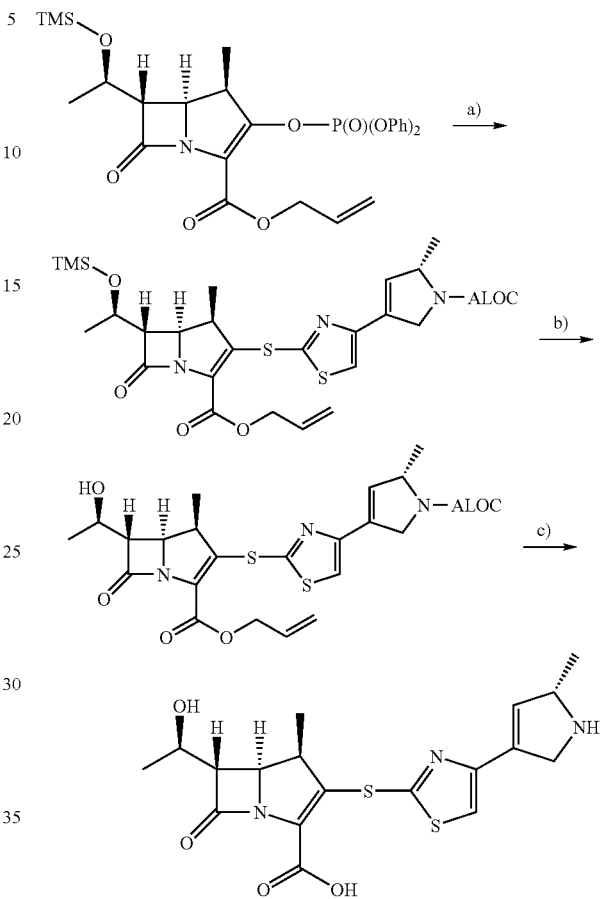

a) A solution of lithium hexamethyldisilazide in THF (1M, 0.20 ml, 0.20 mmol) was added at 0° C. to a suspension of allyl (2S)-2-methyl-4-(2-mercapt-1,3-thiazol-4-yl)-2,5-dihydro-1H-pyrrole-1-carboxylate (54 mg, 0.20 mmol) in THF (0.20 ml)/DMF (0.20 ml) and the mixture was stirred for 25 minutes. To the reaction mixture was added at 0° C. a solution of allyl (4R,5R,6S)-(3-[(diphenoxyphosphino)oxy]-4-methyl-7-oxo-6-{(1R)-1-[(trimethylsilyl)oxy]ethyl}-1-azabicyclo[3.2.0]hept-2-ene-2-carboxylate in acetonitrile (30%, 0.76 g, 0.40 mmol) and the solution was allowed to stand in a refrigerator for 15 hours. To the reaction solution was added ice water and the reaction mixture was extracted with ethyl acetate. The organic layer was washed with a saturated aqueous sodium chloride solution and dried over anhydrous sodium sulfate. After removal of the solvent in vacuo, the residue was purified with silica gel chromatography (hexane/ethyl acetate) to give allyl (4R,5S,6S)-3-[(4-{(5S)-1-[(allyloxy)carbonyl]-5-methyl-2,5-dihydro-1H-pyrrol-3-yl}-1,3-thiazol-2-yl)sulfanyl]-4-methyl-7-oxo-6-{(1R)-1-[(trimethylsilyl)oxy]ethyl}-1-azabicyclo[3.2.0]hept-2-ene-2-carboxylate (85 mg, 70%).

$^1$H NMR (300 MHz, CDCl$_3$) δ 0.09 (9 H, s), 1.06–1.10 (3 H, m), 1.15–1.40 (6 H, m), 3.21–3.24 (1 H, m), 3.40–3.59 (1 H, m), 4.15–4.22 (2 H, m), 4.37–4.85 (7 H, m), 5.15–5.48 (4 H, m), 5.87–6.02 (2 H, m), 6.31–6.36 (1 H, m), 7.09–7.12 (1 H, m).

b) To a solution of allyl (4R,5S,6S)-3-[(4-{(5S)-1-[(allyloxy)carbonyl]-5-methyl-2,5-dihydro-1H-pyrrol-3-yl}-1,3-thiazol-2-yl)sulfanyl]-4-methyl-7-oxo-6-{(1R)-1-[(trimethylsilyl)oxy]ethyl}-1-azabicyclo[3.2.0]hept-2-ene-2-carboxylate (85 mg, 0.14 mmol) in THF (6 ml) was added at 0° C. water and then the solution was adjusted to pH about 3 with 1N hydrochloric acid and stirred for 10 minutes. To the reaction solution was added an aqueous sodium hydrogen carbonate solution and the reaction mixture was extracted twice with ethyl acetate. The organic layer was washed with a saturated aqueous sodium chloride solution and dried over anhydrous sodium sulfate. After removal of the solvent in vacuo, the residue was purified with silica gel chromatography (hexane/ethyl acetate=1/2) to give allyl (4R,5S,6S)-3-[(4-{(5S)-1-[(allyloxy)carbonyl]-5-methyl-2,5-dihydro-1H-pyrrol-3-yl}-1,3-thiazol-2-yl)sulfanyl]-6-[(1R)-1-hydroxyethyl]-4-methyl-7-oxo-1-azabicyclo[3.2.0]hept-2-ene-2-carboxylate (60 mg, 80%) as a pale yellowish amorphous.

c) To a solution of allyl (4R,5S,6S)-3-[(4-{(5S)-1-[(allyloxy)carbonyl]-5-methyl-2,5-dihydro-1H-pyrrol-3-yl}-1,3-thiazol-2-yl)sulfanyl]-6-[(1R)-1-hydroxyethyl]-4-methyl-7-oxo-1-azabicyclo[3.2.0]hept-2-ene-2-carboxylate (70 mg, 0.13 mmol) in dichloromethane (2 ml) were added acetic acid (19 μl) and tributyltin hydride (0.32 ml, 1.2 mmol) and added at room temperature bis(triphenylphosphine)palladium chloride(II) (91 mg, 0.013 mmol). Ten minutes later the reaction mixture was poured into a mixture of ice (10 g) and phosphate buffer (pH7.0, 10 ml). After separation of the mixture with a separating funnel, the organic layer was extracted twice with water and the aqueous layer was washed twice with dichloromethane (3 ml). The organic solvent in the aqueous layer was evaporated under reduced pressure, and the residue was purified by polymer chromatography (CHP-20P). The fractions eluted with 1–3% aqueous THF solution were combined and lyophilized to give (4R,5S,6S)-6-[(1R)-1-hydroxyethyl]-4-methyl-3-({4-[(5S)-5-methyl-2,5-dihydro-1H-pyrrol-3-yl}-1,3-thiazol-2-yl)sulfanyl]-7-oxo-1-azabicyclo[3.2.0]hept-2-ene-2-carboxylic acid (26.9 mg) as a white amorphous.

IR (KBr) 3406, 2969, 1760, 1599, 1391 cm$^{-1}$ $^1$H NMR (300 MHz, D$_2$O) δ 0.94(3 H, d, J=7.3 Hz), 1.12(3 H, d, J=6.4 Hz), 1.38(3 H, d, J=6.8 Hz), 3.10–3.24 (1 H, m), 3.35 (1 H, dd, J=2.6, 6.0 Hz), 4.05–4.15 (2 H, m), 4.23–4.37 (2 H, m), 6.25 (1 H, s), 7.50 (1 H, s).

EXAMPLE 2

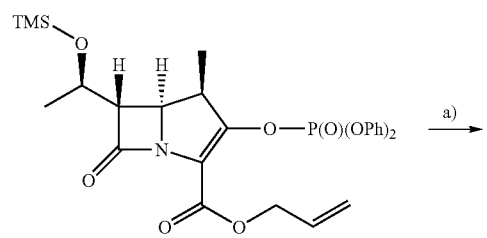

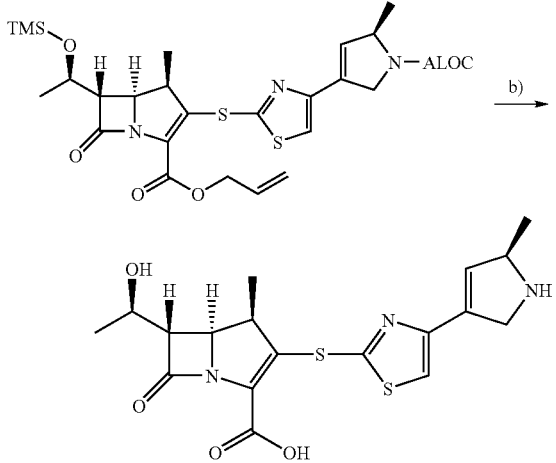

a) In the same manner as in Example 1, by using allyl (2R)-2-methyl-4-(2-mercapto-1,3-thiazol-4-yl)-2,5-dihydro-1H-pyrrole-1-carboxylate as a thiol compound, there was obtained allyl (4R,5S,6S)-3-[(4-{(5R)-1-[(allyloxy)carbonyl]-5-methyl-2,5-dihydro-1H-pyrrol-3-yl}-1,3-thiazol-2-yl)sulfanyl]-4-methyl-7-oxo-6-{(1R)-1-[(trimethylsilyl)oxy]ethyl}-1-azabicyclo[3.2.0]hept-2-ene-2-carboxylate.

$^1$H NMR (300 MHz, CDCl$_3$) δ 0.11 (9 H, s), 1.08–1.12 (3 H, m), 1.22–1.25 (3 H, m), 1.37–1.43 (3 H, m), 3.24 (1H, dd, J=6.2, 2.9 Hz), 3.37–3.58 (1 H, m), 4.17–4.24 (2H, m), 4.40–4.87 (7 H, m), 5.21–5.50 (4 H, m), 5.91–6.05 (2 H, m), 6.34–6.38 (1H, m), 7.10–7.14 (1 H, m).

b) To a solution of allyl (4R,5S,6S)-3-[(4-{(5R)-1-[(allyloxy)carbonyl]-5-methyl-2,5-dihydro-1H-pyrrol-3-yl}-1,3-thiazol-2-yl)sulfanyl]-4-methyl-7-oxo-6-[(1R)-1-[(trimethylsilyl)oxy]ethyl]-1-azabicyclo[3.2.0]hept-2-ene-2-carboxylate (42 mg, 0.070 mmol) in ethyl acetate (4 ml) was added water and then 2N hydrochloric acid and the solution was adjusted to pH 2. After stirring for 10 minutes, THF was further added thereto and the solution was stirred for 20 minutes. To the obtained mixture was added a saturated aqueous sodium hydrogen carbonate solution and the solution was extracted twice with ethyl acetate. The organic layer was washed with a saturated aqueous sodium chloride solution and dried over anhydrous sodium sulfate. The solvent was removed under reduced pressure. To a solution of the residue (37.6 mg) in dichloromethane (2 ml) were added at 0° C. tributyltin hydride (0.17 ml), acetic acid (10 μl) and bis(triphenylphosphine)palladium chloride(5 mg) and the mixture was stirred at the same temperature for 10 minutes. To the reaction mixture were added phosphate buffer (50 mM, pH7, 25 ml) and dichloromethane (20 ml). The aqueous layer was separated and the dichloromethane layer was extracted twice with water. The combined aqueous layer was washed with dichloromethane (3 ml). The organic solvent in the aqueous layer was evaporated under reduced pressure, and the residue was purified by polymer chromatography (CHP-20P). The fractions eluted with 1–3% aqueous THF solution were combined and lyophilized to give (4R,5S,6S)-6-[(1R)-1-hydroxyethyl]-4-methyl-3-({4-[(5R)-5-methyl-2,5-dihydro-1H-pyrrol-3-yl]-1,3-thiazol-2-yl}sulfanyl)-7-oxo-1-azabicyclo[3.2.0]hept-2-ene-2-carboxylic acid.

$^1$H NMR (300 MHz, D$_2$O) δ 0.92 (3 H, d, J=7.2 Hz), 1.10 (3 H, d, J=6.4 Hz), 1.31 (3 H, d, J=6.8 Hz), 3.10–3.20 (1 H, m), 3.32 (1 H, dd, J=5.9, 2.9 Hz), 4.03–4.28 (4 H, m), 6.23 (1 H, br s), 7.45 (1 H, s).

EXAMPLE 3

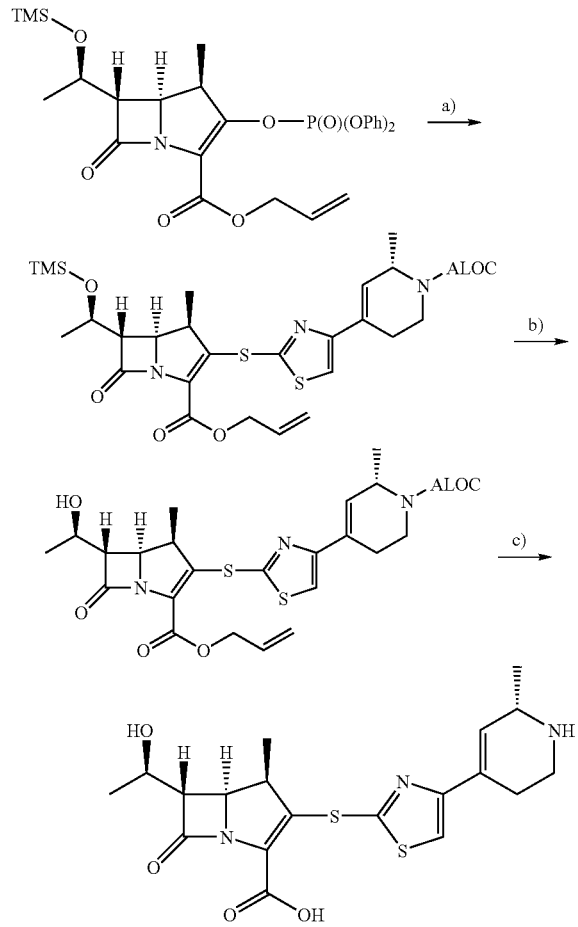

a) A solution of lithium hexamethyldisilazide in THF (1M, 1.26 ml, 1.26 mmol) was added at 0° C. to a solution of allyl (6S)-6-methyl-4-(2-mercapto-1,3-thiazol-4-yl)-3,6-dihydro-1(2H)-pyridine carboxylate (373 mg, 1.26 mmol) in THF (15 ml) and the mixture was stirred for 10 minutes. To the reaction solution was added at 0° C. a solution of allyl (4R,5R,6S)-3-[(diphenoxyphosphino)oxy]-4-methyl-7-oxo-6-{(1R)-1-[(trimethylsilyl)oxy]ethyl}-1-azabicyclo[3.2.0]hept-2-ene-2-carboxylate in acetonitrile (30%, 4.80 g, 2.52 mmol) and the solution was allowed to stand in a refrigerator for 60 hours. To the reaction solution was added ice water and the reaction mixture was extracted with ethyl acetate. The organic layer was washed with a saturated aqueous sodium chloride solution and dried over anhydrous sodium sulfate. After removal of the solvent in vacuo, the residue was purified with silica gel chromatography (hexane/ethyl acetate) to give allyl (4R,5S,6S)-3-[(4-{(6S)-1-[(allyloxy)carbonyl]-6-methyl-1,2,3,6-tetrahydro-4-pyridinyl}-1,3-thiazol-2-yl)sulfanyl]-4-methyl-7-oxo-6-{(1R)-1-[(trimethylsilyl)oxy]ethyl}-1-azabicyclo[3.2.0]hept-2-ene-2-carboxylate (590 mg, 76%).

$^1$H NMR (300 MHz, CDCl$_3$) δ 0.12 (9 H, s), 1.06–1.12 (3 H, m), 1.24 (3 H, d, J=6.0 Hz), 1.29–1.32 (3 H, m), 2.37–2.45 (1 H, m), 2.46–2.59 (1 H, m), 3.00–3.12 (1 H, m), 3.24 (1 H, dd, J=6.4, 2.9 Hz), 3.42–3.61 (1 H, m), 4.16–4.40 (3 H, m), 4.62–4.87 (5 H, m), 5.20–5.50 (4 H, m), 5.90–6.04 (2 H, m), 6.61–6.64 (1 H, m), 7.10–7.13 (1 H, m).

b) To a solution of allyl (4R,5S,6S)-3-[(4-{(6S)-1-[(allyloxy)carbonyl]-6-methyl-1,2,3,6-tetrahydro-4-pyridinyl}-1,3-thiazol-2-yl)sulfanyl]-4-methyl-7-oxo-6-{(1R)-1-[(trimethylsilyl)oxy]ethyl}-1-azabicyclo[3.2.0]hept-2-ene-2-carboxylate (640 mg, 1.04 mmol) in THF (30 ml) was added at 0° C. water and then the solution was adjusted to pH about 3 with 1N hydrochloric acid and stirred for 10 minutes. To the reaction solution was added an aqueous sodium hydrogen carbonate solution and the reaction mixture was extracted twice with ethyl acetate. The organic layer was washed with a saturated aqueous sodium chloride solution and dried over anhydrous sodium sulfate. After removal of the solvent in vacuo, the residue was purified with silica gel chromatography (hexane/ethyl acetate=1/2) to give allyl (4R,5S,6S)-3-[(4-{(6S)-1-[(allyloxy)carbonyl]-6-methyl-1,2,3,6-tetrahydro-4-pyridinyl}-1,3-thiazol-2-yl)sulfanyl]-6-[(1R)-1-hydroxyethyl]-4-methyl-7-oxo-1-azabicyclo[3.2.0]hept-2-ene-2-carboxylate (547 mg, 97%) as a pale yellowish amorphous.

c) To a solution of allyl (4R,5S,6S)-3-[(4-{(6S)-1-[(allyloxy)carbonyl]-6-methyl-1,2,3,6-tetrahydro-4-pyridinyl}-1,3-thiazol-2-yl)sulfanyl]-6-[(1R)-1-hydroxyethyl]-4-methyl-7-oxo-1-azabicyclo[3.2.0]hept-2-ene-2-carboxylate (270 mg, 0.49 mmol) in dichloromethane (10 ml) were added acetic acid (73 μl) and tributyltin hydride (1.23 ml, 4.6 mmol) and added at room temperature bis(triphenylphosphine)palladium chloride(II) (36 mg, 0.051 mmol). Ten minutes later the reaction mixture was poured into a mixture of ice (log) and phosphate buffer (pH7.0, 10 ml). After separation of the mixture with a separating funnel, the organic layer was extracted twice with water and the aqueous layer was washed twice with dichloromethane (3 ml). The organic solvent in the aqueous layer was evaporated under reduced pressure, and the residue was purified by polymer chromatography (CHP-20P). The fractions eluted with 3–5% aqueous THF solution were combined and lyophilized to give (4R,5S,6S)-6-[(1R)-1-hydroxyethyl]-4-methyl-3-({4-[(6S)-6-methyl-1,2,3,6-tetrahydro-4-pyridinyl]-1,3-thiazol-2-yl}sulfanyl)-7-oxo-1-azabicyclo[3.2.0]hept-2-ene-2-carboxylic acid (151.5 mg) as a white amorphous.

IR (KBr) 3409, 2971, 1760, 1596, 1390, 1264, 1148, 1028 cm$^{-1}$ $^1$H NMR (300 MHz, D$_2$O) δ 0.91(3 H, d, J=7.0 Hz),1.10(3 H, d, J=5.7 Hz), 1.32(3 H, d, J=6.8 Hz), 2.58–2.63 (2 H, m), 3.09–3.26 (2 H, m), 3.30–3.34 (1 H, m), 3.42–3.51 (1 H, m), 4.01–4.11 (3 H, m), 6.28 (1 H, s), 7.44 (1 H, s).

EXAMPLE 4

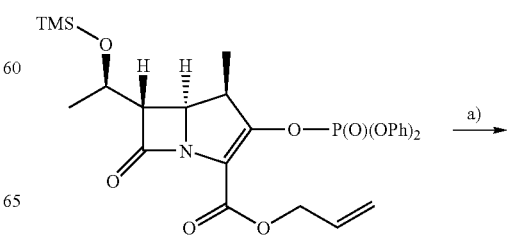

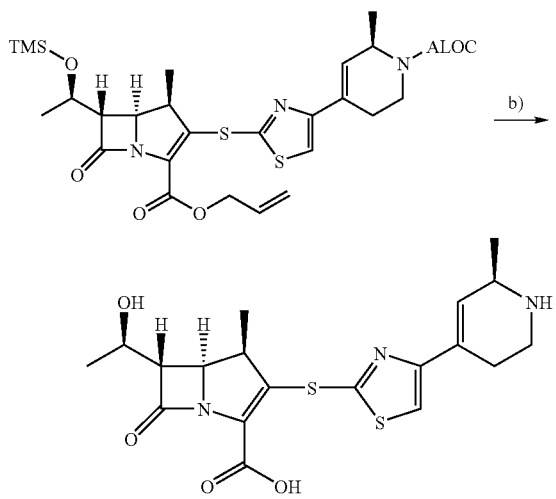

a) In the same manner as in Example 1, by using allyl (6R)-6-methyl-4-(2-mercapto-1,3-thiazol-4-yl)-3,6-dihydro-1(2 H)-pyridine carboxylate as a thiol compound, there was obtained allyl (4R,5S,6S)-3-[(4-{(6R)-1-[(allyloxy)carbonyl]-6-methyl-1,2,3,6-tetrahydro-4-pyridinyl}-1,3-thiazol-2-yl)sulfanyl]-4-methyl-7-oxo-6-{(1R)-1-[(trimethylsilyl)oxy]ethyl}-1-azabicyclo[3.2.0]hept-2-ene-2-carboxylate.

$^1$H NMR (300 MHz, CDCl$_3$) δ 0.09 (9 H, s), 1.04–1.10 (3 H, m), 1.15–1.29 (6 H, m), 2.34–2.57 (2 H, m), 2.96–3.11 (1 H, m), 3.19–3.24 (1 H, m), 3.38–3.58 (1 H, m), 4.13–4.38 (3 H, m), 4.59–4.85 (5 H, m), 5.16–5.48 (4 H, m), 5.85–6.02 (2 H, m), 6.61 (1 H, m), 7.08–7.10 (1 H, m).

b) In the same manner as in Example 2, by using allyl (4R,5S,6S)-3-[(4-{(6R)-1-[(allyloxy)carbonyl]-6-methyl-1,2,3,6-tetrahydro-4-pyridinyl}-1,3-thiazol-2-yl)sulfanyl]-4-methyl-7-oxo-6-{(1R)-1-[(trimethylsilyl)oxy]ethyl}-1-azabicyclo[3.2.0]hept-2-ene-2-carboxylate, there was obtained (4R,5S,6S)-6[(1R)-1-hydroxyethyl]-4-methyl-3-({4-[(6R)-6-methyl-1,2,3,6-tetrahydro-4-pyridinyl]-1,3-thiazol-2-yl}sulfanyl)-7-oxo-1-azabicyclo[3.2.0]hept-2-ene-2-carboxylate.

$^1$H NMR (300 MHz, D$_2$O) δ 0.89–0.91 (3 H, m), 1.09 (3 H, d, J=6.4 Hz), 1.33 (3 H, d, J=7.0 Hz), 2.58–2.67 (2 H, m), 3.07–3.35 (3 H, m), 3.43–3.53 (1 H, m), 4.00–4.12 (3 H, m), 6.28 (1 H, s), 7.44 (1 H, s). IR (KBr) 3422, 1771 cm$^{-1}$

EXAMPLE 5

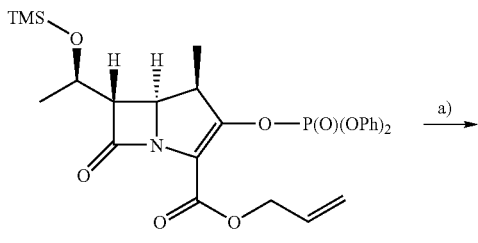

a) A solution of lithium hexamethyldisilazide in THF (1M, 0.62 ml, 0.62 mmol) was added at 0–5° C. to a solution of allyl (6S)-6-isopropyl-4-(2-mercapto-1,3-thiazol-4-yl)-3,6-dihydro-1(2 H)-pyridinecarboxylate (202 mg, 0.62 mmol) in THF (11.0 ml) and the mixture was stirred for 15 minutes. To the reaction solution was added at 0° C. a solution of allyl (4R,5R,6S)-3-[(diphenoxyphosphino)oxy]-4-methyl-7-oxo-6-{(1R)-1-[(trimethylsilyl)oxy]ethyl}-1-azabicyclo[3.2.0]hept-2-ene-2-carboxylate in acetonitrile (30%, 2.37 g, 1.2 mmol) and the solution was allowed to stand in a refrigerator for 16 hours. To the reaction solution was added ice water and the reaction mixture was extracted with ethyl acetate. The organic layer was washed with a saturated aqueous sodium chloride solution and dried over anhydrous sodium sulfate. After removal of the solvent in vacuo, the residue was purified with silica gel chromatography (hexane/ethyl acetate: 1/5→1/3) to give allyl (4R,5S,6S)-3-[(4-{(6S)-1-[(allyloxy)carbonyl]-6-isopropyl-1,2,3,6-tetrahydro-4-pyridinyl}-1,3-thiazol-2-yl)sulfanyl]-4-methyl-7-oxo-6-{(1R)-1-[(trimethylsilyl)oxy]ethyl}-1-azabicyclo[3.2.0]hept-2-ene-2-carboxylate (0.24 g, 61%).

$^1$H NMR (300 MHz, CDCl$_3$) δ 0.00 (9 H, s), 0.88–1.00 (9 H, m), 1.11–1.14 (3 H, m), 1.87 (1 H, sesq, J=7.3 Hz), 2.22–2.48 (2 H, m), 2.88–3.14 (2 H, m), 3.27–3.47 (1 H, m), 3.97–4.77 (8 H, m), 5.06–5.38 (4 H, m), 5.77–5.93 (2 H, m), 6.71 (1 H, brs), 6.99 (1 H, brs).

b) To a solution of allyl (4R,5S,6S)-3-[(4-{(6S)-1-[(allyloxy)carbonyl]-6-isopropyl-1,2,3,6-tetrahydro-4-pyridinyl-1,3-thiazol-2-yl)sulfanyl]-4-methyl-7-oxo-6-{(1R)-1-[(trimethylsilyl)oxy]ethyl}-1-azabicyclo[3.2.0]hept-2-ene-2-carboxylate (204 mg, 0.32 mmol) in THF (20 ml) was added at 0° C. water and then 1N hydrochloric acid. The solution was adjusted to pH about 3 and stirred for 1 hour. To the reaction solution was added a saturated aqueous sodium hydrogen carbonate solution and the reaction mixture was extracted twice with ethyl acetate. The organic layer was washed with an aqueous saturated sodium chloride solution and dried over anhydrous sodium sulfate. After removal of the solvent in vacuo, the residue (0.25 g) was dissolved in dichloromethane (25 ml). To the solution were added acetic acid (46 μl, 0.80 mmol) and tributyltin hydride (0.86 ml, 3.2 mmol) and then was added at room temperature bis(triphenylphosphine)palladium chloride(II) (22.5 mg, 0.032 mmol). Ten minutes later the reaction mixture was poured into a mixture of ice (10 g) and phosphate buffer (pH7.0, 10 ml). After separation of the mixture with a separating funnel, the organic layer was extracted twice with water and the aqueous layer was washed twice with dichloromethane (3 ml). The organic solvent in the aqueous layer was evaporated under reduced pressure, and the residue was purified by polymer chromatography (CHP-20P). The fractions eluted with 3% aqueous THF solution were combined and lyophilized to give (4R,5S,6S)-6-[(1R)-1-hydroxyethyl]-3-({4-[(6S)-6-isopropyl-1,2,3,6-tetrahydro-4-pyridinyl]-1,3-thiazol-2-yl}sulfanyl]-4-methyl-7-oxo-1-azabicyclo[3.2.0]hept-2-ene-2-carboxylic acid (74.2 mg, purity 95%, yield 50%) as a white amorphous.

$^1$H NMR (300 MHz, D$_2$O) δ 0.90–0.95 (9 H, m), 1.09 (3 H, d, J=6.4 Hz), 1.93 (1 H, sesq, J=6.6 Hz), 2.59–2.67 (2 H, m), 3.06–3.23 (2 H, m), 3.29–3.34 (1 H, m), 3.46–3.53 (1 H, m), 3.72–3.77 (1 H, m), 4.04–4.11 (2 H, m), 6.40 (1 H, s), 7.45 (1 H, s). IR (KBr) 3362, 2968, 1760, 1599, 1390 cm$^{-1}$

EXAMPLE 6

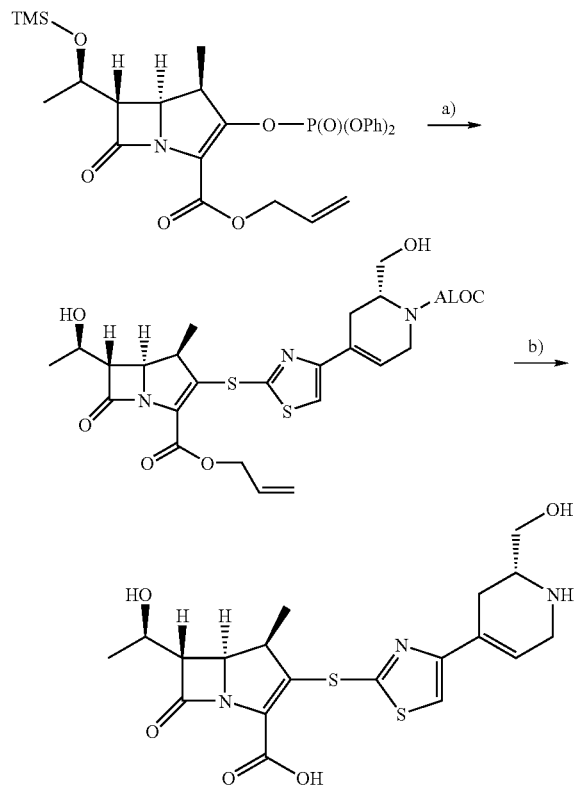

a) A solution of lithium hexamethyldisilazide in THF (1M, 0.29 ml, 0.29 mmol) was added at 0–5° C. to a solution of allyl (2R)-2-({[tert-butyl(dimethyl)silyl]oxy}methyl)-4-(2-mercapto-1,3-thiazol-4-yl)-3,6-dihydro-1(2 H)-pyridinecarboxylate (122 mg, 0.29 mmol) in THF (4.3 ml) and the mixture was stirred for 10 minutes. To the reaction solution was added at 0° C. a solution of allyl (4R,5R,6S)-3-[(diphenoxyphosphino)oxy-4-methyl-7-oxo-6-{(1R)-1-[(trimethylsilyl)oxy]ethyl}-1-azabicyclo[3.2.0]hept-2-ene-2-carboxylate in acetonitrile (30%, 1.09 g, 0.58 mmol) and the solution was allowed to stand in a refrigerator for 19 hours. To the reaction solution was added ice water and the reaction mixture was extracted with ethyl acetate. The organic layer was washed with a saturated aqueous sodium chloride solution and dried over anhydrous sodium sulfate. After removal of the solvent in vacuo, the residue was dissolved in THF (5.65 ml). To the solution were added at 0–5° C. acetic acid (215 µl) and tetrabutylammonium fluoride in THF (1M, 1.5 ml, 1.5 mmol). After reaction for 20 hours, to the reaction mixture was added ice water and the mixture was extracted with ethyl acetate. The organic layer was washed with a saturated aqueous sodium chloride solution and dried over anhydrous sodium sulfate. After removal of the solvent in vacuo, the residue was purified with silica gel chromatography (hexane/ethyl acetate: 1/3→10% methanol in chloroform) to give allyl (4R,5S,6S)-3-({4-[(2R)-1-[(allyloxy)carbonyl]-2-(hydroxymethyl)-1,2,3,6-tetrahydro-4-pyridinyl]-1,3-thiazol-2-yl}sulfanyl)-6-[(1R)-1-hydroxyethyl]-4-methyl-7-oxo-1-azabicyclo[3.2.0]hept-2-ene-2-carboxylate (110 mg, 68%). IR (KBr) 3426, 2933, 1772, 1700, 1559, 1457, 1136 cm$^{-1}$ $^1$H NMR (300 MHz, CDCl$_3$) δ 1.10 (3 H, d, J=7.3 Hz), 1.31 (3 H, d, J=6.2 Hz), 2.50 (1 H, d, J=17.4 Hz), 2.62–2.73 (1 H, m), 3.25 (1 H, d, J=2.8, 7.0 Hz), 3.45–3.96 (4 H, m), 4.17–4.27 (2 H, m), 4.41–4.86 (6 H, m), 5.19–5.47 (4 H, m), 5.87–6.03 (2 H, m), 6.63 (1 H, s), 7.11 (1 H, s).

b) To a solution of allyl (4R,5S,6S)-3-({4-[(2R)-1-[(allyloxy)carbonyl]-2-(hydroxymethyl)-1,2,3,6-tetrahydro-4-pyridinyl]-1,3-thiazol-2-yl}sulfanyl)-6-[(1R)-1-hydroxyethyl]-4-methyl-7-oxo-1-azabicyclo[3.2.0]hept-2-ene-2-carboxylate (110 mg, 0.20 mmol) in dichloromethane (15 ml) were added acetic acid (28 µl) and tributyltin hydride (0.54 ml, 2.6 mmol) and then was added at room temperature bis(triphenylphosphine)palladium chloride(II) (14 mg, 0.020 mmol). Ten minutes later the reaction mixture was poured into a mixture of ice (10 g) and phosphate buffer (pH7.0, 10 ml). After separation of the mixture with a separating funnel, the organic layer was extracted twice with water and the aqueous layer was washed twice with dichloromethane (3 ml). The organic solvent in the aqueous layer was evaporated under reduced pressure, and the residue was purified by polymer chromatography (CHP-20P). The fractions eluted with 1–3% aqueous THF solution were combined and lyophilized to give (4R,5S,6S)-6-[(1R)-1-hydroxyethyl]-3-({4-[(2R)-2-(hydroxymethyl)-1,2,3,6-tetrahydro-4-pyridinyl]-1,3-thiazol-2-yl}sulfanyl)-4-methyl-7-oxo-1-azabicyclo[3.2.0]hept-2-ene-2-carboxylic acid (51 mg, yield 54%) as a white amorphous.

$^1$H NMR (300 MHz, D$_2$O) δ 0.92 (3 H, d, J=7.0 Hz), 1.09 (3 H, d, J=6.4 Hz), 2.35–2.65 (2 H, m), 3.08–3.18 (1 H, m), 3.30–3.44 (2 H, m), 3.60 (1 H, dd, J=6.8, 12.5 Hz), 3.72–3.82 (3 H, m), 4.03–4.13 (2 H, m), 6.38 (1 H, s), 7.41 (1 H, s).

EXAMPLE 7

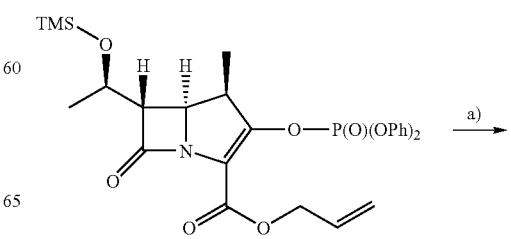

-continued

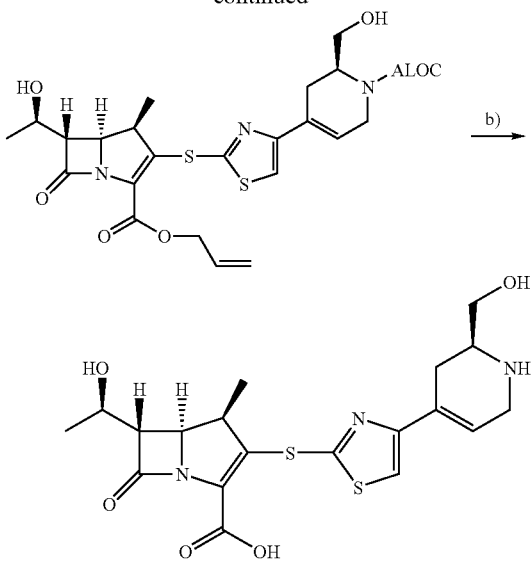

a) Sodium hydride (60 w/w %, 13.3 mg, 0.33 mmol) was added at 0–5° C. to a solution of allyl (2S)-2-(hydroxymethyl)-4-(2-mercapto-1,3-thiazol-4-yl)-3,6-dihydro-1(2H)-pyridinecarboxylate (purity 70%, 139 mg, 0.33 mmol) in a mixture of THF (11.0 ml) and DMF(0.5 ml) and the mixture was stirred for 10 minutes. To the reaction solution was added at 0° C. a solution of allyl (4R,5R,6S)-3-[(diphenoxyphosphino)oxy]-4-methyl-7-oxo-6-{(1R)-1-[(trimethylsilyl)oxy]ethyl}-1-azabicyclo[3.2.0]hept-2-ene-2-carboxylate in acetonitrile (30%, 1.27 g, 0.67 mmol) and the solution was allowed to stand in a refrigerator for 16 hours. To the reaction solution was added ice water and the solution was adjusted to pH 3 at 0–5° C. with 1N hydrochloric acid. After the mixture was stirred for 30 minutes, the reaction mixture was extracted with ethyl acetate. The organic layer was washed with a saturated aqueous sodium chloride solution and dried over anhydrous sodium sulfate. After removal of the solvent in vacuo, the residue was purified with thin layer chromatography (10% methanol in chloroform) to give allyl (4R,5S,6S)-3-({4-[(2S)-1-[(allyloxy)carbonyl]-2-(hydroxymethyl)-1,2,3,6-tetrahydro-4-pyridinyl]-1,3-thiazol-2-yl}sulfanyl)-6-[(1R)-1-hydroxyethyl]-4-methyl-7-oxo-1-azabicyclo[3.2.0]hept-2-ene-2-carboxylate (87 mg, 46%).

$^1$H NMR (300 MHz, CDCl$_3$) δ 0.99 (3 H, d, J=7.3 Hz), 1.21 (3 H, d, J=6.0 Hz), 2.38–2.63 (2 H, m), 3.15 (1 H, dd, J=2.8, 6.8 Hz), 3.37–3.85 (4 H, m), 4.30–4.65 (5 H, m), 4.73 (1 H, dd, J=5.3, 13.2 Hz), 5.10–5.37 (4 H, m), 5.78–5.93 (2 H, m), 6.54 (1 H, brs), 7.01 (1 H, s).

b) To a solution of allyl (4R,5S,6S)-3-({4-[(2S)-1-[(allyloxy)carbonyl]-2-(hydroxymethyl)-1,2,3,6-tetrahydro-4-pyridinyl]-1,3-thiazol-2-yl}sulfanyl)-6-[(1R)-1-hydroxyethyl]-4-methyl-7-oxo-1-azabicyclo[3.2.0]hept-2-ene-2-carboxylate (28 mg, 0.05 mmol) in dichloromethane (4 ml) were added acetic acid (7.2 μl) and tributyltin hydride (135 ml, 0.50 mmol) and then was added at room temperature bis(triphenylphosphine)palladium chloride(II) (3.5 mg, 0.005 mmol). Ten minutes later the reaction mixture was poured into a mixture of ice (10 g) and phosphate buffer (pH7.0, 10 ml). After separation of the mixture with a separating funnel, the organic layer was extracted twice with water and the aqueous layer was washed twice with dichloromethane (3 ml). The organic solvent in the aqueous layer was evaporated under reduced pressure, and the residue was purified by polymer chromatography (CHP-20P). The fractions eluted with 1–3% aqueous THF solution were combined and lyophilized to give (4R,5S,6S)-6-[(1R)-1-hydroxyethyl]-3-({4-[(2S)-2-(hydroxymethyl)-1,2,3,6-tetrahydro-4-pyridinyl]-1,3-thiazol-2-yl}sulfanyl)-4-methyl-7-oxo-1-azabicyclo[3.2.0]hept-2-ene-2-carboxylic acid (3.9 mg) as a white amorphous.

$^1$H NMR (300 MHz, D$_2$O) δ 0.91 (3 H, d, J=7.0 Hz), 1.09 (3 H, d, J=6.4 Hz), 2.20–2.33 (1 H, m), 2.44–2.53 (1 H, m), 3.08–3.73 (7 H, m), 4.02–4.13 (2 H, m), 6.39 (1 H, s), 7.37 (1 H, s).

EXAMPLE 8

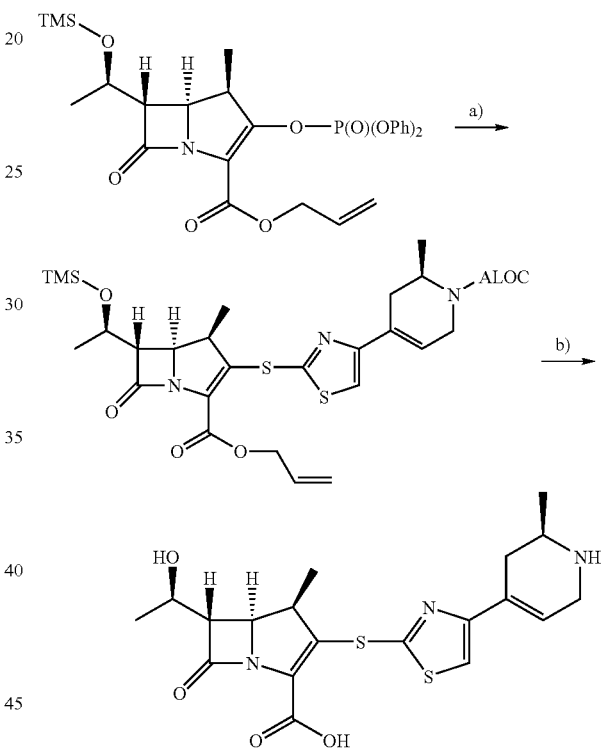

a) A solution of lithium hexamethyldisilazide in THF (1M, 0.58 ml, 0.58 mmol) was added at 0–5° C. to a solution of allyl (2R)-4-(2-mercapto-1,3-thiazol-4-yl)-2-methyl-3,6-dihydro-1(2H)-pyridinecarboxylate (172 mg, 0.58 mmol) in THF (2.0 ml) and the mixture was stirred for 10 minutes. To the reaction solution was added at 0° C. a solution of allyl (4R,5R,6S)-3-[(diphenoxyphosphino)oxy]-4-methyl-7-oxo-6-{(1R)-1-[(trimethylsilyl)oxy]ethyl}-1-azabicyclo[3.2.0]hept-2-ene-2-carboxylate in acetonitrile (30%, 2.21 g, 1.2 mmol) and the solution was allowed to stand in a refrigerator for 16 hours. To the reaction solution was added ice water and the reaction mixture was extracted with ethyl acetate. The organic layer was washed with a saturated aqueous sodium chloride solution and dried over anhydrous sodium sulfate. After removal of the solvent in vacuo, the residue was purified with silica gel chromatography (hexane/ethyl acetate: 1/4→1/3) to give allyl (4R,5S,6S)-3-[(4-{(2R)-1-[(allyloxy)carbonyl]-2-methyl-1,2,3,6-tetrahydro-4-pyridinyl}-1,3-thiazol-2-yl)sulfanyl]-4-methyl-7-oxo-6-{(1R)-1-

[(trimethylsilyl)oxy]ethyl}-1-azabicyclo[3.2.0]hept-2-ene-2-carboxylate (137 mg, 38%).

$^1$H NMR (300 MHz, CDCl$_3$) δ 0.10 (9 H, s), 1.07 (3 H, d, J=7.3 Hz), 1.17 (3 H, d, J=6.8 Hz), 1.21 (3 H, d, J=6.2 Hz), 2.28 (1 H, d, J=17.2 Hz), 2.67–2.79 (1 H, m), 3.22 (1 H, dd, J=2.7, 6.2 Hz), 3.56 (1 H, dd, J=7.3, 9.9 Hz), 3.77–3.87 (1 H, m), 4.15–4.23 (2 H, m), 4.42–4.53 (1 H, m), 4.60–4.85 (5 H, m), 5.18–5.48 (4 H, m), 5.88–6.02 (2 H, m), 6.64 (1 H, brs), 7.06 (1 H, s).

b) To a solution of allyl (4R,5S,6S)-3-[(4-{(2R)-1-[(allyloxy)carbonyl]-2-methyl-1,2,3,6-tetrahydro-4-pyridinyl-1,3-thiazol-2-yl)sulfanyl]-4-methyl-7-oxo-6-{(1R)-1-[(trimethylsilyl)oxy]ethyl}-1-azabicyclo[3.2.0]hept-2-ene-2-carboxylate (137 mg, 0.22 mmol) in THF (20 ml) was added at 0° C. water and then the solution was adjusted to pH about 3 with 1N hydrochloric acid. The solution was stirred for 10 minutes. To the reaction solution was added an aqueous sodium hydrogen carbonate solution and the reaction mixture was extracted twice with ethyl acetate. The organic layer was washed with a saturated sodium chloride solution and dried over anhydrous sodium sulfate. After removal of the solvent in vacuo, the residue was dissolved in dichloromethane (3 ml). To the solution were added acetic acid (3 μl) and tributyltin hydride (0.59 ml, 22 mmol) and then was added at room temperature bis (triphenylphosphine)palladium chloride (II) (15.6 mg, 0.02 mmol). Ten minutes later the reaction mixture was poured into a mixture of ice (10 g) and phosphate buffer (pH7.0, 10 ml). After separation of the mixture with a separating funnel, the organic layer was extracted twice with water and the aqueous layer was washed twice with dichloromethane (3 ml). The organic solvent in the aqueous layer was evaporated under reduced pressure, and the residue was purified by polymer chromatography (CHP-20P). The fractions eluted with 3–8% aqueous THF solution were combined and lyophilized to give (4R,5S,6S)-6-[(1R)-1-hydroxyethyl]-4-methyl-3-({4-[(2R)-2-methyl-1,2,3,6-tetrahydro-4-pyridinyl]-1,3-thiazol-2-yl}sulfanyl)-4-methyl-7-oxo-1-azabicyclo[3.2.0]hept-2-ene-2-carboxylic acid (59.3 mg) as a white amorphous.

IR (KBr) 3428, 2971, 1758, 1602, 1391, 1263 cm$^{-1}$ $^1$H NMR (300 MHz, D$_2$O) δ 0.91 (3 H, d, J=7.1 Hz), 1.10 (3 H, d, J=6.2 Hz), 1.32 (3 H, d, J=6.4 Hz), 2.30–2.45 (1 H, m), 2.67–2.78 (1 H, m), 3.09–3.18 (1 H, m), 3.31–3.34 (1 H, m), 3.41–3.52 (1 H, m), 3.77 (2 H, brs), 4.05–4.13 (2 H, m), 6.35 (1 H, m), 7.42 (1 H, m).

EXAMPLE 9

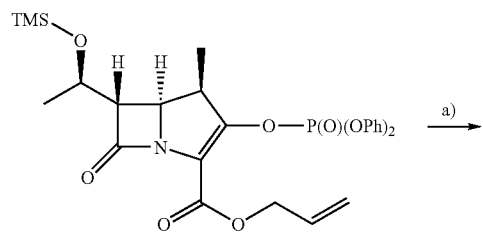

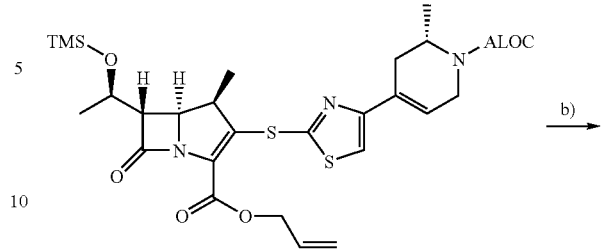

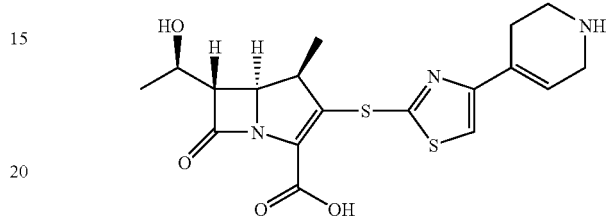

a) A solution of lithium hexamethyldisilazide in THF (1M, 0.30 ml, 0.30 mmol) was added at 0–5° C. to a solution of allyl (2S)-4-(2-mercapto-1,3-thiazol-4-yl)-2-methyl-3,6-dihydro-1(2 H)-pyridinecarboxylate (89 mg, 0.30 mmol) in THF (2.0 ml) and the mixture was stirred for 10 minutes. To the reaction solution was added at 0° C. a solution of allyl (4R,5R,6S)-3-[(diphenoxyphosphino)oxy]-4-methyl-7-oxo-6-{(1R)-1-[(trimethylsilyl)oxy]ethyl}-1-azabicyclo[3.2.0]hept-2-ene-2-carboxylate in acetonitrile (30%, 1.2 g, 0.60 mmol) and the solution was allowed to stand in a refrigerator for 16 hours. To the reaction solution was added ice water and the reaction mixture was extracted with ethyl acetate. The organic layer was washed with a saturated aqueous sodium chloride solution and dried over anhydrous sodium sulfate. After removal of the solvent in vacuo, the residue was purified with silica gel chromatography (hexane/ethyl acetate: 1/4→1/3) to give allyl (4R,5S,6S)-3-[(4-{(2S)-1-[(allyloxy)carbonyl]-2-methyl-1,2,3,6-tetrahydro-4-pyridinyl}-1,3-thiazol-2-yl)sulfanyl]-4-methyl-7-oxo-6-{(1R)-1-[(trimethylsilyl)oxy]ethyl}-1-azabicyclo[3.2.0]hept-2-ene-2-carboxylate (87 mg, 47%).

$^1$H NMR (300 MHz, CDCl$_3$) δ 0.09 (9 H, s), 1.10 (3 H, d, J=7.1 Hz), 1.18 (3 H, d, J=7.0 Hz), 1.21 (3 H, d, J=6.2 Hz), 2.28 (1 H, d, J=16.3 Hz), 2.67–2.79 (1 H, m), 3.22 (1 H, dd, J=2.9, 6.2 Hz), 3.46 (1 H, dd, J=7.4, 9.9 Hz), 3.75–3.86 (1 H, m), 4.15–4.23 (2 H, m), 4.42–4.53 (1 H, m), 4.59–4.86 (5 H, m), 5.16–5.48 (4 H, m), 5.88–6.03 (2 H, m), 6.64 (1 H, brs), 7.08 (1 H, s).

b) To a solution of allyl (4R,5S,6S)-3-[(4-{(2S)-1-[(allyloxy)carbonyl]-2-methyl-1,2,3,6-tetrahydro-4-pyridinyl-1,3-thiazol-2-yl)sulfanyl]-4-methyl-7-oxo-6-{(1R)-1-[(trimethylsilyl)oxy]ethyl}-1-azabicyclo[3.2.0]hept-2-ene-2-carboxylate (87 mg, 0.14 mmol) in THF (10 ml) was added at 0° C. water (7 ml) and then the solution was adjusted to pH about 3 with 1N hydrochloric acid and stirred for 1 hour. To the reaction solution was added an aqueous sodium hydrogen carbonate solution and the reaction mixture was extracted twice with ethyl acetate. The organic layer was washed with a saturated aqueous sodium chloride solution and dried over anhydrous sodium sulfate. After removal of the solvent in vacuo, the residue was dissolved in dichloromethane (2 ml). To the solution were added acetic acid (20

μl) and tributyltin hydride (0.38 ml, 1.4 mmol) and then was added at room temperature bis(triphenylphosphine)palladium chloride(II) (9.8 mg, 0.014 mmol). Ten minutes later the reaction mixture was poured into a mixture of ice (10 g) and phosphate buffer (pH7.0, 10 ml). After separation of the mixture with a separating funnel, the organic layer was extracted twice with water and the aqueous layer was washed twice with dichloromethane (3 ml). The organic solvent in the aqueous layer was evaporated under reduced pressure, and the residue was purified by polymer chromatography (CHP-20P). The fractions eluted with 3–8% aqueous THF solution were combined and lyophilized to give (4R,5S,6S)-6-[(1R)-1-hydroxyethyl]-4-methyl-3-({4-[(2S)-2-methyl-1,2,3,6-tetrahydro-4-pyridinyl]-1,3-thiazol-2-yl}sulfanyl)-4-methyl-7-oxo-1-azabicyclo[3.2.0]hept-2-ene-2-carboxylic acid (59.3 mg) as a white amorphous.

IR (KBr) 3392, 2970, 1758, 1599, 1391, 1263 cm$^{-1}$ $^1$H NMR (300 MHz, D$_2$O) δ 0.91 (3 H, d, J=7.1 Hz), 1.09 (3 H, d, J=6.4 Hz), 1.26 (3 H, d, J=6.4 Hz), 2.24–2.37 (1 H, m), 2.60–2.71 (1 H, m), 3.07–3.18 (1 H, m), 3.28–3.38 (2 H, m), 3.68 (2 H, brs), 4.03–4.10 (2 H, m), 6.35 (1 H, m), 7.39 (1 H, m).

2.63–2.73 (1H, m), 3.24 (1H, dd, J=6.2, 2.9 Hz), 3.39–3.48 (2H, m), 3.34 (3H, s), 3.50–3.64 (1H, m), 3.70–3.87 (1H, m), 4.18–4.26 (2H, m), 4.48–4.88 (6H, m), 5.20–5.51 (4H, m), 5.90–6.04 (2H, m), 6.68 (1H, br s), 7.12 (1H, s).

b) In the same manner as in Example 2, by using allyl (4R,5S,6S)-3-({4-[(2S)-1-[(allyloxy)carbonyl]-2-(methoxymethyl)-1,2,3,6-tetrahydro-4-pyridinyl]-1,3-thiazol-2-yl}sulfanyl)-4-methyl-7-oxo-6-{(1R)-1-[(trimethylsilyl)oxy]ethyl}-1-azabicyclo[3.2.0]hept-2-ene-2-carboxylate, there was obtained (4R,5S,6S)-6-[(1R)-1-[(hydroxyethyl)-3-({4-[(2S)-2-(methoxymethyl)-1,2,3,6-tetrahydro-4-pyridinyl]-1,3-thiazol-2-yl}sulfanyl)-4-methyl-7-oxo-1-azabicyclo[3.2.0]hept-2-ene-2-carboxylate.

$^1$H NMR (300 MHz, D$_2$O) δ 0.91 (3H, d, J=7.1 Hz), 1.09 (3H, d, J=6.4 Hz), 2.38–2.49 (1H, m), 2.59–2.66 (1H, m), 3.09–3.20 (1H, m), 3.30 (3H, s), 3.31–3.33 (1H, m), 3.48–3.65 (3H, m), 3.73 (2H, br s), 4.03–4.12 (2H, m), 6.37 (1H, s), 7.40 (1H, s).

EXAMPLE 11

EXAMPLE 10

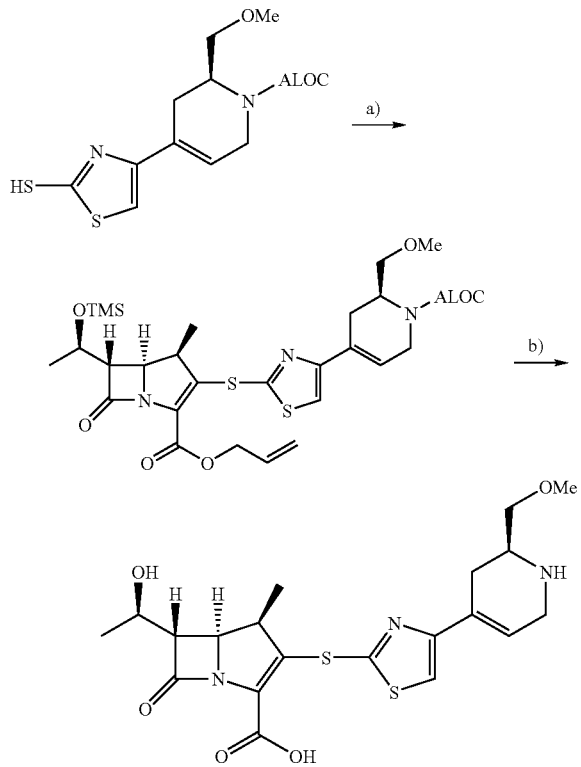

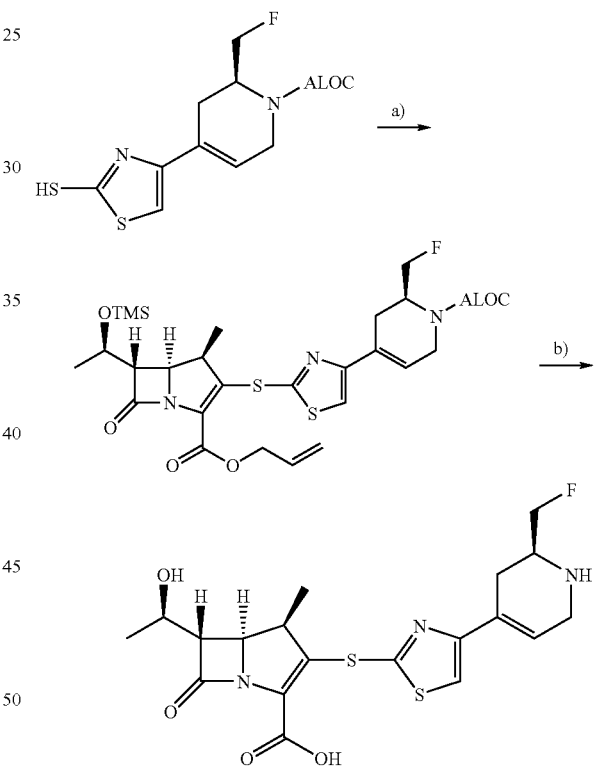

a) In the same manner as in Example 1, by using allyl (2S)-2-(methoxymethyl)-4-(2-sulfanyl-1,3-thiazol-4-yl)-3,6-dihydro-1(2 H)-pyridinecarboxylate as a thiol compound, there was obtained allyl (4R,5S,6S)-3-({4-[(2S)-1-[(allyloxy)carbonyl]-2-(methoxymethyl)-1,2,3,6-tetrahydro-4-pyridinyl]-1,3-thiazol-2-yl}sulfanyl)-4-methyl-7-oxo-6-{(1R)-1-[(trimethylsilyl)oxy]ethyl}-1-azabicyclo[3.2.0]hept-2-ene-2-carboxylate.

$^1$H NMR (300 MHz, CDCl$_3$) δ 0.12 (9H, s), 1.09 (3H, d, J=7.3 Hz), 1.24 (3H, d, J=6.2 Hz), 2.54 (1H, d, J=16.8 Hz), a) In the same manner as in Example 1, by using allyl (2S)-2-(fluoromethyl)-4-(2-sulfanyl-1,3-thiazol-4-yl)-3,6-dihydro-1(2 H)-pyridinecarboxylate was used as a thiol compound, there was obtained allyl (4R,5S,6S)-3-({4-[(2S)-1-[(allyloxy)carbonyl]-2-(fluoromethyl)-1,2,3,6-tetrahydro-4-pyridinyl]-1,3-thiazol-2-yl}sulfanyl)-4-methyl-7-oxo-6-{(1R)-1-[(trimethylsilyl)oxy]ethyl}-1-azabicyclo[3.2.0]hept-2-ene-2-carboxylate.

$^1$H NMR (300 MHz, CDCl$_3$) δ 0.12 (9H, s), 1.10 (3H, d, J=7.3 Hz), 1.24 (3H, d, J=6.0 Hz), 2.57 (1H, d, J=16.7 Hz), 2.69–2.80 (1H, m), 3.24 (1H, dd, J=6.2, 2.9 Hz), 3.49–3.60 (1H, m), 3.78–3.94 (1H, m), 4.08–4.99 (10H, m), 5.22–5.50 (4H, m), 5.90–6.04 (2H, m), 6.69 (1H, br s), 7.14 (1H, s).

b) In the same manner as in Example 2, by using allyl (4R,5S,6S)-3-({4-[(2S)-1-[(allyloxy)carbonyl]-2-(fluoromethyl)-1,2,3,6-tetrahydro-4-pyridinyl]-1,3-thiazol-2-yl)sulfanyl}-4-methyl-7-oxo-6-{(1R)-1-[(trimethylsilyl)oxy]ethyl}-1-azabicyclo[3.2.0]hept-2-ene-2-carboxylate, there was obtained (4R,5S,6S)-3-({4-[(2S)-2-(fluoromethyl)-1,2,3,6-tetrahydro-4-pyridinyl]-1,3-thiazol-2-yl}sulfanyl)-6-[(1R)-1-[(hydroxyethyl)-4-methyl-7-oxo-1-azabicyclo[3.2.0]hept-2-ene-2-carboxylic acid.

$^1$H NMR (300 MHz, D$_2$O) δ 0.92 (3H, d, J=7.3 Hz), 1.10 (3H, d, J=6.2 Hz), 2.24–2.33 (1H, m), 2.43–2.49 (1H, m), 3.12–3.19 (1H, m), 3.30–3.33 (1H, m), 3.53–3.56 (2H, m), 4.05–4.12 (2H, m), 4.31–4.39 (1H, m), 4.46–4.54 (1H, m), 6.40–6.43 (1H, m), 7.36 (1H, s).

EXAMPLE 12

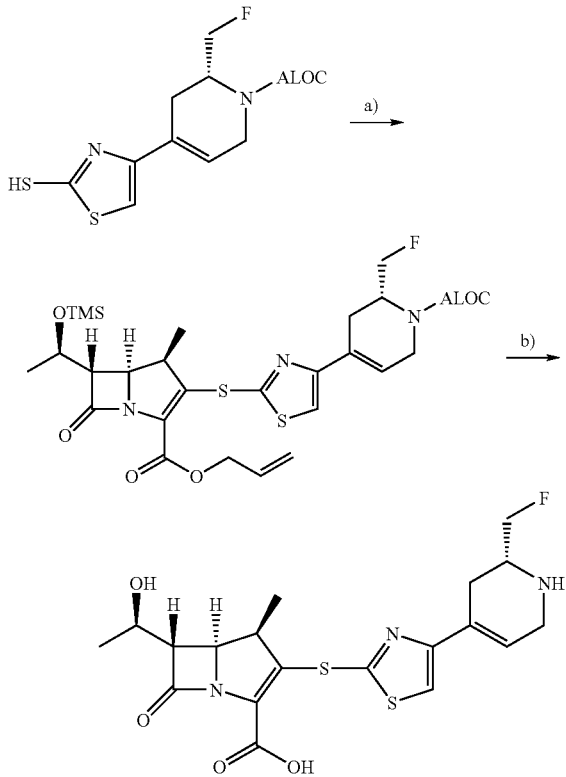

a) In the same manner as in Example 1, by using allyl (2R)-(2-fluoromethyl)-4-(2-sulfanyl-1,3-thiazol-4-yl)-3,6-dihydro-1(2 H)-pyridinecarboxylate as a thiol compound, there was obtained allyl (4R,5S,6S)-3-({4-[(2R)-1-[(allyloxy)carbonyl]-2-(fluoromethyl)-1,2,3,6-tetrahydro-4-pyridinyl]-1,3-thiazol-2-yl}sulfanyl)-4-methyl-7-oxo-6-{(1R)-1-[(trimethylsilyl)oxy]ethyl}-1-azabicyclo[3.2.0]hept-2-ene-2-carboxylate.

$^1$H NMR (300 MHz, CDCl$_3$) δ 0.12 (9H, s), 1.13 (3H, d, J=7.3 Hz), 1.24 (3H, d, J=6.0 Hz), 2.57 (1H, d, J=16.9 Hz), 2.69–2.80 (1H, m), 3.25 (1H, dd, J=6.2, 2.7 Hz), 3.44–3.59 (1H, m), 3.78–3.94 (1H, m), 4.11–5.00 (10H, m), 5.22–5.50 (4H, m), 5.90–6.05 (2H, m), 6.68 (1H, br s), 7.15 (1H, s).

b) In the same manner as in Example 2, by using allyl (4R,5S,6S)-3-({4-[(2R)-1-[(allyloxy)carbonyl]-2-(fluoromethyl)-1,2,3,6-tetrahydro-4-pyridinyl]-1,3-thiazol-2-yl}sulfanyl]-4-methyl-7-oxo-6-{(1R)-1-[(trimethylsilyl) oxy]ethyl}-1-azabicyclo[3.2.0]hept-2-ene-2-carboxylate, there was obtained (4R,5S,6S)-3-({4-[(2R)-2-(fluoromethyl)-1,2,3,6-tetrahydro-4-pyridinyl]-1,3-thiazol-2-yl}sulfanyl)-6-[(1R)-1-[(hydroxyethyl)-4-methyl-7-oxo-1-azabicyclo[3.2.0]hept-2-ene-2-carboxylic acid.

$^1$H NMR (300 MHz, D$_2$O) δ 0.92 (3H, d, J=7.1 Hz), 1.10 (3H, d, J=6.2 Hz), 2.38–2.50 (1H, m), 2.55–2.63 (1H, m), 3.09–3.19 (1H, m), 3.31–3.34 (1H, m), 3.48–3.62 (1H, m), 3.68–3.72 (2H, m), 4.04–4.12 (2H, m), 4.40–4.45 (1H, m), 4.55–4.61 (1H, m), 6.39–6.42 (1H, m), 7.40 (1H, s).

EXAMPLE 13

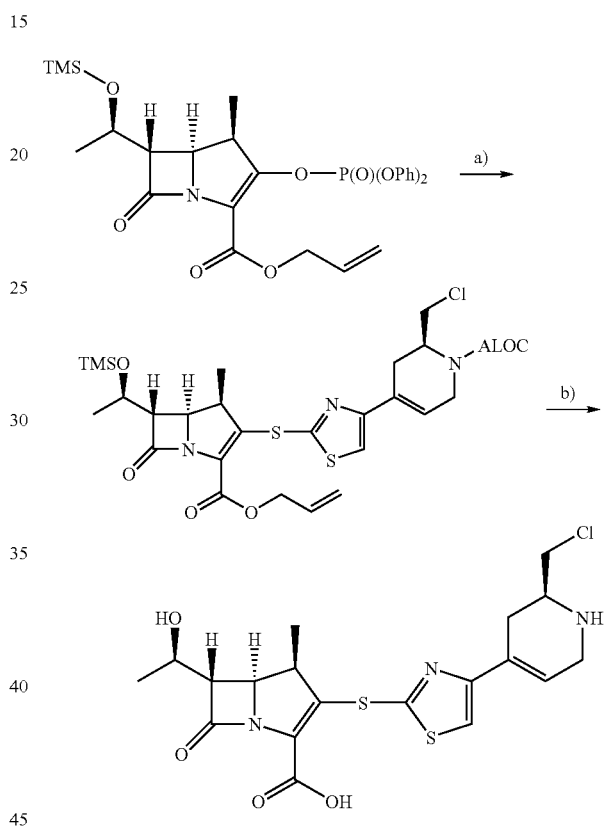

a) A solution of lithium hexamethyldisilazide in THF (1M, 0.19 ml, 0.19 mmol) was added at 0° C. to a solution of (2S)-2-(chloromethyl)-4-(2-mercapto-1,3-thiazol-4-yl)-3,6-dihydro-1(2 H)-pyridinecarboxylate (64 mg, 0.19 mmol) in THF (11.0 ml) and the mixture was stirred for 10 minutes. To the reaction solution was added at 0° C. a solution of allyl (4R,5R,6S)-3-[(diphenoxyphosphino)oxy]-4-methyl-7-oxo-6-{(1R)-1-[(trimethylsilyl)oxy]ethyl}-1-azabicyclo[3.2.0] hept-2-ene-2-carboxylate in acetonitrile (30%, 0.74 g, 0.38 mmol) and the solution was allowed to stand in a refrigerator for 15 hours. To the reaction solution was added ice water and the reaction mixture was extracted with ethyl acetate. The organic layer was washed with a saturated aqueous sodium chloride solution and dried over anhydrous sodium sulfate. After removal of the solvent in vacuo, the residue was purified with silica gel chromatography (hexane/ethyl acetate) to give allyl (4R,5S,6S)-3-({4-[(2S)-1-[(allyloxy) carbonyl]-2-(chloromethyl)-1,2,3,6-tetrahydro-4-pyridinyl]-1,3-thiazol-2-yl]sulfanyl)-4-methyl-7-oxo-6-{(1R)-1-[(trimethylsilyl)oxy]ethyl}-1-azabicyclo[3.2.0]hept-2-ene-2-carboxylate (54 mg, 43%).

$^1$H NMR (300 MHz, CDCl$_3$) δ 0.11 (9 H, s), 1.07 (3 H, d, J=7.4 Hz), 1.21 (3 H, d, J=6.0 Hz), 2.68–2.75 (2 H, m), 3.22 (1 H, dd, J=2.7, 6.4 Hz), 3.47–3.60 (3 H, m), 3.73–3.90 (1 H, m), 4.15–4.22 (2 H, m), 4.42–4.86 (6 H, m), 5.20–5.35 (3 H, m), 5.45 (1 H, dd, J=1.5, 17.2 Hz), 5.88–6.03 (2 H, m), 6.65 (1 H, brs), 7.12 (1 H, s).

b) To a solution of allyl (4R,5S,6S)-3-({4-[(2S)-1-[(allyloxy)carbonyl]-2-(chloromethyl)-1,2,3,6-tetrahydro-4-pyridinyl]-1,3-thiazol-2-yl}sulfanyl)-4-methyl-7-oxo-6-{(1R)-1-[(trimethylsilyl)oxy]ethyl}-1-azabicyclo[3.2.0]hept-2-ene-2-carboxylate (54 mg, 0.083 mmol) in THF (4 ml) was added at 0° C. water (7 ml) and then the solution was adjusted to pH about 2 with 1N hydrochloric acid and stirred for 15 minutes. To the reaction mixture was added a saturated aqueous sodium hydrogen carbonate solution. The solution was adjusted to pH 7.5 and extracted twice with ethyl acetate. The organic layer was washed with a saturated aqueous sodium chloride solution and dried over anhydrous sodium sulfate. After removal of the solvent in vacuo, the residue was dissolved in dichloromethane (2 ml). To the solution were added at 0° C. acetic acid (12 µl), tributyltin hydride (0.23 ml) and bis(triphenylphosphine)palladium chloride (5.8 mg, 0.014 mmol) and the mixture was stirred at the same temperature for 10 minutes. To the reaction mixture were added phosphate buffer (50 mM, pH7, 25 ml) and dichloromethane (20 ml). After separation of the aqueous layer, the dichloromethane layer was extracted with water and the aqueous layer was washed twice with dichloromethane (3 ml). The organic solvent in the aqueous layer was evaporated under reduced pressure, and the residue was purified by polymer chromatography (CHP-20P). The fractions eluted with an 1–3% aqueous THF solution were combined and lyophilized to give (4R,5S,6S)-6-[(1R)-1-hydroxyethyl]-3-({4-[(2S)-2-(chloromethyl)-1,2,3,6-tetrahydro-4-pyridinyl]-1,3-thiazol-2-yl}sulfanyl)-4-methyl-7-oxo-1-azabicyclo[3.2.0]hept-2-ene-2-carboxylic acid (22.5 mg, 46%) as a white amorphous.

IR (KBr) 3398, 2968, 1760, 1601, 1389, 1264 cm$^{-1}$ $^1$H NMR (300 MHz, D$_2$O) δ 0.91 (3 H, d, J=7.1 Hz), 1.08 (3 H, d, J=6.2 Hz), 2.67–2.75 (2 H, m), 3.14 (1 H, dd, J=7.3, 9.7 Hz), 3.31 (1 H, dd, J=2.8, 5.9 Hz), 3.75–3.95 (5 H, m), 4.02–4.11 (2 H, m), 6.37 (1 H, m), 7.43 (1 H, m).

EXAMPLE 14

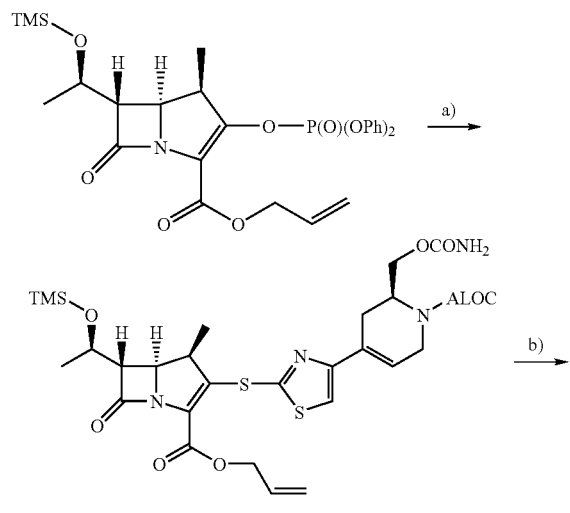

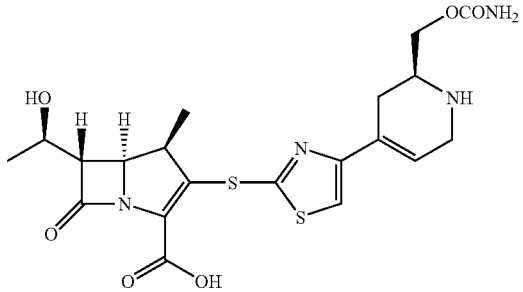

a) A solution of n-butyllithium in hexane (1.56M, 68 ml, 0.11 mmol) was added at –70° C. to a solution of allyl(2S)-2-{[(aminocarbonyl)oxy]methyl}-4-(2-mercapto-1,3-thiazol-4-yl)-3,6-dihydro-1(2 H)-pyridinecarboxylate (37.8 mg, 0.11 mmol) in THF (1 ml)/DMF (0.5 ml). The mixture was warmed to 0° C. and then stirred for 15 minutes. To the reaction solution was added at 0° C. a solution of allyl (4R,5R,6S)-3-[(diphenoxyphosphino)oxy]-4-methyl-7-oxo-6-{(1R)-1-[(trimethylsilyl)oxy]ethyl}-1-azabicyclo[3.2.0]hept-2-ene-2-carboxylate in acetonitrile (30%, 0.42 g, 0.22 mmol) and the solution was allowed to stand in a refrigerator for 13 hours. To the reaction solution was added ice water and the mixture was extracted with ethyl acetate. The organic layer was washed with a saturated aqueous sodium chloride solution and dried over anhydrous sodium sulfate. After removal of the solvent in vacuo, the residue was purified with silica gel chromatography (hexane/ethyl acetate) to give crude allyl (4R,5S,6S)-3-{[4-((2S)-1-[(allyloxy)carbonyl]-2-{[(aminocarbony)oxy]methyl}-1,2,3,6-tetrahydro-4-pyridinyl)-1,3-thiazol-2-yl]sulfanyl}-4-methyl-7-oxo-6-{(1R)-1-[(trimethylsilyl)oxy]ethyl}-1-azabicyclo[3.2.0]hept-2-ene-2-carboxylate (154 mg).

To a solution of thus obtained crude allyl (4R,5S,6S)-3-{[4-((2S)-1-[(allyloxy)carbonyl]-2-{[(aminocarbony)oxy]methyl}-1,2,3,6-tetrahydro-4-pyridinyl)-1,3-thiazol-2-yl]sulfanyl}-4-methyl-7-oxo-6-{(1R)-1-[(trimethylsilyl)oxy]ethyl}-1-azabicyclo[3.2.0]hept-2-ene-2-carboxylate in THF (4 ml) was added at 0° C. water and then the solution was adjusted to pH about 2 with 1N hydrochloric acid and stirred for 15 minutes. To the reaction mixture was added a saturated aqueous sodium hydrogen carbonate solution. The solution was adjusted to pH 7.5 and was extracted twice with ethyl acetate. The organic layer was washed with a saturated sodium chloride solution and dried over anhydrous sodium sulfate. After removal of the solvent in vacuo, the residue was dissolved in dichloromethane (2 ml). To the solution were added at 0° C. acetic acid (47 µl), tributyltin hydride (0.84 ml) and bis(triphenylphosphine)palladium chloride (21.8 mg, 0.014 mmol) and the mixture was stirred at the same temperature for 10 minutes. To the reaction mixture were added phosphate buffer (50 mM, pH7, 25 ml) and dichloromethane (20 ml). After separation of the aqueous layer, the dichloromethane layer was extracted twice with water and the aqueous layer was washed twice with dichloromethane (3 ml). The organic solvent in the aqueous layer was evaporated under reduced pressure, and the residue was purified by polymer chromatography (CHP-20P). The fractions eluted with 3–8% aqueous THF solution were combined and lyophilized to give (4R,5S,6S)-3-{[4-((2S)-2-{[(aminocarbonyl)oxy]methyl}-1,2,3,6-tetrahydro-4-pyridinyl)-1,3-thiazol-2-yl]sulfanyl}-6-[(1R)-1- hydroxyethyl]-4-methyl-7-oxo-1-azabicyclo[3.2.0]hept-2-ene-2-carboxylic acid (10.6 mg) as a white amorphous.

¹H NMR (300 MHz, D₂O) δ 0.95 (3 H, d, J=7.3 Hz), 1.12 (3 H, d, J=6.4 Hz), 2.54–2.80 (2 H, m), 3.15–3.21 (1 H, m), 3.68–3.86 (3 H, m), 4.08–4.38 (5 H, m), 6.41 (1 H, s), 7.46 (1 H, s).

EXAMPLE 15

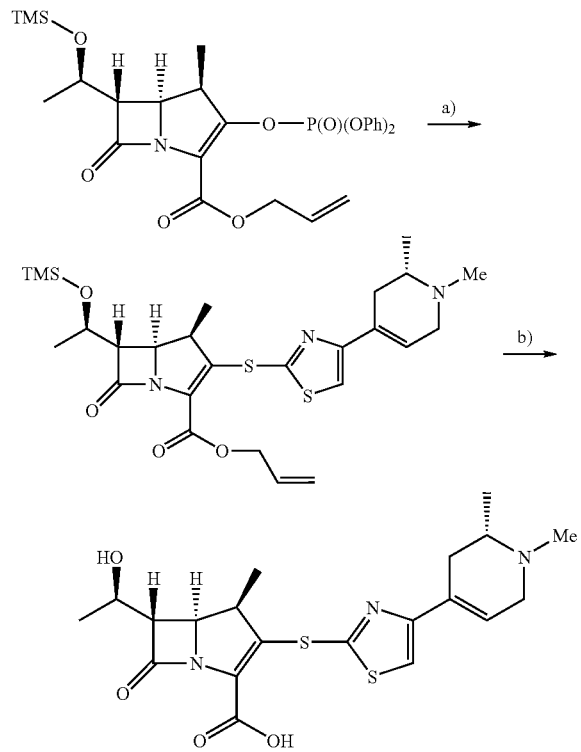

a) In the same manner as in Example 8, by using 4-[(2S)-1,2-dimethyl-1,2,3,6-tetrahydro-4-pyridinyl]-1,3-thiazol-2-thiol as a thiol compound, there was obtained allyl (4R,5S,6S)-3-({4-[(2S)-1,2-dimethyl-1,2,3,6-tetrahydro-4-pyridinyl]-1,3-thiazol-2-yl}sulfanyl)-4-methyl-7-oxo-6-{(1R)-1-[(trimethylsilyl)oxy]ethyl}-1-azabicyclo[3.2.0]hept-2-ene-2-carboxylate.

¹H NMR (300 MHz, CDCl₃) δ 0.10 (9 H, s), 1.05 (3 H, d, J=7.1 Hz), 1.21 (6 H, d, J=6.2 Hz), 2.24–2.36 (1 H, m), 2.41 (3 H, s), 2.50–2.61 (1 H, m), 2.69–3.00 (2 H, m), 3.19–3.22 (1 H, m), 3.47–3.53 (1 H, m), 4.15–4.20 (2 H, m), 4.46–4.85 (3 H, m), 5.25 (1 H, d, J=10.4 Hz), 5.44 (1 H, dd, J=1.4, 17.0 Hz), 5.96 (1 H, ddd, J=5.1, 10.4, 17.0 Hz), 6.61 (1 H, s), 7.07 (1 H, s).

b) In the same manner as in Example 8, by using allyl (4R,5S,6S)-3-({4-[(2S)-1,2-dimethyl-1,2,3,6-tetrahydro-4-pyridinyl]-1,3-thiazol-2-yl}sulfanyl)-4-methyl-7-oxo-6-{(1R)-1-[(trimethylsilyl)oxy]ethyl}-1-azabicyclo[3.2.0]hept-2-ene-2-carboxylate, there was obtained (4R,5S,6S)-3-({4-[(2S)-1,2-dimethyl-1,2,3,6-tetrahydro-4-pyridinyl]-1,3-thiazol-2-yl}sulfanyl)-6-[(1R)-1-hydroxyethyl]-4-methyl-7-oxo-1-azabicyclo[3.2.0]hept-2-ene-2-carboxylic acid.

IR (KBr) 3393, 2970, 1749, 1601, 1393, 1266 cm⁻¹ ¹H NMR (300 MHz, D₂O) δ 0.95 (3 H, d, J=7.5 Hz), 1.13 (3 H, d, J=6.2 Hz), 1.32 (3 H, d, J=6.2 Hz), 2.47–2.58 (1 H, m), 2.74–2.88 (1 H, m), 2.79 (3 H, s), 3.11–3.23 (1 H, m), 3.32–3.38 (1 H, m), 3.75–3.93 (1 H, m), 4.09–4.15 (2 H, m), 6.33 (1 H, s), 7.47 (1 H, s).

EXAMPLE 16

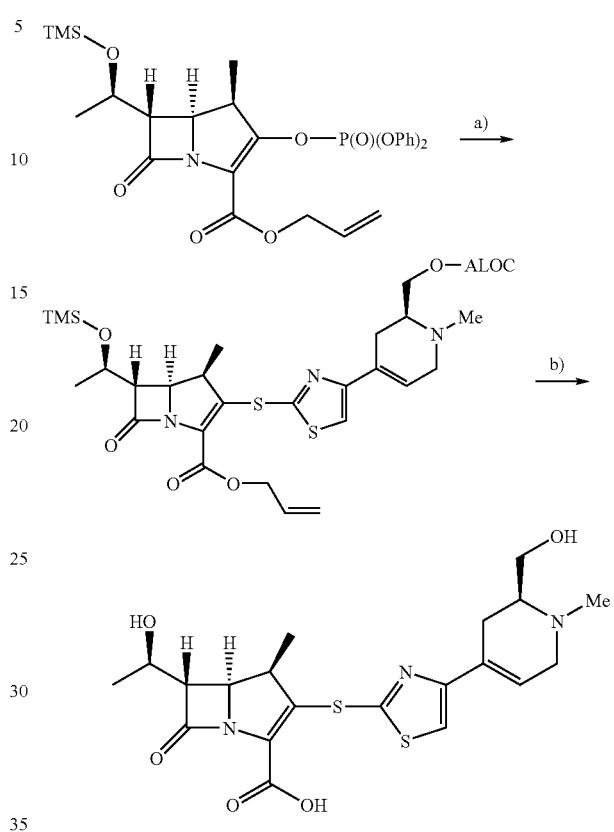

a) In the same manner as in Example 8, by using allyl [(2S)-1-methyl-4-(2-mercapto-1,3-thiazol-4-yl)-1,2,3,6-tetrahydro-2-pyridinyl]methylcarbonate as a thiol compound, there was obtained allyl (4R,5S,6S)-3-({4-[(2S)-2-({[(allyloxy)carbonyl]oxy}methyl)-1-methyl-1,2,3,6-tetrahydro-4-pyridinyl]-1,3-thiazol-2-yl}sulfanyl)-4-methyl-7-oxo-6-{(1R)-1-(trimethylsilyl)oxy]ethyl}-1-azabicyclo[3.2.0]hept-2-ene-2-carboxylate.

¹H NMR (300 MHz, CDCl₃) δ 0.10 (9 H, s), 1.07 (3 H, d, J=7.3 Hz), 1.21 (3 H, d, J=6.2 Hz), 2.37–2.65 (2 H, m), 2.48 (3 H, s), 2.88–3.00 (1 H, m), 3.19–3.29 (2 H, m), 3.37–3.55 (2 H, m), 4.15–4.24 (4 H, m), 4.61–4.85 (4 H, m), 5.17–5.48 (4 H, m), 5.79–6.00 (2 H, m), 6.65 (1 H, s), 7.08 (1 H, s).

b) In the same manner as in Example 8, by using allyl (4R,5S,6S)-3-({4-[(2S)-2-({[(allyloxy)carbonyl]oxy}methyl-1-methyl-1,2,3,6-tetrahydro-4-pyridinyl]-1,3-thiazol-2-yl}sulfanyl)-4-methyl-7-oxo-6-{(1R)-1-[(trimethylsilyl)oxy]ethyl}-1-azabicyclo[3.2.0]hept-2-ene-2-carboxylate, there was obtained (4R,5S,6S)-6-[(1R)-1-hydroxyethyl]-3-({4-[(2S)-2-(hydroxymethyl)-1-methyl-1,2,3,6-tetrahydro-4-pyridinyl]-1,3-thiazol-2-yl}sulfanyl)-6-[(1R)-1-hydroxyethyl]-4-methyl-7-oxo-1-azabicyclo[3.2.0]hept-2-ene-2-carboxylic acid.

IR (KBr) 3489, 1758, 1598, 1393 cm⁻¹ ¹H NMR (300 MHz, D₂O) δ 0.94 (3 H, d, J=7.1 Hz), 1.13 (3 H, d, J=6.4 Hz), 2.62–2.75 (5 H, m), 3.13–3.22 (1 H, m), 3.28–3.33 (1 H, m), 3.53–3.74 (2 H, m), 3.82–4.16 (5 H, m), 6.33 (1 H, s), 7.48 (1 H, s).

EXAMPLE 17

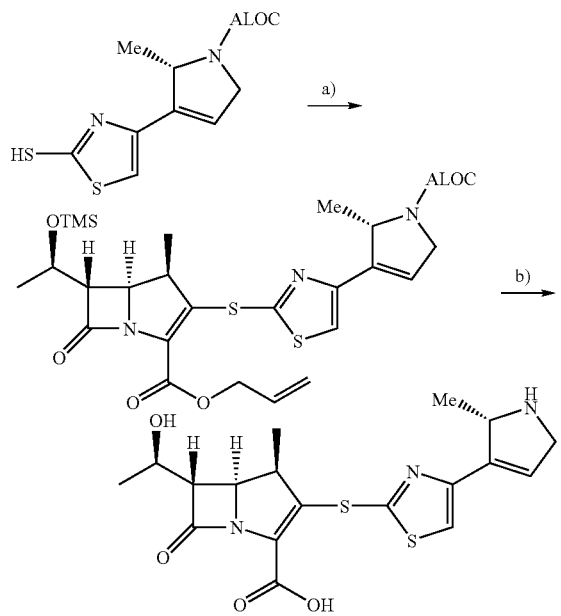

a) In the same manner as in Example 1, by using allyl (2S)-2-methyl-3-(2-sulfanyl-1,3-thiazol-4-yl)-2,5-dihydro-1H-pyrrole-1-carboxylate as a thiol compound, there was obtained allyl (4R,5S,6S)-3-[(4-{(2S)-1-[(allyloxy)carbonyl]-2-methyl-2,5-dihydro-1H-pyrrol-3-yl}-1,3-thiazol-2-yl)sulfanyl]-4-methyl-7-oxo-6-{(1R)-1-[(trimethylsilyl)oxy]ethyl}-1-azabicyclo[3.2.0]hept-2-ene-2-carboxylate.

$^1$H NMR (300 MHz, CDCl$_3$) δ 0.12 (9H, s), 1.12 (3H, d, J=7.1 Hz), 1.23 (3H, d, J=6.2 Hz), 1.44–1.50 (3H, m), 3.25 (1H, dd, J=6.0, 2.7 Hz), 3.42–3.58 (1H, m), 4.12–4.48 (4H, m), 4.60–4.89 (4H, m), 4.98–5.08 (1H, m), 5.22–5.51 (4H, m), 5.91–6.05 (2H, m), 6.36–6.37 (1H, m), 7.18–7.26 (1H, m).

b) In the same manner as in Example 2, by using allyl (4R,5S,6S)-3-[(4-{(2S)-1-[(allyloxy)carbonyl]-2-methyl-2,5-dihydro-1H-pyrrol-3-yl}-1,3-thiazol-2-yl)sulfanyl]-4-methyl-7-oxo-6-{(1R)-1-[(trimethylsilyl)oxy]ethyl}-1-azabicyclo[3.2.0]hept-2-ene-2-carboxylate, there was obtained (4R,5S,6S)-6-[(1R)-1-hydroxyethyl]-4-methyl-3-({4-[(2S)-2-methyl-2,5-dihydro-1H-pyrrol-3-yl]-1,3-thiazol-2-yl}sulfanyl)-7-oxo-1-azabicyclo[3.2.0]hept-2-ene-2-carboxylic acid.

$^1$H NMR (300 MHz, D$_2$O) δ 0.92 (3H, d, J=7.1 Hz), 1.07 (3H, d, J=6.4 Hz), 1.35 (3H, d, J=6.6 Hz), 3.02–3.12 (1H, m), 3.31 (1H, dd, J=6.0, 2.7 Hz), 3.97–4.13 (4H, m), 6.20 (1H, s), 7.53 (1H, s).

EXAMPLE 18

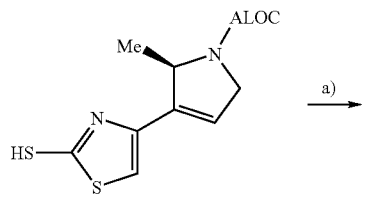

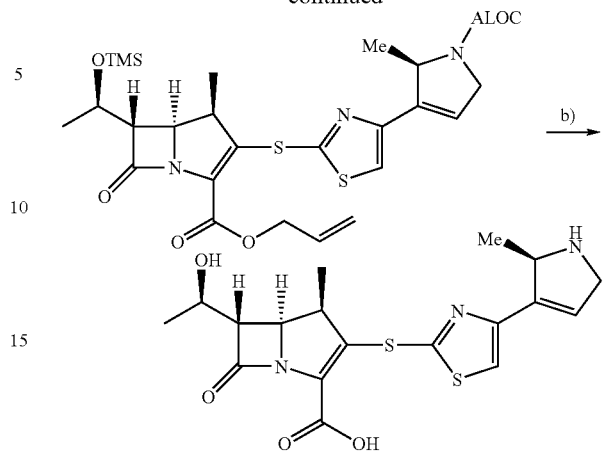

a) In the same manner as in Example 1, by using allyl (2R)-2-methyl-3-(2-sulfanyl-1,3-thiazol-4-yl)-2,5-dihydro-1H-pyrrole-1-carboxylate as a thiol compound, there was obtained allyl (4R,5S,6S)-3-[(4-{(2R)-1-[(allyloxy)carbonyl]-2-methyl-2,5-dihydro-1H-pyrrol-3-yl}-1,3-thiazol-2-yl)sulfanyl]-4-methyl-7-oxo-6-{(1R)-1-[(trimethylsilyl)oxy]ethyl}-1-azabicyclo[3.2.0]hept-2-ene-2-carboxylate.

$^1$H NMR (300 MHz, CDCl$_3$) δ 0.12 (9H, s), 1.07–1.10 (3H, m), 1.23–1.26 (3H, m), 1.44–1.50 (3H, m), 3.23–3.30 (1H, m), 3.53–3.62 (1H, m), 4.12–4.48 (4H, m), 4.60–4.89 (4H, m), 4.99–5.08 (1H, m), 5.22–5.51 (4H, m), 5.90–6.05 (2H, m), 6.33–6.37 (1H, m), 7.18–7.26 (1H, m).

b) In the same manner as in Example 2, by using allyl (4R,5S,6S)-3-[(4-{(2R)-1-[(allyloxy)carbonyl]-2-methyl-2,5-dihydro-1H-pyrrol-3-yl}-1,3-thiazol-2-yl)sulfanyl]-4-methyl-7-oxo-6-{(1R)-1-[(trimethylsilyl)oxy]ethyl}-1-azabicyclo[3.2.0]hept-2-ene-2-carboxylate, there was obtained (4R,5S,6S)-6-[(1R)-1-hydroxyethyl]-4-methyl-3-({4-[(2R)-2-methyl-2,5-dihydro-1H-pyrrol-3-yl]-1,3-thiazol-2-yl})sulfanyl)-7-oxo-1-azabicyclo[3.2.0]hept-2-ene-2-carboxylic acid.

$^1$H NMR (300 MHz, D$_2$O) δ 0.92 (3H, d, J=7.1 Hz), 1.10 (3H, d, J=6.4 Hz), 1.36 (3H, d, J=6.8 Hz), 3.05–3.22 (1H, m), 3.33 (1H, dd, J=5.9, 2.7 Hz), 3.96–4.14 (4H, m), 6.22 (1H, s), 7.53 (1H, s).

EXAMPLE 19

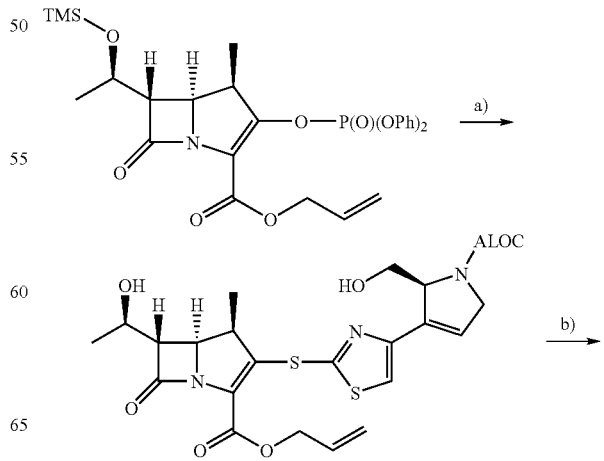

-continued

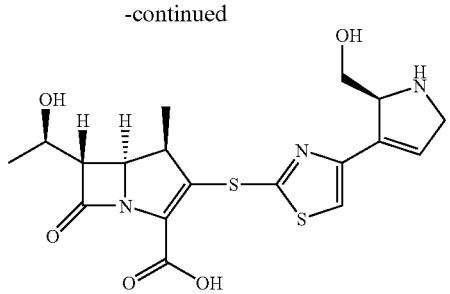

a) A solution of lithium hexamethyldisilazide in THF (1M, 0.16 ml, 0.16 mmol) was added at 0–5° C. to a solution of allyl (2S)-2-({[tert-butyl(dimethyl)silyl]oxy}methyl)-3-(2-mercapto-1,3-thiazol-4-yl)-2,5-dihydro-1H-pyrrole-1-carboxylate (67 mg, 0.16 mmol) in THF (0.3 ml) and the mixture was stirred for 20 minutes. To the reaction solution was added at 0° C. a solution of allyl (4R,5R,6S)-3-[(diphenoxyphosphino)oxy]-4-methyl-7-oxo-6-{(1R)-1-[(trimethylsilyl)oxy]ethyl}-1-azabicyclo[3.2.0]hept-2-ene-2-carboxylate in acetonitrile (30%, 0.62 g, 0.32 mmol) and the solution was allowed to stand in a refrigerator for 12 hours. To the reaction solution was added ice water and the reaction mixture was extracted with ethyl acetate. The organic layer was washed with a saturated aqueous sodium chloride solution and dried over anhydrous sodium sulfate. After removal of the solvent in vacuo, the residue was purified with silica gel chromatography (hexane/ethyl acetate: 1/5→1/3) to give a mixture of a coupling compound and POCA (Starting material). To the mixture in THF (2.4 ml) were added at 0–5° C. acetic acid (92 μl) and tetrabutylammonium fluoride in THF (1M, 0.96 ml, 0.96 mmol). After reaction for 20 hours, to the reaction mixture was added ice water and the solution was extracted with ethyl acetate. The organic layer was washed with a saturated aqueous sodium chloride solution and dried over anhydrous sodium sulfate. After removal of the solvent in vacuo, the residue was purified with silica gel chromatography (hexane/ethyl acetate: 1/3→10% methanol/chloroform) to give allyl (4R,5S,6S)-3-({4-[(2S)-1-[(allyloxy)carbonyl]-2-(hydroxymethyl)-2,5-dihydro-1H-pyrrol-3-yl]-1,3-thiazol-2-yl}sulfanyl)-6-[(1R)-1-hydroxyethyl]-4-methyl-7-oxo-1-azabicyclo[3.2.0]hept-2-ene-2-carboxylate (83 mg, 95%).

$^1$H NMR (300 MHz, CDCl$_3$) δ 1.10 (3 H, d, J=7.3 Hz), 1.32 (3 H, d, J=6.1 Hz), 3.22–3.28 (1 H, m), 3.53–3.64 (1 H, m), 3.72–3.80 (1 H, m), 3.93–4.47 (6 H, m), 4.58–4.88 (4 H, m), 5.12–5.48 (4 H, m), 5.80–6.05 (2 H, m), 6.38 (1 H, s), 7.31 (1 H, s).

b) To a solution of allyl (4R,5S,6S)-3-({4-[(2S)-1-[(allyloxy)carbonyl]-2-(hydroxymethyl)-2,5-dihydro-1H-pyrrol-3-yl]-1,3-thiazol-2-yl}sulfanyl)-6-[(1R)-1-hydroxyethyl]-4-methyl-7-oxo-1-azabicyclo[3.2.0]hept-2-ene-2-carboxylate (33 mg, 0.06 mmol) in dicloromethane (3 ml) were added at 0° C. acetic acid (8.6 μl, 0.15 mmol), tributyltin hydride (165 ml, 0.61 mmol) and bis(triphenylphosphine)palladium chloride (4.2 mg, 0.006 mmol), and the mixture was stirred at the same temperature for 3 minutes. To the reaction mixture were added phosphate buffer (50 mM, pH7, 25 ml) and dichloromethane (5 ml). After separation of the aqueous layer, the dichloromethane layer was extracted twice with water and the aqueous layer was washed twice with dichloromethane (3 ml). The organic solvent in the aqueous layer was evaporated under reduced pressure, and the residue was purified by polymer chromatography (CHP-20P). The fractions eluted with 1–3% aqueous THF solution were combined and lyophilized to give (4R,5S,6S)-6-[(1R)-1-hydroxyethyl]-3-({4-[(2S)-2-(hydroxymethyl)-2,5-dihydro-1H-pyrrol-3-yl]-1,3-thiazol-2-yl}sulfanyl]-4-methyl-7-oxo-1-azabicyclo[3.2.0]hept-2-ene-2-carboxylic acid (12.3 mg, 48%) as a white amorphous.

$^1$H NMR (300 MHz, D$_2$O) δ 0.92 (3 H, d, J=6.8 Hz), 1.10 (3 H, d, J=5.7 Hz), 3.12–3.19 (1 H, m), 3.30–3.35 (1 H, m), 3.73–4.13 (7 H, m), 6.36 (1 H, s), 7.55 (1 H, s).

EXAMPLE 20

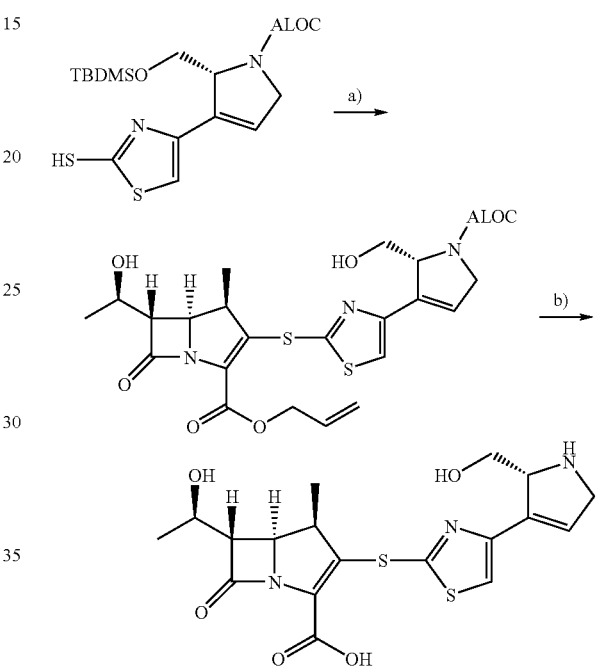

a) In the same manner as in Example 6, by using allyl (2R)-2-({[tert-butyl(dimethyl)silyl]oxy}methyl)-3-(2-sulfanyl-1,3-thiazol-4-yl)-2,5-dihydro-1H-pyrrole-1-carboxylate as a thiol compound, there was obtained allyl (4R,5S,6S)-3-({4-[(2R)-1-[(allyloxy)carbonyl]-2-(hydroxymethyl)-2,5-dihydro-1H-pyrrol-3-yl]-1,3-thiazol-2-yl)sulfanyl)-6-[(1R)-1-hydroxyethyl]-4-methyl-7-oxo-1-azabicyclo[3.2.0]hept-2-ene-2-carboxylate.

$^1$H NMR (300 MHz, CDCl$_3$) δ 1.21 (3H, d, J=7.1 Hz), 1.33 (3H, d, J=6.2 Hz), 3.27 (1H, dd, J=6.9, 2.7 Hz), 3.42–3.60 (1H, m), 3.76–4.50 (7H, m), 4.66–4.89 (4H, m), 5.06–5.50 (5H, m), 5.91–6.05 (2H, m), 6.43–6.46 (1H, m), 7.35–7.40 (1H, m).

b) In the same manner as in Example 6, by using allyl (4R,5S,6S)-3-({4-[(2R)-1-[(allyloxy)carbonyl]-2-(hydroxymethyl)-2,5-dihydro-1H-pyrrol-3-yl]-1,3-thiazol-2-yl}sulfanyl)-6-[(1R)-1-hydroxyethyl]-4-methyl-7-oxo-1-azabicyclo[3.2.0]hept-2-ene-2-carboxylate, there was obtained (4R,5S,6S)-6-[(1R)-1-hydroxyethyl]-3-({4-[(2R)-2-(hydroxymethyl)-2,5-dihydro-1H-pyrrol-3-yl]-1,3-thiazol-2-yl}sulfanyl)-4-methyl-7-oxo-1-azabicyclo[3.2.0]hept-2-ene-2-carboxylic acid.

$^1$H NMR (300 MHz, D$_2$O) δ 0.94 (3H, d, J=7.3 Hz), 1.09 (3H, d, J=6.4 Hz), 3.05–3.16 (1H, m), 3.32 (1H, dd, J=6.0, 2.9 Hz), 3.81–3.93 (2H, m), 4.03–4.19 (4H, m), 4.87–4.90 (1H, m), 6.36 (1H, s), 7.60 (1H, s).

EXAMPLE 21

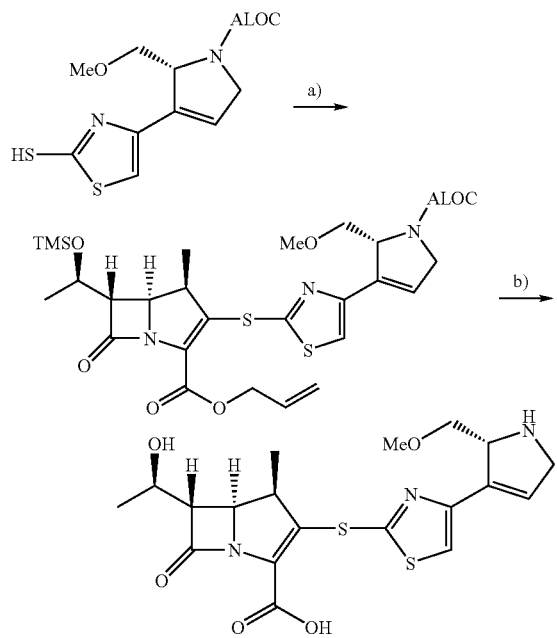

a) In the same manner as in Example 1, by using allyl (2R)-2-(methoxymethyl)-3-(2-sulfanyl-1,3-thiazol-4-yl)-2,5-dihydro-1H-pyrrole-1-carboxylate as a thiol compound, there was obtained allyl (4R,5S,6S)-3-({4-[(2R)-1-[(allyloxy)carbonyl]-2-(methoxymethyl)-2,5-dihydro-1H-pyrrol-3-yl]-1,3-thiazol-2-yl}sulfanyl)-4-methyl-7-oxo-6-{(1R)-1-[(trimethylsilyl)oxy]ethyl}-1-azabicyclo[3.2.0]hept-2-ene-2-carboxylate.

$^1$H NMR (300 MHz, CDCl$_3$) δ 0.12 (9H, s), 1.11 (3H, d, J=7.3 Hz), 1.23 (3H, d, J=6.1 Hz), 3.21–3.30 (4H, m), 3.37–3.53 (1H, m), 3.74–3.93 (2H, m), 4.12–4.49 (4H, m), 4.60–4.89 (4H, m), 5.04–5.09 (1 H., m), 5.22–5.51 (4H, m), 5.91–6.05 (2H, m), 6.47 (1H, s), 7.37–7.42 (1H, m).

b) In the same manner as in Example 2, by using allyl (4R,5S,6S)-3-{4-[(2R)-1-[(allyloxy)carbonyl]-2-(methoxymethyl)-2,5-dihydro-1H-pyrrol-3-yl]-1,3-thiazol-2-yl}sulfanyl)-4-methyl-7-oxo-6-{(1R)-1-[(trimethylsilyl)oxy]ethyl}-1-azabicyclo[3.2.0]hept-2-ene-2-carboxylate, there was obtained (4R,5S,6S)-6-[(1R)-1-hydroxyethyl]-3-({4-[(2R)-2-(methoxymethyl)-2,5-dihydro-1H-pyrrol-3-yl]-1,3-thiazol-2-yl}sulfanyl)-4-methyl-7-oxo-1-azabicyclo[3.2.0]hept-2-ene-2-carboxylic acid.

$^1$H NMR (300 MHz, D$_2$O) δ 0.94 (3H, d, J=7.0 Hz), 1.09 (3H, d, J=6.6 Hz), 3.07–3.13 (1H, m), 3.18 (1H, s), 3.31–3.34 (1H, m), 3.66–3.69 (2H, m), 3.97–4.12 (4H, m), 6.34 (1H, s), 7.58 (1H, s).

EXAMPLE 22

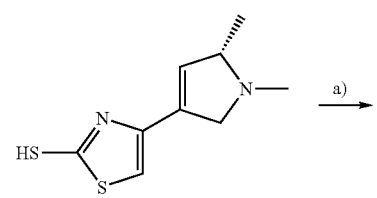

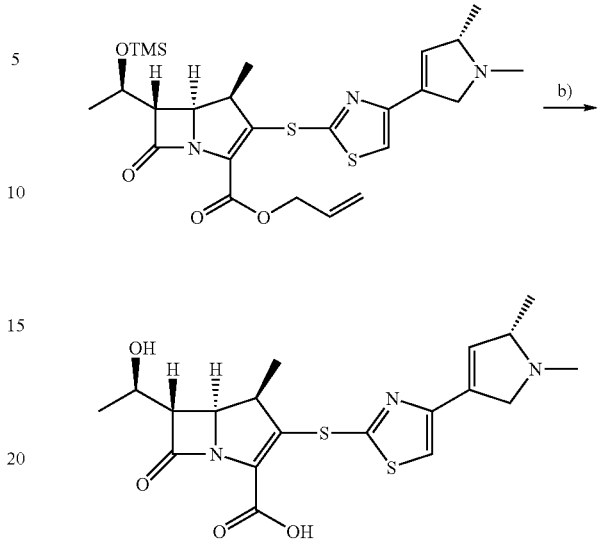

a) In the same manner as in Example 1, by using 4-[(5S)-1,5-dimethyl-2,5-dihydro-1H-pyrrol-3-yl]-1,3-thiazole-2-thiol as a thiol compound, there was obtained allyl (4R,5S,6S)-3-({4-[(5S)-1,5-dimethyl-2,5-dihydro-1H-pyrrol-3-yl]-1,3-thiazol-2-yl}sulfanyl)-4-methyl-7-oxo-6-{(1R)-1-[(trimethylsilyl)oxy]ethyl}-1-azabicyclo[3.2.0]hept-2-ene-2-carboxylate.

$^1$H NMR (300 MHz, CDCl$_3$) δ 0.11–0.12 (9H, m), 1.04–1.09 (3H, m), 1.17–1.28 (6H, m), 2.52 (3H, s), 2.55–2.63 (1H, m), 3.21–3.25 (1H, m), 3.49–3.62 (3H, m), 4.09–4.25 (3H, m), 4.60–4.87 (3H, m), 5.17–5.50 (4H, m), 5.85–6.04 (1H, m), 6.28–6.30 (1H, m), 7.05–7.27 (1H, m).

b) In the same manner as in Example 2, by using allyl (4R,5S,6S)-3-({4-[(5S)-1,5-dimethyl-2,5-dihydro-1H-pyrrol-3-yl]-1,3-thiazol-2-yl}sulfanyl)-4-methyl-7-oxo-6-{(1R)-1-[(trimethylsilyl)oxy]ethyl}-1-azabicyclo[3.2.0]hept-2-ene-2-carboxylate, there was obtained (4R,5S,6S)-3-({4-[(5S)-1,5-dimethyl-2,5-dihydro-1H-pyrrol-3-yl]-1,3-thiazol-2-yl}sulfanyl)-6-[(1R)-1-hydroxyethyl]-4-methyl-7-oxo-1-azabicyclo[3.2.0]hept-2-ene-2-carboxylic acid.

$^1$H NMR (300 MHz, D$_2$O) δ 0.93 (3H, d, J=7.1 Hz), 1.11 (3H, d, J=6.2 Hz), 1.34 (3H, d, J=6.8 Hz), 2.81 (3H, s), 3.13–3.18 (1H, m), 3.34 (1H, dd, J=6.2, 2.8 Hz), 4.03–4.14 (3H, m), 4.21–4.30 (1H, m), 4.38–4.45 (1H, m), 6.22 (1H, s), 7.47 (1H, s).

EXAMPLE 23

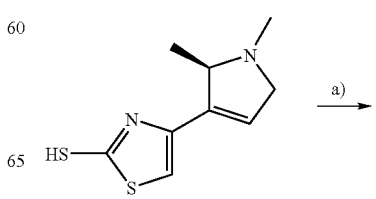

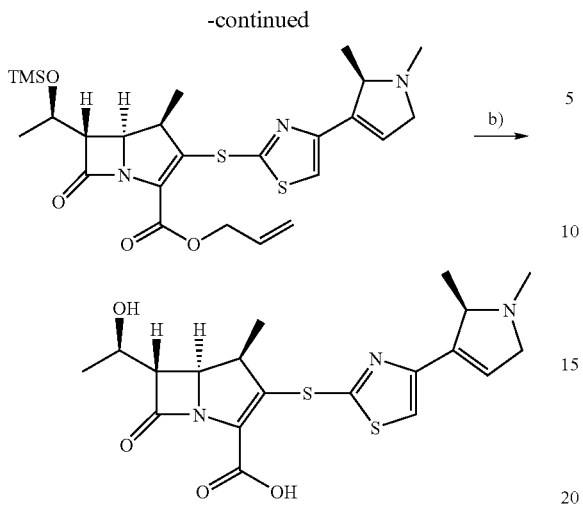

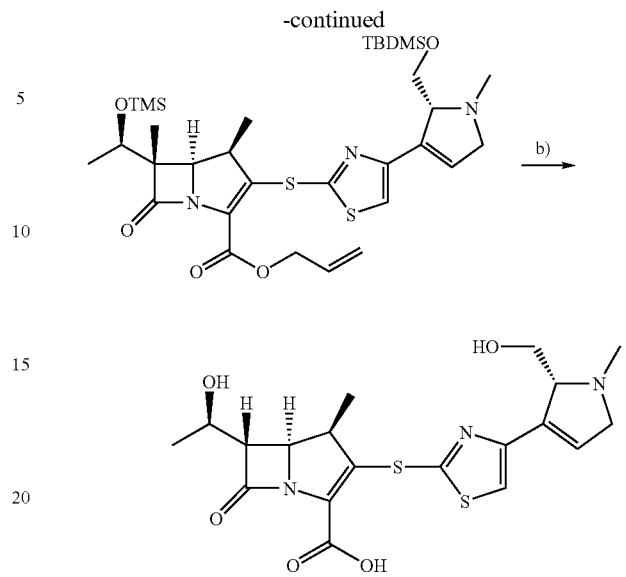

a) In the same manner as in Example 1, by using 4-[(2R)-1,2-dimethyl-2,5-dihydro-1H-pyrrol-3-yl]-1,3-thiazole-2-thiol as a thiol compound, there was obtained allyl (4R,5S,6S)-3-({4-[(2R)-1,2-dimethyl-2,5-dihydro-1H-pyrrol-3-yl]-1,3-thiazol-2-yl}sulfanyl)-4-methyl-7-oxo-6-{(1R)-1-[(trimethylsilyl)oxy]ethyl}-1-azabicyclo[3.2.0]hept-2-ene-2-carboxylate.

$^1$H NMR (300 MHz, CDCl$_3$) δ 0.11 (9H, s), 1.08 (3H, d, J=7.4 Hz), 1.25 (3H, d, J=6.2 Hz), 1.30 (3H, d, J=6.2 Hz), 2.53 (3H, s), 3.23 (1H, dd, J=6.6, 2.7 Hz), 3.39–3.47 (1H, m), 3.53–3.63 (1H, m), 3.80–3.98 (2H, m), 4.16–4.26 (2H, m), 4.56–4.87 (2H, m), 5.25–5.50 (2H, m), 5.87–6.04 (1H, m), 6.29–6.31 (1H, m), 7.18 (1H, s).

b) In the same manner as in Example 2, by using allyl (4R,5S,6S)-3-({4-[(2R)-1,2-dimethyl-2,5-dihydro-1H-pyrrol-3-yl]-1,3-thiazol-2-yl}sulfanyl)-4-methyl-7-oxo-6-{(1R)-1-[(trimethylsilyl)oxy]ethyl}-1-azabicyclo[3.2.0]hept-2-ene-2-carboxylate, there was obtained (4R,5S,6S)-3-({4-[(2R)-1,2-dimethyl-2,5-dihydro-1H-pyrrol-3-yl]-1,3-thiazol-2-yl}sulfanyl)-6-[(1R)-1-hydroxyethyl]-4-methyl-7-oxo-1-azabicyclo[3.2.0]hept-2-ene-2-carboxylic acid.

$^1$H NMR (300 MHz, D$_2$O) δ 0.94 (3H, d, J=7.3 Hz), 1.12 (3H, d, J=6.4 Hz), 1.37 (3H, d, J=6.6 Hz), 2.80 (3H, s), 3.13–3.23 (1H, m), 3.35 (1H, dd, J=6.0, 2.9 Hz), 3.84–3.89 (1H, m), 4.06–4.15 (2H, m), 4.21–4.27 (1H, m), 4.45–4.51 (1H, m), 6.21 (1H, s), 7.55 (1H, s).

EXAMPLE 24

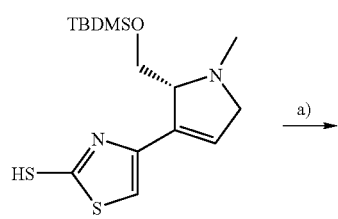

a) In the same manner as in Example 1, by using 4-[(2R)-2-({[tert-butyl(dimethyl)silyl]oxy}methyl)-1-methyl-2,5-dihydro-1H-pyrrol-3-yl]-1,3-thiazole-2-thiol as a thiol compound, there was obtained allyl (4R,5S,6S)-3-({4-[(2R)-2-({[tert-butyl(dimethyl)silyl]oxy}methyl)-1-methyl-2,5-dihydro-1H-pyrrol-3-yl]-1,3-thiazol-2-yl}sulfanyl)-4-methyl-7-oxo-6-{(1R)-1-[(trimethylsilyl)oxy]ethyl}-1-azabicyclo[3.2.0]hept-2-ene-2-carboxylate.

$^1$H NMR (300 MHz, CDCl$_3$) δ−0.03 (3H, s), 0.00 (3H, s), 0.12 (9H, s), 0.86 (9H, s), 1.09 (3H, d, J=7.3 Hz), 1.23 (3H, d, J=6.2 Hz), 2.59 (3H, s), 3.23 (1H, dd, J=6.4, 2.9 Hz), 3.41–3.58 (2H, m), 3.67–3.97 (4H, m), 4.16–4.26 (2H, m), 4.65–4.88 (2H, m), 5.18–5.51 (2H, m), 5.82–6.04 (1H, m), 6.46 (1H, s), 7.41 (1H, s).

b) A solution of allyl (4R,5S,6S)-3-({4-[(2R)-2-({[tert-butyl(dimethyl)silyl]oxy}methyl)-1-methyl-2,5-dihydro-1H-pyrrol-3-yl]-1,3-thiazol-2-yl}sulfanyl)-4-methyl-7-oxo-6-{(1R)-1-[(trimethylsilyl)oxy]ethyl}-1-azabicyclo[3.2.0]hept-2-ene-2-carboxylate (106 mg, 0.16 mmol) in THF (2.7 ml) was cooled at 0° C. and to the solution were added acetic acid (0.073 ml, 1.28 mmol) and tetrabutylammonium fluoride in THF (1M, 0.64 ml, 0.64 mmol). The solution was stirred at the same temperature for 1 hour and then was allowed to stand in a refrigerator for 63 hours. To the reaction mixture was added water, and the solution was extracted three times with ethyl acetate. The organic layer was washed with a saturated aqueous sodium chloride solution and dried over anhydrous sodium sulfate. After removal of the solvent in vacuo, the residue was purified with silica gel chromatography and then was subjected to de-allyl reaction in the same manner as Example 1.c) to give (4R,5S,6S)-6-[(1R)-1-hydroxyethyl]-3-({4-[(2R)-2-hydroxymethyl-1-methyl-2,5-dihydro-1H-pyrrol-3-yl]-1,3-thiazol-2-yl}sulfanyl)-4-methyl-7-oxo-1-azabicyclo[3.2.0]hept-2-ene-2-carboxylic acid.

$^1$H NMR (300 MHz, D$_2$O) δ 0.98 (3H, d, J=7.3 Hz), 1.13 (3H, d, J=6.4 Hz), 2.97 (3H, s), 3.09–3.19 (1H, m), 3.36 (1H, dd, J=6.0, 2.9 Hz), 3.87–4.02 (3H, m), 4.06–4.15 (2H, m), 4.40–4.45 (1H, m), 6.38 (1H, s), 7.63 (1H, s).

EXAMPLE 25

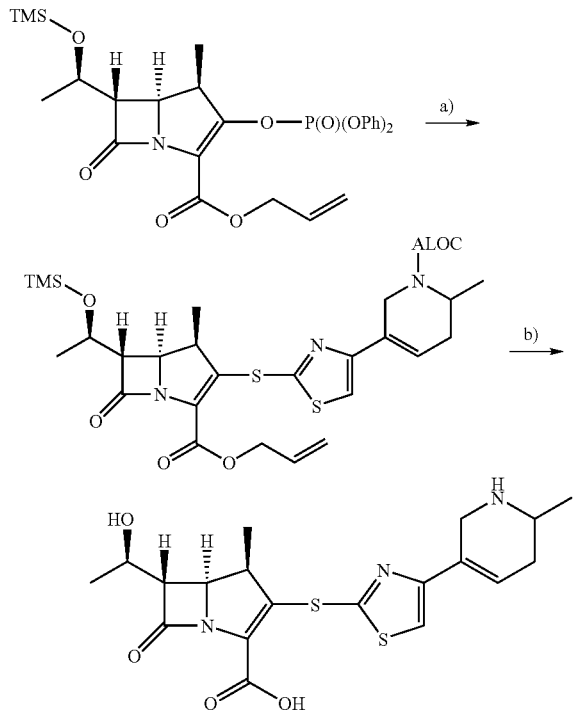

a) A solution of lithium hexamethyldisilazide in THF (1M, 1.24 ml, 1.24 mmol) was added at 0° C. to a solution of allyl 2-methyl-5-(2-mercapto-1,3-thiazol-4-yl)-3,6-dihydro-1(2 H)-pyridinecarboxylate (368 mg, 1.24 mmol) in THF (2.4 ml) and the mixture was stirred for 10 minutes. To the reaction solution was added at 0° C. a solution of allyl (4R,5R,6S)-3-[(diphenoxyphosphino)oxy]-4-methyl-7-oxo-6-{(1R)-1-[(trimethylsilyl)oxy]ethyl}-1-azabicyclo[3.2.0] hept-2-ene-2-carboxylate in acetonitrile (30%, 4.73 g, 2.5 mmol) and the solution was allowed to stand in a refrigerator for 13 hours. To the reaction solution was added ice water and the reaction mixture was extracted with ethyl acetate. The organic layer was washed with a saturated aqueous sodium chloride solution and dried over anhydrous sodium sulfate. After removal of the solvent in vacuo, the residue was purified with silica gel chromatography (hexane/ethyl acetate: 4/1→3/1) to give allyl (4R,5S,6S)-3-[(4-(1-[(allyloxy)carbonyl]-6-methyl-1,2,5,6-tetrahydro-3-pyridinyl}-1, 3-thiazol-2-yl)sulfanyl]-4-methyl-7-oxo-6-{(1R)-1-[(trimethylsilyl)oxy]ethyl}-1-azabicyclo[3.2.0]hept-2-ene-2-carboxylate (544 mg, 71%).

$^1$H NMR (300 MHz, CDCl$_3$) δ 0.09 (9H, s), 1.06–1.22 (9 H,m), 2.04–2.15 (1 H, m), 2.58–2.70 (1 H, m), 3.22 (1 H, dd, J=2.7, 6.0 Hz), 3.40–3.60 (1 H, m), 3.82–3.93 (1 H, m), 4.13–4.23 (2 H, m), 4.60–4.86 (6 H, m), 5.19–5.33 (3 H, m), 5.45 (1 H, d, J=17.0 Hz), 5.89–6.02 (2 H, m), 6.72 (1 H, brs), 7.10 (0.5 H, s), 7.11 (0.5 H, s).

b) To a solution of allyl (4R,5S,6S)-3-[(4-{1-[(allyloxy) carbonyl]-6-methyl-1,2,5,6-tetrahydro-3-pyridinyl}-1,3-thiazol-2-yl)sulfanyl]-4-methyl-7-oxo-6-{(1R)-[(trimethylsilyl)oxy]ethyl}-1-azabicyclo[3.2.0]hept-2-ene-2-carboxylate (544 mg, 0.88 mmol) in THF (4 ml) was added at 0° C. water and then the solution was adjusted to pH about 3 with 1N hydrochloric acid and stirred for 1 hour. To the reaction mixture was added a saturated aqueous sodium hydrogen carbonate solution and the solution was adjusted to pH 7.5. The solution was extracted twice with ethyl acetate. The organic layer was washed with a saturated aqueous sodium chloride solution and dried over anhydrous sodium sulfate. After removal of the solvent in vacuo, the residue was dissolved in dichloromethane (10 ml). To the solution were added at 0° C. acetic acid (126 μl), tributyltin hydride (2.4 ml, 8.9 mmol) and bis(triphenylphosphine) palladium chloride (61.8 mg, 0.088 mmol) and the mixture was stirred at the same temperature for 5 minutes. To the reaction mixture were added phosphate buffer (50 mM, pH7, 25 ml) and dichloromethane (20 ml). After separation of the aqueous layer, the dichloromethane layer was extracted twice with water and the aqueous layer was washed with dichloromethane (3 ml). The organic solvent in the aqueous layer was evaporated under reduced pressure, and the residue was purified by polymer chromatography (CHP-20P). The fractions eluted with 3–8% aqueous THF solution were combined and lyophilized to give (4R,5S,6S)-6-[(1R)-1-hydroxyethyl]-4-methyl-3-{[4-(6-methyl-1,2,5,6-tetrahydro-3-pyridinyl)-1,3-thiazol-2-yl]sulfanyl}-7-oxo-1-azabicyclo[3.2.0]hept-2-ene-2-carboxylic acid (230 mg, 62%) as a white amorphous.

$^1$H NMR (300 MHz, D$_2$O) δ 0.90 (3 H, d, J=7.1 Hz), 1.08 (3 H, d, J=6.2 Hz), 1.27 (3 H, d, J=6.6 Hz), 2.16–2.29 (1 H, m), 2.47–2.58 (1 H, m), 3.11 (1 H, dd, J=7.3, 9.5 Hz), 3.30 (1 H, dd, J=2.7, 5.9 Hz), 3.34–3.46 (1 H, m), 3.88–4.10 (4 H, m), 6.50 (1 H, brs), 7.36 (1 H, s).

EXAMPLE 26

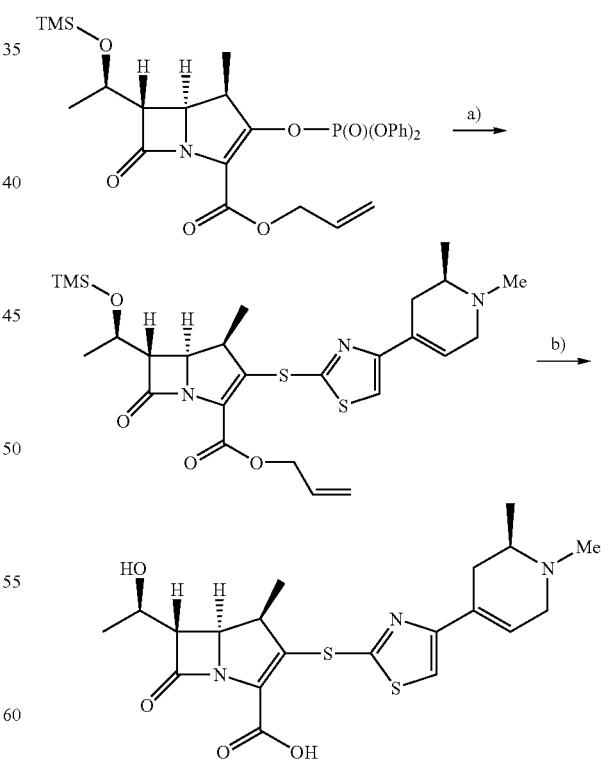

a) In the same manner as in Example 8, by using 4-[(2R)-1,2-dimethyl-1,2,3,6-tetrahydro-4-pyridinyl]-1,3-thiazole-2-thiol as a thiol compound, there was obtained allyl (4R, 5S,6S)-3-({4-[(2R)-1,2-dimethyl-1,2,3,6-tetrahydro-4- pyridinyl]-1,3-thiazol-2-yl}sulfanyl)-4-methyl-7-oxo-6-{(1R)-1-[(trimethylsilyl)oxy]ethyl}-1-azabicyclo[3.2.0]hept-2-ene-2-carboxylate.

b) In the same manner as in Example 8, by using allyl (4R,5S,6S)-3-({4-[(2R)-1,2-dimethyl-1,2,3,6-tetrahydro-4-pyridinyl]-1,3-thiazol-2-yl}sulfanyl)-4-methyl-7-oxo-6-{(1R)-1-[(trimethylsilyl)oxy]ethyl}-1-azabicyclo[3.2.0]hept-2-ene-2-carboxylate, there was obtained (4R,5S,6S)-3-({4-[(2R)-1,2-dimethyl-1,2,3,6-tetrahydro-4-pyridinyl]-1,3-thiazol-2-yl}sulfanyl)-6-[(1R)-1-hydoxyethyl]-4-methyl-7-oxo-1-azabicyclo[3.2.0]hept-2-ene-2-carboxylic acid.

REFERENCE EXAMPLE

One example of the process for a mercapto compound represented by the formula [3] is explained below.

Reference Example 1

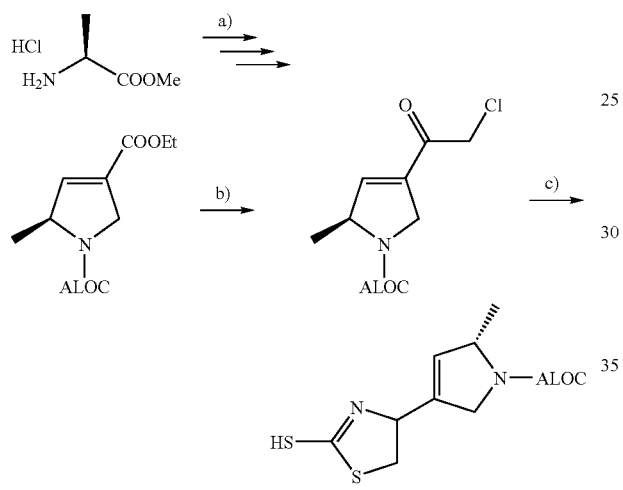

a) In accordance to the method for preparing N-(tert-butoxycarbonyl)-2-methyl-4-ethoxycarbonyl-3-pyrroline (JP 1-233270B), by using methyl L-alaninate hydrochloride as a staring compound, (2S)-N-(allyloxycarbonyl)-2-methyl-4-ethoxycarbonyl-3-pyrroline was obtained.

$^1$H NMR (300 MHz, CDCl$_3$) δ 1.22–1.40 (6 H, m), 4.24 (2 H, q, J=6.9 Hz), 4.29–4.49 (2 H, m), 4.56–4.84 (3 H, m), 5.23 (1 H, d, J=10.4 Hz), 5.32 (1 H, d, J=17.4 Hz), 5.89–6.02 (1 H, m), 6.62–6.67 (1 H, m).

b) To a solution of (2S)-N-(allyloxycarbonyl)-2-methyl-4-ethoxycarbonyl-3-pyrroline(0.44 g, 1.8 mmol) and bromochloromethane(0.19 ml, 2.9 mmol) in THF (3.7 ml) was added at −70° C. a solution of n-butyllithium in hexane (1.59M, 1.7 ml, 2.7 mmol). Twenty minutes later the mixture was poured into a mixture of ice (10 g) and phosphate buffer (pH7.0, 10 ml). To the mixture was added ethyl acetate and after separation of the mixture with a separating funnel, the aqueous layer was extracted twice with ethyl acetate. The organic layer was washed with a saturated aqueous sodium chloride solution, dried over magnesium sulfate and the organic solvent was removed under reduced pressure. The residue was purified by silica gel chromatography to give allyl (2S)-(4-chloroacetyl)-2-methyl-2,5-dihydro-1H-pyrrole-1-carboxylate (151 mg).

$^1$H NMR (300 MHz, CDCl$_3$) δ 1.37–1.42 (3 H, m), 4.30–4.70 (6 H, m), 4.80–4.95 (1 H, m), 5.18–5.24 (1 H, m), 5.26–5.34 (1 H, m), 5.86–5.99 (1 H, m), 6.64–6.68 (1 H, m). IR (KCl) 1683, 1649, 1629, 1404 cm$^{-1}$.

c) To a solution of allyl (2S)-4-(chloroacetyl)-2-methyl-2,5-dihydro-1H-pyrrole-1-carboxylate(0.15 g, 0.62 mmol) in methanol (2 ml) were added at 0–5° C. thioisonicotinamide (5 mg) and ammonium dithiocarbamate (82 mg, 0.74 mmol). The temperature was raised to room temperature and the mixture was stirred for 15 minute, followed with stirring at 55–60° C. for 1 hour. The solvent was removed under reduced pressure and the residue was washed with ethanol to give allyl (2S)-2-methyl-4-(2-mercapto-1,3-thiazol-4-yl)-2,5-dihydro-1H-pyrrole-1-carboxylate(60 mg, 34%).

$^1$H NMR (300 MHz, CDCl$_3$) δ 1.34–1.39 (3 H, m), 4.32–4.53 (2 H, m), 4.61–4.66 (2 H, m), 4.72–4.85 (1 H, m), 5.22 (1 H, d, J=10.4 Hz), 5.27–5.35 (1 H, m), 5.87–6.09 (2 H, m), 6.37 (0.5 H, s), 6.40 (0.5 H, m).

Reference Example 2

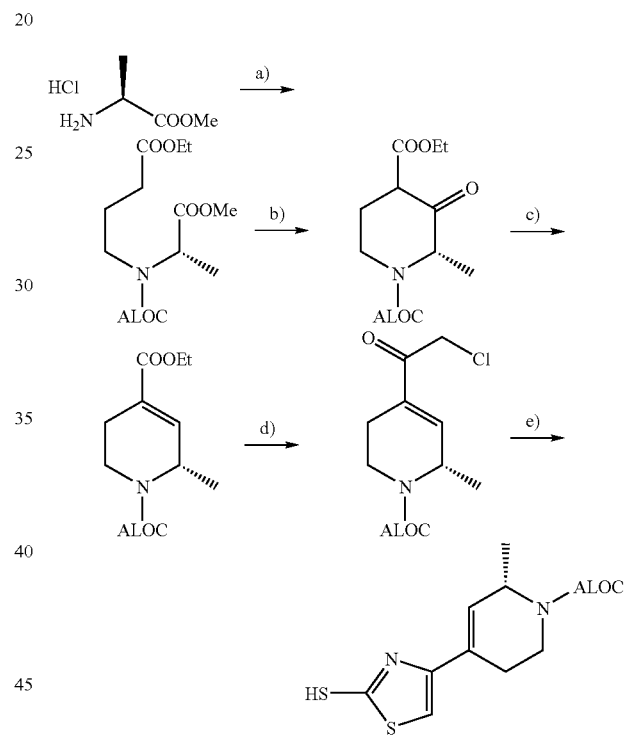

a) To a suspension of methyl L-alaninate hydrochloride (100 mg, 0.72 mmol) in DMF (2.5 ml) were added potassium carbonate (500 mg, 3.6 mmol), potassium iodide (60 mg, 0.36 mmol) and 4-bromolactic acid ethyl ester (0.103 ml, 0.72 mmol) and the resulting mixture was stirred at 60° C. for 2 hours. To the mixture was again added ethyl 4-bromolactate (0.103 ml, 0.70 mmol) and the resulting mixture was stirred at the same temperature for more than 2 hours. To the reaction mixture was added water and the mixture was extracted three times with ethyl acetate and the organic layers were combined. The combined organic layer was washed with water and then a saturated aqueous sodium chloride solution, dried over magnesium sulfate. The organic solvent was removed under reduced pressure, and the residue was dissolved in chloroform (5 ml). To the solution were added at room temperature diisopropylethylamine (0.25 ml, 1.44 mmol) and allyl chloroformate (0.15 ml, 1.42 mmol) and the mixture was stirred for 1 hour. After adding water to the reaction mixture and separating the mixture with a separating funnel, the aqueous layer was extracted twice with chloroform. The organic layer was washed with a saturated aqueous sodium chloride solution, and dried over magnesium sulfate. The organic solvent was removed under reduced pressure, and the residue was purified by silica gel chromatography to give methyl N-[(allyloxy)carbonyl]-N-(4-ethoxy-4-oxobutyl)-L-alaninate (134 mg).

$^1$H NMR (300 MHz, CDCl$_3$) δ 1.26 (3 H, t, J=7.1 Hz), 1.49 (3 H, d, J=7.4 Hz), 1.80–1.98 (2 H, m), 2.30–2.40 (2 H, m), 3.12–3.27 (1 H, m), 3.38–3.51 (1 H, m), 3.71 (3 H, s), 4.13 (2 H, q, J=7.1 Hz), 4.45–4.62 (3 H, m), 5.18–5.33 (2 H, m), 5.81–6.00 (1 H, m).

b) To a suspension of potassium tert-butoxide (3.42 g, 30 mol) in THF which was warmed at 60° C. was added a solution of methyl N-[(allyloxy)carbonyl]-N-(4-ethoxy-4-oxobutyl)-L-alaninate(4.60 g, 15 mmol) in THF (30 ml) and after stirring for 1 minute, the reaction solution was poured into an aqueous sodium dihydrogenphosphate solution (1M, 50 ml). The solution was adjusted to pH 2–3 and thereto was added ethyl acetate. After separating the mixture with a separating funnel, the aqueous layer was extracted twice with ethyl acetate. The organic layer was washed with a saturated aqueous sodium chloride solution, and dried over magnesium sulfate. The organic solvent was removed under reduced pressure, and the residue was purified by silica gel chromatography to give 1-allyl 4-ethyl (2S)-2-methyl-3-oxo-1,4-piperidinedicarboxylate (2.03 g) and 1-allyl 4-methyl (2S)-2-methyl-3-oxo-1,4-piperidinedicarboxylate (1.20 g).

1-allyl 4-ethyl (2S)-2-methyl-3-oxo-1,4-piperidinedicarboxylate $^1$H NMR (300 MHz, CDCl$_3$) δ1.31 (3 H, t, J=7.1 Hz), 1.40 (3 H, d, J=7.0 Hz), 2.25–2.42 (2 H, m), 2.86–3.08 (1 H, m), 4.07–4.28 (1 H, m), 4.23 (2 H, q, J=7.1 Hz), 4.57–4.72 (3 H, m), 5.20–5.34 (2 H, m), 5.88–6.00 (1 H, m), 12.2 (1 H, s).

1-allyl 4-methyl (2S)-2-methyl-3-oxo-1,4-piperidinedicarboxylate $^1$H NMR (300 MHz, CDCl$_3$) δ 1.40 (3 H, d, J=6.8 Hz), 2.25–2.42 (2 H, m), 2.86–3.03 (1 H, m), 3.78 (3 H, s), 4.07–4.28 (1 H, m), 4.57–4.72 (3 H, m), 5.20–5.34 (2 H, m), 5.88–6.01 (1 H, m), 12.1 (1 H, s).

c) To a solution of 1-allyl 4-ethyl (2S)-2-methyl-3-oxo-1,4-piperidinedicarboxylate (1.40 g, 5.2 mmol) in methanol (27 ml) were added acetic acid (0.36 ml, 6.3 mmol) and sodium cyanoborohydride (0.39 g, 6.3 mmol), and the mixture was stirred at room temperature for 1 hour. The solvent was removed in vacuo and the residue was purified by silica gel chromatography to give 1-allyl 4-ethyl (2S)-3-hydroxy-2-methyl-1,4-piperidinedicarboxylate (1.36 g). A solution of this compound in dichloromethane (24 ml) was cooled at −30° C. and to the solution were added methanesulfonyl chloride (0.58 ml, 7.5 mmol), triethylamine (1.4 ml, 10.0 ml) and dimethylaminopyridine (61 mg, 0.50 mmol). The mixture was stirred at 0° C. for 20 minutes and poured into 1N hydrochloric acid and the solution was extracted three times with chloroform. The organic layer was washed with a saturated aqueous sodium chloride solution, dried over magnesium sulfate and the organic solvent was removed under reduced pressure. The residue was dissolved in toluene (10 ml) and dichloromethane (5 ml). To the solution was added DBU (2.3 ml, 15.4 mmol) and the solution was stirred at room temperature for 5 hours. To the reaction solution was added water and after separating the mixture with a separating funnel the aqueous layer was extracted with ethyl acetate. The organic layer was washed with a saturated aqueous sodium chloride solution, dried over magnesium sulfate and the organic solvent was removed under reduced pressure. The residue was purified by silica gel chromatography to give 1-allyl 4-ethyl (6S)-6-methyl-3,6-dihydro-1,4(2 H)-pyridinedicarboxylate (825 mg) with an intermediate, a methanesulfonylated compound (409 mg).

$^1$H NMR (300 MHz, CDCl$_3$) δ 1.27 (3 H, d, J=7.0 Hz), 1.30 (3 H, t, J=7.1 Hz), 2.23–2.36 (1 H, m), 2.40–2.46 (1 H, m), 2.80–2.96 (1 H, m), 4.14–4.29 (3 H, m), 4.57–4.72 (3 H, m), 5.20–5.34 (2 H, m), 5.87–6.01 (1 H, m), 6.82 (1 H, s).

d) To a solution of 1-allyl 4-ethyl (6S)-6-methyl-3,6-dihydro-1,4(2 H)-pyridinedicarboxylate (200 mg, 0.79 mmol) and bromochloromethane (0.082 ml, 1.3 mmol) in THF (4 ml) was added at −90° C. a solution of n-butyllithium in hexane (1.59M, 0.74 ml, 1.2 mmol). Twenty minute later, the reaction mixture was poured into a mixture of ice (5 g) and phosphate buffer (pH 7.0, 10 ml). To the solution was added ethyl acetate and after separating the mixture with a separating funnel, the aqueous layer was extracted twice with ethyl acetate. The organic layer was washed with a saturated aqueous sodium chloride solution, dried over magnesium sulfate and the organic solvent was removed under reduced pressure. The residue was purified by silica gel chromatography to give allyl (6S)-4-(chloroacetyl)-6-methyl-3,6-dihydro-1(2 H)-pyridinecarboxylate (167 mg).

$^1$H NMR (300 MHz, CDCl$_3$) δ 1.32 (3 H, d, J=7.0 Hz), 2.18–2.31 (1 H, m), 2.49–2.56 (1 H, m), 2.80–2.94 (1 H, m), 4.16–4.31 (1 H, m), 4.39 (1 H, d, J=14.1 Hz), 4.42 (1 H, d, J=14.1 Hz), 4.60–4.64 (2 H, m), 4.74–4.83 (1 H, m), 5.20–5.34 (2 H, m), 5.86–6.02 (1 H, m), 6.73 (1 H, s).

e) To a solution of allyl 6S)-4-(chloroacetyl)-6-methyl-3,6-dihydro-1(2 H)-pyridinecarboxylate (167 mg, 0.65 mmol) in methanol (2 ml) were added at 0–5° C. thioisonicotinamide (5 mg) and ammonium thiocarbamate (87 mg, 0.79 mmol). The temperature was raised to room temperature and the mixture was stirred for 15 minute. To the mixture was added ethanol (4 ml) and the solution was refluxed for 3 hours under stirring. The solvent was removed under reduced pressure and the residue was dissolved in a 1N aqueous sodium hydroxide solution. The solution was washed with ether. The aqueous layer of the solution was adjusted to pH 2–3 with 6N hydrochloric acid and the aqueous layer was extracted three times with ethyl acetate. The organic layer was washed with a saturated aqueous sodium chloride solution, dried over magnesium sulfate and the organic solvent was removed under reduced pressure to give allyl (6S)-6-methyl-4-(2-mercapto-1,3-thiazol-4-yl)-3,6-dihydro-1(2 H)-pyridinecarboxylate (115 mg).

$^1$H NMR (300 MHz, CDCl$_3$) δ 1.29 (3 H, d, J=6.9 Hz), 2.20–2.28 (1 H, m), 2.38–2.50 (1 H, m), 2.83–3.05 (1 H, m), 4.25–4.33 (1 H, m), 4.60–4.65 (1 H, m), 4.66–4.78 (1 H, m), 5.21–5.35 (2 H, m), 5.89–6.02 (2 H, m), 6.40 (1 H, s).

Reference Example 3

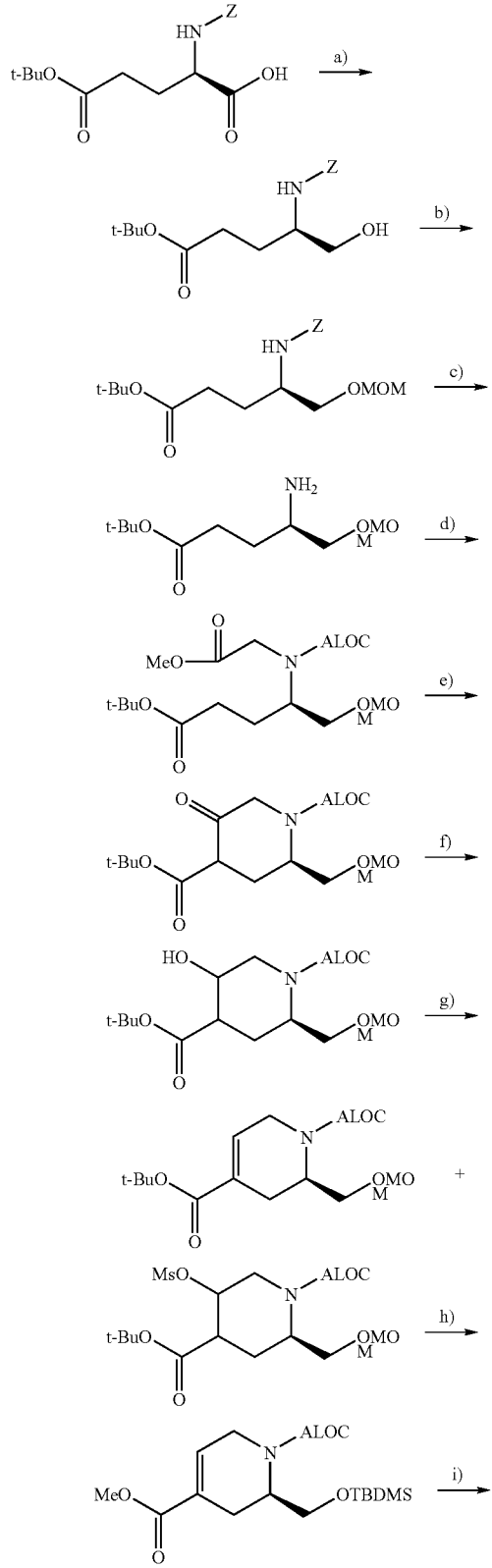

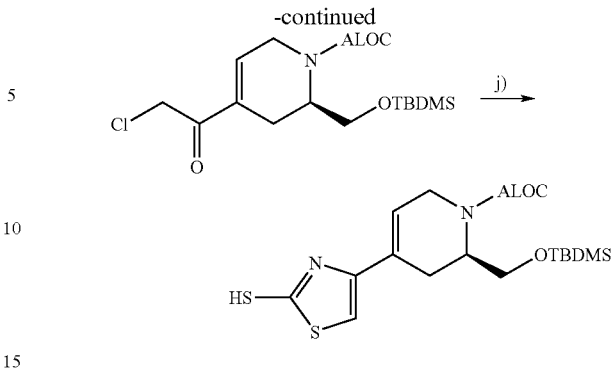

a) To a solution of N-(benzyloxy)carbonyl-D-glutamic acid 5-tert-butyl ester (35 g, 102 mol) in THF (500 ml) was added at −30° C. triethylamine (17 ml, 122 mmol), followed by addition of ethyl chloroformate (12 ml, 122 mmol) and the mixture was stirred at the same temperature. Then to the mixture was added at −30° C. a solution of sodium borohydride (11.6 g, 306 mmol) in water (51 ml) and the mixture was stirred for 30 minutes. Then the solution was raised to 0° C. and stirred for 30 minutes. To the reaction mixture was added water and the solution was extracted three times with ethyl acetate and the organic layer was washed with a saturated aqueous sodium chloride solution, dried over magnesium sulfate and the organic solvent was removed under reduced pressure. The residue was purified by silica gel (210 g) chromatography (Hexane/ethyl acetate: 3/2→1/1) to give tert-butyl (4R)-4-{[(benzyloxy)carbonyl]amino}-5-hydroxypentanoate (16.5 g, 50%).

$^1$H NMR (300 MHz, CDCl$_3$) δ 1.40 (9 H, s), 1.67–1.91 (2 H, m), 2.19–2.38 (2 H, m), 2.61 (1 H, brs), 3.48–3.70 (3 H, m), 5.06 (2 H, s), 5.17 (1 H, brs), 7.25–7.36 (5 H, m).

b) To a solution of tert-butyl (4R)-4-{[(benzyloxy)carbonyl]amino}-5-hydroxypentanoate (15.05 g, 46.5 mmol) in dichloromethane (150 ml) were added under the ice cooling 4-dimethylaminopyridine (120 mg, 1 mmol), diisopropylethylamine (26 ml, 150 mmol) and chloromethyl methyl ether (12 ml, 150 mmol), and the mixture was raised to the room temperature. Ten hours later the mixture was adjusted to pH about 3 with ice water and 1N hydrochloric acid under cooling in an ice bath. After adding a saturated aqueous sodium chloride solution and separating the mixture with a separating funnel, the organic layer was washed once with water and twice with a saturated aqueous sodium chloride solution. The organic layer was dried over magnesium sulfate and the organic solvent was removed under reduced pressure to give tert-butyl (4R)-4-{[(benzyloxy)carbonyl]amino}-5-(methoxymethoxy)pentanoate (16.87 g, 99%).

$^1$H NMR (300 MHz, CDCl$_3$) δ 1.41 (9 H, s), 1.75–1.92 (2 H, m), 2.22–2.35 (2 H, m), 3.31 (3 H, s), 3.47–3.58 (2 H, m), 3.75–3.86 (1 H, m), 4.58 (2 H, s), 5.02 (1 H, brd, J=8.1 Hz), 5.07 (2 H, s), 7.26–7.37 (5 H, m).

c) To a solution of tert-butyl (4R)-4-{[(benzyloxy)carbonyl]amino}-5-(methoxymethoxy)pentanoate (16.42 g, 44 mmol) in methanol (164 ml) was added 10% Pd—C (1.7 g) and the mixture was stirred under a hydrogen atmosphere for 3.5 hours. Catalyst was removed by filtration and the solvent was removed in vacuo to give tert-butyl (4R)-4-amino-5-(methoxymethoxy)pentanoate (10.87 g, 106%).

¹H NMR (300 MHz, CDCl₃) δ 1.41 (9 H, s), 1.89 (2 H, q, J=7.1 Hz), 2.41 (2 H, t, J=7.5 Hz), 3.24–3.33 (2 H, m), 3.36 (3 H, s), 3.53 (1 H, dd, J=6.8, 10.1 Hz), 3.68 (1 H, dd, J=3.8, 10.3 Hz), 4.57–4.83 (5 H, m).

d) To a solution of tert-butyl (4R)-4-amino-5-(methoxymethoxy)pentanoate (2.33 g, 10 mmol) and diisopropylethylamine (2.6 ml, 15 mmol) in methanol (70 ml) was dropped at room temperature methyl bromoacetate (1.4 ml, 15 mmol) in methanol (10 ml) and the mixture was stirred at 60° C. for 1 hour. Thereto were added additional methyl bromoacetate (0.5 ml, 5 mmol) and diisopropylethylamine (0.9 ml, 5 mmol). After stirring for 1 hour, the mixture was cooled to room temperature and the solvent was removed in vacuo. The residue was dissolved in chloroform (50 ml) and thereto was dropped allyl chloroformate (2.15 ml, 20 mmol) and then diisopropylethylamine (3.5 ml, 20 mmol). The mixture was stirred at the same temperature for 1 hour and at room temperature for 1 hour, respectively. Water was added thereto under cooling in an ice bath. The mixture was extracted three times with chloroform. The organic layer was washed with a saturated aqueous sodium chloride solution and was dried over magnesium sulfate. The solvent was removed under reduced pressure, and the residue was purified by silica gel (51 g) chromatography (hexane/ethyl acetate: 2/1~hexane/ethyl acetate: 1/1) to give tert-butyl (4R)-4-[[(allyloxy)carbonyl](2-methoxy-2-oxoethyl)amino}-5-(methoxymethoxy)pentanoate (3.01 g, 77%).

¹H NMR (300 MHz, CDCl₃) δ 1.44 (9 H, s), 1.78–1.91 (2 H, m), 2.31–2.37 (2 H, m), 3.33 (3 H, s), 3.62 (2 H, t, J=6.8 Hz), 3.71 (1.8 H, s), 3.72 (1.2 H, s), 3.99 (2 H, s), 4.22–4.38 (1 H, m), 4.52–4.66 (4 H, m), 5.15–5.35 (2 H, m), 5.81–5.97 (1 H, m).

e) To a suspension of potassium tert-butoxide (299 mg, 2.66 mmol) in THF (26 ml) was added tert-butyl (4R)-4-[[(allyloxy)carbonyl](2-methoxy-2-oxoethyl)amino}-5-(methoxymethoxy)pentanoate (0.52 g, 1.33 mmol) in THF (2.5 ml) and the mixture was stirred for 1 minutes. After cooling to 0° C., the reaction mixture was poured into diluted hydrochloric acid. The solution was adjusted to pH about 3 and after adding a saturated aqueous sodium chloride solution, the solution was extracted with ethyl acetate. The organic layer was washed with water and then a saturated aqueous sodium chloride solution. The organic layer was dried over magnesium sulfate and the organic solvent was removed under reduced pressure. The residue was purified by silica gel (15 g) chromatography (Hexane/ethyl acetate: 3/1) to give 1-allyl 4-tert-butyl (2R)-2-[(methoxymethoxy)methyl]-5-oxo-1,4-piperidinedicarboxylate (0.26 g, 54%).

¹H NMR (300 MHz, CDCl₃) δ1.50 (9 H, s), 2.29–2.44 (2 H, m), 3.33 (3 H, s), 3.49–3.76 (3 H, m), 4.31–4.48 (1 H, m), 4.56–4.70 (5 H, m), 5.22 (1 H, d, J=10.4 Hz), 5.31 (1 H, d, J=17.4 Hz), 5.94 (1 H, ddd, J=5.1, 10.4, 17.2 Hz), 12.23 (1 H, s).

f) To a solution of 1-allyl 4-tert-butyl (2R)-2-[(methoxymethoxy)methyl]-5-oxo-1,4-piperidinedicarboxylate (1.21 g, 3.4 mmol) in methanol (40 ml) was added acetic acid (0.235 ml, 4.1 mmol) and sodium cyanoborohydride (0.255 g, 4.1 mmol) and the mixture were stirred at room temperature for 20 minutes. The solvent was removed in vacuo and it was confirmed whether a starting material run out by TLC. When the starting material remained, methanol (40 ml) was added thereto to dissolve the reaction mixture and then the solvent was again removed. Until the starting material run out, the procedure was repeated. After the starting material run out, the residue was purified by silica gel (30 g) chromatography to give 1-allyl 4-tert-butyl (2R)-5-hydroxy-2-[(methoxymethoxy)methyl]-1,4-piperidinedicarboxylate (1.22 g, quantitatively).

¹H NMR (300 MHz, CDCl3) δ 1.45 (9 H, s), 1.63–1.74 (2 H, m), 2.44–2.56 (1 H, m), 2.61–2.79 (1 H, m), 3.34 (3 H, s), 3.53–3.76 (3 H, m), 4.10–4.36 (1 H, m), 4.41–4.67 (5 H, m), 5.18 (1 H, d, J=10.3 Hz), 5.28 (1 H, dd, J=1.7, 17.2 Hz), 5.84–5.96 (1 H, m).

g) To a solution of 1-allyl 4-tert-butyl (2R)-5-hydroxy-2-[(methoxymethoxy)methyl]-1,4-piperidinedicarboxylate (1.22 g, 3.4 mmol) in dichloromethane (9.4 ml) were added at −30° C. methanesulfonyl chloride (0.4 ml, 5.1 mmol), triethylamine (0.95 ml, 6.8 mmol) and 4-dimethylaminopyridine ((41.5 mg, 0.34 mmol), and the mixture was stirred 0° C. for 40 minutes. The reaction mixture was poured into diluted hydrochloric acid and the mixture was extracted three times with chloroform. The organic layer was washed with a saturated aqueous sodium chloride, and dried over magnesium sulfate. The organic solvent was removed under reduced pressure, and the residue was dissolved in toluene (5 ml) and dichloromethane (10 ml). The mixture was cooled to 0° C. and thereto was added DBU (0.76 ml, 5.1 mmol). The mixture was raised to room temperature and was stirred accurately for 20 minutes. The reaction mixture was poured into diluted hydrochloric acid and extracted three times with ethyl acetate. The organic layer was washed with water and then a saturated aqueous sodium chloride solution. The organic layer was dried over magnesium sulfate and the organic solvent was removed under reduced pressure. The residue was purified by silica gel (30 g) chromatography (Hexane/ethyl acetate: 2/1) to give 1-allyl 4-tert-butyl (2R)-2-[(methoxymethoxy)methyl]-5-[(methylsulfonyl)oxy]-1,4-piperidinedicarboxylate (0.24 g, 15%) and 1-allyl 4-tert-butyl (2R)-2-[(methoxymethoxy)methyl]-3,6-dihydro-1,4(2 H)-pyridinedicarboxylate (0.79 g, 68%).

1-allyl 4-tert-butyl (2R)-2-[(methoxymethoxy)methyl]-5-[(methylsulfonyl)oxy]-1,4-piperidinedicarboxylate ¹H NMR (300 MHz, CDCl₃) δ 1.43 (9 H, s), 1.79 (1 H, dt, J=5.9, 13.4 Hz), 2.07–2.18 (1 H, m), 2.75–2.87 (1 H, m), 3.03 (3 H, s), 3.34 (3 H, s), 3.57–3.68 (2 H, m), 4.45–4.75 (8 H, m), 5.20 (1 H, dd, J=0.9, 10.3 Hz), 5.29 (1 H, d, J=16.9 Hz), 5.84–5.96 (1 H, m).

1-allyl 4-tert-butyl (2R)-2-[(methoxymethoxy)methyl]-3,6-dihydro-1,4(2 H)-pyridinedicarboxylate ¹H NMR (300 MHz, CDCl₃) δ 1.47 (9 H, s), 2.41–2.47 (2 H, m), 3.30 (3 H, s), 3.43 (2 H, d, J=7.9 Hz), 3.64–3.80 (1 H, m), 4.37–4.80 (6 H, m), 5.19 (1 H, dd, J=1.3, 10.4 Hz), 5.29 (1 H, d, J=17.2 Hz), 5.87 (1 H, ddt, J=5.3, 10.4, 17.2 Hz), 6.77 (1 H, brs).

h) A solution of 1-allyl 4-tert-butyl (2R)-2-[(methoxymethoxy)methyl]-3,6-dihydro-1,4(2 H)-pyridinedicarboxylate (1.15 g, 3.4 mmol) in methanol (15 ml) was added hydrochloric acid/methanol (50 ml) and the mixture was stirred overnight. To the mixture was added toluene and the solvent was removed in vacuo. To the residue were added methanol and toluene, and the solvent was again removed in vacuo. The residue was dissolved in dichloromethane (20 ml) and to the solution were added at 0–5° C. 2,6-lutidine (3.6 ml, 31 mmol) and tert-butyldimethylsilyltriflate (4.2 ml, 18 mmol). One hour later a saturated aqueous sodium chloride solution was added thereto and the mixture was separated with a separating funnel. The organic layer was dried over magnesium sulfate and the solvent was removed under reduced pressure. The residue was purified by silica gel (40 g) chromatography (Hexane/ethyl acetate: 1/5) to give 1-allyl 4-methyl (2R)-2-({[tert-butyl(dimethyl) silyl]oxy}methyl)-3,6-dihydro-1,4(2 H)-pyridinedicarboxylate (1.09 g, 81%).

$^1$H NMR (300 MHz, CDCl$_3$) δ −0.01 (6 H, s), 0.83 (9 H, s), 2.33–2.46 (1 H, m), 2.47–2.62 (1 H, m), 3.40–3.53 (2 H, m), 3.63–3.92 (1 H, m), 3.73 (3 H, s), 4.33–4.65 (4 H, m), 5.20 (1 H, dd, J=1.5, 10.4 Hz), 5.29 (1 H, d, J=16.7 Hz), 5.92 (1 H, ddt, J=5.3, 10.4, 16.7 Hz), 6.78–6.92 (1 H, m). IR (KBr) n 2953, 1715, 1417, 1251, 1112 cm$^{-1}$ i) To a solution of 1-allyl 4-methyl (2R)-2-({[tert-butyl (dimethyl)silyl]oxy}methyl)-3,6-dihydro-1,4(2 H)-pyridinedinedicarboxylate (0.52 g, 1.39 mmol) in THF (10 ml) was added −90 to −80° C. a solution of n-butyllithium in hexane (1.59M, 1.31 ml, 2.1 mmol) over a 20 minute period. After stirring for additional 15 minutes, the reaction mixture was poured into a mixture of ice (10 g) and phosphate buffer (pH 7.0, 10 ml). After ethyl acetate was added and the mixture was separated with a separating funnel, the aqueous layer was extracted twice with ethyl acetate. The organic layer was washed with a saturated aqueous sodium chloride, dried over magnesium sulfate and the organic solvent was removed under reduced pressure. The residue was purified by silica gel (30 g) chromatography to give 1-allyl (2R)-2-({[tert-butyl(dimethyl)silyl]oxy}methyl)-4-(chloroacetyl)-3,6-dihydro-1(2 H)-pyridinecarboxylate (244 mg, 45%).

$^1$H NMR (300 MHz, CDCl$_3$) δ−0.02 (6 H, s), 0.82 (9 H, s), 2.23–2.43 (1 H, m), 2.57–2.68 (1 H, m), 3.40–3.53 (2 H, m), 3.63–3.92 (2 H, m), 4.33–4.65 (5 H, m), 5.20 (1 H, dd, J=1.3, 12.1 Hz), 5.29 (1 H, dd, J=1.5, 17.2 Hz), 5.92 (1 H, ddt, J=5.3, 12.1, 17.2 Hz), 6.73–6.85 (1 H, m). IR (KBr) n 2954, 2858, 1692, 1650, 1414, 1113 cm$^{-1}$ j) To a solution of 1-allyl (2R)-2-({[tert-butyl(dimethyl) silyl]oxy}methyl-4-(chloroacetyl)-3,6-dihydro-1(2 H)-pyridinecarboxylate (0.345 g, 0.88 mmol) in methanol (5 ml) were added at 0–5° C. thioisonicotinamide (5 mg) and ammonium dithiocarbamate (149 mg, 1.35 mmol). The reaction mixture was raised to room temperature. The mixture was stirred for 15 minutes and then stirred at 55–60° C. for 1 hour. The solvent was removed in vacuo and the residue was purified by silica gel chromatography to give allyl (2R)-2-({[tert-butyl(dimethyl)silyl]oxy}methyl)-4-(2-mercapto-1,3-thiazol-4-yl)-3,6-dihydro-1(2 H)-pyridinecarboxylate (170 mg, 38%).

$^1$H NMR (300 MHz, CDCl$_3$) δ 0.00 (3 H, s), 0.02 (3 H, s), 0.84 (9 H, s), 2.40–2.57 (2 H, m), 3.45–3.85 (3 H, m), 3.38–3.65 (4 H, m), 5.18–5.35 (2 H, m), 5.88–6.01 (1 H, m), 6.07 (1 H, brs), 6.40 (1 H, s).

Reference Example 4

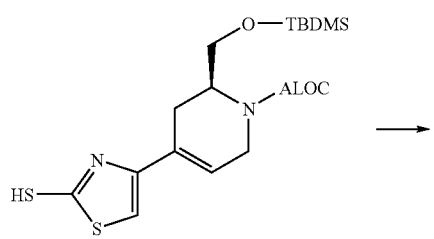

-continued

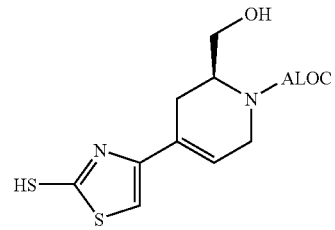

To a solution of allyl (2S)-2-({[tert-butyl(dimethyl)silyl] oxy}methyl)-4-(2-mercapto-1,3-thiazol-4-yl)-3,6-dihydro-1(2 H)-pyridinecarboxylate (539 mg, 1.30 mmol) in ethanol (40 ml)/THF(3 ml) was added p-toluenesulfonic acid monohydrate (50 ml). Four hours later the solvent was removed in vacuo. The residue was made alkaline by adding an aqueous 1N NaOH solution. To the mixture were added ethyl acetate and hexane, and the mixture was separated with a separating funnel. To the aqueous layer was added 6N hydrochloric acid, and the mixture was separated with a separating funnel. The aqueous layer was extracted with ethyl acetate. The organic layer was washed twice with a saturated aqueous sodium chloride solution, was dried over magnesium sulfate and the organic solvent was removed under reduced pressure to give allyl (2S)-2-(hydroxymethyl)-4-(2-mercapto-1,3-thiazol-4-yl)-3,6-dihydro-1(2 H)-pyridinecarboxylate (218 mg, 55%).

$^1$H NMR (300 MHz, CDCl$_3$) δ 2.40 (1 H, d, J=17.4 Hz), 2.52–2.64 (1 H, m), 3.54–3.93 (3 H, m), 4.38–4.69 (2 H, m), 4.62 (2 H, d, J=5.5 Hz), 5.22 (1 H, dd, J=1.1, 10.3 Hz), 5.30 (1 H, dd, J=1.5, 17.2 Hz), 5.93 (1 H, ddd, J=5.7, 10.3, 17.2 Hz), 6.12 (1 H, s), 6.41 (1 H, s).

Reference Example 5

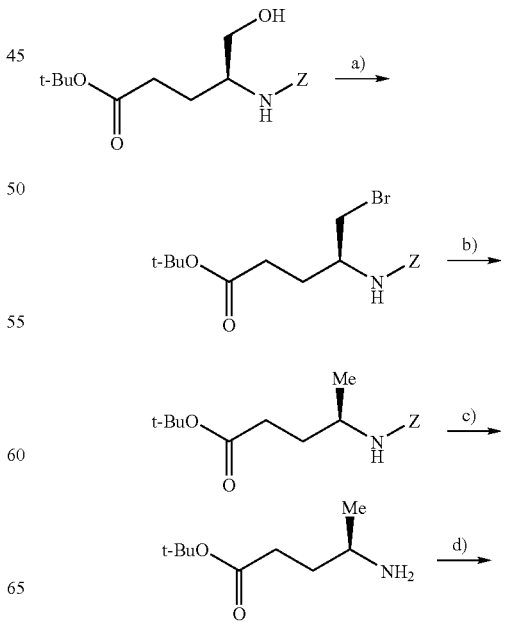

-continued

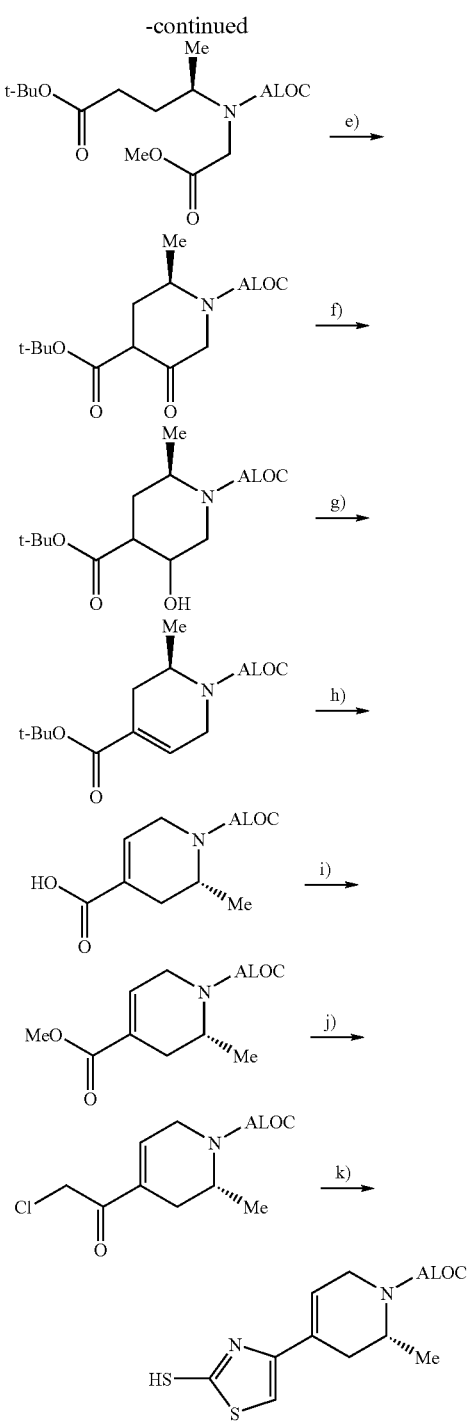

a) A solution of tert-butyl(4S)-4-{[(benzyloxy)carbonyl]amino}-5-hydroxypentanoate (5.0 g, 15.5 mmol) in dichloromethane (50 ml) was cooled to 0° C. and carbontetrabromide (6.15 g, 18.5 mmol) was added thereto. At the same temperature triphenylphosphine (5.68 g, 21.7 mmol) was divided to five portions and they were added to the reaction mixture for every 2 minutes and the mixture was stirred for 30 minutes. The solvent was removed in vacuo. To the residue was added diethyl ether and mixture was stirred. After removal of the resulting crystal by filtration, the filtrate was condensed in vacuo and the residue was purified with silica gel chromatography to give tert-butyl(4S)-4-{[(benzyloxy)carbonyl]amino}-5-bromopentanoate (4.5 g, 80%).

$^1$H NMR (300 MHz, CDCl$_3$) δ 1.43 (9H, s), 1.84–1.92 (2H, m), 2.23–2.41 (2H, m), 3.50 (1H, dd, J=10.4, 3.5 Hz), 3.57 (1H, dd, J=10.4, 4.4 Hz), 3.86–3.97 (1H, m), 5.04–5.16 (3H, m), 7.27–7.40 (5H, m).

b) To a solution of tert-butyl(4S)-4-{[(benzyloxy)carbonyl]amino}-5-bromopentanoate (4.5 g, 11.7 mmol) and tributyltin hydride (6.3 ml, 23.4 mmol) in toluene (45 ml) was added 2,2'-azobisisobutyronitrile (0.19 g, 1.2 mmol) and the mixture was stirred at 80° C. for 20 minutes. To the reaction mixture was added water, and the solution was extracted three times with ethyl acetate. The organic layer was washed with a saturated aqueous sodium chloride solution, dried over anhydrous sodium sulfate and the organic solvent was removed under reduced pressure. The residue was purified with silica gel chromatography to give tert-butyl (4R)-4-{[(benzyloxy)carbonyl]amino}pentanoate (3.5 g, 98%).

$^1$H NMR (300 MHz, CDCl$_3$) δ 1.16 (3H, d, J=6.6 Hz), 1.43 (9H, s), 1.68–1.79 (2H, m), 2.26–2.31 (2H, m), 3.69–3.80 (1H, m), 4.63–4.70 (1H, m), 5.04–5.12 (2H, m), 7.30–7.37 (5H, m).

c) To a solution of tert-butyl (4R)-4-{[(benzyloxy)carbonyl]amino}pentanoate (3.5 g, 11.4 mmol) in methanol (35 ml) was added Pd—C (0.7 g) and the mixture was stirred under a hydrogen atomosphere for 3 hours. Catalyst was removed by filtration and the solvent was removed in vacuo to give tert-butyl(4R)-4-aminopentanoate (2.1 g).

$^1$H NMR. (300 MHz, CDCl$_3$) δ 1.08 (3H, d, J=6.4 Hz), 1.45 (9H, s), 1.53–1.73 (2H, m), 2.20–2.36 (2H, m), 2.86–2.96 (1H, m).

d) A solution of tert-butyl(4R)-4-aminopentanoate (2.1 g) prepared above, methyl bromoacetate (1.6 ml, 16.9 mmol) and diisopropylethylamine (3.0 ml, 17.2 mmol) in methanol (60 ml) was stirred at 60° C. for 1 hour. Additional methyl bromoacetate (0.3 ml, 3.2 mmol) and diisopropylethylamine (0.6 ml, 3.4 mmol) were added thereto and the mixture was stirred for 1 hour. The mixture was cooled to room temperature and the solvent was removed in vacuo. The residue was dissolved in chloroform (40 ml). To the solution was added ally chloroformate (2.4 ml, 22.6 mmol) and then diisopropylethylamine (4.0 ml, 23.0 mmol). The mixture was stirred at the same temperature for 1 hour. To the reaction mixture was added water and the mixture was extracted three times with chloroform. The organic layer was washed with a saturated aqueous sodium chloride solution, dried over magnesium sulfate and the solvent was removed under reduced pressure. The residue was purified with silica gel chromatography to give tert-butyl(4R)-4-[[(allyloxy)carbonyl](2-methoxy-2-oxoethyl)amino]pentanoate (3.1 g).

$^1$H NMR (300 MHz, CDCl$_3$) δ 1.13–1.17 (3H, m), 1.43 (9H, s), 1.64–1.74 (2H, m), 2.25–2.39 (2H, m), 3.69–3.94 (5H, m), 4.18–4.37 (1H, m), 4.56–4.64 (2H, m), 5.15–5.35 (2H, m), 5.81–6.00 (1H, m).

e) In the same manner as Reference example 2.b), by using tert-butyl (4R)-4-[[(allyloxy)carbonyl](2-methoxy-2-oxoethyl)amino]pentanoate, there was obtained 1-allyl 4-tert-butyl (2R)-2-methyl-5-oxo-1,4-piperidinedicarboxylate.

$^1$H NMR (300 MHz, CDCl$_3$) δ 1.15 (3H, d, J=6.8 Hz), 1.51 (9H, s), 2.13 (1H, d, J=15.8 Hz), 2.43–2.52 (1H, m), 3.68 (1H, d, J=18.7 Hz), 4.38 (1H, d, J=18.7 Hz), 4.57–4.62 (3H, m), 5.19–5.35 (2H, m), 5.86–6.00 (1H, m), 12.2 (1H, s).

f) To a solution of 1-allyl 4-tert butyl (2R)-2-methyl-5-oxo-1,4-piperidinedicarboxylate (1.93 g, 6.5 mmol) in methanol (40 ml) were added acetic acid (0.45 ml, 7.9 mmol) and sodium cyanoborohydride (0.49 g, 7.8 mmol), and the mixture was stirred at room temperature for 20 minutes. The solvent was removed in vacuo and the residue was purified by silica gel chromatography to give 1-allyl 4-tert-butyl (2R)-5-hydroxy-2-methyl-1,4-piperidinedicarboxylate (1.85 g, 95%).

$^1$H NMR (300 MHz, CDCl$_3$) δ 1.20 (3H, d, J=6.9 Hz), 1.47 (9H, s), 1.69–1.87 (2H, m), 2.47–2.56 (1H, m), 2.70–2.80 (1H, m), 3.23 (1H, br s), 3.70–3.87 (1H, m), 4.12–4.28 (1H, m), 4.51 (1H, br s), 4.57–4.60 (2H, m), 5.17–5.33 (2H, m), 5.87–6.00 (1H, m).

g) To a solution of 1-allyl 4-tert-butyl (2R)-5-hydroxy-2-methyl-1,4-piperidinedicarboxylate (1.85 g, 6.2 mmol) in dichloromethane (40 ml) were added at −30° C. methanesulfonyl chloride and triethylamine, and the mixture was stirred 0° C. for 2 hours. The reaction mixture was poured into diluted hydrochloric-acid and the mixture was extracted three times with chloroform. The organic layer was washed with a saturated aqueous sodium chloride solution, dried over magnesium sulfate and the solvent was removed under reduced pressure. The residue was dissolved in a mixture of toluene (5 ml) and dichloromethane (10 ml). The solution was cooled to 0° C. and thereto was added DBU. The mixture was stirred for 1 hour. The reaction mixture was poured into diluted hydrochloric acid and extracted three times with ethyl acetate. The organic layer was washed with water and then a saturated aqueous sodium chloride solution, and dried over magnesium sulfate. The solvent was removed under reduced pressure and the residue was purified by silica gel (30 g) chromatography to give 1-allyl 4-tert-butyl (2R)-2-methyl-3,6-dihydro-1,4(2 H)-pyridinedicarboxylate (1.33 g, 76%).

$^1$H NMR (300 MHz, CDCl$_3$) δ 1.10 (3H, d, J=6.8 Hz), 1.50 (9H, s), 2.30 (1H, d, J=16.8 Hz), 2.42–2.53 (1H, m), 3.73 (1H, d, J=20.3 Hz), 4.44 (1H, d, J=20.3 Hz), 4.61–4.67 (3H, m), 5.19–5.34 (2H, m), 5.88–6.00 (1H, m), 6.78 (1H, s).

h) To a solution of 1-allyl 4-tert-butyl (2R)-2-methyl-3,6-dihydro-1,4(2 H)-pyridinedicarboxylate (0.64 g, 2.3 mmol) in methanol (10 ml) was added hydrochloric acid/methanol (10 ml) and the mixture was stirred overnight. Toluene was added thereto and the solvent was removed in vacuo. To the residue were added methanol and toluene, and the solvent was again removed in vacuo. The residue was dissolved in THF (10 ml) and to the solution was added at 0–5° C. a solution of trimethylsilyldiazomethane in hexane (2M, 1.15 ml, 2.3 mmol). Fifteen minutes later 1N hydrochloric acid was added thereto. Ethyl acetate and a saturated aqueous sodium chloride solution were added thereto. The mixture was separated with a separating funnel. The aqueous layer was extracted twice with ethyl acetate. The organic layer was washed twice with a saturated aqueous sodium chloride solution and dried over magnesium sulfate. The solvent was removed under reduced pressure, and the residue was purified by silica gel (20 g) chromatography (hexane/ethyl acetate: 1/6→1/4) to give 1-allyl 4-methyl (2R)-2-methyl-3,6-dihydro-1,4(2 H)-pyridinedicarboxylate (0.31 g)

$^1$H NMR (300 MHz, CDCl$_3$) δ 1.07 (3 H, d, J=6.8 Hz), 2.33 (1H, d, J=16.8 Hz), 2.44–2.56 (1H, m), 3.70–3.80 (1 H, m), 3.74 (3 H, s), 4.38–4.50 (1 H, m), 4.55–4.70 (3 H, m), 5.20 (1 H, ddd, J=1.5, 2.7, 10.4 Hz), 5.29 (1 H, ddd, J=1.7, 3.1, 17.2 Hz), 5.93 (1 H, ddd, J=5.5, 10.4, 17.2 Hz), 6.87 (1 H, brs).

i) To a solution of 1-allyl 4-methyl (2R)-2-methyl-3,6-dihydro-1,4(2 H)-pyridinedicarboxylate (0.30 g, 1.25 mmol) and bromochloromethane (125 μl) in THF (15 ml) was added −90 to −80° C. a solution of n-butyllithium in hexane (1.59M, 1.15 ml) over a 15 minutes period. After stirring for additional 15 minutes, the reaction mixture was poured into a mixture of-ice (10 g) and phosphate buffer (pH 7.0, 10 ml). After ethyl acetate was added thereto and the mixture was separated by a separating funnel, the aqueous layer was extracted twice with ethyl acetate. The organic layer was washed with a saturated aqueous sodium chloride solution, dried over magnesium sulfate and the organic solvent was removed under reduced pressure. The residue was purified by silica gel (25 g) chromatography to give allyl (2R)-4-(chloroacetyl)-2-methyl-3,6-dihydro-1(2 H)-pyridinecarboxylate (255 mg, 80%).

$^1$H NMR (300 MHz, CDCl$_3$) δ 1.06 (3 H, d, J=6.8 Hz), 2.43 (2 H, brs), 3.77–3.88 (1 H, m), 4.35–4.7 (6 H, m), 5.21 (1 H, ddd, J=1.5, 2.7, 10.4 Hz), 5.29 (1 H, ddd, J=1.7, 2.9, 17.2 Hz), 5.93 (1 H, ddd, J=5.5, 10.4, 17.2 Hz), 6.81 (1 H, brs).

j) To a solution of allyl (2R)-4-(chloroacetyl)-2-methyl-3,6-dihydro-1(2 H)-pyridinecarboxylate (0.255 g, 1.0 mmol) in methanol (5 ml) were added at 0–5° C. thioisonicotinamide (5 mg) and ammonium dithiocarbamate (0.22 g, 2.0 mmol). The reaction mixture was raised to room temperature, stirred for 15 minutes and then stirred at 55–60° C. for 1.5 hour. The solvent was removed in vacuo and to the residue was added aqueous 1N NaOH solution to make the solution alkaline. To the solution were added ethyl acetate and hexane, and the mixture was separated with a separating funnel. The aqueous layer was acidified with 6N hydrochloric acid, and extracted with ethyl acetate. The organic layer was washed twice with a saturated aqueous sodium chloride solution and dried over magnesium sulfate. The solvent was removed in vacuo to give allyl (2R)-4-(2-mercapto-1,3-thiazol-4-yl)-2-methyl-3,6-dihydro-1(2 H)-pyridinecarboxylate (170 mg, 59%).

$^1$H NMR (300 MHz, CDCl$_3$) δ 1.14 (3 H, d, J=6.9 Hz), 2.05–2.14 (1 H, m), 2.59–2.70 (1 H, m), 3.72–3.84 (1 H, m), 4.43–4.74 (4 H, m), 5.21 (1 H, ddd, J=1.5, 2.7, 10.4 Hz), 5.29 (1 H, ddd, J=1.5, 2.9, 17.2 Hz), 5.93 (1 H, ddd, J=5.7, 10.4, 17.2 Hz), 6.19 (1 H, brs), 6.38 (1 H, s).

Reference Example 6

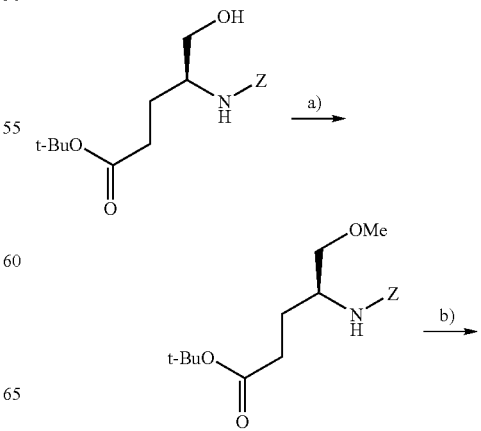

-continued

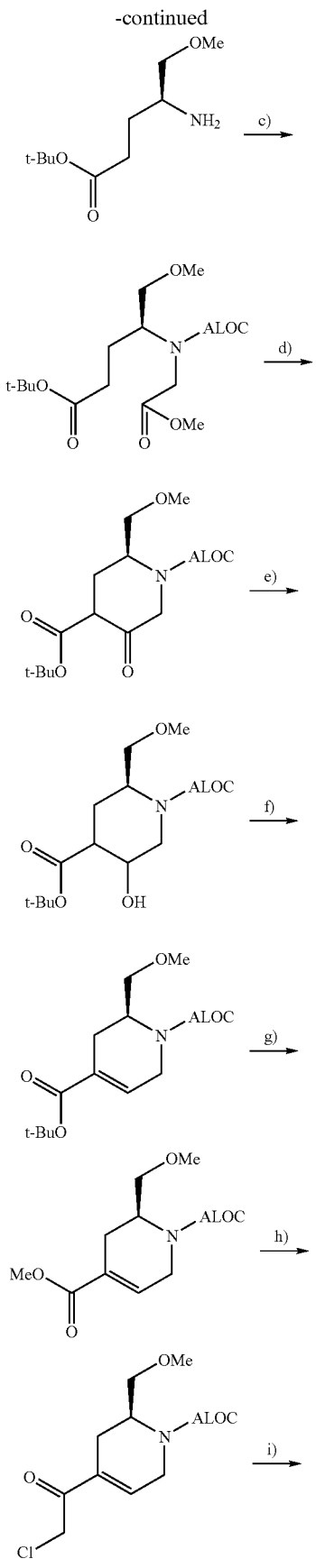

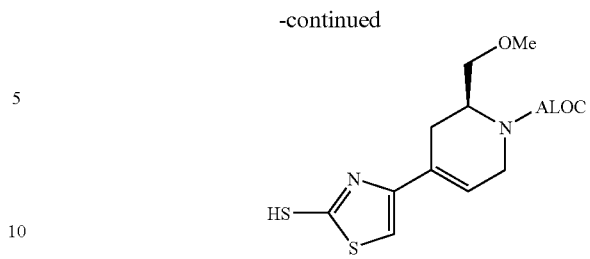

a) To a solution of tert-butyl (4S)-4-{[(benzyloxy)carbonyl]amino}-5-hydroxypentanoate (4.0 g, 12.4 mmol) in acetonitrile (80 ml) were added silveroxide (14.3 g, 61.7 mmol) and methyliodide (7.7 ml, 124 mmol), and the mixture was stirred for 19 hours. After removal of the insoluble materials, the solvent was removed in vacuo and the residue was purified with silica gel chromatography to give tert-butyl (4S)-4-{[(benzyloxy)carbonyl]amino}-5-methoxypentanoate (2.98 g, 71%).

$^1$H NMR (300 MHz, CDCl$_3$) δ 1.43 (9H, s), 1.75–1.91 (2H, m), 2.28–2.33 (2H, m), 3.33 (3H, s), 3.36–3.42 (2H, m), 3.75–3.85 (1H, m), 4.99–5.03 (1H, m), 5.09 (2H, s), 7.27–7.37 (5H, m).

b) In the same manner as Reference example 2.b), by using tert-butyl (4S)-4-{[(benzyloxy)carbonyl]amino}-5-methoxypentanoate (2.98 g, 8.8 mmol), there was obtained tert-butyl (4S)-4-amino-5-methoxypentanoate (1.88 g).

$^1$H NMR (300 MHz, CDCl$_3$) δ 1.44 (9H, s), 1.84–1.91 (2H, m), 2.40–2.45 (2H, m), 3.22–3.30 (1H, m), 3.37–3.55 (5H, m), 4.41 (2H, br s).

c) In the same manner as Reference example 5.d), by using tert-butyl (4S)-4-amino-5-methoxypentanoate (1.88 g), there was obtained tert-butyl (4S)-4-[[(allyloxy)carbonyl](2-methoxy-2-oxoethyl)amino]-5-methoxypentanoate (2.48 g).

$^1$H NMR (300 MHz, CDCl$_3$) δ 1.44 (9H, s), 1.74–1.92 (2H, m), 2.27–2.33 (2H, m), 3.24–3.25 (3H, m), 3.38–3.53 (2H, m), 3.68–3.73 (3H, m), 3.91–4.07 (2H, m), 4.20–4.36 (1H, m), 4.54–4.65 (2H, m), 5.16–5.34 (2H, m), 5.81–5.59 (1H, m).

d) In the same manner as Reference example 2.b), by using tert-butyl (4S)-4-[[(allyloxy)carbonyl](2-methoxy-2-oxoethyl)amino]-5-methoxypentanoate (1.66 g, 4.6 mmol and 0.82 g, 2.3 mmol), there was obtained 1-allyl 4-tert-butyl (2S)-2-(methoxymethyl)-5-oxo-1,4-piperidinedicarboxylate (1.24 g, 55%).

$^1$H NMR (300 MHz, CDCl$_3$) δ 1.51 (9H, s), 2.28 (1H, d, J=16.0 Hz), 2.39–2.48 (1H, m), 3.27–3.46 (5H,m), 3.60–3.72 (1H, m), 4.34–4.72 (4H, m), 5.20–5.35 (2H, m), 5.88–6.00 (1H, m), 12.2 (1H, s).

e) In the same manner as Reference example 5.f), by using 1-allyl 4-tert-butyl (2S)-2-(methoxymethyl)-5-oxo-1,4-piperidinedicarboxylate (1.24 g, 3.8 mmol), there was obtained 1-allyl 4-tert-butyl (2S)-5-hydroxy-2-(methoxymethyl)-1,4-piperidinedicarboxylate (1.19 g, 94%).

$^1$H NMR (300 MHz, CDCl$_3$) δ 1.47 (9H, s), 1.63–1.74 (1H, m), 2.04–2.12 (1H, m), 2.47–2.57 (1H, m), 2.69–2.84 (1H, m), 3.08–3.52 (5H, m), 3.70–3.81 (1H, m), 4.20–4.63 (4H, m), 5.17–5.35 (2H, m), 5.86–6.00 (1H, m).

f) In the same manner as Reference example 5.g), by using 1-allyl 4-tert-butyl (2S)-5-hydroxy-2-(methoxymethyl)-1,4-piperidinedicarboxylate (1.19 g, 3.6 mmol), there was obtained 1-allyl 4-tert-butyl (2S)-2-(methoxymethyl)-3,6-dihydro-1,4(2 H)-pyridinedicarboxylate (0.74 g, 66%).

¹H NMR (300 MHz, CDCl₃) δ 1.49 (9H, s), 2.41–2.45 (2H, m), 3.23–3.39 (2H, m), 3.33 (3H, s), 3.65–3.79 (1H, m), 4.40–4.82 (4H, m), 5.19–5.36 (2H, m), 5.88–6.00 (1H, m), 6.78 (1H, s).

g) To methanol (19 ml, 470 mmol) was added at 0° C. acetyl chloride (12 ml, 169 mmol) and the mixture was stirred at the same temperature for 30 minutes. This solution was added to a solution of 1-allyl 4-tert-butyl (2S)-2-(methoxymethyl)-3,6-dihydro-1,4(2 H)-pyridinedicarboxylate (744 mg, 2.4 mmol) in methanol (3 ml) and the mixture was stirred at room temperature for 2 hours. The solvent was removed and the residue was dissolved in ethyl acetate. The solution was washed with a saturated sodium hydrogen carbonate solution and a saturated aqueous sodium chloride solution and dried over magnesium sulfate. The solvent was removed in vacuo to give 1-allyl 4-methyl (2S)-2-(methoxymethyl)-3,6-dihydro-1,4(2 H)-pyridinedicarboxylate (600 mg, 93%).

¹H NMR (300 MHz, CDCl₃) δ 2.40–2.56 (2H, m), 3.23–3.40 (2H, m), 3.33 (3H, s), 3.66–3.84 (1H, m), 3.77 (3H, s), 4.42–4.82 (4H, m), 5.20–5.38 (2H, m), 5.89–6.01 (1H, m), 6.89 (1H, s).

h) In the same manner as Reference example 2.d), by using 1-allyl 4-methyl (2S)-2-(methoxymethyl)-3,6-dihydro-1,4(2 H)-pyridinedicarboxylate (600 mg, 2.2 mmol), there was obtained allyl (2S)-4-(chloroacetyl)-2-(methoxymethyl)-3,6-dihydro-1(2 H)-pyridinecarboxylate (547 mg, 71%).

¹H NMR (300 MHz, CDCl₃) δ 2.18–2.65 (2H, m), 3.21–3.38 (2H, m), 3.31 (3H, s), 3.65–3.90 (2H, m), 4.41 (1H, d, J=14.1 Hz), 4.43 (1H, d, J=14.1 Hz), 4.50–4.80 (3H, m), 5.20–5.36 (2H, m), 5.89–6.02 (1H, m), 6.83 (1H, s).

i) In the same manner as Reference example 2.e), by using allyl (2S)-4-(chloroacetyl)-2-(methoxymethyl)-3,6-dihydro-1(2 H)-pyridinecarboxylate (547 mg, 1.9 mmol), there was obtained allyl (2S)-2-(methoxymethyl)-4-(2-sulfanyl-1,3-thiazol-4-yl)-3,6-dihydro-1(2 H)-pyridinecarboxylate (286 mg, 46%).

¹H NMR (300 MHz, CDCl₃) δ 2.42 (2H, d, J=16.8 Hz), 2.52–2.63 (1H, m), 3.21–3.43 (2H, m), 3.34 (3H, s), 3.65–3.86 (1H, m), 4.43–4.82 (4H, m), 5.21–5.36 (2H, m), 5.89–6.02 (1H, m), 6.10 (1H, br s), 6.43 (1H, s).

Reference Example 7

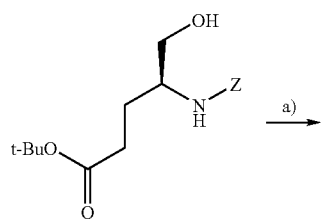

a)

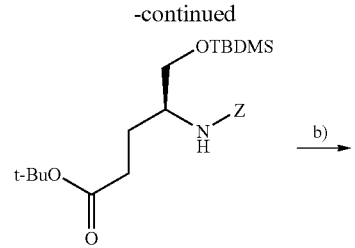

b)

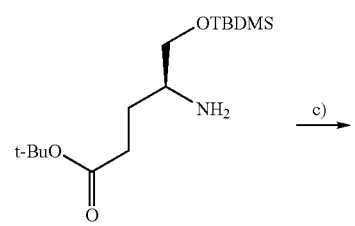

c)

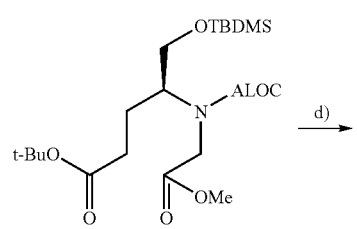

d)

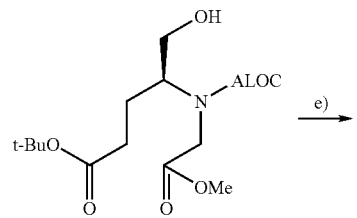

e)

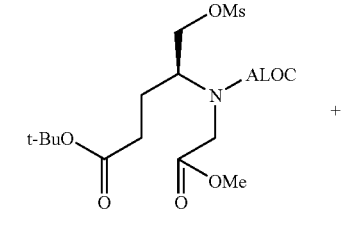

+

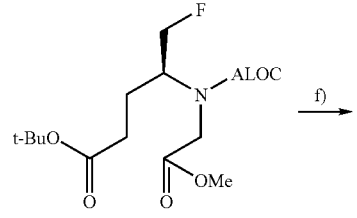

f)

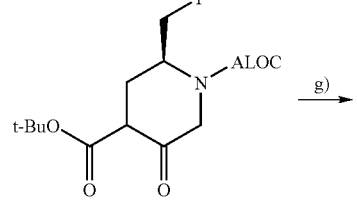

g)

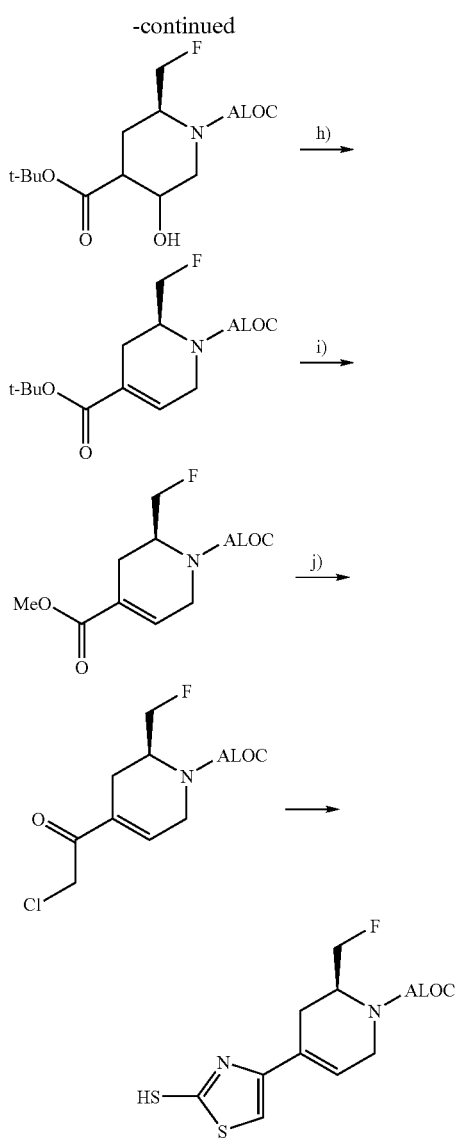

a) To a solution of tert-butyl (4S)-4-{[(benzyroxy)carbonyl]amino}-5-hydroxypentanoate (8.09 g, 25 mmol) in DMF (100 ml) were added at 0° C. tert-butyldimethylsilyl chloride (4.90 g, 32 mmol) and imidazole (2.21 g, 32 mmol), and the mixture was stirred for 30 minutes. The reaction mixture was poured into water and extracted three times with ethyl acetate. The organic layer was washed with water and then a saturated aqueous sodium chloride solution, dried over anhydrous sodium sulfate and the solvent was removed. The residue was purified with silica gel chromatography to give tert-butyl (4S)-4-{[(benzloxy)carbonyl]amino}-5-{[tert-butyl(dimethyl)silyl]oxy}pentanoate (10.4 g, 95%).

$^1$H NMR (300 MHz, CDCl$_3$) δ 0.04 (6H, s), 0.88 (9H, s), 1.43 (9H, s), 1.74–1.89 (2H, m), 2.28–2.33 (2H, m), 3.60–3.72 (3H, m), 4.95 (1H, d, J=9.2 Hz), 5.09 (2H, s), 7.27–7.37 (5H, m).

b) In the same manner as Reference example 2.b), by using tert-butyl (4S)-4-{[(benzyloxy)carbonyl]amino}-5-{[tert-butyl(dimethyl)silyl]oxy}pentanoate (10.4 g, 24 mmol), there was obtained tert-butyl (4S)-4-amino-5-{[tert-butyl(dimethyl)silyl]oxy}pentanoate (7.39 g).

c) In the same manner as Reference example 5.d), by using tert-butyl (4S)-4-amino-5-{[tert-butyl(dimethyl)silyl]oxy}pentanoate (7.39 g), there was obtained tert-butyl (4S)-4-[[(allyloxy)carbonyl](2-methoxy-2-oxoethyl)amino]-5-{[tert-butyl(dimethyl)silyl]oxy}pentanoate (8.79 g).

$^1$H NMR (300 MHz, CDCl$_3$) δ 0.05 (6H, s), 0.87 (9H, s), 1.44 (9H, s), 1.75–1.89 (2H, m), 2.28–2.36 (2H, m), 3.59–3.82 (5H, m), 3.98–4.01 (2H, m), 4.09–4.23 (1H, m), 4.54–4.63 (2H, m), 5.14–5.33 (2H, m), 5.80–5.59 (1H, m).

d) To a solution of tert-butyl (4S)-4-[[(allyloxy)carbonyl](2-methoxy-2-oxoethyl)amino]-5-{[tert-butyl(dimethyl)silyl]oxy}pentanoate (5.29 g, 1.2 mmol) in methanol (106 ml) was added p-toluenesulfonic acid monohydrate (0.22 g, 1.2 mmol) and the mixture was stirred for 30 minutes. To the mixture was further added p-toluenesulfonic acid monohydrate (0.22 g, 1.2 mmol) and the mixture was stirred for 1 hour. The reaction mixture was poured into water and extracted three times with ethyl acetate. The organic layer was washed with water and then a saturated aqueous sodium chloride solution, dried over anhydrous sodium sulfate and the solvent was removed. The residue was purified with silica gel chromatography to give tert-butyl (4S)-4-[[(allyloxy)carbonyl](2-methoxy-2-oxoethyl)amino]-5-hydroxypentanoate (3.7 g, 93%).

$^1$H NMR (300 MHz, CDCl$_3$) δ 1.44 (9H, s), 1.61–1.75 (2H, m), 2.21–2.30 (2H, m), 3.36–3.74 (3H, m), 3.78–3.80 (3H, m), 4.01–4.13 (1H, m), 4.24–4.36 (1H, m), 4.52–4.66 (2H, m), 5.17–5.37 (2H, m), 5.80–6.00 (1H, m).

e) To a solution of tert-butyl (4S)-4-[[(allyloxy)carbonyl](2-methoxy-2-oxoethyl)amino]-5-hydroxypentanoate (2.38 g, 6.9 mmol) in dichloromethane (72 ml) were added at 0° C. methanesulfonyl chloride (0.81 ml, 10.4 mmol) and triethylamine (1.45 ml, 10.4 mmol) and the mixture was stirred for 10 minutes. The reaction mixture was poured into water and extracted three times with ethyl acetate. The organic layer was washed with 1N hydrochloric acid, a saturated aqueous sodium hydrogen carbonate solution and a saturated aqueous sodium chloride solution in order, dried over anhydrous sodium sulfate and the solvent was removed in vacuo.

The residue was dissolved in acetonitrile (72 ml) and to the solution was added a solution of tetrabutylammonium fluoride in THF (1M, 13.8 ml, 13.8 mmol). The mixture was stirred at 80° C. for 30 minutes. The reaction mixture was poured into water and extracted three times with ethyl acetate. The organic layer was washed with 1N hydrochloric acid, a saturated aqueous sodium hydrogen carbonate solution and a saturated aqueous sodium chloride solution in order, dried over anhydrous sodium sulfate and the solvent was removed in vacuo. The residue was purified with silica gel chromatography to give tert-butyl (4S)-4-[[(allyloxy)carbonyl](2-methoxy-2-oxoethyl)amino]-5-[(methylsulfonyl)oxy]pentanoate (1.1 g, 38%) and tert-butyl (4S)-4-[[(allyloxy)carbonyl](2-methoxy-2-oxoethyl)amino]-5-fluoropentanoate (0.47 g, 20%).

tert-Butyl (4S)-4-[[(allyloxy)carbonyl](2-methoxy-2-oxoethyl)amino]-5-[(methylsulfonyl)oxy]pentanoate $^1$H NMR (300 MHz, CDCl$_3$) δ 1.44 (9H, s), 1.75–1.99 (2H, m), 2.32–2.37 (2H, m), 3.01 (3H, s), 3.74–3.75 (3H, m), 3.88–4.03 (2H, m), 4.20–4.42 (3H, m), 4.55–4.71 (2H, m), 5.19–5.35 (2H, m), 5.80–5.99 (1H, m).

tert-Butyl (4S)-4-[[(allyloxy)carbonyl](2-methoxy-2-oxoethyl)amino]-5-fluoropentanoate ¹H NMR (300 MHz, CDCl₃) δ 1.44 (9H, s), 1.75–1.99 (2H, m), 2.31–2.36 (2H, m), 3.69–3.77 (3H, m), 3.88–4.14 (2H, m), 4.20–4.73 (5H, m), 5.18–5.33 (2H, m), 5.80–5.99 (1H, m).

f) In the same manner as Reference example 2.b), by using tert-butyl (4S)-4-{[(allyloxy)carbonyl](2-methoxy-2-oxoethyl)amino}-5-fluoropentanoate (877 mg, 2.5 mmol), there was obtained 1-allyl 4-tert-butyl (2S)-2-(fluoromethyl)-5-oxo-1,4-piperidinedicarboxylate (460 mg, 55%).

¹H NMR(300 MHz, CDCl₃) δ 1.51 (9H, s), 2.34 (1H, d, J=15.7 Hz), 2.45–2.55 (1H, m), 3.64–3.80 (1H, m), 4.28–4.81 (6H, m), 5.20–5.35 (2H, m), 5.88–6.00 (1H, m), 12.2 (1H, s).

g) In the same manner as Reference example 5.f), by using 1-allyl 4-tert-butyl (2S)-2-(fluoromethyl)-5-oxo-1,4-piperidinedicarboxylate (460 mg, 1.5 mmol), there was obtained 1-allyl 4-tert-butyl (2S)-2-(fluoromethyl)-5-hydroxy-1,4-piperidinedicarboxylate (400 mg, 86%).

¹H NMR (300 MHz, CDCl₃) δ 1.48 (9H, s), 1.67–1.84 (1H, m), 2.09–2.30 (1H, m), 2.42–2.60 (1H, m), 2.70–2.88 (1H, m), 3.11–3.32 (1H, m), 3.70–3.83 (1H, m), 3.96–4.67 (6H, m), 5.21–5.34 (2H, m), 5.88–6.00 (1H, m).

h) In the same manner as Reference example 5.g), by using 1-allyl 4-tert-butyl (2S)-2-(fluoromethyl)-5-hydroxy-1,4-piperidinedicarboxylate (400 mg, 1.3 mmol), there was obtained 1-allyl 4-tert-butyl (2S)-2-(fluoromethyl)-3,6-dihydro-1,4(2 H)-pyridinedicarboxylate (272 mg, 72%).

¹H NMR (300 MHz, CDCl₃) δ 1.50 (9H, s), 2.46–2.58 (2H, m), 3.71–3.87 (1H, m), 4.22–4.91 (6H, m), 5.21–5.35 (2H, m), 5.88–6.01 (1H, m), 6.81 (1H, br s).

i) In the same manner as Reference example 6.g), by using 1-allyl 4-tert-butyl (2S)-2-(fluoromethyl)-3,6-dihydro-1,4(2 H)-pyridinedicarboxylate (272 mg, 0.91 mmol), there was obtained 1-allyl 4-methyl (2S)-2-(fluoromethyl)-3,6-dihydro-1,4(2 H)-pyridinedicarboxylate (183 mg, 78%).

¹H NMR (300 MHz, CDCl₃) δ 2.48–2.60 (2H, m), 3.77 (3H, s), 3.78–3.90 (1H, m), 4.24–4.91 (6H, m), 5.21–5.36 (2H, m), 5.89–6.01 (1H, m), 6.91 (1H, br s).

j) In the same manner as Reference example 2.d), by using 1-allyl 4-methyl (2S)-2-(fluoromethyl)-3,6-dihydro-1,4(2 H)-pyridinedicarboxylate (180 mg, 0.70 mmol), there was obtained allyl (2S)-4-(chloroacetyl)-2-(fluoromethyl)-3,6-dihydro-1(2 H)-pyridinecarboxylate (127 mg, 66%).

¹H NMR (300 MHz, CDCl₃) δ 2.44–2.53 (1H, m), 2.64 (1H, d, J=17.9 Hz), 3.87–4.00 (1H, m), 4.18–4.91 (8H, m), 5.21–5.36 (2H, m), 5.89–6.02 (1H, m), 6.85 (1H, br s).

k) In the same manner as Reference example 2.e), by using allyl (2S)-4-(chloroacetyl)-2-(fluoromethyl)-3,6-dihydro-1(2 H)-pyridinecarboxylate (127 mg, 0.46 mmol), there was obtained allyl (2S)-2-(fluoromethyl)-4-(2-sulfanyl-1,3-thiazol-4-yl)-3,6-dihydro-1(2 H)-pyridinecarboxylate (120 mg, 83%).

¹H NMR (300 MHz, CDCl₃) δ 2.37–2.46 (1H, m), 2.52–2.63 (1H, m), 3.79–3.84 (1H, m), 4.24–4.91 (6H, m), 5.22–5.37 (2H, m), 5.89–6.02 (1H, m), 6.13 (1H, br s), 6.45 (1H, s).

Reference Example 8

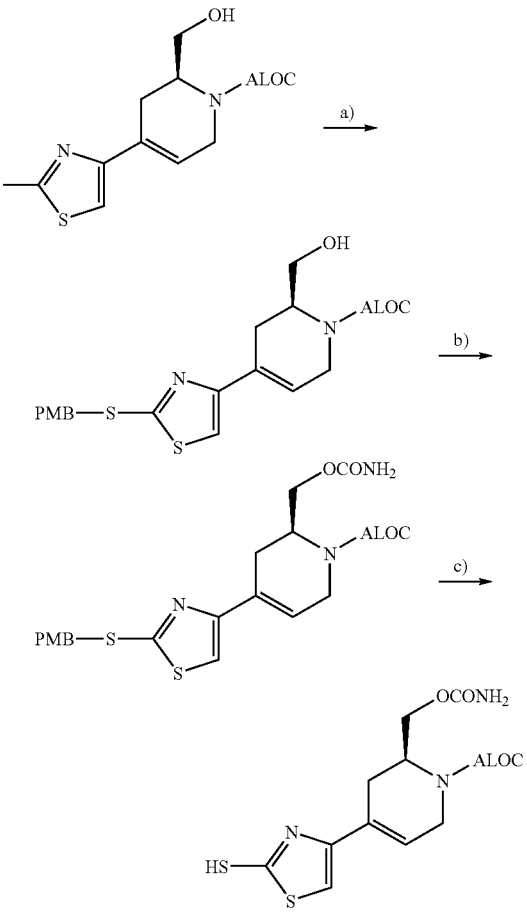

a) To a solution of allyl (2S)-2-(hydroxymethyl)-4-(2-mercapto-1,3-thiazol-4-yl)-3,6-dihydro-1(2 H)-pyridinecarboxylate (218 mg, 0.7 mmol) in THF (3 ml) were added at 0–5° C. 4-methoxybenzyl chloride (95 ml, 0.70 mmol) and triethylamine (98 ml, 0.7 mmol). The mixture was stirred for 3 hours and then at room temperature for 45 minutes. To the solution were added an aqueous sodium hydrogen carbonate solution and ethy acetate. The mixture was separated with a separating funnel. The organic layer was washed with a saturated aqueous sodium solution, dried over magnesium sulfate and the organic layer was removed in vacuo. The residue was purified with preparative TLC to give allyl (2S)-2-(hydroxymethyl)-4-{2-[(4-methoxybenzyl)sulfanyl]-1,3-thiazol-4-yl}-3,6-dihydro-1(2 H)-pyridinecarboxylate (150 mg, 50%).

¹H NMR (300 MHz, CDCl₃) δ 2.40 (1 H, d, J=16.7 Hz), 2.53–2.65 (1 H, m), 3.50–3.80 (3 H, m), 3.69 (3 H, s), 4.29–4.67 (2 H, m), 4.30 (2 H, s), 4.56 (2 H, d, J=5.5 Hz), 5.13 (1 H, dd, J=1.5, 10.4 Hz), 5.23 (1 H, dd, J=1.5, 17.2 Hz), 5.87(1 H, ddd, J=5.5, 10.4, 17.2 Hz), 6.56 (1 H, s), 6.75 (2 H, d, J=8.6 Hz), 6.81 (1 H, s), 7.21 (2 H, d, J=8.6 Hz).

b) To a solution of allyl (2S)-2-(hydroxymethyl)-4-{2-[(4-methoxybenzyl)sulfanyl]-1,3-thiazol-4-yl}-3,6-dihydro-1(2 H)-pyridinecarboxylate (75 mg, 0.17 mmol) in chloroform (1 ml) was added at 0–5° C. chlorosulfonylisocyanate (17 ml, 0.20 mmol). Three hours later, chlorosulfonylisocyanate (10 ml, 0.11 mmol) was further added thereto. Three hours later, to the mixture was added water and the mixture was stirred for 10 minutes. To the solution was added ethyl acetate and the solution was separated with a separating funnel. The organic layer was washed with a saturated aqueous sodium chloride solution, dried over magnesium sulfate and the organic layer was removed in vacuo. The residue was purified with preparative TLC to give allyl (2S)-2-{[(aminocarbonyl)oxy]methyl}-4-{2-[(4-methoxybenzyl)sulfanyl]-1,3-thiazol-4-yl}-3,6-dihydro-1(2 H)-pyridinecarboxylate (74.5 mg, 90%).

$^1$H NMR (300 MHz, CDCl$_3$) δ 2.37–2.45 (1 H, m), 2.61–2.78 (1 H, m), 3.72–4.95 (9 H, m), 3.77 (3 H, s), 4.38 (2 H, s), 5.21 (1 H, dd, J=1.3, 10.4 Hz), 5.31 (1 H, d, J=17.2 Hz), 5.95(1 H, ddd, J=5.5, 10.4, 17.2 Hz), 6.64 (1 H, brs), 6.83 (2 H, d, J=8.6 Hz), 6.88 (1 H, s), 7.29 (2 H, d, J=8.6 Hz).

c) Allyl (2S)-2-{[(aminocarbonyl)oxy]methyl}-4-{2-[(4-methoxybenzyl)sulfanyl]-1,3-thiazol-4-yl}-3,6-dihydro-1(2 H)-pyridinecarboxylate (74.5 mg, 0.16 mmol) and anisole (35 ml, 0.32 mmol) were dissolved in trifluoroacetic acid (6 ml). And then thioisonicotinamide (3 mg) was added to the solution and the mixture was refluxed at 80–90° C. Four hours later the solvent was removed in vacuo. To the residue was added an aqueous 1N NaOH solution to make the solution alkaline. To the solution were added ethyl acetate and hexane, and the solution was separated with a separating funnel. To the aqueous layer was added 6N hydrochloric acid and the solution was separated with a separating funnel by addition of ethyl acetate. The aqueous layer was extracted with ethyl acetate and the organic layer was washed twice with a saturated aqueous sodium chloride solution and dried over magnesium sulfate. The solvent was removed in vacuo to give allyl (2S)-2-{[(aminocarbonyl)oxy]methyl}-4-(2-mercapto-1,3-thiazol-4-yl)-3,6-dihydro-1(2 H)-pyridinecarboxylate (37.3 mg, 67%).

$^1$H NMR (300 MHz, CDCl$_3$) δ 2.21–2.70 (2 H, m), 3.73–4.65 (8 H, m), 4.80 (1 H, brs), 5.18 (1 H, d, J=10.3 Hz), 5.26 (1 H, d, J=17.2 Hz), 5.88(1 H, ddd, J=5.1, 10.3, 17.2 Hz), 6.22 (1 H, brs), 6.40 (1 H, s).

Reference Example 9

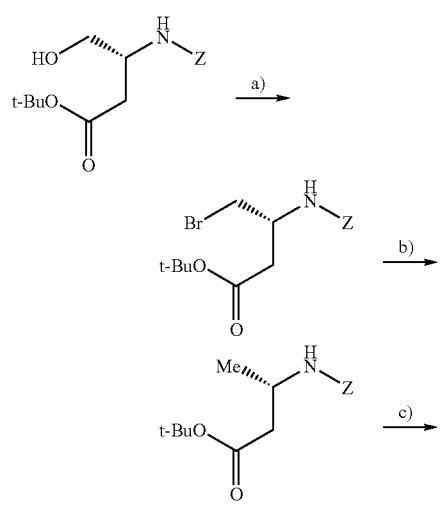

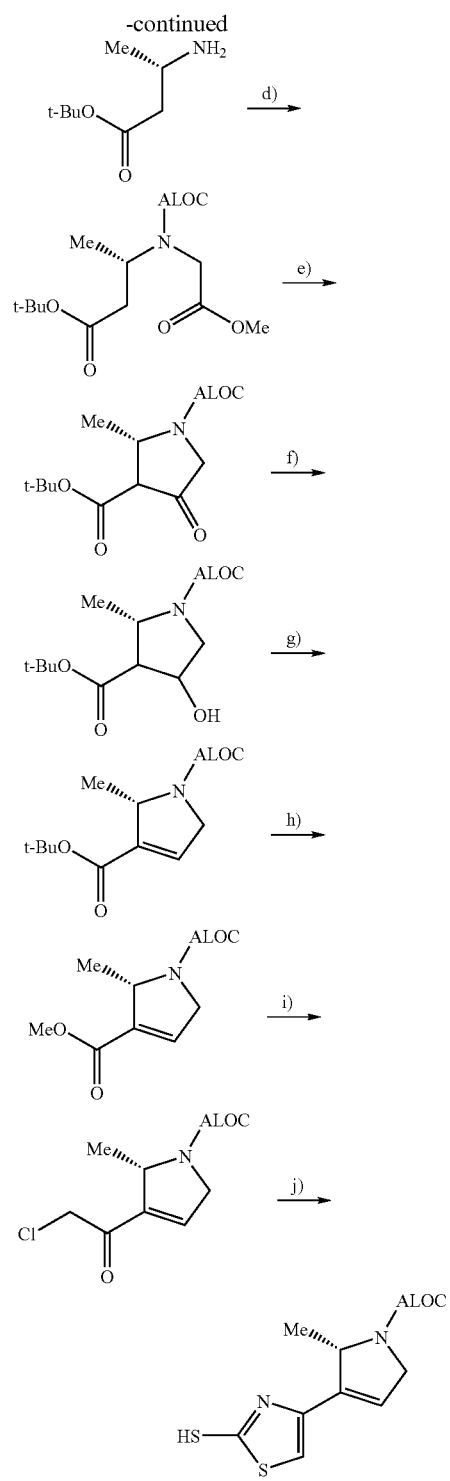

a) In the same manner as Reference example 5.a), by using tert-butyl (3R)-3-{[(benzyloxy)carbonyl]amino}-4-hydroxybutanoate (2.12 g, 6.9 mmol), there was obtained tert-butyl (3R)-3-{[(benzyloxy)carbonyl]amino}-4-bromobutanoate (2.09 g, 82%).

$^1$H NMR (300 MHz, CDCl$_3$) δ 1.44 (9H, s), 2.55–2.70 (2H, m), 3.47–3.64 (2H, m), 4.21–4.32 (1H, m), 5.03–5.18 (2H, m), 5.40 (1H, d, J=8.6 Hz), 7.27–7.43 (5H, m).

b) In the same manner as Reference example 5.b), by using tert-butyl (3R)-3-{[(benzyloxy)carbonyl]amino}-4-bromobutanoate (2.08 g, 5.6 mmol), there was obtained tert-butyl (3S)-3-{[(benzyloxy)carbonyl]amino}butanoate (1.45 g, 88%).

$^1$H NMR (300 MHz, CDCl$_3$) δ 1.22 (3H, d, J=6.8 Hz), 1.44 (9H, s), 2.34–2.51 (2H, m), 4.01–4.14 (1H, m), 5.01–5.17 (2H, m), 5.22–5.33 (1H, m), 7.28–7.36 (5H, m).

c) In the same manner as Reference example 2.b), by using tert-butyl (3S)-3-{[(benzyloxy)carbonyl]amino}butanoate (1.45 g, 3.7 mmol), there was obtained tert-butyl (3S)-3-aminobutanoate (586 mg, 75%).

$^1$H NMR (300 MHz, CDCl$_3$) δ 1.11 (3H, d, J=6.4 Hz), 1.46 (9H, s), 2.22 (1H, dd, J=15.5, 8.2 Hz), 2.32 (1H, dd, J=15.5, 4.7 Hz), 3.28–3.39 (1H, m).

d) In the same manner as Reference example 5.d), by using tert-butyl (3S)-3-aminobutanoate (586 mg, 4.9 mmol), there was obtained tert-butyl (3S)-3-[[(allyloxy)carbonyl](2-methoxy-2-oxoethyl)amino]butanoate (917 mg, 79%).

$^1$H NMR (300 MHz, CDCl$_3$) δ 1.22–1.28 (3H, m), 1.43 (9H, s), 2.09–2.64 (2H, m), 3.68–3.73 (5H, m), 4.42–4.55 (1H, m), 4.55–4.66 (2H, m), 5.15–5.38 (2H, m), 5.80–6.02 (1H, m).

e) In the same manner as Reference example 2.b), by using tert-butyl (3S)-3-[[(allyloxy)carbonyl](2-methoxy-2-oxoethyl)amino]butanoate (917 mg, 2.9 mmol), there was obtained 1-allyl 3-tert-butyl (2S)-2-methyl-4-oxo-1,3-pyrrolidinedicarboxylate (166 mg, 20%).

$^1$H NMR (300 MHz, CDCl$_3$) δ 1.31–1.51 (12H, m), 4.10–4.33 (2H, m), 4.55–4.72 (3H, m), 5.20–5.38 (2H, m), 5.86–6.03 (1H, m), 10.39 (1H, br s).

f) In the same manner as Reference example 5.f), by using 1-allyl 3-tert-butyl (2S)-2-methyl-4-oxo-1,3-pyrrolidinedicarboxylate (166 mg, 0.59 mmol), there was obtained 1-allyl 3-tert-butyl (2S)-4-hydroxy-2-methyl-1,3-pyrrolidinedicarboxylate (127 mg, 76%).

$^1$H NMR (300 MHz, CDCl$_3$) δ 1.43–1.50 (12H, m), 2.38–2.62 (2H, m), 3.27 (1H, dd, J=11.2, 7.0 Hz), 3.95 (1H, br s), 4.04 (1H, quint, J=6.4 Hz), 4.39–4.46 (1H, m), 4.55–4.64 (2H, m), 5.18–5.35 (2H, m), 5.87–6.00 (1H, m).

g) In the same manner as Reference example 5.g), by using 1-allyl 3-tert-butyl (2S)-4-hydroxy-2-methyl-1,3-pyrrolidinedicarboxylate (127 mg, 0.45 mmol), there was obtained 1-allyl 3-tert-butyl (2S)-2-methyl-2,5-dihydro-1H-pyrrole-1,3-dicarboxylate (120 mg, 100%).

$^1$H NMR (300 MHz, CDCl$_3$) δ 1.40–1.45 (3H, m), 1.50 (9H, s), 4.18–4.41 (2H, m), 4.60–4.70 (2H, m), 4.73–4.86 (1H, m), 5.20–5.38 (2H, m), 5.89–6.03 (1H, m), 6.60–6.67 (1H, m).

h) In the same manner as Reference example 6.g) by using 1-allyl 3-tert-butyl (2S)-2-methyl-2,5-dihydro-1H-pyrrole-1,3-dicarboxylate (120 mg, 0.45 mmol), there was obtained 1-allyl 3-methyl (2S)-2-methyl-2,5-dihydro-1H-pyrrole-1,3-dicarboxylate (62 mg, 61%).

$^1$H NMR (300 MHz, CDCl$_3$) δ 1.41–1.47 (3H, m), 3.78 (3H, s), 4.21–4.45 (2H, m), 4.60–4.71 (2H, m), 4.80–4.90 (1H, m), 5.20–5.38 (2H, m), 5.89–6.02 (1H, m), 6.69–6.77 (1H, m).

i) In the same manner as Reference example 2.d), by using 1-allyl 3-methyl (2S)-2-methyl-2,5-dihydro-1H-pyrrole-1,3-dicarboxylate (62 mg, 0.28 mmol), there was obtained allyl (2S)-3-(chloroacetyl)-2-methyl-2,5-dihydro-1H-pyrrole-1-carboxylate (37 mg, 55%).

$^1$H NMR (300 MHz, CDCl$_3$) δ 1.39–1.44 (3H, m), 4.31–4.58 (4H, m), 4.60–4.71 (2H, m), 4.89–5.00 (1H, m), 5.21–5.38 (2H, m), 5.89–6.02 (1H, m), 6.67–6.87 (1H, m).

j) In the same manner as Reference example 2.e), by using allyl (2S)-3-(chloroacetyl)-2-methyl-2,5-dihydro-1H-pyrrole-1-carboxylate (37 mg, 0.15 mmol), there was obtained allyl (2S)-2-methyl-3-(sulfanyl-1,3-thiazol-4-yl)-2,5-dihydro-1H-pyrrole-1-carboxylate (36 mg, 84%).

$^1$H NMR (300 MHz, CDCl$_3$) δ 1.42–1.46 (3H, m), 4.26–4.50 (2H, m), 4.56–4.72 (2H, m), 4.87–5.00 (1H, m), 5.21–5.38 (2H, m), 5.88–6.03 (1H, m), 6.25–6.45 (2H, m).

Reference Example 10

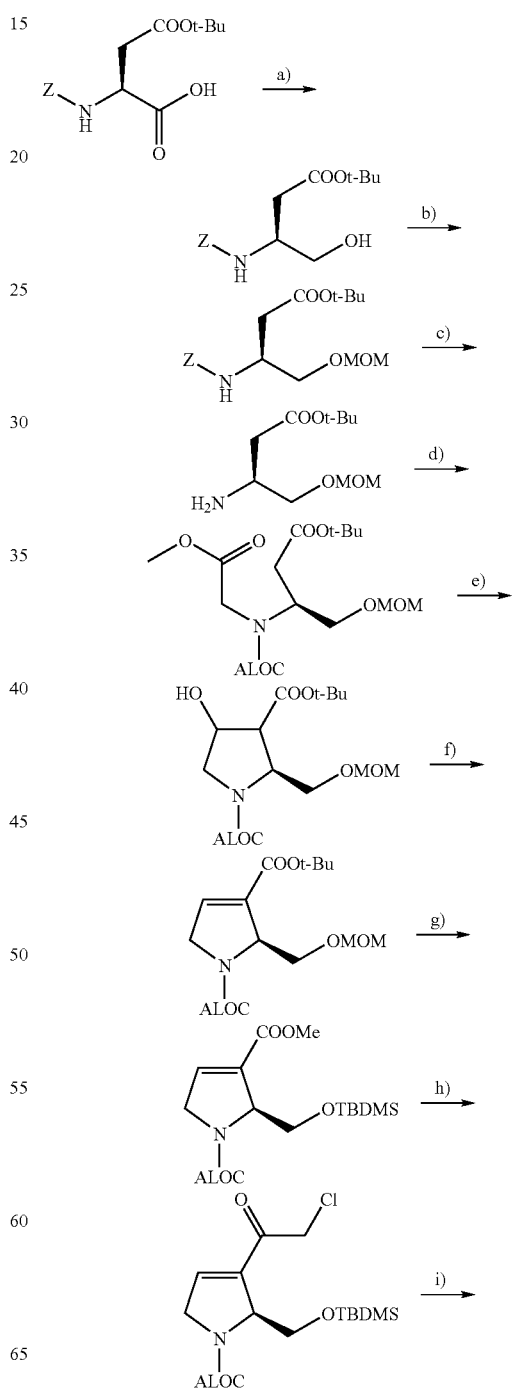

-continued

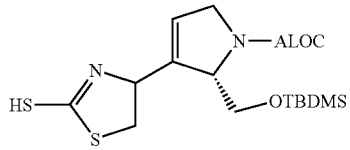

a) To a solution of N-(benzyloxy)carbonyl-L-asparagic acid 4-tert-butyl ester (35 g, 108 mol) in THF (500 ml) was added at −30° C. triethylamine (18 ml, 130 mmol), and then ethyl chloroformate (12.5 ml, 130 mmol), and the mixture was stirred at the same temperature. To the mixture was dropped at −30° C. a solution of sodium borohydride (12.3 g, 324 mmol) in water and the mixture was stirred for 30 minutes. The mixture was raised to 0° C. and then stirred for 30 minutes. To the reaction mixture was added water and the mixture was extracted three times with ethyl acetate. The organic layer was washed with a saturated aqueous sodium hydrogen carbonate solution and then a saturated aqueous sodium chloride solution, and was dried over anhydrous sodium sulfate. The solvent was removed in vacuo and the residue was purified with silica gel (210 g) chromatography (hexane/ethyl acetate=3/2→1/1) to give tert-butyl (3S)-3-{[(benzyloxy)carbonyl]amino}-4-hydroxybutanoate (27.1 g, 81%)

$^1$H NMR (300 MHz, CDCl$_3$) δ 1.41 (9 H, s), 2.40–2.62 (3 H, m), 3.69 (2 H, d, J=4.6 Hz), 3.97–4.07 (1 H, m), 5.08 (2 H, s), 5.48 (1 H, brs), 7.27–7.37 (5 H, m).

b) To a solution of tert-butyl (3S)-3-{[(benzyloxy)carbonyl]amino}-4-hydroxybutanoate (14.26 g, 46.1 mmol) in dichloromethane (190 ml) were added under ice cooling 4-dimethylaminopyridine (0.28 g, 2.3 mmol), diisopropylethylamine (24 ml, 138 mmol) and chloromethyl methyl ether (105 ml, 138 mmol). The mixture was raised to room temperature. Twelve hours later, to the mixture were added ice water and 1N hydrochloric acid under cooling in an ice bath to adjust pH to about 3. To the mixture was added a saturated aqueous sodium chloride solution and the solution was separated with a separating funnel. The organic layer was washed once with water and twice with a saturated aqueous sodium chloride solution and dried over magnesium sulfate. The solvent was removed in vacuo to give tert-butyl (3S)-3-{[(benzyloxy)carbonyl]amino}-4-(methoxymethoxy)butanoate (16.4 g, 100%).

$^1$H NMR (300 MHz, CDCl$_3$) δ 1.41 (9 H, s), 2.53 (2 H, d, J=6.1 Hz), 3.32 (3 H, s), 3.54 (1 H, dd, J=5.0, 9.5 Hz), 3.63 (1 H, dd, J=3.8, 9.5 Hz), 4.12–4.23 (1 H, m), 4.58 (2 H, s), 5.08 (2 H, s), 5.41 (1 H, d, J=8.6 Hz), 7.27–7.38 (5 H, m).

c) To a solution of tert-butyl(3S)-3-{[(benzyloxy)carbonyl]amino}-4-(methoxymethoxy)butanoate (16.3 g, 53 mmol) in methanol (150 ml) was added 10% Pd—C (3.3 g) and the mixture was stirred for 6 hours at a hydrogen atmosphere. Additional 10% Pd—C (0.75 g) was added thereto and the mixture was stirred for 1.5 hours. After removal of catalyst by filtration, the solvent was removed in vacuo to give tert-butyl(3S)-3-amino-4-(methoxymethoxy)butanoate (9.7 g, 84%).

$^1$H NMR (300 MHz, CDCl$_3$) δ1.43 (9 H, s), 2.42–2.57 (2 H, m), 3.28–3.65 (5 H, m), 3.35 (3 H, s), 4.63 (2 H, s).

d) To a solution of tert-butyl(3S)-3-amino-4-(methoxymethoxy)butanoate (9.7 g, 44 mmol) and diisopropylethylamine (11.5 ml, 66 mmol) in methanol (300 ml) was dropped at room temperature methyl bromoacetate (6.2 ml, 66 mmol). The solution was stirred for 1 hour at 60° C. Additional methyl bromoacetate (2.1 ml, 22 mmol) and diisopropylethylamine (3.8 ml, 22 mmol) were added thereto and the mixture was stirred for 1 hour, cooled to room temperature and the solvent was removed. The residue was dissolved in chloroform (100 ml) and thereto were dropped at 0° C. allyl chloroformate (94 ml, 88 mmol) and then diisopropylethylamine (15.5 ml, 88 mmol). The mixture was stirred at the same temperature for 1 hour and at room temperature for 13 hours. To the reaction mixture was added water under cooling in an ice bath and the mixture was extracted three times with chloroform. The organic layer was washed with a saturated aqueous sodium chloride solution and dried over magnesium sulfate. The residue was purified with silica gel (230 g) chromatography (hexane/ethyl acetate=2/1→1/1) to give tert-butyl (3S)-3-[[(allyloxy)carbonyl](2-methoxy-2-oxoethyl)amino]-4-(methoxymethoxy)butanoate (11.7 g, 71%).

$^1$H NMR (300 MHz, CDCl$_3$) δ 1.43 (9 H, s), 2.54–2.75 (2 H, m), 3.33 (3 H, s), 3.54–3.82 (5 H, m), 4.04–4.09 (2 H, m), 4.50–4.71 (5 H, m), 5.15–5.38 (2 H, m), 5.80–6.02 (1 H, m).

e) To a suspension of potassium tert-butoxide (3.14 g, 28 mmol) in THF (130 ml) heated at 60° C. was added tert-butyl (3S)-3-[[(allyloxy)carbonyl](2-methoxy-2-oxoethyl)amino]-4-(methoxymethoxy)butanoate (5.24 g, 14 mmol) in THF (50 ml) and the mixture was stirred for 5 minutes. After cooled to 0° C. the reaction mixture was poured into diluted hydrochloric acid (after confirming that pH was about 3), a saturated aqueous sodium chloride solution was added thereto and the mixture was extracted three times with ethyl acetate. The organic layer was washed with water, then a saturated aqueous sodium chloride solution and dried over magnesium sulfate. The solvent was removed in vacuo. To a solution of the residue (4.17 g) in methanol (100 ml) were added acetic acid (1.45 ml, 25 mmol) and sodium cyanoborohydride (1.06 g, 17 mmol) and the mixture was stirred at room temperature for 30 minutes. The solvent was removed in vacuo. The residue was purified with silica gel (60 g) chromatography (hexane/ethyl acetate=2/1→1/1) to give 1-allyl 3-tert-butyl (2S)-4-hydroxy-2-[(methoxymethoxy)methyl]-1,3-pyrrolidinedicarboxylate (1.47 g, 30%).

$^1$H NMR (300 MHz, CDCl$_3$) δ 1.46 (9 H, s), 2.98 (0.6 H, brs), 3.02 (0.4 H, brs), 3.33 (3 H, s), 3.36 (3 H, s), 3.46–3.80 (3 H, m), 4.02–4.70 (8 H, m), 5.22 (1 H, d, J=10.4 Hz), 5.31 (1 H, d, J=17.2 Hz), 5.94 (1 H, ddd, J=5.5, 10.4, 17.2 Hz).

f) To a solution of 1-allyl 3-tert-butyl (2S)-4-hydroxy-2-[(methoxymethoxy)methyl]-1,3-pyrrolidinedicarboxylate (1.47 g, 4.26 mmol) in dichloromethane (20 ml) were added at −30° C. methanesulfonyl chloride (0.50 ml, 6.5 mmol), triethylamine (1.2 ml, 8.6 mmol) and 4-dimethylaminopyridine (52 mg, 0.43 mmol) and the mixture was stirred at 0° C. for 75 minutes. The reaction mixture was poured into diluted hydrochloric acid and the mixture was extracted three times with chloroform. The organic layer was washed with a saturated aqueous sodium chloride solution and dried over anhydrous sodium sulfate. The solvent was removed in vacuo. The residue was dissolved in dicholomethane (10 ml) and the solution was cooled to 0° C. and thereto was added DBU (0.95 ml, 6.4 mmol). The mixture was raised to room temperature and stirred just for 30 minutes. The reaction mixture was poured into diluted hydrochloric acid and the solution was extracted three times with ethyl acetate. The organic layer was washed with water and then a saturated aqueous sodium chloride solution and dried over anhydrous sodium sulfate. The solvent was removed in vacuo. The residue was purified with silica gel (30 g) chromatography (hexane/ethyl acetate=4/1→2/1) to give 1-allyl 3-tert-butyl (2S)-2-[(methoxy)methyl]-2,5-dihydro-1H-pyrrole-1,3-dicarboxylate (0.92 g, 66%).

$^1$H NMR (300 MHz, CDCl$_3$) δ 1.48 (9 H, s), 3.25 (3 H, s), 3.91–4.42 (4 H, m), 4.50–4.65 (4 H, m), 4.79–4.87 (1 H, m), 5.20 (1 H, d, J=10.4 Hz), 5.29 (1 H. d, J=17.2 Hz), 5.93 (1 H, ddd, J=5.5, 10.4, 17.2 Hz), 6.72–6.78 (1 H, m).

g) To a solution of 1-allyl 3-tert-butyl (2S)-2-[(methoxymethoxy)methyl]-2,5-dihydro-1H-pyrrole-1,3-dicarboxylate (296 mg, 0.90 mmol) in methanol (2 ml) was added hydrochloric acid/methanol(5 ml) and the mixture was stirred overnight. To the solution was added toluene and the solvent was removed in vacuo. To the residue were added methanol and toluene and the solvent was again removed in vacuo. The residue was dissolved in THF (8 ml) and thereto were added at 0–5° C. 2,6-lutidine (0.84 ml, 7.2 mmol) and tert-butyldimethylsilyltriflate (0.83 ml, 3.6 mmol). The mixture was stirred at room temperature for 1 hour and thereto was added at 0–5° C. a solution of trimethylsilyldiazomethane in hexane (2M, 0.45 ml, 0.90 mmol). Thirty minutes later the mixture was raised to room temperature and stirred for 30 minutes. Thirty minutes later to the mixture were added 1N hydrochloric acid and a saturated aqueous sodium chloride solution, and the mixture was separated with a separating funnel. The organic layer was dried over magnesium sulfate, and the solvent was removed in vacuo. The residue was purified with silica gel (26 g) chromatography (hexane/ethyl acetate=1/5) to give 1-allyl 3-methyl (2S)-2-({[tert-butyl(dimethyl)silyl]oxy}methyl)-2,5-dihydro-1H-pyrrole-1,3-dicarboxylate (71 mg, 22%).

$^1$H NMR (300 MHz, CDCl$_3$) δ –0.08 (3 H, s), –0.07 (3 H, s), 0.78 (9 H, s), 3.75 (3 H, s), 3.84–4.42 (4 H, m), 4.58–4.64 (2 H, m), 4.77–4.84 (1 H, m), 5.18–5.23 (1 H, m), 5.29 (1 H, dt, J=1.7, 17.2 Hz), 5.92(1 H, ddd, J=5.5, 10.4, 17.2 Hz), 6.77–6.84 (1 H, m).

h) To a solution of 1-allyl 3-methyl (2S)-2-({[tert-butyl(dimethyl)silyl]oxy}methyl)-2,5-dihydro-1H-pyrrole-1,3-dicarboxylate (0.20 g, 0.55 mmol) and bromochloromethane (54 ml, 0.83 mmol) in THF (6 ml) was added at –90 to –80° C. a solution of n-butyllithium in hexane (1.59M, 0.52 ml, 0.83 mmol) over a 10 minutes period. After stirring for additional 30 minutes, the reaction mixture was poured into a mixture of ice (10 g) and phosphate buffer (pH 7.0, 10 ml). After ethyl acetate was added and the mixture was separated with a separating funnel, the aqueous layer was extracted twice with ethyl acetate. The organic layer was washed with a saturated aqueous sodium chloride, dried over magnesium sulfate and the organic solvent was removed under reduced pressure. The residue was purified by silica gel (27 g) chromatography to give allyl (2S)-2-({[tert-butyl(dimethyl)silyl]oxy}methyl)-3-(chloroacetyl)-2,5-dihydro-1H-pyrrole-1-carboxylate (163 mg, 79%).

$^1$H NMR (300 MHz, CDCl$_3$) δ –0.08 (3 H, s), –0.06 (3 H, s), 0.78 (9 H, s), 3.86–4.13 (2 H, m), 4.23–4.63 (6 H, m), 4.87–4.96 (1 H, m), 5.21 (1 H, dd, J=2.9, 10.4 Hz), 5.29 (1 H, d, J=17.0 Hz), 5.92(1 H, ddd, J=5.7, 10.4, 17.0 Hz), 6.79 (0.5 H, brs), 6.85 (0.5 H, brs).

i) To a solution of allyl (2S)-2-({[tert-butyl(dimethyl)silyl]oxy}methyl)-3-(chloroacetyl)-2,5-dihydro-1H-pyrrole-1-carboxylate (163 mg, 0.44 mmol) in methanol (2 ml) were added at 0–5° C. thioisonicotinamide (2 mg) and ammonium dithiocarbamate (72 mg, 0.65 mmol). The reaction mixture was raised to room temperature and stirred for 40 minutes. The mixture was stirred at 65–70° C. for 30 minutes and then at 75–85° C. for 1 hour. The solvent was removed in vacuo. To the solution was added ethyl acetate and the solution was separated with a separating funnel. The aqueous layer was extracted with ethyl acetate. The organic layer was washed twice with a saturated aqueous sodium chloride solution and dried over magnesium sulfate. The solvent was removed in vacuo and the residue was recrystallized from ethyl acetate/hexane to give allyl (2S)-2-({[tert-butyl(dimethyl)silyl]oxy}methyl)-3-(2-mercapto-1,3-thiazol-4-yl)-2,5-dihydro-1H-pyrrole-1-carboxylate (70.5 mg, 39%).

$^1$H NMR (300 MHz, DMSO-d$_6$) δ –0.15 (3 H, s), –0.12 (3 H, s), 0.76 (9 H, s), 3.90–4.13 (3 H, m), 4.23–4.34 (1 H, m), 4.49–4.70 (2 H, m), 4.88–4.95 (1 H, m), 5.16–5.34 (2 H, m), 5.86–5.99(1 H, m), 6.56 (0.6 H, brs), 6.59 (0.4 H, brs), 7.06 (1 H, s).

Reference Example 11

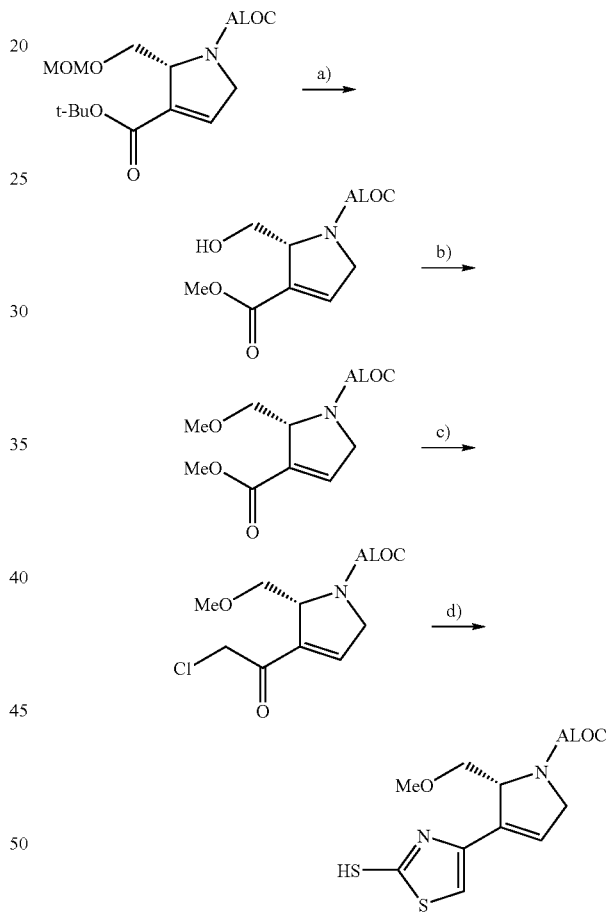

a) In the same manner as Reference example 6.g), by using 1-allyl 3-tert-butyl (2R)-2-[(methoxymethoxy)methyl]-2,5-dihydro-1H-pyrrole-1,3-dicarboxylate (470 mg, 1.4 mmol), there was obtained 1-allyl 3-methyl (2R)-2-(hydroxymethyl)-2,5-dihydro-1H-pyrrole-1,3-dicarboxylate (234 mg, 68%).

$^1$H NMR (300 MHz, CDCl$_3$) δ 3.70–4.59 (7H, m), 4.62–4.67 (2H, m), 4.82–5.01 (1H, m), 5.22–5.38 (2H, m), 5.89–6.02 (1H, m), 6.82–6.92 (1H, m).

b) To a solution of 1-allyl 3-methyl (2R)-2-(hydroxymethyl)-2,5-dihydro-1H-pyrrole-1,3-dicarboxylate (234 mg, 0.97 mmol) in DMF (4.7 ml) was added at 0° C. sodium hydride (60% suspension in oil, 39 mg, 0.98 mmol) and the mixture was stirred for 30 minutes. Then thereto was added at 0° C. methyl iodide (0.95 ml, 9.7 mmol) and the mixture was stirred at room temperature for 1 hour. After cooled to 0° C., the reaction mixture was poured into ice water and extracted three times with ethyl acetate. The organic layer was washed with water and then a saturated aqueous sodium chloride solution and dried over anhydrous sodium sulfate. The solvent was removed in vacuo and the residue was purified with silica gel chromatography to give 1-allyl 3-methyl (2R)-2-(methoxymethyl)-2,5-dihydro-1H-pyrrole-1,3-dicarboxylate (55 mg, 15%).

$^1$H NMR (300 MHz, CDCl$_3$) δ 3.29–3.30 (3H, m), 3.70–3.97 (4H, m), 4.22–4.49 (2H, m), 4.52–4.72 (3H, m), 4.86–4.91 (1H, m), 5.21–5.38 (2H, m), 5.89–6.02 (1H, m), 6.82–6.94 (1H, m).

c) In the same manner as Reference example 2.d), by using 1-allyl 3-methyl (2R)-2-(methoxymethyl)-2,5-dihydro-1H-pyrrole-1,3-dicarboxylate (55 mg, 0.22 mmol) there was obtained allyl (2R)-3-(chloroacetyl)-2-(methoxymethyl)-2,5-dihydro-1H-pyrrole-1-carboxylate (38 mg, 64%).

$^1$H NMR (300 MHz, CDCl$_3$) δ 3.25–3.26 (3H, m), 3.70–3.90 (2H, m), 4.31–4.71 (6H, m), 4.95–5.01 (1H, m), 5.21–5.36 (2H, m), 5.89–6.02 (1H, m), 6.81–6.88 (1H, m).

d) In the same manner as Reference example 2.e), by using allyl (2R)-3-(chloroacetyl)-2-(methoxymethyl)-2,5-dihydro-1H-pyrrole-1-carboxylate (38 mg, 0.22 mmol), there was obtained allyl (2R)-2-(methoxymethyl)-3-(2-sulfanyl-1,3-thiazol-4-yl)-2,5-dihydro-1H-pyrrole-1-carboxylate (37 mg, 85%).

$^1$H NMR (300 MHz, CDCl$_3$) δ 3.44–3.45 (3H, m), 3.53–3.71 (1H, m), 3.87–3.95 (1H, m), 4.20–4.46 (2H, m), 4.63–4.70 (2H, m), 4.86–4.96 (1H, m), 5.22–5.39 (2H, m), 5.89–6.03 (1H, m), 6.29–6.34 (1H, m), 6.62 (1H, s).

Reference Example 12

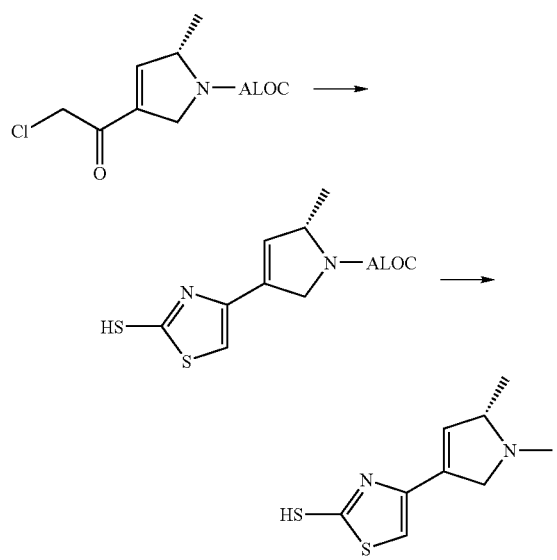

Allyl (2S)-2-methyl-4-(2-sulfanyl-1,3-thiazol-4-yl)-2,5-dihydro-1H-pyrrole-1-carboxylate prepared from allyl (2S)-4-(chloroacetyl)-2-methyl-2,5-dihydro-1H-pyrrole-1-carboxylate (331 mg, 1.36 mmol) in the same manner as Reference example 2.e) was dissolved in THF (3 ml). The solution was dropped into a suspension of LiAlH$_4$ (103 mg, 2.71 mmol) in THF (3 ml) at 0° C. and the mixture was stirred at room temperature for 10 minutes. Thereto was added methanol and the mixture was filtered through a pad of silica gel. The solvent was removed in vacuo and the residue was purified with silica gel chromatography to give 4-[((5S)-1,5-dimethyl-2,5-dihydro-1H-pyrrol-3-yl]-1,3-thiazole-2-thiol (224 mg, 77%).

$^1$H NMR (300 MHz, CDCl$_3$) δ 1.24 (3H, d, J=6.4 Hz), 2.49 (3H, s), 3.43–3.59 (2H, m), 3.97–4.03 (1H, m), 5.89 (1H, br s), 6.30 (1H, s).

Reference Example 13

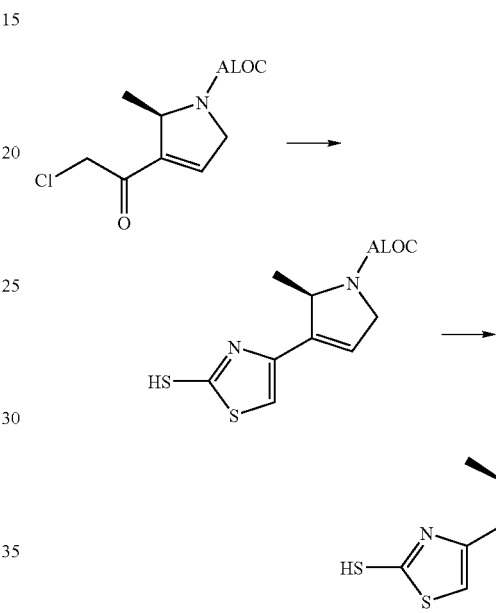

In the same manner as Reference example 12, by using allyl (2R)-3-(chloroacetyl)-2-methyl-2,5-dihydro-1H-pyrrole-1-carboxylate (243 mg, 1.00 mmol) there was obtained 4-[(2R)-1,2-dimethyl-2,5-dihydro-1H-pyrrol-3-yl]-1,3-thiazole-2-thiol (103 mg, 49%).

$^1$H NMR (300 MHz, CDCl$_3$—CD$_3$OD) δ 1.33 (3H, d, J=6.4 Hz), 2.57 (3H, s), 6.20–6.22 (1H, m), 6.43 (1H, s).

Reference Example 14

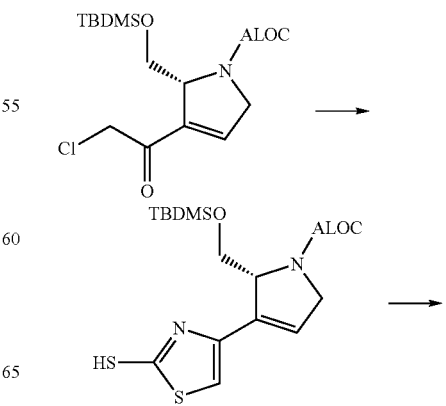

-continued

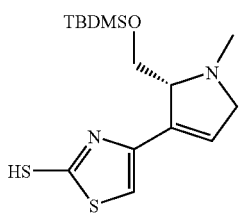

In the same manner as Reference example 12, by using allyl (2R)-2-({[tert-butyl(dimethyl)silyl]oxy}methyl)-3-(chloroacetyl)-2,5-dihydro-1H-pyrrole-1-carboxylate (270 mg, 0.72 mmol), there was obtained 4-[(2R)-2-({[tert-butyl(dimethyl)silyl]oxy}methyl)-1-methyl-2,5-dihydro-1H-pyrrole-3-yl]-1,3-thiazole-2-thiol (97 mg, 39%).

$^1$H NMR (300 MHz, CDCl$_3$) δ 0.24 (3H, s), 0.25 (3H, s), 0.97 (9H, s), 2.51 (3H, s), 3.29–3.37 (1H, m), 3.55–3.61 (1H, m), 3.67–3.73 (1H, m), 3.80–3.96 (2H, m), 6.18–6.20 (1H, m), 6.61 (1H, s).

Reference Example 15

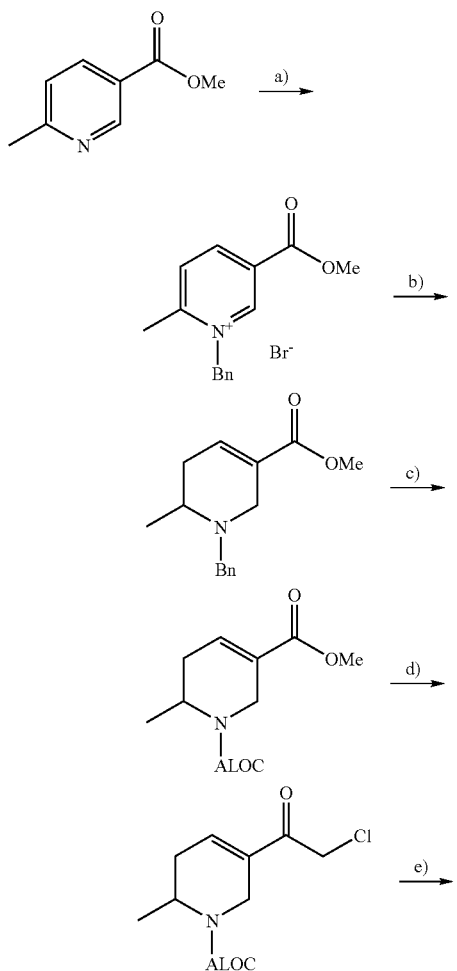

-continued

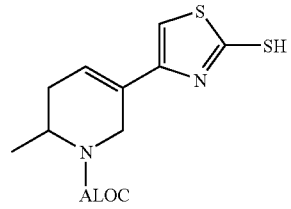

a) To a solution of 6-methylnicotinic acid methyl ester (10 g, 66 mmol) in ethyl acetate (70 ml) was added benzyl bromide (9.5 ml, 80 mmol) and the mixture was stirred at 60–70° C. for 3 hours. The mixture was cooled to room temperature and was filtered. The residue was washed twice with ethyl acetate/hexane and dried in vacuo to give 1-benzyl-5-(methoxycarbonyl)-2-methylpyridinium bromide (1.59 g, 7%).

$^1$H NMR (300 MHz, CDCl$_3$) δ 3.12 (3 H, s), 3.98 (3 H, s), 6.28 (2 H, s), 7.30–7.42 (5 H, m), 8.13 (1 H, d, J=8.3 Hz), 8.78 (1 H, dd, J=1.8, 8.3 Hz), 9.44 (1 H, d, J=1.8 Hz).

b) To a suspension of 1-benzyl-5-(methoxycarbonyl)-2-methylpyridinium bromide (3.2 g, 9.9 mmol) in methanol (50 ml) was added at −70° C. a solution of sodium borohydride (0.75 g, 20 mmol) in water (10 ml). The mixture was raised to 0° C. and stirred for 20 minutes. The reaction mixture was added to ethyl acetate/brine and the mixture was separated with a separating funnel. The aqueous layer was extracted twice with ethyl acetate. The organic layer was washed with a saturated aqueous sodium chloride solution, dried over magnesium sulfate and the solvent was removed in vacuo. The residue (2.34 g) was purified with silica gel (60 g) chromatography (hexane/ethyl acetate=4/1) to give methyl 1-benzyl-6-methyl-1,2,5,6-tetrahydro-3-pyridinecarboxylate (2.05 g, 84%).

$^1$H NMR (300 MHz, CDCl$_3$) δ 1.03 (3 H, d, J=6.6 Hz), 1.97–2.08 (1 H, m), 2.42–2.54 (1 H, m), 2.87–2.97 (1 H, m), 3.21–3.24 (2 H, m), 3.53 (1 H, d, J=13.4 Hz), 3.68 (3 H, s), 3.75 (1 H, d, J=13.4 Hz), 6.94–6.98 (1 H, m), 7.18–7.35 (5 H, m).

c) To a solution of methyl 1-benzyl-6-methyl-1,2,5,6-tetrahydro-3-pyridinecarboxylate (2.05 g, 8.36 mmol) in THF (15 ml) were added at 0–5° C. allyl chloroformate (1.1 ml, 10.4 mmol). The mixture was immediately raised to room temperature and stirred for 18 hours. After cooled to 0–5° C. a saturated aqueous sodium hydrogen carbonate and ethy acetate were added thereto and the mixture was separated with a separating funnel. The aqueous layer was extracted twice with ethyl acetate. The organic layer was washed with a saturated aqueous sodium chloride solution, dried over magnesium sulfate and the solvent was removed in vacuo. The residue was purified with silica gel (55 g) chromatography (hexane/ethyl acetate=6/1→4/1) to give 1-allyl 3-methyl 6-methyl-5,6-dihydro-1,3(2 H)-pyridinedicarboxylate (1.42 g, 71%).

$^1$H NMR (300 MHz, CDCl$_3$) δ 1.09 (3 H, d, J=7.0 Hz), 2.02–2.12 (1 H, m), 2.50–2.63 (1 H, m), 3.65–3.78 (1 H, m), 3.75 (3 H, s), 4.50–4.65 (4 H, m), 5.20 (1 H, d, J=10.3 Hz), 5.29 (1 H, d, J=17.0 Hz), 5.93 (1 H, ddd, J=5.0, 10.3, 17.0 Hz), 6.97–7.03 (1 H, m).

d) To a solution of 1-allyl 3-methyl 6-methyl-5,6-dihydro-1,3(2 H)-pyridinedicarboxylate (0.44 g, 1.85 mmol) and bromochloromethane (0.18 ml, 2.8 mmol) in THF (15 ml) was added −90 to −80° C. a solution of n-butyllithium in hexane (1.59M, 1.75 ml, 2.8 mmol) over a 15 minute period. After stirring for additional 40 minutes, the reaction mixture was poured into a mixture of ice (10 g) and phosphate buffer (pH 7.0, 10 ml). After ethyl acetate was added and the mixture was separated with a separating funnel, the aqueous layer was extracted twice with ethyl acetate. The organic layer was washed with a saturated aqueous sodium chloride, dried over magnesium sulfate and the organic solvent was removed under reduced pressure. The residue was purified by silica gel (25 g) chromatography to give allyl 5-(chloroacetyl)-2-methyl-3,6-dihydro-1(2 H)-pyridinecarboxylate (253 mg, 53%).

$^1$H NMR (300 MHz, CDCl$_3$) δ 1.09 (3 H, d, J=7.0 Hz), 2.10–2.22 (1 H, m), 2.60–2.74 (1 H, m), 3.67–3.78 (1 H, m), 4.40 (2 H, s), 4.55–4.70 (4 H, m), 5.20 (1 H, d, J=10.4 Hz), 5.28 (1 H, d, J=17.0 Hz), 5.92 (1 H, ddd, J=5.0, 10.4, 17.0 Hz), 6.92–6.98 (1 H, m).

e) To a solution of allyl 5-(chloroacetyl)-2-methyl-3,6-dihydro-1(2 H)-pyridinecarboxylate (0.50 g, 1.94 mmol) in methanol (10 ml) were added at 0–5° C. thioisonicotinamide (5 mg) and ammonium dithiocarbamate (0.32 g, 2.9 mmol). The reaction mixture was raised to room temperature, stirred for 10 minutes and then stirred at 60–70° C. for 50 minutes. The solvent was removed in vacuo. To the residue was added an aqueous 1N NaOH solution to made alkaline. To the solution were added ethyl acetate and hexane and the solution was separated with a separating funnel. After 6N hydrochloric acid was added to the aqueous layer and ethyl acetate was added thereto, the mixture was again separated with a separating funnel. The aqueous layer was extracted with ethyl acetate. The organic layer was washed twice with a saturated aqueous sodium chloride solution, dried over magnesium sulfate and the solvent was removed in vacuo to give allyl 2-methyl-5-(2-mercapto-1,3-thiazol-4-yl)-3,6-dihydro-1(2 H)-pyridinecarboxylate (368 mg, 64%).

$^1$H NMR (300 MHz, CDCl$_3$) δ 1.14 (3 H, d, J=6.8 Hz), 2.00–2.20 (1 H, m), 2.56–2.73 (1 H, m), 3.68–3.78 (1 H, m), 4.46–4.67 (4 H, m), 5.17–5.32 (2 H, m), 5.86–6.00 (1 H, m), 6.22 (0.5 H, brs), 6.24 (0.5 H, brs), 6.41 (1 H, s).

Reference Example 16

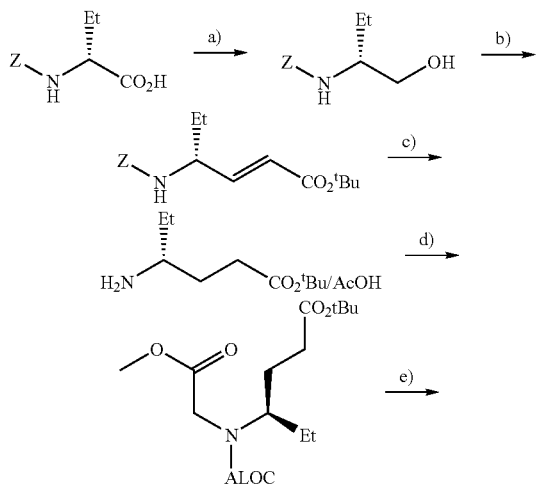

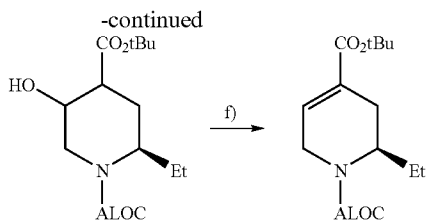

a) In the same manner as Reference example 3.a), by using (2R)-2-{[(benzyloxy)carbonyl]aminobutanoic acid, there was obtained benzyl (1R)-1-(hydroxymethyl)propyl-carbamate.

$^1$H NMR (300 MHz, CDCl$_3$) δ 0.94 (3 H, t, J=7.3 Hz), 1.41–1.64 (2 H, m), 2.12 (1 H, brs), 3.52 (3 H, m), 4.82 (1 H, brs), 5.09 (2 H, s), 7.27–7.37 (5 H, m).

b) To a suspension of benzyl (1R)-1-(hydroxymethyl) propylcarbamate (9.46 g, 42.4 mmol), 2,2,6,6-tetramethyl-1-piperidinyloxy (0.143 g, 0.85 mmol) and sodium bromide (4.36 g, 42 mmol) in a mixture of toluene (125 ml), water (21 ml) and ethyl acetate (125 ml) was added sodium hydrogen carbonate (10.3 g). And thereto was added at 0–5° C. an aqueous sodium hypochlorite solution over an hour period. After separating the solution with a separating funnel, the aqueous layer was extracted with ether. The organic layer was washed with an aqueous 10% potassium hydrogen sulfate solution containing potassium iodide, an aqueous 10% sodium thiosulfate solution and a saturated aqueous sodium chloride solution. The mixture was condensed with an evaporator and the residue was dissolved at 0–5° C. in THF (60 ml). The solution was immediately raised to room temperature and then stirred for 1.5 hours at the same temperature. After condensation with an evaporator the residue was purified with silica gel (200 g) chromatography (ethyl acetate/hexane=1/3) to give tert-butyl (2E, 4R)-4-{[(benzyloxy)carbonyl]amino}-2-hexenoate (9.73 g).

$^1$H NMR (300 MHz, CDCl$_3$) δ 0.93 (3 H, t, J=7.5 Hz), 1.46 (9 H, s), 1.42–1.68 (2 H, m), 4.20–4.32 (1 H, m), 3.65–3.73 (1 H, m), 5.07 (1 H, d, J=15.8 Hz), 5.11 (1 H, d, J=15.8 Hz), 5.82 (1 H, d, J=15.6 Hz), 6.71 (1 H, dd, J=5.7, 15.6 Hz), 7.28–7.37 (5 H, m).

c) To a solution of tert-butyl (2E, 4R)-4-{[(benzyloxy) carbonyl]amino}-2-hexenoate (9.73 g, 30.5 mmol) in methanol (200 ml) were added acetic acid (3.5 ml, 61 mmol) and 10% Palladium carbon (3.2 g). The mixture was stirred under hydrogen atmosphere for 7 hours. Catalyst was filtered off under a nitrogen atomosphere and the filtrate was condensed with an evaporator to give tert-butyl (4R)-4-aminohexanoate acetic acid salt (7.5 g, quantitatively).

$^1$H NMR (300 MHz, CDCl$_3$) δ 0.95 (3 H, t, J=7.5 Hz), 1.46 (9 H, s), 1.53–1.63 (2 H, m), 1.68–1.92 (2 H, m), 2.35 (2 H, t, J=7.5 Hz), 2.90–2.98 (1 H, m).

d) In the same manner as Reference example 3.d), by using tert-butyl (4R)-4-aminohexanoate, there was obtained tert-butyl (4R)-4-[[(allyloxy)carbonyl](2-methoxy-2-oxoethyl)amino]hexanoate.

$^1$H NMR (300 MHz, CDCl$_3$) δ 0.88 (3 H, t, J=7.3 Hz), 1.41 (9 H, s), 1.37–1.79 (4 H, m), 2.21–2.42 (2 H, m), 3.66–3.77 (5 H, m), 3.90–4.20 (1 H, m), 4.50–4.63 (2 H, m), 5.13–5.32 (2 H, m), 5.78–5.97 (1 H, m).

e) In the same manner as Reference example 3.e) and f), by using tert-butyl (4R)-4-[[(allyloxy)carbonyl](2-methoxy-2-oxoethyl)amino]hexanoate, there was obtained 1-allyl 4-tert-butyl (2R)-5-hydroxy-2-ethyl-1,4-piperidinedicarboxylate.

¹H NMR (300 MHz, CDCl₃) δ 0.86 (3 H, t, J=7.3 Hz), 1.44 (9 H, s), 1.36–1.47 (1 H, m), 1.58–1.73 (2 H, m), 1.83–1.93 (1 H, m), 2.39–2.48 (1 H, m), 2.54–2.73 (1 H, m), 3.65–3.77 (1 H, m), 4.04–4.34 (2 H, m), 4.55 (2 H, d, J=5.5 Hz), 5.18 (1 H, dd, J=1.3, 10.4 Hz), 5.26 (1 H, dd, J=1.3, 17.0 Hz), 5.90 (1 H, ddt, J=5.5, 10.4, 17.0 Hz).

f) In the same manner as Reference example 3.g), by using 1-allyl 4-tert-butyl (2R)-5-hydroxy-2-ethyl-1,4-piperidinedicarboxylate, there was obtained 1-allyl 4-tert-butyl (2R)-2-ethyl-3,6-dihydro-1,4(2 H)-pyridinedicarboxylate.

¹H NMR (300 MHz, CDCl₃) δ 0.85 (3 H, t, J=7.5 Hz), 1.32–1.59 (2 H, m), 1.47 (9 H, s), 2.35–2.42 (2 H, m), 3.55–3.73 (1 H, m), 4.29–4.63 (4 H, m), 5.19 (1 H, dd, J=1.5, 10.4 Hz), 5.28 (1 H, dd, J=1.5, 17.0 Hz), 5.92 (1 H, ddt, J=5.5, 10.4, 17.0 Hz), 6.74 (1 H, brs).

Reference Example 17

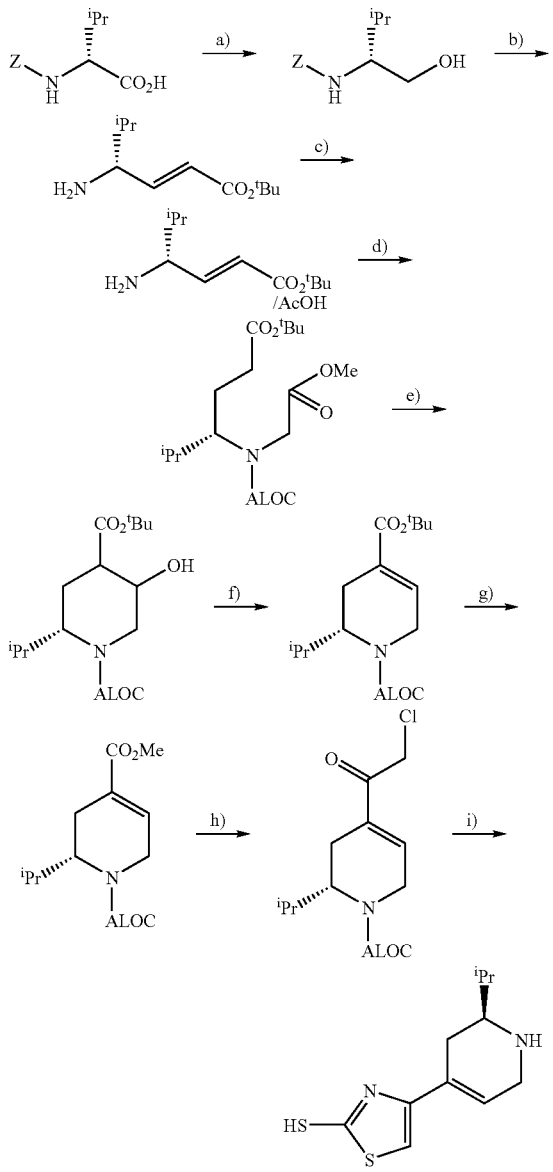

a) In the same manner as Reference example 16.a), by using N-[(benzyoxy)carbonyl]-D-valine, there was obtained benzyl (1R)-1-(hydroxymethyl)-2-methylpropylcarbamate.

¹H NMR (300 MHz, CDCl₃) δ 0.91 (3 H, d, J=7.0 Hz), 0.94 (3 H, d, J=7.9 Hz), 1.78–1.90 (1 H, m), 2.03–2.12 (1 H, m), 3.44–3.75 (3 H, m), 4.84 (1 H, brs), 5.09 (2 H, s), 7.28–7.37 (5 H, m).

b) In the same manner as Reference example 16.b), by using benzyl(1R)-1-(hydroxymethyl)-2-methylpropylcarbamate, there was obtained tert-butyl(2E,4R)-4-{[(benzyloxy)carbonyl]amino}-5-methyl-2-hexenoate.

¹H NMR (300 MHz, CDCl₃) δ 0.89 (3 H, d, J=7.0 Hz), 0.92 (3 H, d, J=6.8 Hz), 1.46 (9 H, s), 1.78–1.92 (1 H, m), 4.16–4.26 (1 H, m), 4.76 (1 H, d, J=9.7 Hz), 5.07 (1 H, d, J=13.9 Hz), 5.11 (1 H, d, J=12.1 Hz), 5.83 (1 H, dd, J=1.3, 15.5 Hz), 6.73 (1 H, dd, J=5.5, 15.5 Hz), 7.28–7.37 (5 H, m).

c) In the same manner as Reference example 16.c), by using tert-butyl(2E,4R)-4-{[(benzyloxy)carbonyl]amino}-5-methyl-2-hexenoate, there was obtained tert-butyl(4S)-4-amino-5-methylhexanoate acetic acid salt.

¹H NMR (300 MHz, CDCl₃) δ 0.94 (3 H, d, J=7.0 Hz), 0.95 (3 H, d, J=6.8 Hz), 1.41 (9 H, s), 1.63–1.91 (3 H, m), 2.28–2.47 (2 H, m), 2.83 (1 H, dt, J=4.4, 8.8 Hz).

d) In the same manner as Reference example 3.d), by using tert-butyl(4S)-4-amino-5-methylhexanoate acetic acid salt, there was obtained tert-butyl (4S)-4-[[(allyloxy)carbonyl](2-methoxy-2-oxoethyl)amino]-5-methylhexanoate.

¹H NMR (300 MHz, CDCl₃) δ 0.87 (3 H, d, J=6.6 Hz), 0.97 (3 H, d, J=6.6 Hz), 1.35–1.65 (2 H, m), 1.42 (9 H, s), 1.88–2.02 (1 H, m), 2.26–2.52 (2 H, m), 3.59–3.93 (5 H, m), 4.51–4.68 (2 H, m), 5.18–5.31 (2 H, m), 5.78–5.96 (1 H, m).

e) In the same manner as Reference example 3.e) and f), by using tert-butyl(4S)-4-[[(allyloxy)carbonyl](2-methoxy-2-oxoethyl)amino]-5-methylhexanoate, there was obtained 1-allyl 4-tert-butyl (2S)-5-hydroxy-2-isopropyl-1,4-piperidinedicarboxylate.

¹H NMR (300 MHz, CDCl₃) δ 0.84–0.97 (6 H, m), 1.45 (9 H, s), 1.50–1.70 (1 H, m), 1.74–2.13 (2 H, m), 2.33–3.09 (2 H, m), 3.64–4.38 (3 H, m), 4.50–4.65 (2 H, m), 5.15–5.34 (2 H, m), 5.85–5.98 (1 H, m).

f) In the same manner as Reference example 3.g), by using 1-allyl 4-tert-butyl (2S)-5-hydroxy-2-isopropyl-1,4-piperidinedicarboxylate, there was obtained 1-allyl 4-tert-butyl (2S)-2-isopropyl-3,6-dihydro-1,4(2 H)-pyridinedicarboxylate.

¹H NMR (300 MHz, CDCl₃) δ 0.84 (3 H, d, J=6.8 Hz), 0.91 (3 H, d, J=6.6 Hz), 1.47 (9 H, s), 1.63–1.73 (1 H, m), 2.23–2.36 (1 H, m), 2.62 (1 H, d, J=17.4 Hz), 3.53–3.72 (1 H, m), 3.90–4.14 (1 H, m), 4.40–4.65 (4 H, m), 5.19 (1 H, dd, J=1.3, 10.4 Hz), 5.28 (1 H, d, J=17.4 Hz), 5.92 (1 H, ddt, J=5.5, 10.4, 17.4 Hz), 6.75 (1 H, brs).

g) In the same manner as Reference example 6.g), by using 1-allyl 4-tert-butyl (2S)-2-isopropyl-3,6-dihydro-1,4(2 H)-pyridinedicarboxylate, there was obtained 1-allyl 4-methyl (2S)-2-isopropyl-3,6-dihydro-1,4(2 H)-pyridinedicarboxylate.

¹H NMR (300 MHz, CDCl₃) δ 0.84 (3 H, d, J=6.6 Hz), 0.90(3H, d, J=6.4 Hz), 1.60–1.72 (1 H, m), 2.28–2.40 (1 H, m), 2.67 (1 H, d, J=17.6 Hz), 3.55–3.77 (1 H, m), 3.74 (3 H, s), 3.93–4.13 (1 H, m), 4.41–4.65 (3 H, m), 5.19 (1 H, ddd, J=1.5, 2.8, 10.4 Hz), 5.28 (1 H, d, J=17.2 Hz), 5.92 (1 H, ddt, J=5.5, 10.4, 17.2 Hz), 6.86 (1 H, brs).

h) In the same manner as Reference example 2.d), by using 1-allyl 4-methyl (2S)-2-isopropyl-3,6-dihydro-1,4(2 H)-pyridinedicarboxylate, there was obtained allyl (2R)-4-(chloroacetyl)-2-isopropyl-3,6-dihydro-1(2 H)-pyridinecarboxylate.

¹H NMR (300 MHz, CDCl₃) δ 0.85 (3 H, d, J=6.8 Hz), 0.89 (3 H, d, J=6.6 Hz), 1.50–1.64 (1 H, m), 2.21–2.34 (1 H, m), 2.78 (1 H, d, J=17.4 Hz), 3.64–3.75 (2 H, m), 4.33–4.44 (2 H, m), 4.50–4.70 (3 H, m), 5.17–5.32 (2 H, m), 5.85–5.99 (1 H, m), 6.80 (1 H, brs).

i) In the same manner as Reference example 2.e), by using allyl (2S)-4-(chloroacetyl)-2-isopropyl-3,6-dihydro-1(2 H)-pyridinecarboxylate, there was obtained allyl (2S)-4-(2-mercapto-1,3-thiazol-4-yl)-2-isopropyl-3,6-dihydro-1(2 H)-pyridinecarboxylate.

¹H NMR (300 MHz, CDCl₃) δ 0.87 (3 H, d, J=6.6 Hz), 0.92 (3 H, d, J=6.6 Hz), 1.67–1.83 (1 H, m), 2.38–2.58 (2 H, m), 3.57–3.80 (1 H, m), 3.97–4.18 (1H, m), 4.44–4.68 (3 H, m), 5.21 (1H, dd, J=1.3, 10.4 Hz), 5.29 (1H, dd, J=1.4, 17.2 Hz), 5.93 (1H, ddt, J=5.5, 10.4, 17.2 Hz), 6.03 (1H, brs), 6.38 (1H, brs).

Reference Example 18

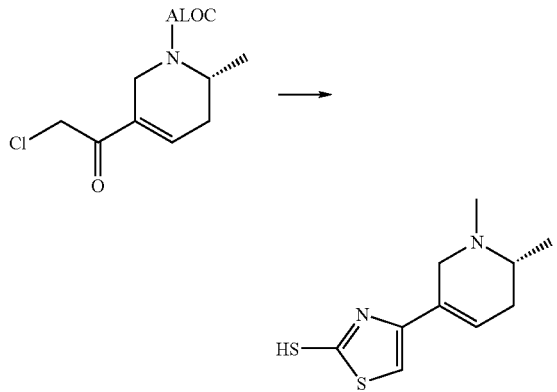

In the same manner as Reference example 12, by using allyl (2R)-5-(chloroacetyl)-2-methyl-3,6-dihydro-1(2 H)-pyridinecarboxylate, there was obtained 4-[(6R)-1,6-dimethyl-1,2,5,6-tetrahydro-3-pyridinyl]-1,3-thiazole-2-thiol.

¹H NMR (300 MHz, CD₃OD) δ 1.23 (3 H, brs), 2.10–2.29 (1 H, m), 2.54 (3 H, brs), 2.80 (2 H, brs), 3.50–3.70 (2 H, m), 6.38 (1 H, brs), 6.71 (1 H, brs).

Reference Example 19

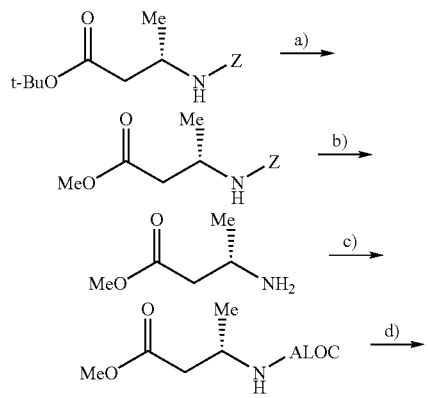

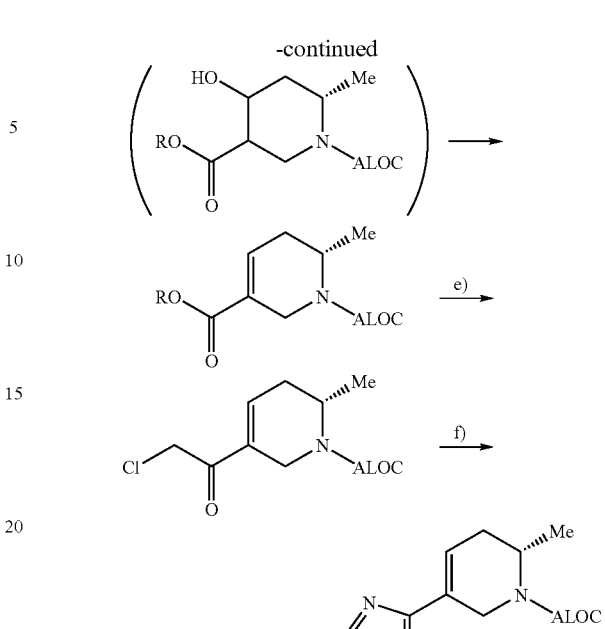

a) In the same manner as Reference example 6.g), by using tert-butyl (3S)-3-{[(benzyloxy)carbonyl]amino}butanoate (5.63 g, 19.2 mmol), there was obtained methyl (3S)-3-{[(benzyloxy)carbonyl]amino}butanoate (3.61 g, 75%).

¹H NMR (300 MHz, CDCl₃) δ 1.24 (3H, d, J=6.8 Hz), 2.54 (2H, d, J=5.5 Hz), 3.67 (3H, s), 4.05–4.18 (1H, m), 5.06–5.13 (2H, m), 5.15–5.24 (1H, m), 7.28–7.39 (5H, m).

b) In the same manner as Reference example 3.c), by using methyl (3S)-3-{[(benzyloxy)carbonyl]amino}butanoate (3.61 g, 14.4 mmol), there was obtained methyl (3S)-3-aminobutanoate (1.47 g, 87%).

¹H NMR (300 MHz, CDCl₃) δ 1.14 (3H, d, J=6.4 Hz), 2.33 (1H, dd, J=15.7, 8.2 Hz), 2.43 (1H, dd, J=15.7, 4.6 Hz), 3.34–3.45 (1H, m), 3.69 (3H, s).

c) To a solution of methyl (3S)-3-aminobutanoate (1.47 g, 12.5 mmol) in THF (30 ml) were added at 0° C. allyl chloroformate (1.60 ml, 15.1 mmol) and diisopropylethylamine (2.62 ml, 15.0 mmol), and the mixture was stirred at the same temperature for 30 minutes. The reaction mixture was poured into water and extracted twice with ethylacetate. The organic layer was washed with a saturated aqueous sodium chloride solution, was dried over magnesium sulfate and the organic solvent was removed under reduced pressure. The residue was purified by silica gel (25 g) chromatography to give methyl (3S)-3-{[(allyloxy)carbonyl]amino}butanoate (2.06 g, 81%).

¹H NMR (300 MHz, CDCl₃) δ 1.25 (3H, d, J=6.8 Hz), 2.24 (3H, d, J=5.5 Hz), 3.69 (3H, s), 4.03–4.16 (1H, m), 4.54–4.58 (2H, m), 5.15–5.34 (3H, m), 5.85–5.98 (1H, m).

d) To a solution of methyl (3S)-3-{[(allyloxy)carbonyl]amino}butanoate (2.06 g, 10.2 mmol) and ethyl acrylate (1.11 ml, 10.2 mmol) in toluene (25 ml) was added at 40° C. sodium hydride (60% suspension in oil, 0.41 g, 10.2 mmol). The mixture was stirred for 2 hours and then was poured into diluted hydrochloric acid. The solution was extracted twice with ethyl acetate. The organic layer was washed with a saturated aqueous sodium chloride solution and dried over magnesium sulfate. The organic solvent was removed in vacuo. To the residue were added methanol (40 ml), acetic acid (0.70 ml, 12.2 mmol) and sodium cyanoborohydride (0.77 g, 12.2 mmol) and the mixture was stirred at room temperature for 20 minutes. The solvent was removed in vacuo and the residue was purified with silica gel chromatography to give a mixture (1.21 g) of 1-allyl 3-ethyl (6S)-4-hydroxy-6-methyl-1,3-piperidinedicarboxylate and 1-allyl 3-methyl (6S)-4-hydroxy-6-methyl-1,3-piperidinedicarboxylate.

By treating the mixture in the same manner as Reference example 3.g), there were obtained 1-allyl 3-ethyl (6S)-6-methyl-5,6-dihydro-1,3(2 H)-pyridinedicarboxylate (127 mg, 5%) and 1-allyl 3-methyl (6S)-6-methyl-5,6-dihydro-1,3(2 H)-pyridinedicarboxylate (252 mg, 10%).

1-allyl 3-ethyl (6S)-6-methyl-5,6-dihydro-1,3(2 H)-pyridinedicarboxylate $^1$H NMR (300 MHz, CDCl$_3$) δ 1.12 (3H, d, J=7.0 Hz), 2.04–2.13 (1H, m), 2.54–2.63 (1H, m), 3.70–3.79 (1H, m), 4.23 (2H, q, J=7.1 Hz), 4.55–4.68 (4H, m), 5.19–5.34 (2H, m), 5.89–6.02 (1H, m), 7.00–7.04 (1H, m).

1-allyl 3-methyl (6S)-6-methyl-5,6-dihydro-1,3(2 H)-pyridinedicarboxylate $^1$H NMR (300 MHz, CDCl$_3$) δ 1.12 (3H, d, J=6.8 Hz), 1.31 (3H, t, J=7.1 Hz), 2.04–2.13 (1H, m), 2.53–2.64 (1H, m), 3.70–3.79 (1H, m), 3.77 (3H, s), 4.55–4.68 (4H, m), 5.19–5.34 (2H, m), 5.89–6.02 (1H, m), 7.00–7.04 (1H, m).

e) In the same manner as Reference example 1.b), by using 1-allyl 3-ethyl (6S)-6-methyl-5,6-dihydro-1,3(2 H)-pyridinedicarboxylate (126 mg, 0.50 mmol), there was obtained allyl (2S)-5-(chloroacetyl)-2-methyl-3,6-dihydro-1(2 H)-pyridinecarboxylate (62 mg, 48%).

$^1$H NMR (300 MHz, CDCl$_3$) δ 1.12 (3H, d, J=7.0 Hz), 2.13–2.24 (1H, m), 2.66–2.75 (1H, m), 3.71–3.79 (1H, m), 4.36–4.46 (2H, m), 4.60–4.71 (4H, m), 5.20–5.34 (2H, m), 5.88–6.01 (1H, m), 6.96–6.99 (1H, m).

f) In the same manner as Reference example 1.c), by using allyl (2S)-5-(chloroacetyl)-2-methyl-3,6-dihydro-1(2 H)-pyridinecarboxylate (141 mg, 0.55 mmol), there was obtained allyl (2S)-2-methyl-5-(2-sulfanyl-1,3-thiazol-4-yl)-3,6-dihydro-1(2 H)-pyridinecarboxylate (160 mg, 99%).

$^1$H NMR (300 MHz, CDCl$_3$) δ 1.16 (3H, d, J=7.0 Hz), 2.08–2.18 (1H, m), 2.60–2.70 (1H, m), 3.71–3.79 (1H, m), 4.52–4.65 (4H, m), 5.22–5.34 (2H, m), 5.89–6.01 (1H, m), 6.18–6.20 (1H, m), 6.42 (1H, s), 10.66 (1H, br s).

Reference Example 20

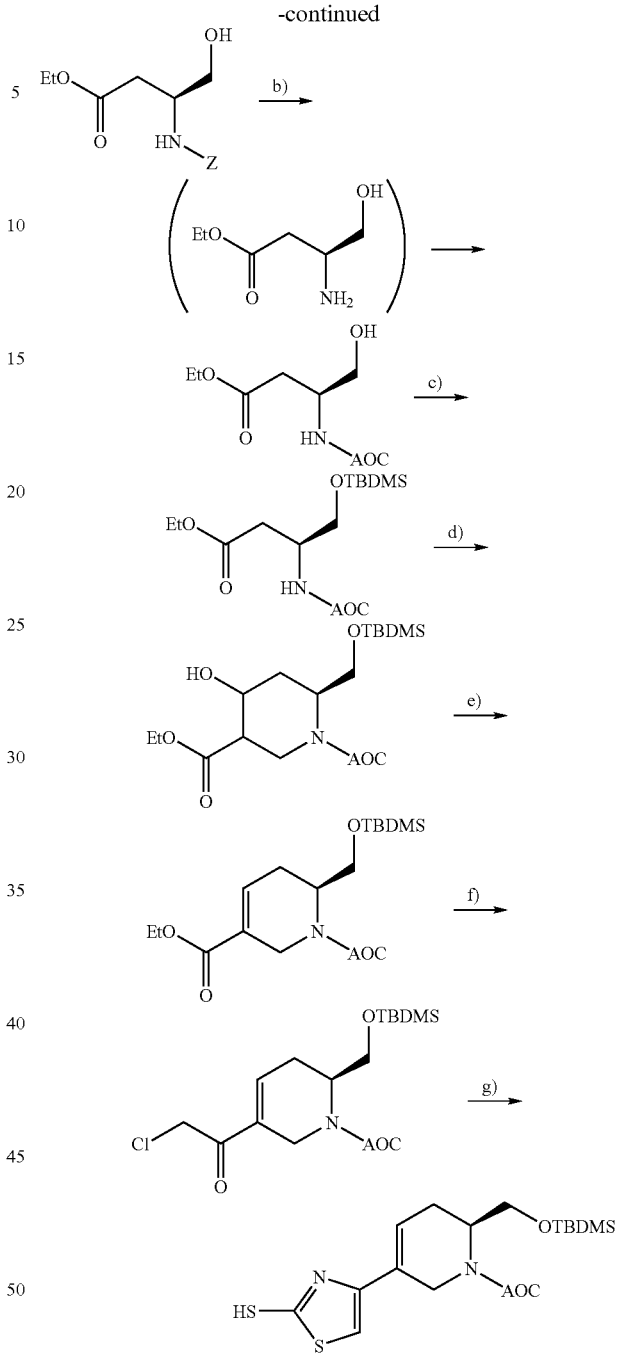

a) To ethanol (188 ml, 3.24 mol) was added at 0° C. acetyl chloride (46 ml, 0.65 mol). The mixture was stirred at the same temperature for 30 minutes and added to tert-butyl (3S)-3-{[(benzyloxy)carbonyl]amino}-4-hydroxybutanoate (10.0 g, 32.3 mmol) in ethanol (20 ml). The mixture was stirred overnight. After removal of the solvent, the residue was dissolved in ethyl acetate and the solution was washed with a saturated aqueous sodium hydrogen carbonate solution and then a saturated aqueous sodium chloride solution and dried over anhydrous sodium sulfate. The organic solvent was removed under reduced pressure, and the residue was purified by silica gel chromatography to give ethyl (3S)-3-{[(benzyloxy)carbonyl]amino}-4-hydroxybutanoate (2.92 g, 32%) with a lactone compound, benzyl (3S)-5-oxotetrahydro-3-furanylcarbamate (4.24 g, 56%) as by-product.

Ethyl (3S)-3-{[(benzyloxy)carbonyl]amino}-4-hydroxybutanoate $^1$H NMR (300 MHz, CDCl$_3$) δ 1.24 (3H, t, J=7.1 Hz), 2.61–2.65 (2H, m), 2.78 (1H, br s), 3.68–3.73 (2H, m), 4.02–4.17 (3H, m), 5.07–5.10 (2H, m), 5.50–5.58 (1H, m), 7.28–7.39 (5H, m).

Benzyl (3S)-5-oxotetrahydro-3-furanylcarbamate $^1$H NMR (300 MHz, CDCl$_3$) δ 1.24 (3H, t, J=7.1 Hz), 2.46 (1H, dd, J=3.5, 17.9 Hz), 2.81 (1H, dd, J=7.5, 17.9 Hz), 4.17–4.24 (1H, m), 4.44–4.53 (2H, m), 5.10 (2H, s), 5.40–5.45 (1H, m), 7.28–7.39 (5H, m).

b) In the same manner as Reference example 3.c), by using ethyl (3S)-3-{[(benzyloxy)carbonyl]amino}-4-hydroxybutanoate (2.92 g, 10.4 mmol), there was obtained ethyl (3S)-3-amino-4-hydroxybutanoate.

By allyloxycarbonylation of the above compound without further purification in the same manner as Reference example 19.c), there was obtained ethyl (3S)-3-{[(allyloxy)carbonyl]amino}-4-hydroxybutanoate (0.96 g, 40%).

$^1$H NMR (300 MHz, CDCl$_3$) δ 1.27 (3H, t, J=7.1 Hz), 2.42 (1H, br s), 2.64–2.68 (2H, m), 3.71–3.76 (2H, m), 4.01–4.11 (1H, m), 4.16 (2H, q, J=7.1), 4.54–4.58 (2H, m), 5.19–5.34 (2H, m), 5.47 (1H, br s), 5.85–5.98 (1H, m).

c) In the same manner as Reference example 7.a), by using ethyl (3S)-3-{[(allyloxy)carbonyl]amino}-4-hydroxybutanoate (0.96 g, 4.2 mmol), there was obtained ethyl (3S)-3-{[(allyloxy)carbonyl]amino}-4-{[tert-butyl(dimethyl)silyl]oxy}butanoate (1.25 g, 87%).

$^1$H NMR (300 MHz, CDCl$_3$) δ 0.04 (6H, s), 0.89 (9H, s), 1.25 (3H, t, J=7.1 Hz), 2.58–2.62 (2H, m), 3.64 (1H, dd, J=5.1, 9.9 Hz), 3.70 (1H, dd, J=3.8, 9.9 Hz), 4.04–4.16 (1H, m), 4.13 (2H, q, J=7.1), 4.54–4.58 (2H, m), 5.19–5.34 (3H, m), 5.85–5.98 (1H, m).

d) To a solution of ethyl (3S)-3-{[(allyloxy)carbonyl]amino}-4-{[tert-butyl(dimethyl)silyl]oxy}butanoate (1.25 g, 3.6 mmol) and ethyl acrylate (0.39 ml, 3.6 mmol) in toluene (10 ml) was added at 40° C. sodium hydride (60% suspension in oil, 145 mg, 3.6 mmol). The mixture was stirred at 60° C. for 1 hour and then poured into diluted hydrochloric acid. The solution was extracted three times with ethyl acetate. The organic layer was washed with a saturated aqueous sodium chloride solution and dried over anhydrous sodium sulfate. The solvent was removed in vacuo. The residue was dissolved in methanol(25 ml) and to the solution were added acetic acid (0.25 ml, 4.4 mmol) and sodium cyanoborohydride (0.27 g, 4.3 mmol). The mixture was stirred at room temperature for 30 minutes. The solvent was removed in vacuo and the residue was purified with silica gel chromatography to give 1-allyl 3-ethyl (6S)-6-({[tert-butyl(dimethyl)silyl]oxy}methyl)-4-hydroxy-1,3-piperidinedicarboxylate (0.48 g, 33%).

$^1$H NMR (300 MHz, CDCl$_3$) δ 0.04 (6H, s), 0.89 (9H, s), 1.26 (3H, t, J=7.1 Hz), 2.48–2.66 (3H, m), 3.60–3.73 (3H, m), 4.04–4.23 (4H, m), 4.14 (2H, q, J=7.1), 4.54–4.62 (2H, m), 5.19–5.34 (2H, m), 5.85–5.98 (1H, m).

e) In the same manner as Reference example 5.g), by using 1-allyl 3-ethyl (6S)-6-({[tert-butyl(dimethyl)silyl]oxy}methyl)-4-hydroxy-1,3-piperidinedicarboxylate (484 mg, 1,2 mmol), there was obtained 1-allyl 3-ethyl (6S)-6-({[tert-butyl(dimethyl)silyl]oxy}methyl)-5,6-dihydro-1,3(2H)-pyridinedicarboxylate (151 mg, 33%).

$^1$H NMR (300 MHz, CDCl$_3$) δ 0.01–0.04 (6H, m), 0.84–0.89 (9H, m), 1.23–1.33 (3H, m), 2.18–2.65 (2H, m), 3.45–3.92 (3H, m), 4.07–4.26 (2H, m), 4.45–4.68 (3H, m), 5.19–5.35 (2H, m), 5.86–6.02 (1H, m), 7.01 (1H, br s).

f) In the same manner as Reference example 1.b), by using 1-allyl 3-ethyl (6S)-6-({[tert-butyl(dimethyl)silyl]oxy}methyl)-5,6-dihydro-1,3(2H)-pyridinedicarboxylate (151 mg, 0.39 mmol), there was obtained allyl (2S)-2-({[tert-butyl(dimethyl)silyl]oxy}methyl)-5-(chloroacetyl)-3,6-dihydro-1(2H)-pyridinecarboxylate (79 mg, 52%).

$^1$H NMR (300 MHz, CDCl$_3$) δ 0.02 (3H, s), 0.03 (3H, s), 0.86 (9H, s), 2.42–2.65 (2H, m), 3.45–3.57 (3H, m), 3.67–3.78 (1H, m), 4.40 (2H, s), 4.50–4.65 (4H, m), 5.19–5.34 (2H, m), 5.88–6.01 (1H, m), 6.98 (1H, br s).

g) In the same manner as Reference example 1.c), by using allyl (2S)-2-({[tert-butyl (dimethyl)silyl]oxy}methyl)-5-(chloroacetyl)-3,6-dihydro-1(2H)-pyridinecarboxylate (79 mg, 0.20 mmol), there was obtained allyl (2S)-2-({[tert-butyl(dimethyl)silyl]oxy}methyl)-5-(2-sulfanyl-1,3-thiazol-4-yl)-3,6-dihydro-1(2H)-pyridinecarboxylate (90 mg, quantitatively).

$^1$H NMR (300 MHz, CDCl$_3$) δ 0.03 (6H, s), 0.86 (9H, s), 2.27–2.38 (1H, m), 2.50–2.61 (1H, m), 3.48–3.82 (3H, m), 4.40–4.66 (4H, m), 5.19–5.34 (2H, m), 5.88–6.01 (1H, m), 6.29 (1H, br s), 6.44 (1H, br s), 11.49 (1H, br s).

Reference Example 21

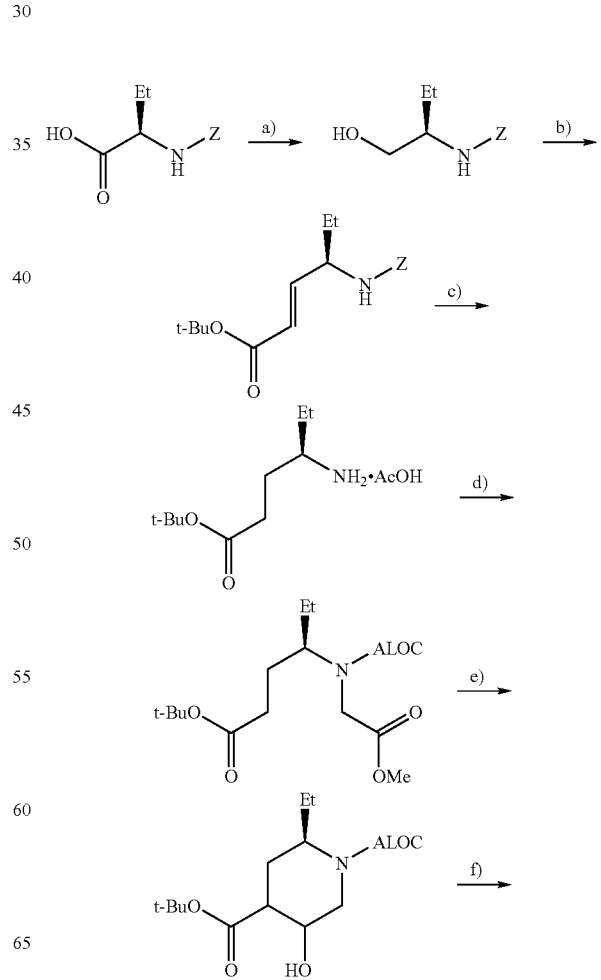

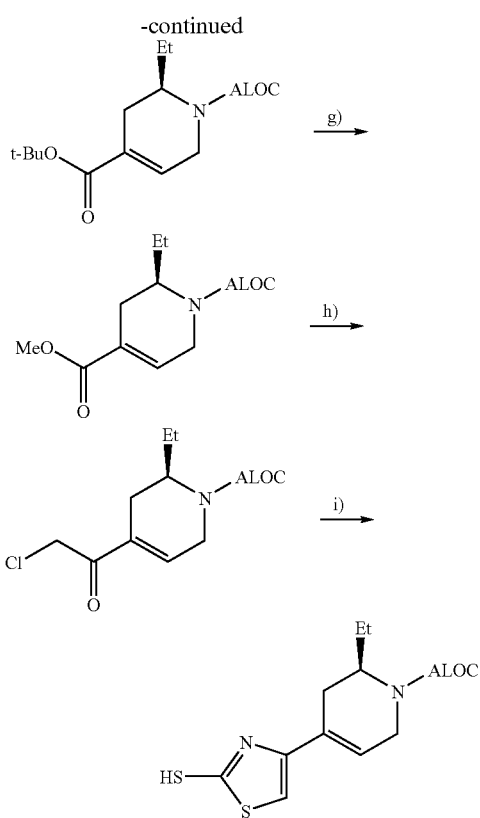

a) In the same manner as Reference example 3.a), by using (2R)-N-benzyloxycarbonyl-2-aminopropanecarboxylic acid, there was obtained benzyl (1R)-1-(hydroxymethyl)propylcarbamate.

$^1$H NMR (300 MHz, CDCl$_3$) δ 0.94 (3H, t, J=7.3 Hz), 1.41–1.64 (2H, m), 2.12 (1H, brs), 3.52 (3H, m), 4.82 (1H, brs), 5.09 (2H, s), 7.27–7.37 (5H, m).

b) To a suspension of benzyl (1R)-1-(hydroxymethyl)propylcarbamate (9.46 g, 42.4 mmol), 2,2,6,6-tetramethyl-1-piperidinyloxy (0.143 g, 0.85 mmol) and sodium bromide (4.36 g, 42 mmol) in a mixture of toluene (125 ml), water (21 ml) and ethyl acetate (125 ml) was added sodium hydrogen carbonate (10.3 g). And then thereto was added at 0–5° C. an aqueous sodium hypochlorite solution over an hour period. After separating the solution with a separating funnel, the aqueous layer was extracted with ether. The organic layer was washed with a 10% potassium hydrogen sulfate solution containing potassium iodide, a 10% sodium thiosulfate solution and a saturated aqueous sodium chloride solution. The mixture was condensed with an evaporator and the residue was dissolved at 0–5° C. in THF (60 ml). The solution was immediately raised to room temperature and the solution was stirred for 1.5 hours at the same temperature. After condensed with an evaporator the residue was purified with silica gel (200 g) chromatography (ethyl acetate/hexane=1/3) to give tert-butyl (2E, 4R)-4-{[(benzyloxy)carbonyl]amino}-2-hexenoate (9.73 g).

$^1$H NMR (300 MHz, CDCl$_3$) δ 0.93 (3H, t, J=7.5 Hz), 1.46 (9H, s)., 1.42–1.68 (2H, m), 4.20–4.32 (1H, m), 3.65–3.73 (1H, m), 5.07 (1H, d, J=15.8 Hz), 5.11 (1H, d, J=15.8 Hz), 5.82 (1H, d, J=15.6 Hz), 6.71 (1H, dd, J=5.7, 15.6 Hz), 7.28–7.37 (5H, m).

c) To a solution of tert-butyl (2E, 4R)-4-{[(benzyloxy)carbonyl]amino}-2-hexenoate (9.73 g, 30.5 mmol) in methanol (200 ml) were added acetic acid (3.5 ml, 61 mmol) and 10% Palladium carbon (3.2 g). The mixture was stirred under a hydrogen atmosphere for 7 hours. Catalyst was filtered off under a nitrogen gas and the filtrate was condensed with an evaporator to give tert-butyl (4R)-4-aminohexanoate acetic acid salt (7.5 g, quantitatively).

$^1$H NMR (300 MHz, CDCl$_3$) δ 0.95 (3H, t, J=7.5 Hz), 1.46 (9H, s), 1.53–1.63 (2H, m), 1.68–1.92 (2H, m), 2.35 (2H, t, J=7.5 Hz), 2.90–2.98 (1H, m).

d) In the same manner as Reference example 3.d), by using tert-butyl(4R)-4-aminohexanoate, there was obtained tert-butyl (4R)-4-[[(allyloxy)carbonyl](2-methoxy-2-oxoethyl)amino]hexanoate.

$^1$H NMR (300 MHz, CDCl$_3$) δ 0.88 (3H, t, J=7.3 Hz), 1.41 (9H, s), 1.37–1.79 (4H, m), 2.21–2.42 (2H, m), 3.66–3.77 (5H, m), 3.90–4.20 (1H, m), 4.50–4.63 (2H, m), 5.13–5.32 (2H, m), 5.78–5.97 (1H, m).

e) In the same manner as Reference example 3.e) and f), by using tert-butyl(4R)-4-[[(allyloxy)carbonyl](2-methoxy-2-oxoethyl)amino]hexanoate, there was obtained 1-allyl 4-tert-butyl (2R)-5-hydroxy-2-ethyl-1,4-piperidinedicarboxylate.

$^1$H NMR (300 MHz, CDCl$_3$) δ 0.86 (3H, t, J=7.3 Hz), 1.44 (9H, s), 1.36–1.47 (1H, m), 1.58–1.73 (2H, m), 1.83–1.93 (1H, m), 2.39–2.48 (1H, m), 2.54–2.73 (1H, m), 3.65–3.77 (1H, m), 4.04–4.34 (2H, m), 4.55 (2H, d, J=5.5 Hz), 5.18 (1H, dd, J=1.3, 10.4 Hz), 5.26 (1H, dd, J=1.3, 17.0 Hz), 5.90 (1H, ddt, J=5.5, 10.4, 17.0 Hz).

f) In the same manner as Reference example 3.g), by using 1-allyl 4-tert-butyl (2R)-5-hydroxy-2-ethyl-1,4-piperidinedicarboxylate, there was obtained 1-allyl 4-tert-butyl (2R)-2-ethyl-3,6-dihydro-1,4(2H)-pyridinedicarboxylate.

$^1$H NMR (300 MHz, CDCl$_3$) δ 0.85(3H, t, J=7.5 Hz), 1.32–1.59(2H, m), 1.47(9H, s), 2.35–2.42 (2H, m), 3.55–3.73 (1H, m), 4.29–4.63 (4H, m), 5.19 (1H, dd, J=1.5, 10.4 Hz), 5.28 (1H, dd, J=1.5, 17.0 Hz), 5.92 (1H, ddt, J=5.5, 10.4, 17.0 Hz), 6.74 (1H, brs).

g) In the same manner as Reference example 6.g), by using 1-allyl 4-tert-butyl (2R)-2-ethyl-3,6-dihydro-1,4(2H)-pyridinedicarboxylate (1.40 g, 4.72 mmol), there was obtained 1-allyl 4-methyl (2R)-2-ethyl-3,6-dihydro-1,4(2H)-pyridinedicarboxylate (1.09 g, 91%).

$^1$H NMR (300 MHz, CDCl$_3$) δ 0.88 (3H, t, J=7.4 Hz), 1.32–1.57 (2H, m), 2.44–2.47 (2H, m), 3.63–3.79 (1H, m), 3.76 (3H, s), 4.35–4.65 (4H, m), 5.19–5.34 (2H, m), 5.88–6.01 (1H, m), 6.88 (1H, br s).

h) In the same manner as Reference example 1.b), by using 1-allyl 4-methyl (2R)-2-ethyl-3,6-dihydro-1,4(2H)-pyridinedicarboxylate (435 mg, 1.72 mmol), there was obtained allyl (2R)-4-(chloroacetyl)-2-ethyl-3,6-dihydro-1(2H)-pyridinecarboxylate (177 mg, 38%).

$^1$H NMR (300 MHz, CDCl$_3$) δ 0.88 (3H, t, J=7.3 Hz), 1.32–1.57 (2H, m), 2.34–2.46 (1H, m), 2.50–2.57 (1H, m), 3.70–3.82 (1H, m), 4.34–4.48 (1H, m), 4.39 (1H, d, J=14.1), 4.43 (1H, d, J=14.1), 4.60–4.65 (1H, m), 5.19–5.34 (2H, m), 5.88–6.01 (1H, m), 6.81 (1H, br s).

i) In the same manner as Reference example 1.c), by using allyl (2R)-4-(chloroacetyl)-2-ethyl-3,6-dihydro-1(2H)-pyridinecarboxylate (167 mg, 0.61 mmol), there was obtained allyl (2R)-2-ethyl-4-(2-sulfanyl-1,3-thiazol-4-yl)-3,6-dihydro-1(2H)-pyridinecarboxylate (105 mg, 55%).

$^1$H NMR (300 MHz, CDCl$_3$) δ 0.90 (3H, t, J=7.4 Hz), 1.37–1.66 (2H, m), 2.17–2.24 (1H, m), 2.58–2.68 (1H, m), 3.65–3.79 (1H, m), 4.43–4.67 (4H, m), 5.21–5.34 (2H, m), 5.89–6.01 (1H, m), 6.08 (1H, br s), 6.39 (1H, s), 10.94 (1H, br s).

EXAMPLE 27

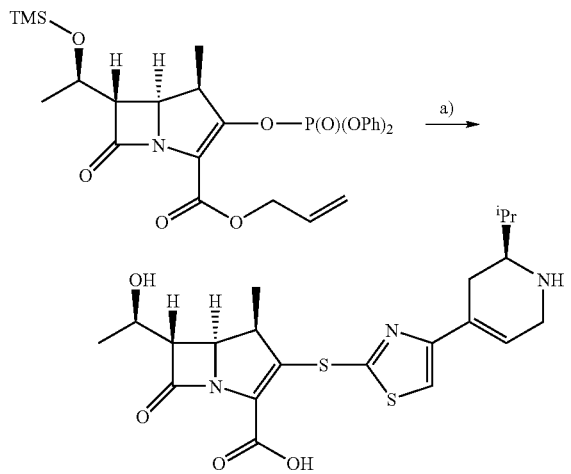

a) A solution of lithium hexamethyldisilazide in THF (1M, 0.25 ml, 0.25 mmol) was added at 0–5° C. to a solution of allyl (2S)-4-(2-mercapto-1,3-thiazol-4-yl)-2-isopropyl-3,6-dihydro-1(2H)-pyridinecarboxylate (80 mg, 0.25 mmol) in THF (4.3 ml) and the mixture was stirred for 10 minutes. To the reaction solution was added at 0° C. a solution of allyl (4R,5R,6S)-3-[(diphenoxyphosphino)oxy]-4-methyl-7-oxo-6-{(1R)-1-[(trimethylsilyl)oxy]ethyl}-1-azabicyclo[3.2.0]hept-2-ene-2-carboxylate in acetonitrile (30%, 0.94 g, 0.50 mmol) and the solution was allowed to stand in a refrigerator for 12 hours. To the reaction solution was added ice water and the reaction mixture was extracted with ethyl acetate. The organic layer was washed with a saturated aqueous sodium chloride solution and dried over anhydrous sodium sulfate. After removal of the solvent in vacuo, the residue was dissolved in THF (5.65 ml) and thereto were added at 0° C. water and 1N hydrochloric acid to adjust pH about 3. The solution was stirred for 1 hour. To the reaction mixture was added an aqueous sodium hydrogen carbonate and the solution was extracted twice with ethyl acetate. The organic layer was washed with a saturated aqueous sodium chloride solution, dried over anhydrous sodium sulfate and the solvent was removed in vacuo. The residue was dissolved in dichloromethane (5 ml). To the solution was added at 0° C. acetic acid (36 μl, 0.63 mmol) and tributyltin hydride (0.67 ml, 2.5 mmol) and then was added at room temperature bis(triphenylphosphine)palladium chloride(II) (17.5 mg, 0.025 mmol). The mixture was stirred at the same temperature for 10 minutes. The reaction mixture was poured into a mixture of ice (5 g) and phosphate buffer (pH7.0, 5 ml). After separation with a separating funnel, the organic layer was extracted twice with water. The organic solvent in the aqueous layer was removed in vacuo and was purified by polymer chromatography (CHP-20P). The fractions eluted with an 3–8% aqueous THF solution were combined and lyophilized to give (4R,5S,6S)-6-[(1R)-1-hydroxyethyl]-3-({4-[(6S)-6-isopropyl-1,2,5,6-tetrahydro-3-pyridinyl]-1,3-thiazol-2-yl}sulfanyl)-4-methyl-7-oxo-1-azabicyclo[3.2.0]hept-2-ene-2-carboxylic acid (29.9 mg, 17%) as a white amorphous.

$^1$H NMR (300 MHz, D$_2$O) δ 0.95 (6 H, d, J=6.8 Hz), 0.97 (3 H, d, J=6.8 Hz), 1.12 (3 H, d, J=6.4 Hz), 1.95–2.07 (1 H, m), 2.47–2.76 (2 H, m), 3.16–3.36 (3 H, m), 3.82 (2 H, brs), 4.08–4.15 (2 H, m), 6.38 (1 H, brs), 7.48 (1 H, s). IR (KBr) 3434, 2969, 1753, 1598 cm$^{-1}$

EXAMPLE 28

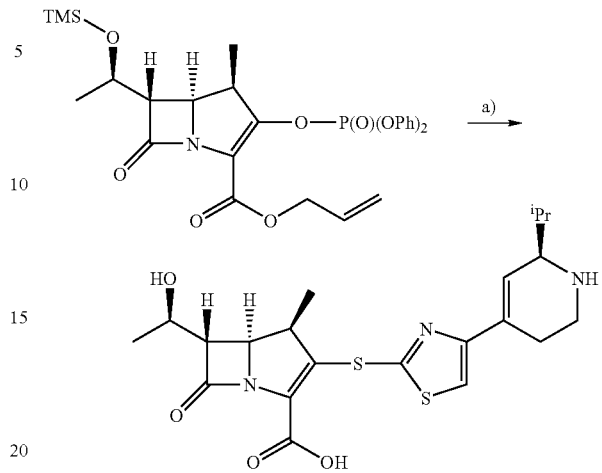

a) In the same manner as Example 27.a), by using allyl (6R)-6-isopropyl-4-(2-mercapto-1,3-thiazol-4-yl)-3,6-dihydro-1(2H)-pyridinecarboxylate, there was obtained (4R,5S,6S)-6-[(1R)-1-hydroxyethyl]-3-({4-[(6R)-6-isopropyl-1,2,3,6-tetrahydro-4-pyridinyl]-1,3-thiazol-2-yl}sulfanyl)-4-methyl-7-oxo-1-azabicyclo[3.2.0]hept-2-ene-2-carboxylic acid.

$^1$H NMR (300 MHz, D$_2$O) δ 0.92–0.98 (9 H, s), 1.12 (3 H, d=6.4 Hz), 1.90–2.03 (1 H, m), 2.62–2.73 (2 H, m), 3.09–3.38 (3 H, m), 3.48–3.65 (1 H, m), 3.77–3.83 (1 H, m), 4.04–4.16 (2 H, m), 6.42 (1 H, s), 7.48 (1 H, m). IR (KBr) 3412, 2968, 1755, 1599, 1393 cm$^{-1}$

EXAMPLE 29

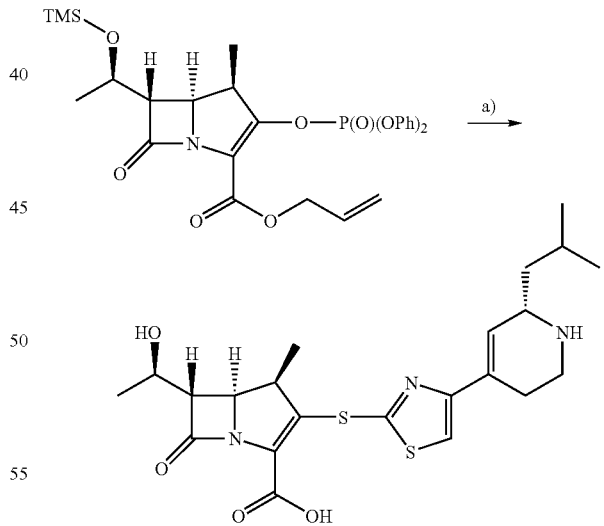

a) In the same manner as Example 27.a), by using allyl(6S)-6-isobutyl-4-(2-mercapto-1,3-thiazol-4-yl)-3,6-dihydro-1(2H)-pyridinecarboxylate, there was obtained (4R,5S,6S)-6-[(1R)-1-hydroxyethyl]-3-({4-[(6S)-6-isobutyl-1,2,3,6-tetrahydro-4-pyridinyl]-1,3-thiazol-2-yl}sulfanyl)-4-methyl-7-oxo-1-azabicyclo[3.2.0]hept-2-ene-2-carboxylic acid.

$^1$H NMR (300 MHz, D$_2$O) δ 0.86 (6 H, d, J=6.2 Hz), 0.95 (3 H, d, J=7.7 Hz), 1.12 (3 H, d, J=6.2 Hz), 1.50–1.79 (3 H, m), 2.63–2.70 (2 H, m), 3.13–3.37 (3 H, m), 3.47–3.65 (2 H, m), 3.98–4.15 (2 H, m), 6.39 (1 H, brs), 7.47 (1 H, s). IR (KBr) 3386, 2966, 1756, 1600, 1388 cm$^{-1}$

EXAMPLE 30

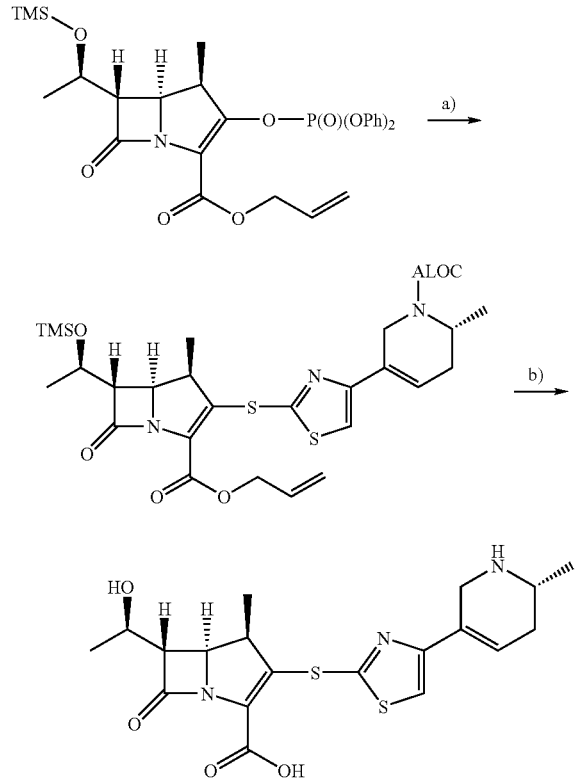

a) In the same manner as Example 2.a), by using allyl (2R)-2-methyl-5-(2-mercapto-1,3-thiazol-4-yl)-3,6-dihydro-1(2H)-pyridinecarboxylate, there was obtained allyl (4R,5S,6S)-3-[4-{(6R)-1-[(allyloxy)carbonyl]-6-methyl-1,2,5,6-tetrahydro-3-pyridinyl}-1,3-thiazol-2-yl)sulfanyl]-4-methyl-7-oxo-6-{(1R)-1-[(trimethylsilyl)oxy]ethyl}-1-azabicyclo[3.2.0]hept-2-ene-2-carboxylate.

$^1$H NMR (300 MHz, CDCl$_3$) δ 0.10 (9 H, s), 1.11 (3 H, d, J=7.3 Hz), 1.17 (3 H, d, J=6.8 Hz), 1.21 (3 H, d, J=6.1 Hz), 2.04–2.15 (1 H, m), 2.58–2.71 (1 H, m), 3.18–3.24 (1 H, m), 3.37–3.48 (1 H, m), 3.82–3.93 (1 H, m), 4.06–4.21 (2 H, m), 4.62–4.86 (6 H, m), 5.15–5.48 (4 H, m), 5.87–6.03 (2 H, m), 6.71 (1 H, brs), 7.11 (1 H, s).

b) In the same manner as Example 2.b), by using allyl (4R,5S,6S)-3-[(4-{(6R)-1-[(allyloxy)carbonyl]-6-methyl-1,2,5,6-tetrahydro-3-pyridinyl}-1,3-thiazol-2-yl)sulfanyl]-4-methyl-7-oxo-6-{(1R)-1-[(trimethylsilyl)oxy]ethyl}-1-azabicyclo[3.2.0]hept-2-ene-2-carboxylate, there was obtained (4R,5S,6S)-6-[(1R)-1-hydroxyethyl]4-methyl-3-({4-[(6R)-6-methyl-1,2,5,6-tetrahydro-3-pyridinyl]-1,3-thiazol-2-yl}sulfanyl)-7-oxo-1-azabicyclo[3.2.0]hept-2-ene-2-carboxylic acid.

$^1$H NMR (300 MHz, D$_2$O) δ 0.95 (3 H, d, J=7.3 Hz), 1.12 (3 H, d, J=6.0 Hz), 1.31 (3 H, d, J=6.4 Hz), 2.18–2.33 (1 H, m), 2.50–2.64 (1 H, m), 3.10–3.49 (3 H, m), 3.95–4.16 (4 H, m), 6.54 (1 H, s), 7.41 (1 H, s). IR (KBr) 3428, 2970, 1759, 1599, 1392 cm$^{-1}$

EXAMPLE 31

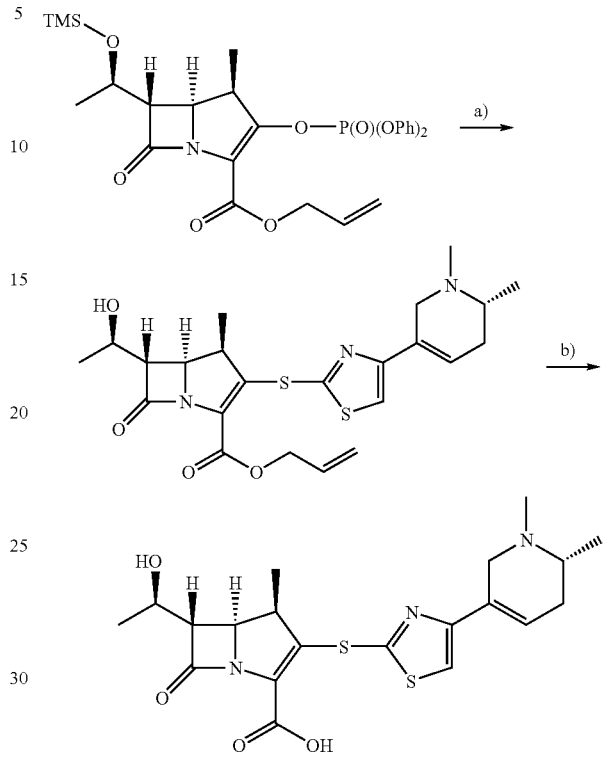

a) In the same manner as Example 1.a) and 1.b), by using 4-[(6R)-1,6-dimethyl-1,2,5,6-tetrahydro-3-pyridinyl]-1,3-thiazole-2-thiol, there was obtained allyl (4R,5S,6S)-3-({4-[(6R)-1,6-dimethyl-1,2,5,6-tetrahydro-3-pyridinyl]-1,3-thiazol-2-yl}sulfanyl)-4-methyl-7-oxo-6-{(1R)-1-[(trimethylsilyl)oxy]ethyl}-1-azabicyclo[3.2.0]hept-2-ene-2-carboxylate.

$^1$H NMR (300 MHz, CDCl$_3$) δ 1.06 (3 H, d, J=7.3 Hz), 1.16 (3 H, d, J=6.4 Hz), 1.29 (3 H, d, J=6.4 Hz), 2.17–2.30 (2 H, m), 2.46 (3 H, s), 2.64–2.76 (1 H, m), 3.21–3.25 (1 H, m), 3.32–3.43 (1 H, m), 3.48–3.61 (2 H, m), 4.15–4.27 (2 H, m), 4.71 (1 H, dd, J=5.7, 13.4 Hz), 4.83 (1 H, dd, J=5.3, 13.4 Hz), 5.26 (1 H, d, J=10.4 Hz), 5.44 (1 H, d, J=17.2 Hz), 5.96 (1 H, dddd, J=5.3, 5.7, 10.4, 17.2 Hz), 6.60 (1 H, s), 7.07 (1 H, s).

b) In the same manner as Example 1.c), by using allyl (4R,5S,6S)-3-({4-[(6R)-1,6-dimethyl-1,2,5,6-tetrahydro-3-pyridinyl]-1,3-thiazol-2-yl}sulfanyl)-4-methyl-7-oxo-6-{(1R)-1-[(trimethylsilyl)oxy]ethyl}-1-azabicyclo[3.2.0]hept-2-ene-2-carboxylate, there was obtained (4R,5S,6S)-3-({4-[(6R)-1,6-methyl-1,2,5,6-tetrahydro-3-pyridinyl]-1,3-thiazol-2-yl}sulfanyl)-6-[(1R)-1-hydroxyethyl]-4-methyl-7-oxo-1-azabicyclo[3.2.0]hept-2-ene-2-carboxylic acid.

$^1$H NMR (300 MHz, D$_2$O) δ 0.95 (3 H, d, J=7.3 Hz), 1.12 (3 H, d, J=6.4 Hz), 1.28 (3 H, d, J=6.6 Hz), 2.27–2.40 (1 H, m), 2.58–2.72 (1 H, m), 2.83 (3 H, s), 3.13–3.38 (4 H, m), 3.90–4.14 (3 H, m), 6.52 (1 H, s), 7.40 (1 H, s) IR (KBr) 3400, 2968, 1764, 1602, 1386 cm$^{-1}$

EXAMPLE 32

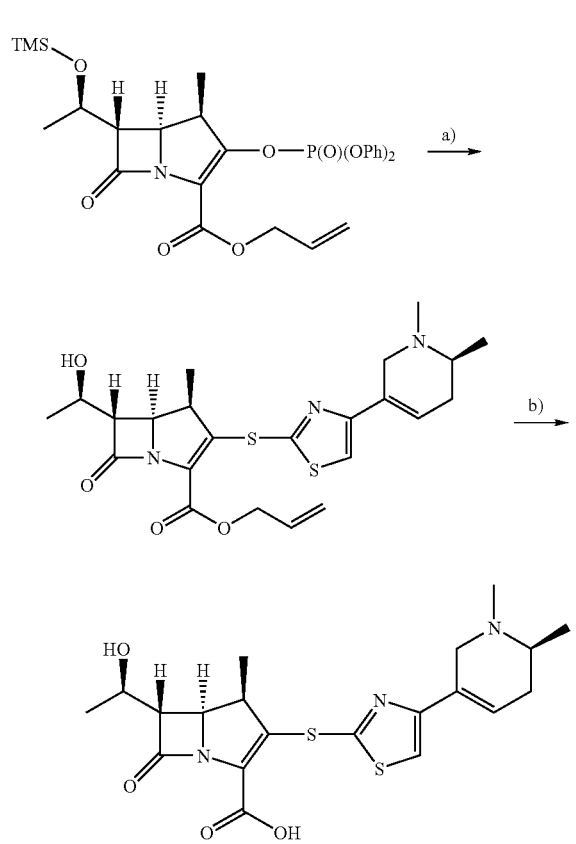

a) In the same manner as Example 1.a) and 1.b), by using 4-[(6S)-1,6-dimethyl-1,2,5,6-tetrahydro-3-pyridinyl]-1,3-thiazole-2-thiol, there was obtained allyl (4R,5S,6S)-3-({4-[(6S)-1,6-dimethyl-1,2,5,6-tetrahydro-3-pyridinyl]-1,3-thiazol-2-yl}sulfanyl)-4-methyl-7-oxo-6-{(1R)-1-[(trimethylsilyl)oxy]ethyl}-1-azabicyclo[3.2.0]hept-2-ene-2-carboxylate.

$^1$H NMR (300 MHz, CDCl$_3$) δ 1.04–1.31 (9 H, m), 2.07–2.20 (2 H, m), 2.43 (3 H, s), 2.54–2.64 (1 H, m), 3.21–3.24 (1 H, m), 3.48–3.99 (3 H, m), 4.14–4.26 (2 H, m), 4.62–4.86 (2 H, m), 5.14–5.47 (2 H, m), 5.89–6.03 (1 H, m), 6.59 (1 H, s), 7.05 (1 H, s).

b) In the same manner as Example 1.c), by using allyl (4R,5S,6S)-3-({4-[(6S)-1,6-dimethyl-1,2,5,6-tetrahydro-3-pyridinyl]-1,3-thiazol-2-yl}sulfanyl)-4-methyl-7-oxo-6-{(1R)-1-[(trimethylsilyl)oxy]ethyl}-1-azabicyclo[3.2.0]hept-2-ene-2-carboxylate, there was obtained (4R,5S,6S)-3-({4-[(6S)-1,6-methyl-1,2,5,6-tetrahydro-3-pyridinyl]-1,3-thiazol-2-yl}sulfanyl)-6-[(1R)-1-hydroxyethyl]-4-methyl-7-oxo-1-azabicyclo[3.2.0]hept-2-ene-2-carboxylic acid.

$^1$H NMR (300 MHz, D$_2$O) δ 0.95 (3 H, d, J=7.1 Hz), 1.12 (3 H, d, J=6.2 Hz), 1.27 (3 H, d, J=7.0 Hz), 2.27–2.40 (1 H, m), 2.58–2.72 (1 H, m), 2.81 (3 H, s), 3.13–3.38 (4 H, m), 3.90–4.14 (3 H, m), 6.51 (1 H, s), 7.40 (1 H, s). IR (KBr) 3280, 2965, 1788, 1602, 1384 cm$^{-1}$

EXAMPLE 33

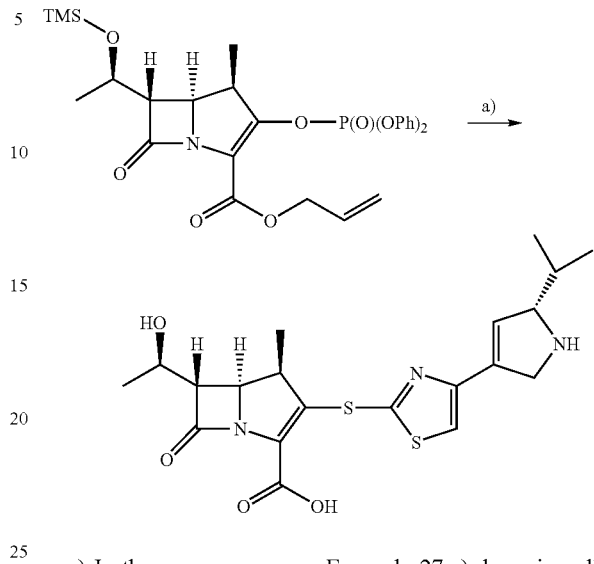

a) In the same manner as Example 27.a), by using allyl (2S)-2-isopropyl-4-(2-sulfanyl-1,3-thiazol-4-yl)-2,5-dihydro-1H-pyrrole-1-carboxylate, there was obtained (4R,5S,6S)-6-[(1R)-1-hydroxyethyl]-3-({4-[(5S)-5-isopropyl-2,5-dihydro-1H-pyrrol-3-yl]-1,3-thiazol-2-yl}sulfanyl)-4-methyl-7-oxo-1-azabicyclo[3.2.0]hept-2-ene-2-carboxylic acid.

$^1$H NMR (300 MHz, D$_2$O) δ 0.91–0.96 (9 H, m), 1.11 (3 H, d, J=6.4 Hz), 1.93–2.05 (1 H, m), 3.11–3.22 (1 H, m), 3.34 (1 H, dd, J=2.7, 6.0 Hz), 4.05–4.13 (2 H, m), 4.25–4.42 (3 H, m), 6.35 (1 H, s), 7.51 (1 H, s).

EXAMPLE 34

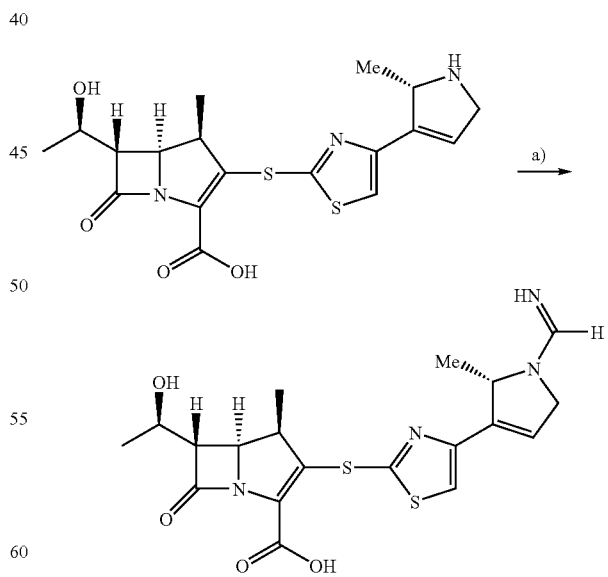

To a phosphate buffer solution of (4R,5S,6S)-6-[(1R)-1-hydroxyethyl]-4-methyl-3-({4-[(2S)-2-methyl-2,5-dihydro-1H-pyrrol-3-yl]-1,3-thiazol-2-yl}sulfanyl)-7-oxo-1-azabicyclo[3.2.0]hept-2-ene-2-carboxylic acid (7.3 mg, 0.018 mmol) was added at 0° C. benzyl formimidate hydrochloride (22.3 mg, 0.13 mmol). The solution was adjusted pH to 8.5 with an aqueous 1N NaOH solution and was stirred at the same temperature for 1.5 hours. Then the solution was adjusted pH to 7.0 with 1N hydrochloric acid and was purified by polymer chromatography (CHP-20P). The fractions eluted with 3–8% aqueous THF solution were combined and lyophilized to give (4R,5S,6S)-6-[(1R)-1-hydroxyethyl]-3-({4-[(5S)-1-(iminomethyl)-5-methyl-2,5-dihydro-1H-pyrrol-3-yl]-1,3-thiazol-2-yl}sulfanyl)-4-methyl-7-oxo-1-azabicyclo[3.2.0]hept-2-ene-2-carboxylic acid (5.9 mg, 75%) as a white amorphous.

$^1$H NMR (300 MHz, D$_2$O) δ 0.96 (3 H, d, J=7.3 Hz), 1.11 (3 H, d, J=6.4 Hz), 1.40 (3 H, d, J=6.6 Hz), 3.05–3.16 (1 H, m), 3.34 (1 H, dd, J=2.7, 5.9 Hz), 4.05–4.14 (2 H, m), 4.30–4.37 (1 H, m), 5.03–5.20 (1 H, m), 6.27 (1 H, s), 7.55 (1 H, s), 8.04 (1 H, s). IR (KBr) 3402, 2974, 1758, 1710, 1597, 1391 cm$^{-1}$

EXAMPLE 35

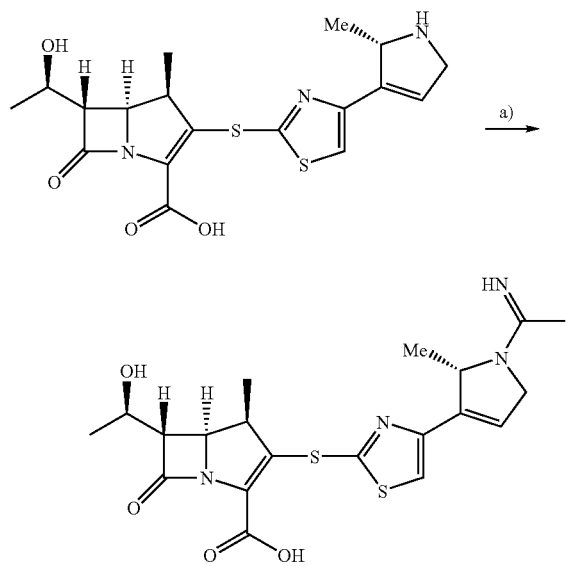

To a phosphate buffer solution of (4R,5S,6S)-6-[(1R)-1-hydroxyethyl]-4-methyl-3-({4-[(2S)-2-methyl-2,5-dihydro-1H-pyrrol-3-yl]-1,3-thiazol-2-yl}sulfanyl)-7-oxo-1-azabicyclo[3.2.0]hept-2-ene-2-carboxylic acid (7.6 mg, 0.019 mmol) was added at 0° C. ethyl acetimidate hydrochloride (18.4 mg, 0.15 mmol). The solution was adjusted pH to 8.5 with an aqueous 1N NaOH solution and was stirred for 6 hours. Then the solution was adjusted pH to 7.0 with 1N hydrochloric acid and was purified by polymer chromatography (CHP-20P). The fractions eluted with an 3–8% aqueous THF solution were combined and lyophilized to give (4R,5S,6S)-3-({4-[(5S)-1-ethanimidoyl-5-methyl-2,5-dihydro-1H-pyrrol-3-yl]-1,3-thiazol-2-yl}sulfanyl)-6-[(1R)-1-hydroxyethyl]-4-methyl-7-oxo-1-azabicyclo[3.2.0]hept-2-ene-2-carboxylic acid (7.9 mg, 93%) as a white amorphous.

$^1$H NMR (300 MHz, D$_2$O) δ 0.94 (3 H, d, J=7.3 Hz), 1.10 (3 H, d, J=6.4 Hz), 1.31 (1.65 H, d, J=6.2 Hz), 1.34 (1.35 H, d, J=6.4 Hz), 2.18 (1.65 H, s), 2.30 (1.35 H, s), 3.05–3.15 (1 H, m), 3.33 (1 H, dd, J=2.6, 6.0 Hz), 4.03–4.13 (2 H, m), 4.27–4.33 (0.45 H, m), 4.43–4.48 (0.55 H, m), 4.97–5.07 (0.55 H, m), 5.16–5.25 (0.45 H, m), 6.26 (1 H, s), 7.53 (0.45 H, s), 7.54 (0.55 H, s). IR (KBr) 3406, 1760, 1682, 1605, 1385 cm$^{-1}$

EXAMPLE 36

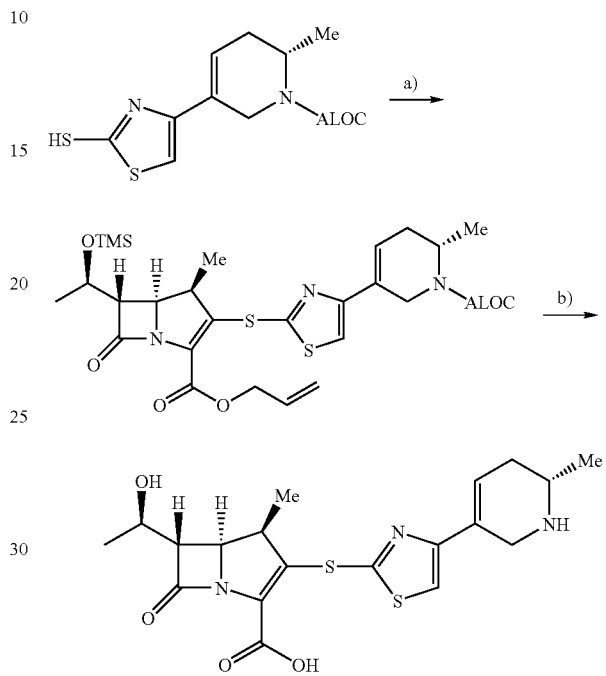

a) In the same manner as Example 1.a), by using allyl (2S)-2-methyl-5-(2-sulfanyl-1,3-thiazol-4-yl)-3,6-dihydro-1(2H)-pyridinecarboxylate(160 mg, 0.54 mmol), there was obtained allyl(4R,5S,6S)-3-[(4-{(6S)-1-[(allyloxy)carbonyl]-6-methyl-1,2,5,6-tetrahydro-3-pyridinyl]-1,3-thiazol-2-yl}sulfanyl)-4-methyl-7-oxo-6-[(1R)-1-[(trimethylsilyl)oxy]ethyl}-1-azabicyclo[3.2.0]hept-2-ene-2-carboxylate (175 mg, 52%).

$^1$H NMR (300 MHz, CDCl$_3$) δ 0.12 (9H, s), 1.10 (3H, d, J=7.1 Hz), 1.19(3H, d, J=6.8 Hz), 1.24 (3H, d, J=6.2 Hz), 2.09–2.17 (1H, m), 2.62–2.70 (1H, m), 3.25 (1H, dd, J=3.5, 6.2 Hz), 3.51–3.61 (1H, m), 3.88–3.94 (1H, m), 4.17–4.25 (2H, m), 4.64–4.88 (6H, m), 5.21–5.51 (4H, m), 5.91–6.04 (2H, m), 6.73–6.76 (1H, m), 7.12 (1H, s).

b) In the same manner as Example 2.b), by using allyl (4R,5S,6S)-3-[(4-{(6S)-1-[(allyloxy)carbonyl]-6-methyl-1,2,5,6-tetrahydro-3-pyridinyl}-1,3-thiazol-2-yl)sulfanyl]-4-methyl-7-oxo-6-{(1R)-1-[(trimethylsilyl)oxy]ethyl}-1-azabicyclo[3.2.0]hept-2-ene-2-carboxylate (175 mg, 0.28 mmol), there was obtained (4R,5S,6S)-6-[(1R)-1-hydroxyethyl]-4-methyl-3-({4-[(6S)-6-methyl-1,2,5,6-tetrahydro-3-pyridinyl]-1,3-thiazol-2-yl]sulfanyl)-7-oxo-1-azabicyclo[3.2.0]hept-2-ene-2-carboxylic acid (70 mg, 59%).

$^1$H NMR (300 MHz, D$_2$O) δ 0.95 (3H, d, J=7.7 Hz), 1.13 (3H, d, J=6.2 Hz), 1.31 (3H, d, J=6.4 Hz), 2.20–2.31 (1H, m), 2.52–2.62 (1H, m), 3.14–3.20 (1H, m), 3.33–3.37 (1H, m), 3.41–3.51 (1H, m), 3.96–4.01 (2H, m), 4.09–4.15 (2H, m), 6.53–6.65 (1H, m), 7.41 (1H, s). IR (KBr) 3404, 2971, 1758, 1597, 1456, 1389, 1265, 1148, 1028, 767 cm$^{-1}$

EXAMPLE 37

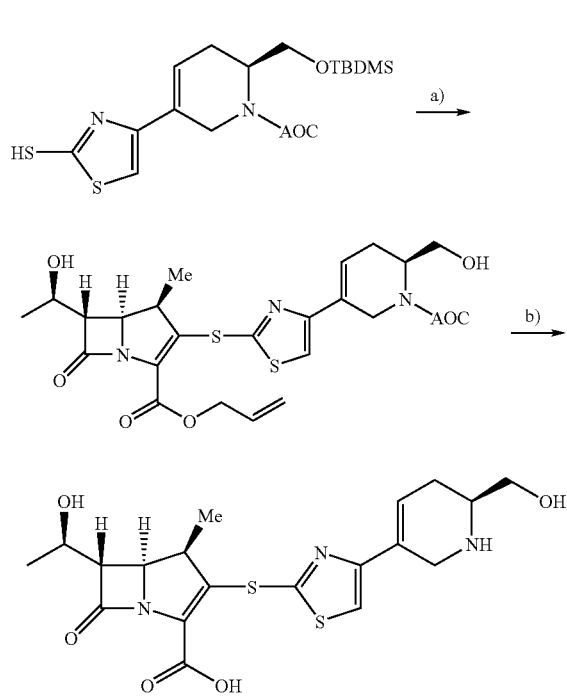

a) In the same manner as Example 6.a), by using allyl (2S)-2-({[tert-butyl(dimethyl)silyl]oxy}methyl)-5-(2-sulfanyl-1,3-thiazol-4-yl)-3,6-dihydro-1(2H)-pyridinecarboxylate(90 mg, 0.20 mmol), there was obtained allyl(4R,5S,6S)-3-({4-[(6S)-1-[(allyloxy)carbonyl]-6-(hydroxymethyl)-1,2,5,6-tetrahydro-3-pyridinyl]-1,3-thiazol-2-yl}sulfanyl)-6-[(1R)-1-hydoxyethyl]-4-methyl-7-oxo-1-azabicyclo[3.2.0]hept-2-ene-2-carboxylate (40 mg, 34%).

$^1$H NMR (300 MHz, CDCl$_3$) δ 1.12 (3H, d, J=7.4 Hz), 1.33 (3H, d, J=6.2 Hz), 2.24–2.33 (1H, m), 2.57–2.65 (1H, m), 3.27 (1H, dd, J=2.9, 6.0 Hz), 3.50–3.73 (3H, m), 3.89–4.06 (1H, m), 4.18–4.31 (2H, m), 4.56–4.88 (6H, m), 5.22–5.50 (4H, m), 5.90–6.05 (2H, m), 6.68–6072 (1H, m), 7.15 (1H, s).

b) In the same manner as Example 1.c), by using allyl (4R,5S,6S)-3-({4-[(6S)-1-[(allyloxy)carbonyl]-6-(hydroxymethyl)-1,2,5,6-tetrahydro-3-pyridinyl]-1,3-thiazol-2-yl}sulfanyl)-6-[(1R)-1-hydoxyethyl]-4-methyl-7-oxo-1-azabicyclo[3.2.0]hept-2-ene-2-carboxylate (40 mg, 0.053 mmol), there was obtained (4R,5S,6S)-6-[(1R)-1-hydroxyethyl]-3-({4-[(6S)-6-(hydroxymethyl)-1,2,5,6-tetrahydro-3-pyridinyl]-1,3-thiazol-2-yl}sulfanyl)-4-methyl-7-oxo-1-azabicyclo[3.2.0]hept-2-ene-2-carboxylic acid (16.9 mg, 54%).

$^1$H NMR (300 MHz, D$_2$O) δ 0.94 (3H, d, J=7.5 Hz), 1.11 (3H, d, J=6.4 Hz), 2.26–2.53 (2H, m), 3.09–3.21 (1H, m), 3.32–3.35 (1H, m), 3.38–3.49 (1H, m), 3.57–3.64 (1H, m), 3.77–3.83 (1H, m), 3.98–4.13 (4H, m), 6.52–6.56 (1H, m), 7.41 (1H, s). IR (KBr) 3380, 2969, 1760, 1596, 1389, 1263, 1056 cm$^{-1}$

EXAMPLE 38

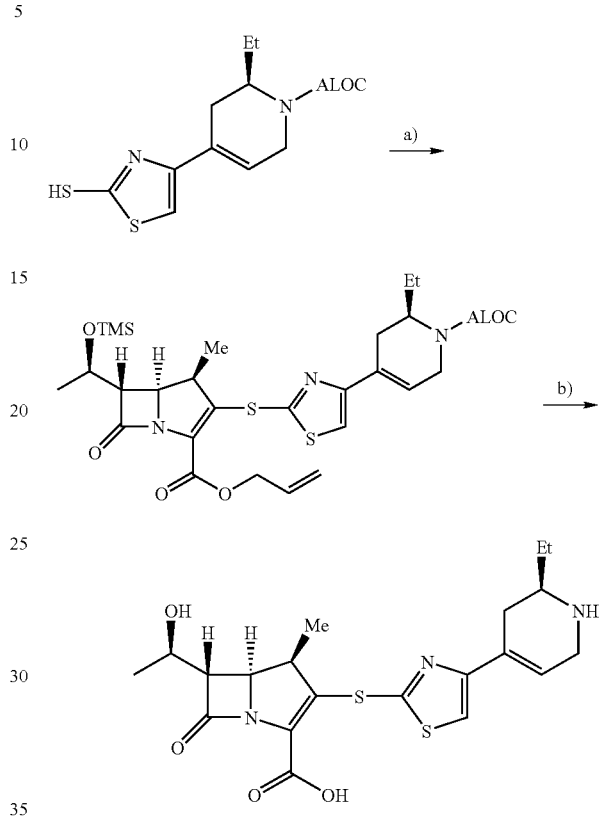

a) In the same manner as Example 1.a), by using allyl (2R)-2-ethyl-4-(2-sulfanyl-1,3-thiazol-4-yl)-3,6-dihydro-1(2H)-pyridinecarboxylate(105 mg, 0.34 mmol), there was obtained allyl (4R,5S,6S)-3-[(4-{(2R)-1-[(allyloxy) carbonyl]-2-ethyl-1,2,3,6-tetrahydro-4-pyridinyl}-1,3-thiazol-2-yl) sulfanyl]-4-methyl-7-oxo-6-{(1R)-1-[(trimethylsilyl) oxy]ethyl}-1-azabicyclo[3.2.0]hept-2-ene-2-carboxylate (108 mg, 51%).

$^1$H NMR (300 MHz, CDCl$_3$) δ 0.12 (9H, s), 0.91 (3H, t, J=6.7 Hz), 1.09 (3H, d, J=7.1 Hz), 1.24 (3H, d, J=6.2 Hz), 1.41–1.69 (2H, m), 2.35–2.42 (1H, m), 2.67–2.76 (1H, m), 3.24 (1H, dd, J=2.9, 6.2 Hz), 3.51–3.63 (1H, m), 3.70–3.81 (1H, m), 4.17–4.24 (2H, m), 4.45–4.68 (4H, m), 4.70–4.87 (2H, m), 5.18–5.50 (4H, m), 5.90–6.05 (2H, m), 6.64 (1H, br s), 7.09 (1H, s).

b) In the same manner as Example 2.b), by using allyl (4R,5S,6S)-3-[(4-{(2R)-1-[(allyloxy)carbonyl]-2-ethyl-1,2,3,6-tetrahydro-4-pyridinyl}-1,3-thiazol-2-yl)sulfanyl]-4-methyl-7-oxo-6-[(1R)-1-[(trimethylsilyl)oxy]ethyl]-1-azabicyclo[3.2.0]hept-2-ene-2-carboxylate (108 mg, 0.17 mmol), there was obtained (4R,5S,6S)-3-({4-[(2R)-2-ethyl-1,2,3,6-tetrahydro-4-pyridinyl]-1,3-thiazol-2-yl}sulfanyl)-6-[(1R)-1-hydroxyethyl]-4-methyl-7-oxo-1-azabicyclo[3.2.0]hept-2-ene-2-carboxylic acid (35 mg, 47%).

$^1$H NMR (300 MHz, D$_2$O) δ 0.94 (3H, t, J=7.5 Hz), 0.95 (3H, d, J=6.1 Hz), 1.12 (3H, d, J=6.2 Hz), 1.59–1.81 (2H, m), 2.35–2.46 (1H, m), 2.72–2.81 (1H, m), 3.13–3.22 (1H, m), 3.25–3.37 (2H, m), 3.76–3.80 (2H, m), 4.08–4.14 (2H, m), 6.37–6.40 (1H, m), 7.46 (1H, s). IR (KBr) 3248, 2969, 1760, 1599, 1392, 1264, 1028 cm$^{-1}$

EXAMPLE 39

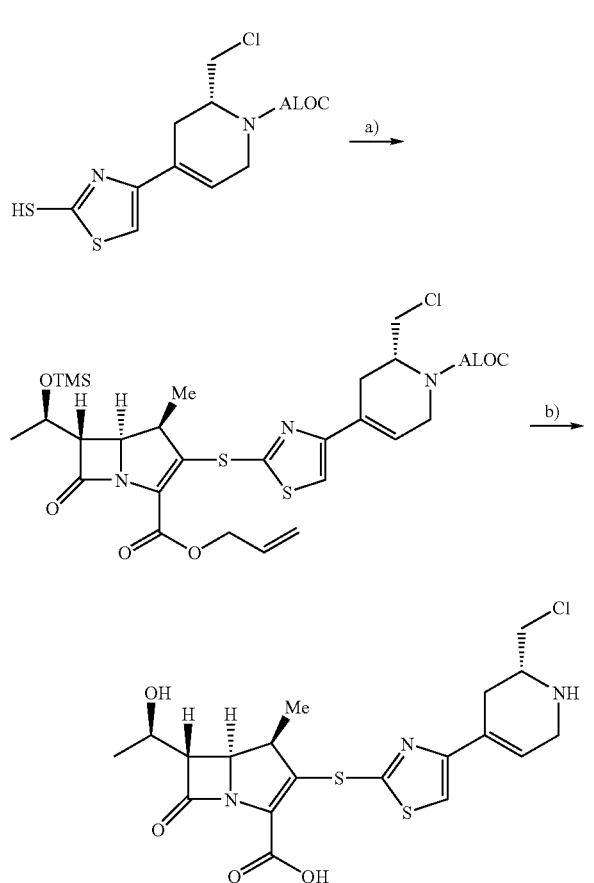

a) In the same manner as Example 1.a), by using allyl (2R)-2-(chloromethyl)-4-(2-sulfanyl-1,3-thiazol-4-yl)-3,6-dihydro-1(2H)-pyridinecarboxylate(150 mg, 0.45 mmol), there 5 was obtained allyl(4R,5S,6S)-3-({4-[(2R)-1-[(allyloxy)carbonyl]-2-(chloromethyl)-1,2,3,6-tetrahydro-4-pyridinyl]-1,3-thiazol-2-yl}sulfanyl]-4-methyl-7-oxo-6-{(1R)-1-[(trimethylsilyl)oxy]ethyl}-1-azabicyclo[3.2.0]hept-2-ene-2-carboxylate (140 mg, 47%).

$^1$H NMR (300 MHz, CDCl$_3$) δ 0.12 (9H, s), 1.13 (3H, d, J=7.1 Hz), 1.23 (3H, d, J=6.2 Hz), 2.71–2.76 (2H, m), 3.25 (1H, dd, J=2.9, 6.0 Hz), 3.45–3.63 (3H, m), 3.76–3.91 (1H, m), 4.18–4.26 (2H, m), 4.45–4.88 (6H, m), 5.22–5.50 (4H, m), 5.90–6.04 (2H, m), 6.68 (1H, br s), 7.15 (1H, s).

b) In the same manner as Example 2.b), by using allyl (4R,5S,6S)-3-({4-[(2R)-1-[(allyloxy)carbonyl]-2-(chloromethyl)-1,2,3,6-tetrahydro-4-pyridinyl]-1,3-thiazol-2-yl}sulfanyl)-4-methyl-7-oxo-6-{(1R)-1-[(trimethylsilyl)oxy]ethyl}-1-azabicyclo[3.2.0]hept-2-ene-2-carboxylate (140 mg, 0.21 mmol), there was obtained (4R,5S,6S)-3-({4-[(2R)-2-(chloromethyl)-1,2,3,6-tetrahydro-4-pyridinyl]-1,3-thiazol-2-yl}sulfanyl)-6-[(1R)-1-hydroxyethyl]-4-methyl-7-oxo-1-azabicyclo[3.2.0]hept-2-ene-2-carboxylic acid (51 mg, 52%).

$^1$H NMR (300 MHz, D$_2$O) δ 1.02 (3H, d, J=7.1 Hz), 1.19 (3H, d, J=6.4 Hz), 2.64–2.82 (2H, m), 3.19–3.28 (1H, m), 3.40–3.43 (1H, m), 3.69–4.00 (5H, m), 4.13–4.20 (2H, m), 6.47–6.50 (1H, m), 7.51 (1H, s). IR (KBr) 3412, 2968, 1758, 1600, 1393, 1264, 1028 cm$^{-1}$

EXAMPLE 40

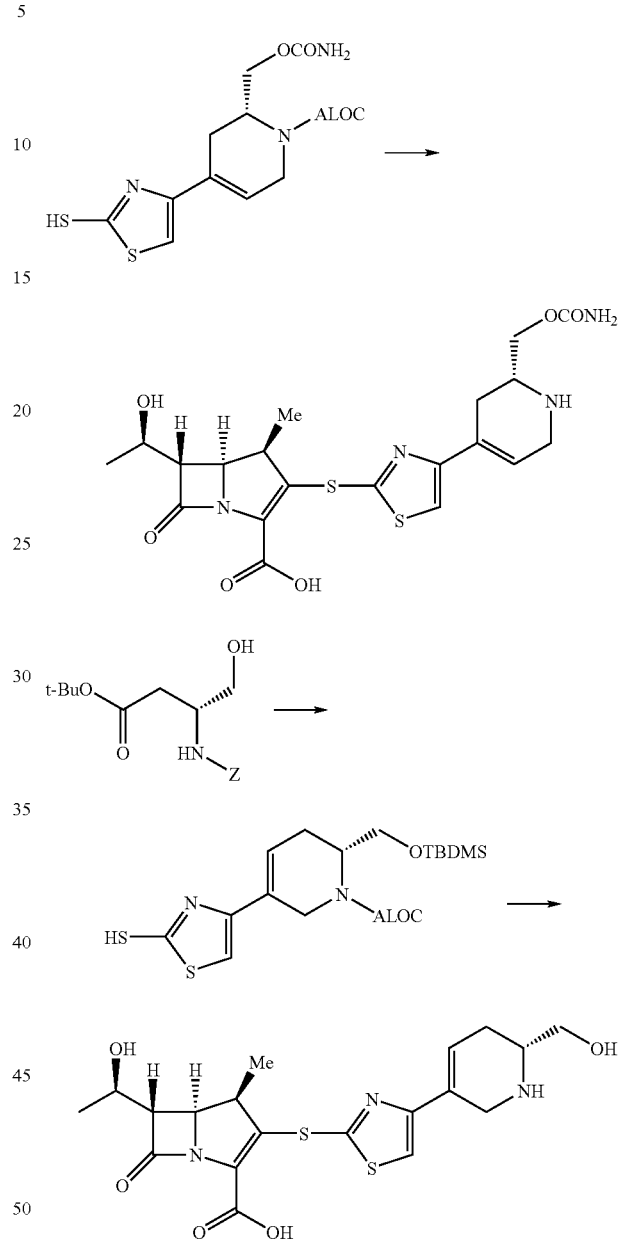

In the same manner as Example 14, by using allyl (2R)-2-{[(2-aminocarbonyl)oxy]methyl}-4-(2-sulfanyl-1,3-thiazol-4-yl)-3,6-dihydro-1(2H)-pyridinecarboxylate(503 mg, 1.42 mmol), there was obtained (4R,5S,6S)-3-{[4-((2R)-2-{[(aminocarbonyl)oxy]methyl}-1,2,3,6-tetrahydro-4-pyridinyl]-1,3-thiazol-2-yl]sulfanyl}-6-[(1R)-1-hydroxyethyl]-4-methyl-7-oxo-1-azabicyclo[3.2.0]hept-2-ene-2-carboxylic acid (19 mg, 3%).

$^1$H NMR (300 MHz, D$_2$O) δ 0.95 (3H, d, J=7.3 Hz), 1.12 (3H, d, J=6.0 Hz), 2.49–2.92 (2H, m), 3.14–3.20 (1H, m), 3.33–3.35 (1H, m), 3.82–3.85 (2H, m), 4.08–4.23 (2H, m), 4.30–4.37 (1H, m), 6.39–6.42 (1H, m), 7.46 (1H, s). IR (KBr) 3406, 2969, 1759, 1728, 1602, 1391, 1264, 1087 cm$^{-1}$

Reference Example 22

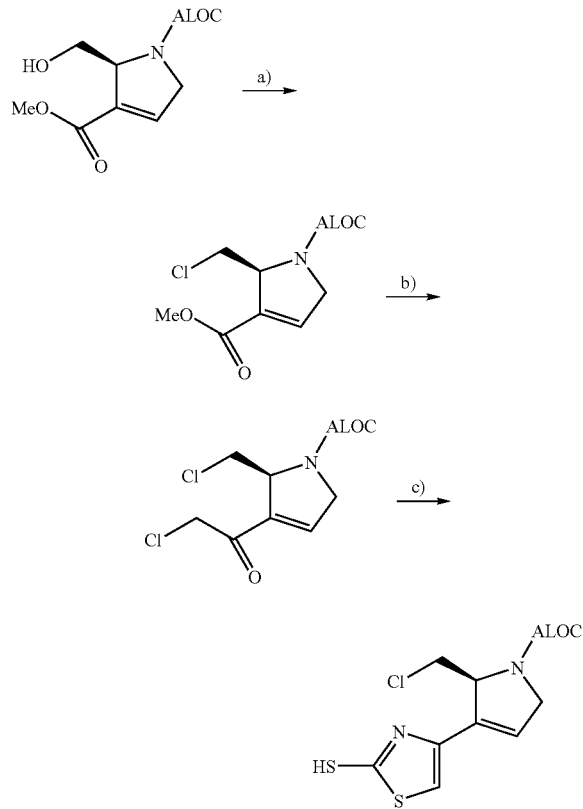

a) To a solution of 1-allyl 3-methyl(2S)-2-(hydroxymethyl)-2,5-dihydro-1H-pyrrole-1,3-dicarboxylate (1.29 g, 4.28 mmol) in carbontetrachloride (16 ml) was added at room temperature triphenylphosphine (1.35 g) and the mixture was refluxed under heating for 6 hours. The insoluble materials were dissolved in chloroform and the solvent was removed in vacuo. The residue was purified with silica gel (150 g) column chromatography (hexane/ethyl acetate 4/1→2/1) to give 1-allyl 3-methyl (2S)-2-(chloromethyl)-2,5-dihydro-1H-pyrrole-1,3-dicarboxylate (268 mg, 24%).

$^1$H-NMR (300 MHz, CDCl$_3$) δ 3.70 (3H, s), 3.92–4.06 (2H, m), 4.17–4.38 (2H, m), 4.52–4.58 (2H, m), 5.00–5.07 (1H, m), 5.11–5.17 (1H, m), 5.18–5.25 (1H, m), 5.76–5.92 (1H, m), 6.81–6.88 (1H, m).

b) In the same manner as Reference example 2.d), by using 1-allyl 3-methyl (2S)-2-(chloromethyl)-2,5-dihydro-1H-pyrrole-1,3-dicarboxylate (268 mg, 1.03 mmol), there was obtained allyl (2S)-3-(chloroacetyl)-2-(chloromethyl)-2,5-dihydro-1H-pyrrole-1-carboxylate (86 mg, 30%).

$^1$H-NMR (300 MHz, CDCl$_3$) δ 3.98–4.03 (1H, m), 4.09–4.34 (1H, m), 4.37–4.61 (4H, m), 4.63–4.68 (2H, m), 5.22–5.36 (3H, m), 5.88–6.02 (1H, m), 6.95–7.03 (1H, m).

c) In the same manner as Reference example 2.e), by using allyl (2S)-3-(chloroacetyl)-2-(chloromethyl)-2,5-dihydro-1H-pyrrole-1-carboxylate (86 mg, 0.31 mmol), there was obtained allyl (2S)-2-(chloromethyl)-3-(2-mercapto-1,3-thiazol-4-yl)-2,5-dihydro-1H-pyrrole-1-carboxylate (87 mg, 89%).

$^1$H-NMR (300 MHz, CDCl$_3$) δ 3.73–3.80 (1H, m), 4.26–4.43 (1H, m), 4.62–4.68 (4H, m), 5.24–5.38 (4H, m), 5.89–6.02 (1H, m), 6.48–6.54 (2H, m).

EXAMPLE 41

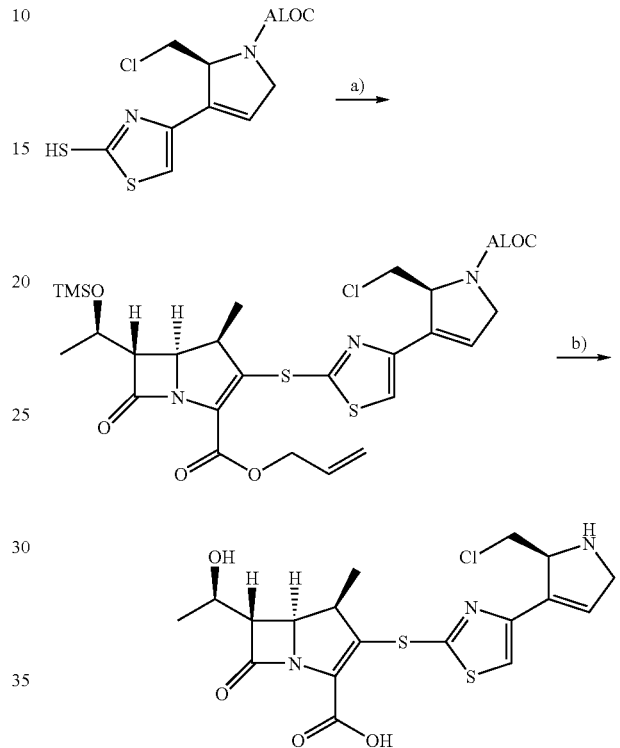

a) In the same manner as Example 1.a), by using allyl (2S)-2-(chloromethyl)-3-(2-mercapto-1,3-thiazol-4-yl)-2,5-dihydro-1H-pyrrole-1-carboxylate(87 mg, 0.27 mmol), there was obtained allyl (4R,5S,6S)-3-({4-[(2S)-1-[(allyloxy)carbonyl]-2-(chloromethyl)-2,5-dihydro-1H-pyrrol-3-yl]-1,3-thiazol-2-yl}thio)-4-methyl-7-oxo-6-{(1R)-1-[(trimethylsilyl)oxy]ethyl}-1-azabicyclo[3.2.0]hept-2-ene-2-carboxylate (30 mg, 17%).

$^1$H-NMR (300 MHz, CDCl$_3$) 0.12 (9H, s), 1.08 (3H, d, J=7.1 Hz), 1.24 (3H, d, J=6.1 Hz), 3.24 (1H, dd, J=2.9, 6.6 Hz), 3.42–3.51 (1H, m), 4.07–4.24 (4H, m), 4.35–4.44 (2H, m), 4.66–4.88 (4H, m), 5.23–5.38 (4H, m), 5.47 (1H, qd, J=1.5, 17.2 Hz), 5.91–6.05 (2H, m), 6.45 (1H, br), 7.38 (1H, s).

b) In the same manner as Example 2.b), by using allyl (4R,5S,6S)-3-({4-(2S)-1-[(allyloxy)carbonyl]-2-(chloromethyl)-2,5-dihydro-1H-pyrrol-3-yl]-1,3-thiazol-2-yl}thio)-4-methyl-7-oxo-6-{(1R)-1-[(trimethylsilyl)oxy]ethyl}-1-azabicyclo[3.2.0]hept-2-ene-2-carboxylate (30 mg, 0.047 mmol), there was obtained (4R,5S,6S)-3-({4-[(2S)-2-(chloromethyl)-2,5-dihydro-1H-pyrrol-3-yl]-1,3-thiazol-2-yl}thio)-6-[(1R)-1-hydroxyethyl]-4-methyl-7-oxo-1-azabicyclo[3.2.0]hept-2-ene-2-carboxylic acid (3.0 mg, 14%).

$^1$H-NMR (300 MHz, D$_2$O) 0.92 (3H, d, J=7.5 Hz), 1.11 (3H, d, J=6.4 Hz), 3.12–3.19 (1H, m), 3.32–3.36 (1H, m), 3.94–4.11 (6H, m), 5.18 (1H, br), 6.41 (1H, br), 7.64 (1H, br). IR (KBr) 3418, 2968, 1758, 1602, 1394, 1280, 1029 cm$^{-1}$.

EXAMPLE 42

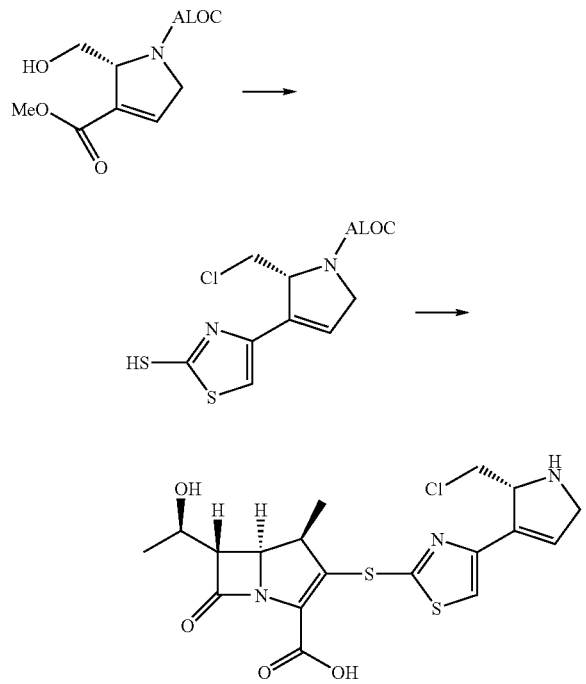

In the same manner as Example 22, by using 1-allyl 3-methyl (2R)-2-(hydroxymethyl)-2,5-dihydro-1H-pyrrole-1,3-dicarboxylate, there was obtained allyl (2R)-2-(chloromethyl)-3-(2-mercapto-1,3-thiazol-4-yl)-2,5-dihydro-1H-pyrrole-1-carboxylate. And then in the same manner as Example 41, there was obtained (4R,5S,6S)-3-({4-[(2R)-2-(chloromethyl)-2,5-dihydro-1H-pyrrol-3-yl]-1,3-thiazol-2-yl}thio)-6-[(1R)-1-hydroxyethyl]-4-methyl-7-oxo-1-azabicyclo[3.2.0]hept-2-ene-2-carboxylic acid.

EXAMPLE 43

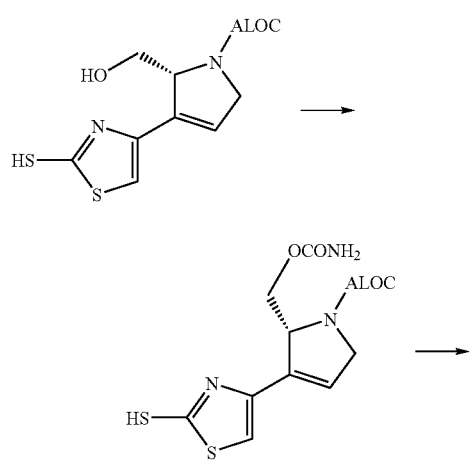

-continued

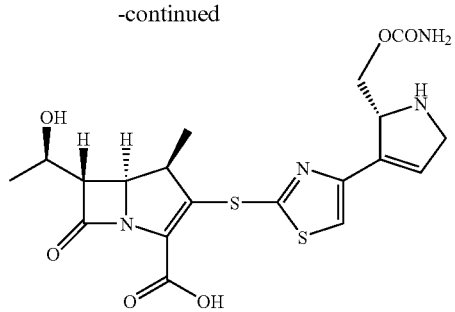

In the same manner as Reference example 8, by using allyl (2R)-2-(hydroxymethyl)-3-(2-mercapto-1,3-thiazol-4-yl)-2,5-dihydro-1H-pyrrole-1-carboxylate, there was obtained allyl (2R)-2-{[(aminocarbonyl)oxy]methyl}-3-(2-mercapto-1,3-thiazol-4-yl)-2,5-dihydro-1H-pyrrole-1-carboxylate. And then in the same manner as Example 14, there was obtained (4R,5S,6S)-3-{[4-((2R)-2-{[(aminocarbonyl)oxy]methyl}-2,5-dihydro-1H-pyrrol-3-yl)-1,3-thiazol-2-yl]thio}-6-[(1R)-1-hydroxyethyl]-4-methyl-7-oxo-1-azabicyclo[3.2.0]hept-2-ene-2-carboxylic acid.

EXAMPLE 44

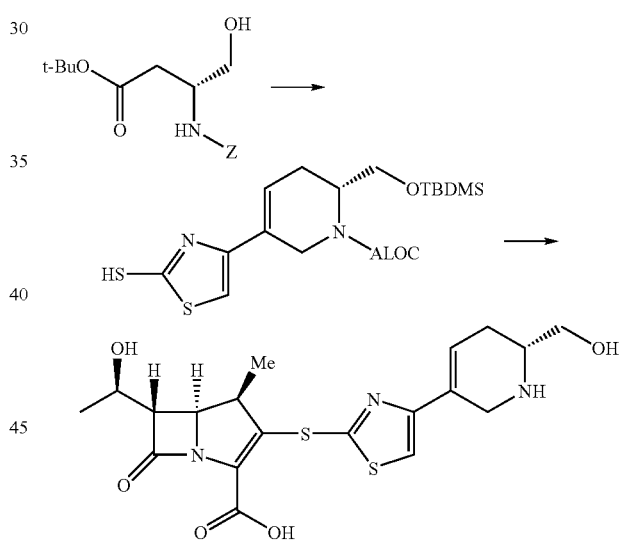

In the same manner as Reference example 20 by using tert-butyl (3R)-3-{[(benzyloxy)carbonyl]amino}-4-hydroxybutanoate, there was obtained allyl (2R)-2-({[tert-butyl(dimethyl)silyl]oxy}methyl)-5-(2-sulfanyl-1,3-thiazol-4-yl)-3,6-dihydro-1(2H)-pyridinecarboxylate. And then in the same manner as Example 37, there was obtained (4R,5S,6S)-6-[(1R)-1-hydroxyethyl]-3-({4-[(6R)-6-(hydroxymethyl)-1,2,5,6-tetrahydro-3-pyridinyl]-1,3-thiazol-2-yl}sulfanyl)-4-methyl-7-oxo-1-azabicyclo[3.2.0]hept-2-ene-2-carboxylic acid.

INDUSTRIAL APPLICABILITY

By the present invention, it becomes possible to provide β-lactam antibiotics having an excellent antibacterial activity against Gram-positive bacteria, especially against MRSA and MRCNS.

What is claimed is:

1. A β-lactam compound of the following formula [1a];

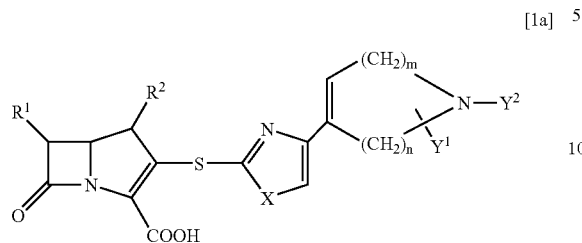

wherein $R^1$ is 1-(R)-hydroxyethyl group, $R^2$ is a methyl, X is a sulfur atom, and when (1) when m=1, n=1, $Y^1$ is a methyl, hydroxymethyl or isopropyl; and $Y^2$ is a hydrogen atom; or
(2) m=1, n=2, $Y^1$ is a fluoromethyl, hydroxymethyl, metoxymethyl or carbamoyloxymethyl; and $Y^2$ is a hydrogen atom; or
(3) a compound of the following formula (a), (b), (c) or (d):

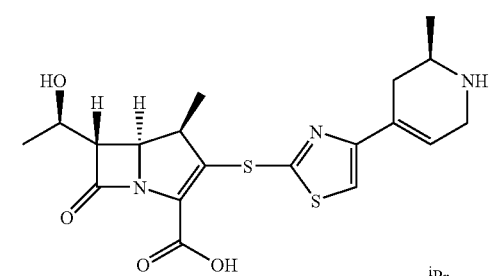
(a)

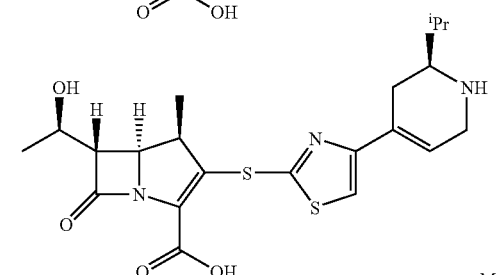
(b)

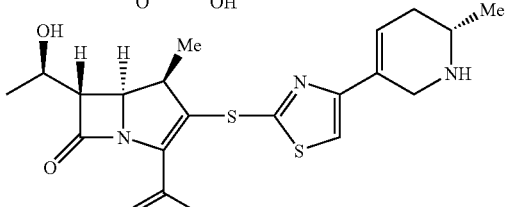
(c)

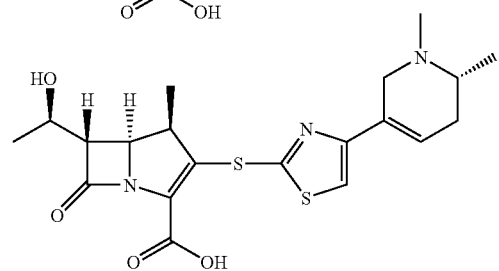
(d)

or a pharmaceutically acceptable salt thereof, or a non-toxic ester thereof.

2. The β-lactam compound according to claim 1, which is a compound of the formula:

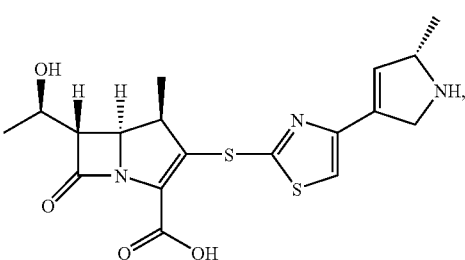

or a pharmaceutically acceptable salt thereof.

3. The β-lactam compound according to claim 1, which is a compound of the formula:

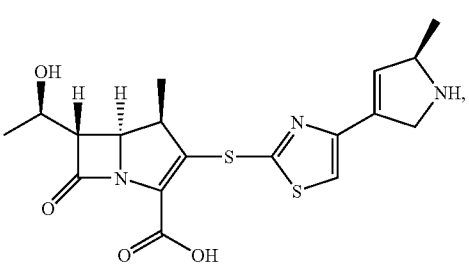

or a pharmaceutically acceptable salt thereof.

4. The β-lactam compound according to claim 1, which is a compound of the formula:

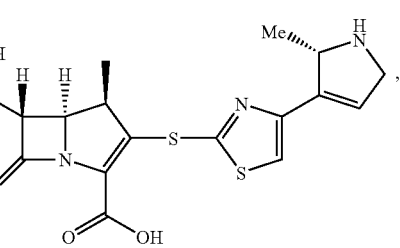

or a pharmaceutically acceptable salt thereof.

5. The β-lactam compound according to claim 1, which is a compound of the formula:

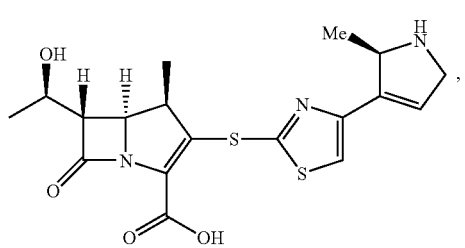

or a pharmaceutically acceptable salt thereof.

6. The β-lactam compound according to claim 1, which is a compound of the formula:

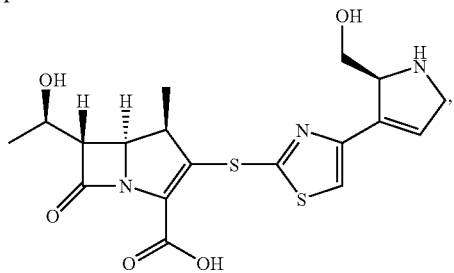

or a pharmaceutically acceptable salt thereof.

7. The β-lactam compound according to claim 1, which is a compound of the formula:

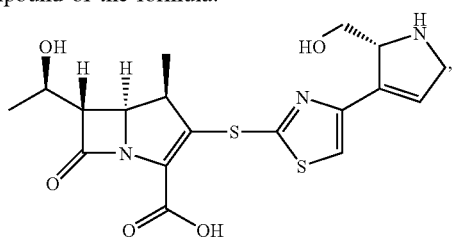

or a pharmaceutically acceptable salt thereof.

8. The β-lactam compound according to claim 1, which is a compound of the formula:

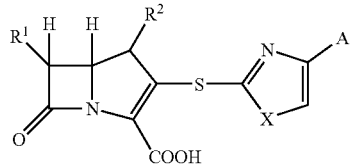

wherein $R^1$ is CH(OH)CH$_3$, $R^2$ is CH$_3$, X is S and A is

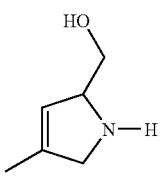

or a pharmaceutically acceptable salt thereof.

9. The β-lactam compound according to claim 1, which is a compound of the formula:

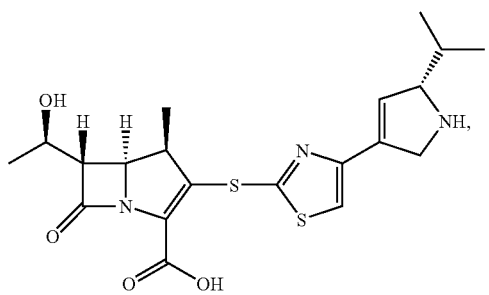

or a pharmaceutically acceptable salt thereof.

10. The β-lactam compound according to claim 1, which is a compound of the formula:

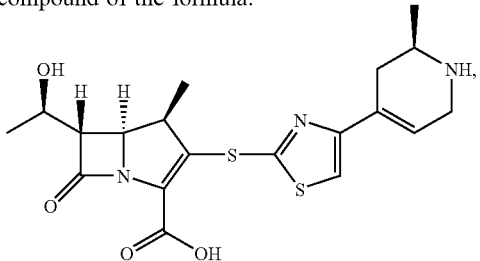

or a pharmaceutically acceptable salt thereof.

11. The β-lactam compound according to claim 1, which is a compound of the formula:

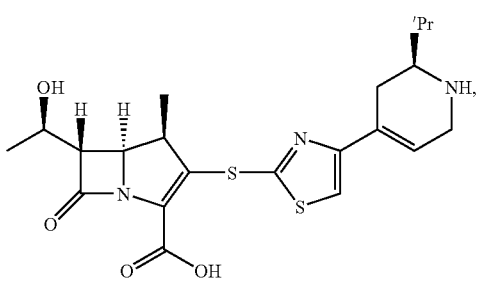

or a pharmaceutically acceptable salt thereof.

12. The β-lactam compound according to claim 1, which is a compound of the formula:

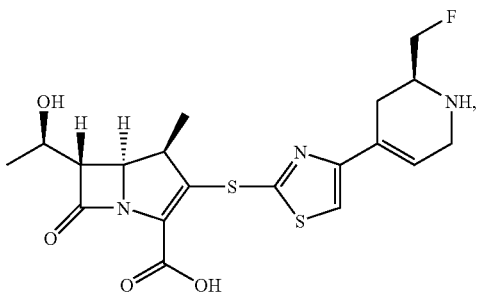

or a pharmaceutically acceptable salt thereof.

13. The β-lactam compound according to claim 1, which is a compound of the formula:

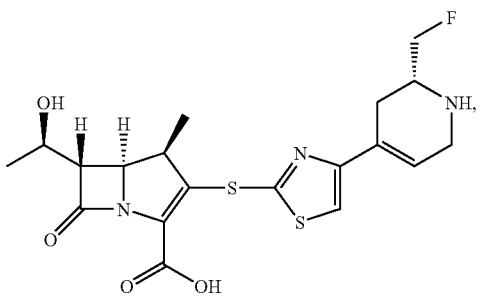

or a pharmaceutically acceptable salt thereof.

14. The β-lactam compound according to claim 1, which is a compound of the formula:

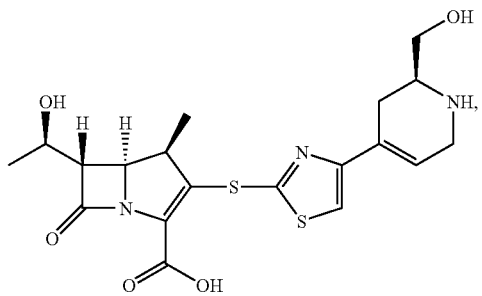

or a pharmaceutically acceptable salt thereof.

15. The β-lactam compound according to claim 1, which is a compound of the formula:

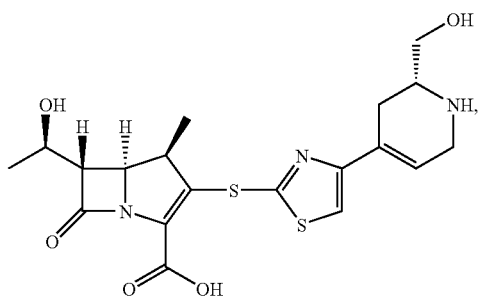

or a pharmaceutically acceptable salt thereof.

16. The β-lactam compound according to claim 1, which is a compound of the formula:

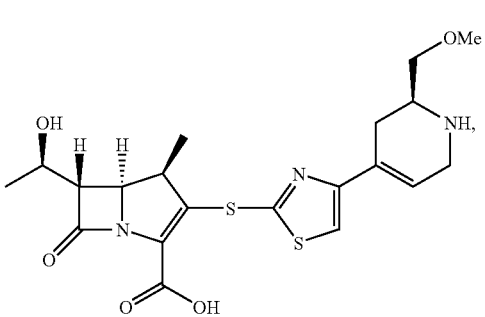

or a pharmaceutically acceptable salt thereof.

17. The β-lactam compound according to claim 1, which is a compound of the formula:

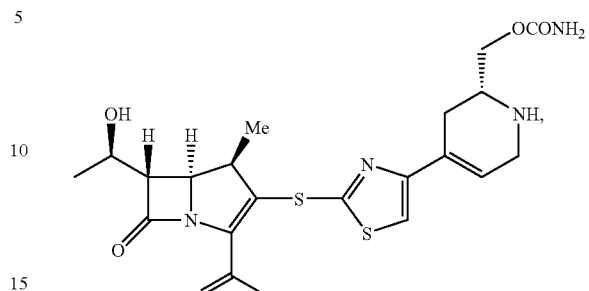

or a pharmaceutically acceptable salt thereof.

18. The β-lactam compound according to claim 1, which is a compound of the formula:

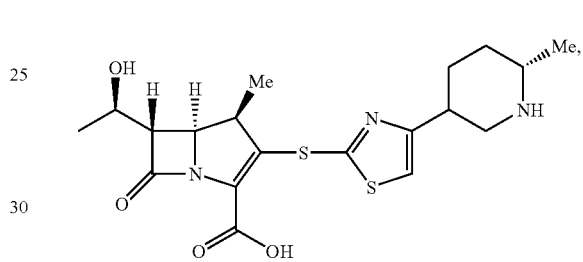

or a pharmaceutically acceptable salt thereof.

19. The β-lactam compound according to claim 1, which is a compound of the formula:

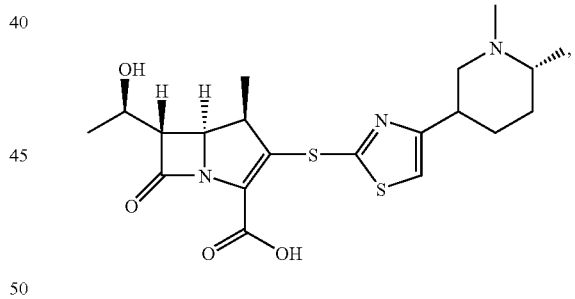

or a pharmaceutically acceptable salt thereof.

* * * * *

UNITED STATES PATENT AND TRADEMARK OFFICE
CERTIFICATE OF CORRECTION

| | |
|---|---|
| PATENT NO. | : 7,163,936 B2 |
| APPLICATION NO. | : 10/416334 |
| DATED | : January 16, 2007 |
| INVENTOR(S) | : Makoto Sunagawa et al. |

It is certified that error appears in the above-identified patent and that said Letters Patent is hereby corrected as shown below:

Column 115, Claim 1, line 17, delete "when";

line 18, change "m=1, n=1" to -- m=1 and n=1 --;

line 19, change "isopropyl;" to -- isopropyl, --;

line 20, change "m=1, n=2" to -- when m=1 and n=2 --;

line 21, change "carbamoyloxymethyl;" to -- carbamoyloxymethyl, --;

Signed and Sealed this

Tenth Day of April, 2007

JON W. DUDAS
*Director of the United States Patent and Trademark Office*